(12) United States Patent
Bretschneider et al.

(10) Patent No.: US 7,897,543 B2
(45) Date of Patent: Mar. 1, 2011

(54) SPIROKETAL-SUBSTITUTED CYCLIC KETOENOLS

(75) Inventors: Thomas Bretschneider, Lohmar (DE); Reiner Fischer, Monheim (DE); Oliver Gaertzen, Köln (DE); Stefan Lehr, Liederbach (DE); Mark Wilhelm Drewes, Langenfeld (DE); Dieter Feucht, Eschborn (DE); Olga Malsam, Rösrath (DE); Udo Reckmann, Köln (DE); Christian Arnold, Langenfeld (DE); Thomas Auler, Leichlingen (DE); Waltraud Hempel, Liederbach (DE); Martin Jeffrey Hills, Idstein (DE); Heinz Kehne, Hofheim (DE); Christopher Hugh Rosinger, Hofheim (DE); Erich Sanwald, Keil (DE)

(73) Assignee: Bayer CropScience AG, Monheim (DE)

( * ) Notice: Subject to any disclaimer, the term of this patent is extended or adjusted under 35 U.S.C. 154(b) by 380 days.

(21) Appl. No.: 11/884,887

(22) PCT Filed: Feb. 8, 2006

(86) PCT No.: PCT/EP2006/001089

§ 371 (c)(1),
(2), (4) Date: Apr. 3, 2008

(87) PCT Pub. No.: WO2006/089633

PCT Pub. Date: Aug. 31, 2006

(65) Prior Publication Data

US 2008/0305955 A1 Dec. 11, 2008

(30) Foreign Application Priority Data

Feb. 22, 2005 (DE) .................. 10 2005 008 021

(51) Int. Cl.
*A01N 43/08* (2006.01)
*A01N 43/38* (2006.01)
*C07D 209/54* (2006.01)
*C07D 307/94* (2006.01)

(52) U.S. Cl. .................. 504/140; 548/408; 549/331
(58) Field of Classification Search .................. 548/408; 549/331
See application file for complete search history.

(56) References Cited

U.S. PATENT DOCUMENTS

| | | | |
|---|---|---|---|
| 4,021,224 A | 5/1977 | Pallos et al. |
| 4,186,130 A | 1/1980 | Teach |
| 4,623,727 A | 11/1986 | Hübele |
| 4,639,266 A | 1/1987 | Heubach et al. |
| 4,881,966 A | 11/1989 | Nyffeler et al. |
| 4,891,057 A | 1/1990 | Sohn et al. |
| 4,902,340 A | 2/1990 | Hubele |
| 4,925,868 A | 5/1990 | Terao et al. |
| 4,985,063 A | 1/1991 | Fischer et al. |
| 5,045,560 A | 9/1991 | Fischer et al. |
| 5,094,681 A | 3/1992 | Krämer et al. |
| 5,116,836 A | 5/1992 | Fischer et al. |
| 5,225,434 A | 7/1993 | Bertram et al. |
| 5,258,527 A | 11/1993 | Krauskopf et al. |
| 5,262,383 A | 11/1993 | Fischer et al. |
| 5,314,863 A | 5/1994 | Löher et al. |
| 5,380,852 A | 1/1995 | Schütze et al. |
| 5,401,700 A | 3/1995 | Sohn et al. |
| 5,407,897 A | 4/1995 | Cary et al. |
| 5,462,913 A | 10/1995 | Fischer et al. |
| 5,504,057 A | 4/1996 | Fischer et al. |
| 5,508,436 A | 4/1996 | Fischer et al. |
| 5,516,750 A | 5/1996 | Willms et al. |
| 5,567,671 A | 10/1996 | Fischer et al. |
| 5,589,469 A | 12/1996 | Fischer et al. |
| 5,610,122 A | 3/1997 | Fischer et al. |
| 5,622,917 A | 4/1997 | Fischer et al. |
| 5,683,965 A | 11/1997 | Bachmann et al. |

(Continued)

FOREIGN PATENT DOCUMENTS

CA 2 492 096 A1 1/2004

(Continued)

OTHER PUBLICATIONS

J. Patrick Parkman. Pest Management Strategic Plan for Beef Cattle in Tennessee and Kentucky. Summary of Workshops held in Jan. 2005 Princeton, KY and Nashville, TN (2005).*

(Continued)

*Primary Examiner*—Shawquia Young
(74) *Attorney, Agent, or Firm*—Sterne, Kessler, Goldstein & Fox P.L.L.C.

(57) ABSTRACT

The invention relates to novel spiroketal-substituted cyclic ketoenols of the formula (I)

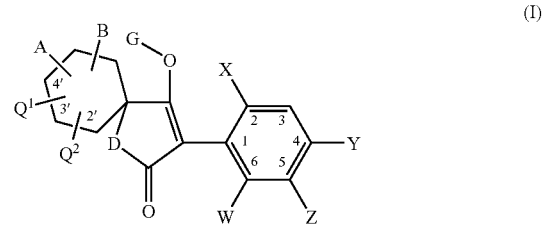

(I)

in which
A, B, $Q^1$, $Q^2$, D, G, W, X, Y, and Z are as defined above,
to processes and intermediates for their preparation and to their use as pesticides and/or microbicides and/or herbicides.

Moreover, the invention relates to selective herbicidal compositions comprising, firstly, spiroketal-substituted cyclic ketoenols and, secondly, a crop plant compatibility-improving compound.

16 Claims, No Drawings

U.S. PATENT DOCUMENTS

| | | | |
|---|---|---|---|
| 5,700,758 | A | 12/1997 | Rösch et al. |
| 5,739,079 | A | 4/1998 | Holdgrün et al. |
| 5,811,374 | A | 9/1998 | Bertram et al. |
| 5,830,825 | A | 11/1998 | Fischer et al. |
| 5,830,826 | A | 11/1998 | Fischer et al. |
| 5,922,732 | A | 7/1999 | Urch et al. |
| 5,945,444 | A | 8/1999 | Fischer et al. |
| 6,114,374 | A | 9/2000 | Lieb et al. |
| 6,133,296 | A | 10/2000 | Lieb et al. |
| 6,140,358 | A | 10/2000 | Lieb et al. |
| 6,200,932 | B1 | 3/2001 | Fischer et al. |
| 6,235,680 | B1 | 5/2001 | Ziemer et al. |
| 6,251,827 | B1 | 6/2001 | Ziemer et al. |
| 6,251,830 | B1 | 6/2001 | Fischer et al. |
| 6,316,486 | B1 | 11/2001 | Lieb et al. |
| 6,358,887 | B1 | 3/2002 | Fischer et al. |
| 6,417,370 | B1 | 7/2002 | Lieb et al. |
| 6,451,843 | B1 | 9/2002 | Lieb et al. |
| 6,458,965 | B1 | 10/2002 | Lieb et al. |
| 6,472,419 | B1 | 10/2002 | Fischer et al. |
| 6,511,942 | B1 | 1/2003 | Lieb et al. |
| 6,589,976 | B1 | 7/2003 | Fischer et al. |
| 6,608,211 | B1 | 8/2003 | Hagemann et al. |
| 6,861,391 | B1 | 3/2005 | Fischer et al. |
| 6,894,005 | B1 | 5/2005 | Maetzke et al. |
| 2002/0061913 | A1 | 5/2002 | Urch et al. |
| 2002/0072617 | A1 | 6/2002 | Hagemann et al. |
| 2003/0171220 | A1 | 9/2003 | Ziemer et al. |
| 2003/0216260 | A1 | 11/2003 | Ruther et al. |
| 2005/0054535 | A1 | 3/2005 | Fischer et al. |
| 2005/0090399 | A1 | 4/2005 | Friedmann et al. |
| 2006/0160847 | A1 | 7/2006 | Fischer et al. |
| 2006/0166829 | A1 | 7/2006 | Fischer et al. |

FOREIGN PATENT DOCUMENTS

| | | |
|---|---|---|
| CA | 2 497 074 A1 | 3/2004 |
| CA | 2 518 620 A1 | 9/2004 |
| CA | 2 544 537 A1 | 5/2005 |
| CA | 2 544 548 A1 | 5/2005 |
| CA | 2 546 815 A1 | 6/2005 |
| CA | 2 546 817 A1 | 6/2005 |
| CA | 2 552 737 A1 | 7/2005 |
| CA | 2 561 076 A1 | 10/2005 |
| CA | 2 572 141 A1 | 1/2006 |
| EP | 0 346 620 A1 | 12/1989 |
| GB | 2 266 888 A | 11/1993 |
| JP | 2000/53670 A | 2/2000 |
| JP | 2002/205984 A | 7/2002 |

OTHER PUBLICATIONS

Mio, et al., Document 133:362702, retrieved on Sep. 10, 2010 from CAPLUS.*

Avenoza, A., et al., "A New Efficient Synthesis of 2-Phenyl-4-oxo-1-aminocyclohexanecarboxylic Acids," *Tetrahedron* 50:12989-12998, Elsevier Science Ltd. (1994).

Bhattacharya, B., "Isoquinoline Derivatives: Part XVIII—Formation of I-Alkyl-(alkaryl or aryl)-3-methyl-7-chloro-(or 5-chloro)-isoquinolines," *Indian J. Chem.* 6:341-345, Council of Scientific and Industrial Research (1968).

Campbell, A.C., et al., "Synthesis of (E)- and (Z)-Pulvinones," *J. Chem. Soc. Perkins Trans. I* 8:1567-1576, Chemical Society (1985).

Compagnon, P.L., and Miocque, M., "Addition des Réactifs Nucleophiles sur la Triple Liaison Nitrile," *Ann. Chim.* 5:11-22, Masson (1970).

Edward, J.T., and Jitrangsri, C., "Stereochemistry of the Bucherer-Bergs and Strecker Reactions of 4-tert-Butylcyclohexanone," *Can J. Chem.* 53:3339-3350, NRC Research Press (1975).

Felice, E., et al., "Easy Access to α-Amino β-Oxo Esters from β-Enamino Ester," *Tetrahedron Letts.* 40:4413-4416, Elsevier Science Ltd. (1999).

Fischer, R., and Benet-Buchholz, J., "Chemistry and stereochemistry of spirodiclofen (BAJ 2740)," *Pflanzenschutz-Nachrichten Bayer* 55:137-148, Leverkusen: Bayer CropScience AG (2002).

Harrison, H.R., et al., "Use of molecular sieves in the methyl esterification of carboxylic acids," *Chem. Ind.*, pp. 1568, Society of Chemical Industry (1968).

Ito, M., et al., "Synthesis and Insecticidal Activity of Novel N-Oxydihydropyrrole Derivatives with a Substituted Spirocyclohexyl Group," *Biosci. Biotechnol. Biochem.* 67:1230-1238, Japan Society for Bioscience, Biotechnology, and Agrochemistry (2003).

Ito, M., et al., "Synthesis and Insecticidal Activity of N-Oxydihydropyrroles: 4-Hydroxy-3-mesityl-5,5-dimethyl Derivatives with Various Substituents at the 1-Position," *Biosci. Biotechnol. Biochem.* 66:2406-2414, Japan Society for Bioscience, Biotechnology, and Agrochemistry (2002).

Lednicer, D., et al., "4-Aryl-4-aminocyclohexanones and Their Derivatives, a Novel Class of Analgesics. 3. *m*-Hydroxyphenyl Derivatives," *J Med. Chem.* 24:341-346, American Chemical Society (1981).

Munday, L., "Amino-acids of the Cyclohexane Series. Part I.," *J. Chem. Soc.*, pp. 4372-4379, Royal Society of Chemistry (1961).

Ota, H., et al., "A novel synthesis of cyclic α-amino aldehydes, amino alcohols, and α-amino acid methyl esters from cyclic ketones through sulfinylaziridines," *Tetrahedron Letts.* 45:3903-3907, Elsevier Ltd. (Mar. 2004).

Satoh, T., et al.,"1-Chloroallcyl-p-Tolyl Sulfoxides as Useful Agents for Homologation of Carbonyl Compounds: Conversion of Carbonyl Compounds to α-Hydroxy Acids, Esters, and Amides and α,. α'-Dihydroxy Ketones," *J. Org. Chem.* 56:4129-4134, American Chemical Society (1991).

Schmierer, R., and Mildenberger, H., "Cyclisierung von N-Acylalanin-und N-Acylglycinestern," *Liebigs Ann. Chem.* 6:1095-1098, VCH Verlagsgesellschaft mbH (1985).

Sonntag, N.O.V., "The Reactions of Aliphatic Acid Chlorides," *Chem. Rev.* 52:237-416, American Chemical Society (1953).

Suzuki, S., et al., "Studies on antiviral agents. IV. Biological activity of tenuazonic acid derivatives," *Chem. Pharm. Bull.* 15:1120-1122, Pharmaceutical Society of Japan (1967).

Database Bellstein, Citation Number: 156279, Britten, A., and Lockwood G., *J. Chem. Soc. Perkin Trans. I*, pp. 1824-1827, Chemical Society (1974).

Database CAPLUS on STN, Chemical Accession No. 1985:437721 English language abstract, Schmierer, R., and Mildenberger, H., "Cyclization of N-acylalanine and N-acylglycine esters," *Liebigs Ann. Chem.* 5:1095-1098, (1985) (Abstract for document NPL15).

Dialog File 347, Accession No. 4963457, Derwent WPI English language abstract for EP 0 346 620 A1 (listed as document FP1 on accompanying form PTO/SB/08A).

Dialog File 351, Accession No. 6468095, Derwent WPI English language abstract for JP 2000/053670 A (listed as document FP3 on accompanying form PTO/SB/08A).

Dialog File 351, Accession No. 7337495, Derwent WPI English language abstract for JP 2002/205984 a (listed as document FP4 on accompanying form PTO/SB/08A).

International Search Report for International Application No. PCT/EP2006/001089, European Patent Office, Netherlands, mailed on Aug. 11, 2005.

* cited by examiner

SPIROKETAL-SUBSTITUTED CYCLIC KETOENOLS

This application is a National Stage of International Application No. PCT/EP2006/001089, filed Feb. 8, 2006, which claims the benefit of German Patent Application No. 10 2005 008 021.9, filed Feb. 22, 2005. The entirety of each of these applications is incorporated by reference herein.

The present invention relates to novel spiroketal-substituted cyclic ketoenols, to a plurality of processes for their preparation and to their use as pesticides and/or herbicides and/or microbicides. The invention also provides selective herbicidal compositions comprising, firstly, spiroketal-substituted cyclic ketoenols and, secondly, a crop plant compatibility-improving compound.

Pharmaceutical properties of 3-acylpyrrolidine-2,4-diones are described in the prior art (S. Suzuki et al. Chem. Pharm. Bull. 15 1120 (1967)). Furthermore, R. Schmierer and H. Mildenberger (Liebigs Ann. Chem. 1985, 1095) synthesized N-phenylpyrrolidine-2,4-diones. A biological activity of these compounds has not been described.

EP-A-0 262 399 and GB-A-2 266 888 disclose compounds of a similar structure (3-aryl-pyrrolidine-2,4-diones); however, a herbicidal, insecticidal or acaricidal action of the compounds is not known. Known to have a herbicidal, insecticidal or acaricidal action are unsubstituted bicyclic 3-arylpyrrolidine-2,4-dione derivatives (EP-A-355 599, EP-A-415 211 and JP-A-12-053 670), and also substituted monocyclic 3-arylpyrrolidine-2,4-dione derivatives (EP-A-377 893 and EP-A-442 077).

Also known are polycyclic 3-arylpyrrolidine-2,4-dione derivatives (EP-A-442 073), and also 1H-arylpyrrolidine dione derivatives (EP-A-456 063, EP-A-521 334, EP-A-596 298, EP-A-613 884, EP-A-613 885, WO 94/01 997, WO 95/26 954, WO 95/20 572, EP-A-0 668 267, WO 96/25 395, WO 96/35 664, WO 97/01 535, WO 97/02 243, WO 97/36 868, WO 97/43275, WO 98/05638, WO 98/06721, WO 98/25928, WO 99/24437, WO 99/43649, WO 99/48869 and WO 99/55673, WO 01/17972, WO 01/23354, WO 01/74770, WO 03/013249, WO 03/062244, WO 2004/007448, WO 2004/024688, WO 04/065366, WO 04/080962, WO 04/111042, WO 05/044791, WO 05/044796, WO 05/048710, WO 05/049596, WO 05/066125, WO 05/092897 and DE-A-04 030 753). Further well known are ketal-substituted 1H-arylpyrrolidine-2,4-diones from WO 99/16748 and (spiro)-ketal-substituted N-alkoxyalkoxy-substituted arylpyrrolidinediones from JP-A-14 205 984 and Ito M. et al., Bioscience, Biotechnology and Biochemistry 67, 1230-1.238, (2003).

It is known that certain substituted $\Delta^3$-dihydrofuran-2-one derivatives have herbicidal properties (cf. DE-A-4 014 420). The synthesis of the tetronic acid derivatives (such as, for example, 3-(2-methylphenyl)-4-hydroxy-5-(4-fluorophenyl)-$\Delta^3$-dihydrofuran-2-one) used as starting materials is also described in DE-A-4 014 420. Compounds of a similar structure with no stated insecticidal and/or acaricidal activity are known from the publication Campbell et al., J. Chem. Soc., Perkin Trans. 1, 1985, (8) 1567-76. Furthermore, 3-aryl-$\Delta^3$-dihydrofuranone derivatives having herbicidal, acaricidal and insecticidal properties are known from EP-A-528 156, EP-A-0 647 637, WO 95/26 345, WO 96/20 196, WO 96/25 395, WO 96/35 664, WO 97/01 535, WO 97/02 243, WO 97/36 868, WO 98/05638, WO 98/25928, WO 99/16748, WO 99/43649, WO 99/48869, WO 99/55673, WO 01/17972, WO 01/23354 and WO 01/74770, WO 03/013 249, WO 2004/024 688, WO 04/080962, WO 04/111042, WO 05/092897 and DE-A-04 030 753.

However, the herbicidal and/or acaricidal and/or insecticidal activity and/or activity spectrum and/or the plant compatibility of the known compounds, in particular with respect to crop plants, is/are not always satisfactory.

This invention now provides novel compounds of the formula (I)

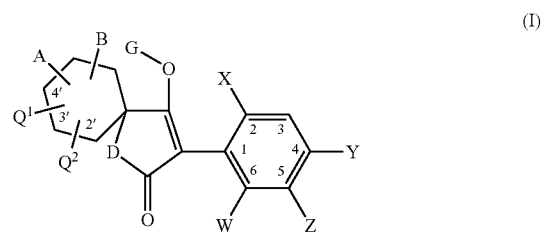

in which
W represents hydrogen, alkyl, alkenyl, alkynyl, halogen, alkoxy, alkenyloxy, haloalkyl, haloalkoxy or cyano,
X represents halogen, alkyl, alkenyl, alkynyl, alkoxy, alkenyloxy, alkylthio, alkylsulphinyl, alkylsulphonyl, haloalkyl, haloalkoxy, haloalkenyloxy, nitro or cyano,
Y and Z independently of one another represent hydrogen, alkyl, alkenyl, alkynyl, alkoxy, halogen, haloalkyl, haloalkoxy, cyano, nitro or in each case optionally substituted aryl or hetaryl,
with the proviso that at least one of the radicals W or Z has to be different from hydrogen if X and Y represent methyl,
A and B and the carbon atom to which they are attached represent five- to seven-membered ketal, thioketal or dithioketal which may optionally be interrupted by a further heteroatom, each of which radicals is optionally substituted by alkyl, haloalkyl, alkoxy, alkoxyalkyl or optionally substituted phenyl,
D represents NH and oxygen,
$Q^1$, $Q^2$ independently of one another represent hydrogen, alkyl, haloalkyl or alkoxy,
G represents hydrogen (a) or represents one of the groups (b)

(c)

(d)

(e)

(f)

(g)

in which

E represents a metal ion or an ammonium ion,

L represents oxygen or sulphur,

M represents oxygen or sulphur, $R^1$ represents in each case optionally halogen- or cyano-substituted alkyl, alkenyl, alkoxyalkyl, alkylthioalkyl or polyalkoxyalkyl or represents in each case optionally halogen-, alkyl- or alkoxy-substituted cycloalkyl or heterocyclyl or represents in each case optionally substituted phenyl, phenylalkyl, hetaryl, phenoxyalkyl or hetaryloxyalkyl, $R^2$ represents in each case optionally halogen- or cyano-substituted alkyl, alkenyl, alkoxyalkyl or polyalkoxyalkyl or represents in each case optionally substituted cycloalkyl, phenyl or benzyl, $R^3$, $R^4$ and $R^5$ independently of one another represent in each case optionally halogen-substituted alkyl, alkoxy, alkylamino, dialkylamino, alkylthio, alkenylthio or cycloalkylthio or represent in each case optionally substituted phenyl, benzyl, phenoxy or phenylthio, $R^6$ and $R^7$ independently of one another represent hydrogen, represent in each case optionally halogen- or cyano-substituted alkyl, cycloalkyl, alkenyl, alkoxy, alkoxyalkyl, represent in each case optionally substituted phenyl or benzyl, or together with the N atom to which they are attached form an optionally substituted cycle which optionally contains oxygen or sulphur.

Depending inter alia on the nature of the substituents, the compounds of the formula (I) can be present as optical isomers or isomer mixtures of varying composition which, if appropriate, may be separated in a customary manner. The present invention provides both the pure isomers and the isomer mixtures, their preparation and use, and compositions comprising them. However, for the sake of simplicity, hereinbelow only compounds of the formula (I) are referred to, although what is meant are both the pure compounds and, if appropriate, also mixtures having varying proportions of isomeric compounds.

Including D for NH (1) and D for O (2), the following principal structures (I-1) and (I-2) result:

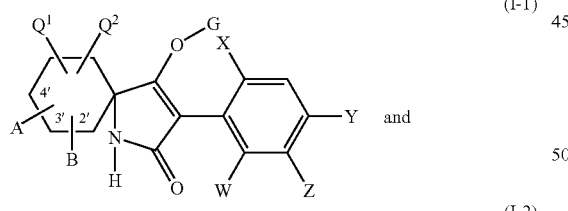

(I-1)

and

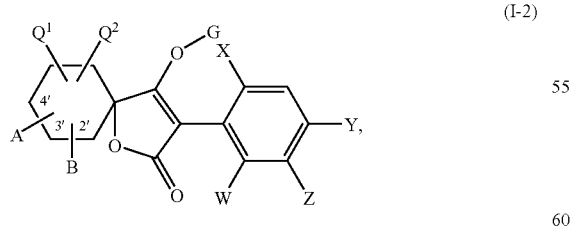

(I-2)

in which

A, B, G, $Q^1$, $Q^2$, W, X, Y and Z are as defined above.

Including the different meanings (a), (b), (c), (d), (e), (f) and (g) of the group G, the following principal structures (I-1-a) to (I-1-g) result if D represents NH (1)

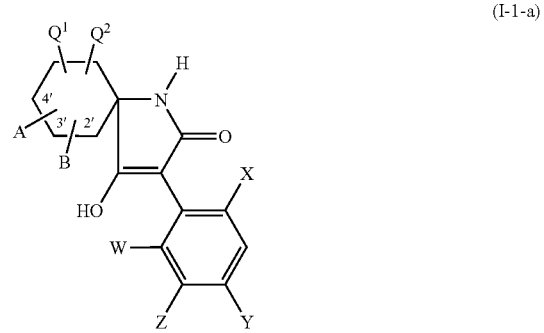

(I-1-a)

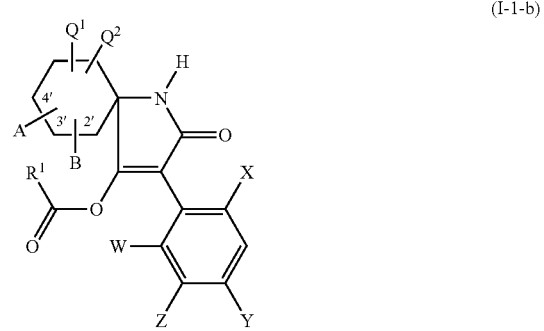

(I-1-b)

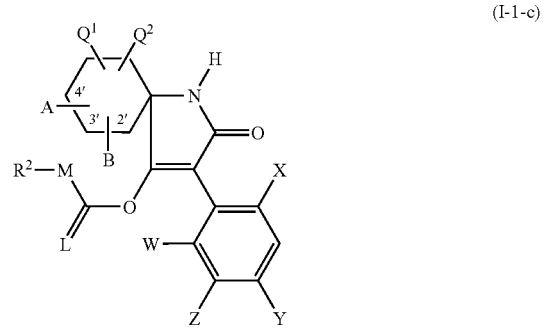

(I-1-c)

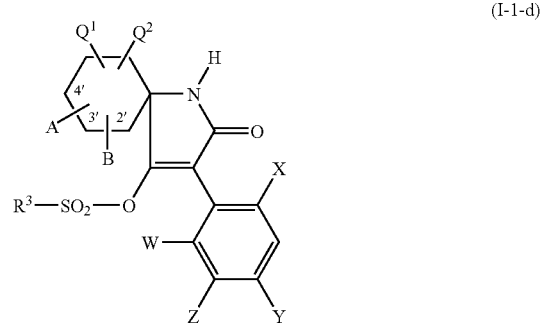

(I-1-d)

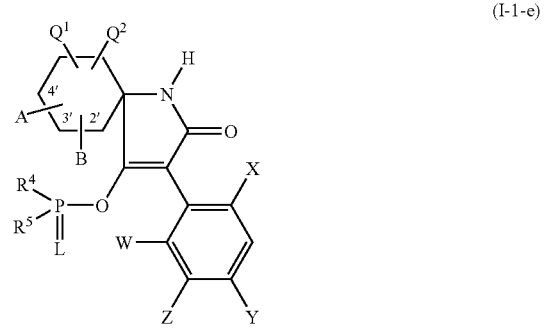

(I-1-e)

-continued (I-1-f)

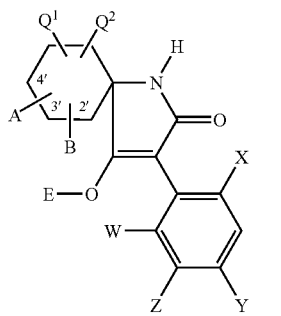

(I-1-g)

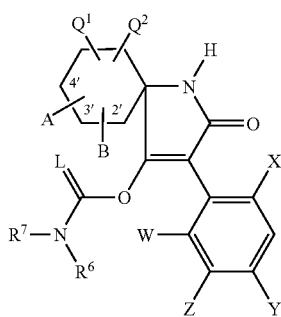

in which

A, B, E, L, M, $Q^1$, $Q^2$, W, X, Y, Z, $R^1$, $R^2$, $R^3$, $R^4$, $R^5$, $R^6$ and $R^7$ are as defined above.

Including the different meanings (a), (b), (c), (d), (e), (f) and (g) of the group G, the following principal structures (I-2-a) to (I-2-g) result if D represents O (2)

(I-2-a)

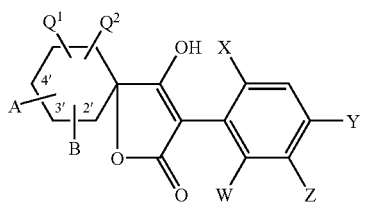

(I-2-b)

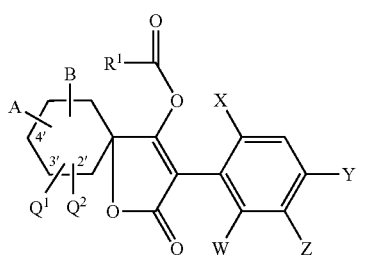

(I-2-c)

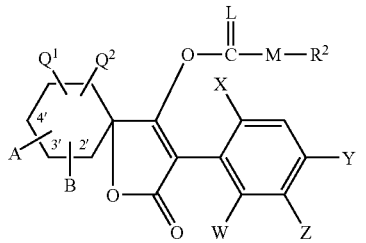

(I-2-d)

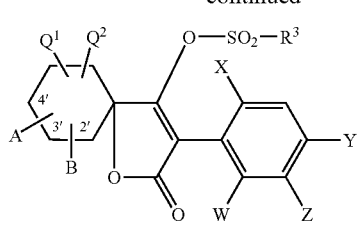

(I-2-e)

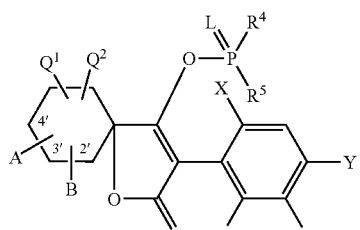

(I-2-f)

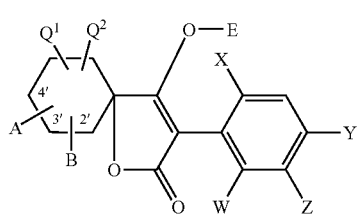

(I-2-g)

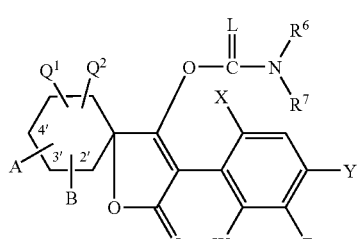

in which

A, B, E, L, M, $Q^1$, $Q^2$, W, X, Y, Z, $R^1$, $R^2$, $R^3$, $R^4$, $R^5$, $R^6$ and $R^7$ are as defined above.

Furthermore, it has been found that the novel compounds of the formula (I) are obtained by the processes described below:

(A) compounds of the formula (I-1-a)

(I-1-a)

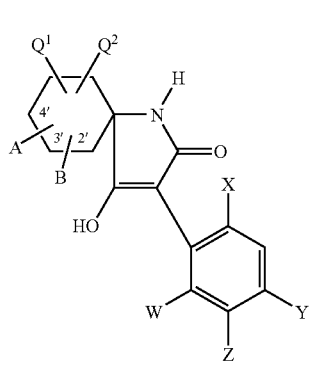

in which
A, B, $Q^1$, $Q^2$, W, X, Y and Z are as defined above are obtained when compounds of the formula (II)

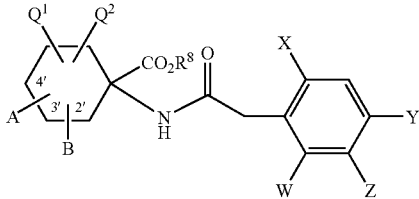

in which
A, B, $Q^1$, $Q^2$, W, X, Y and Z are as defined above
and
$R^8$ represents alkyl (preferably $C_1$-$C_6$-alkyl),
are condensed intramolecularly in the presence of a diluent and in the presence of a base.

(B) Moreover, it has been found that compounds of the formula (I-2-a)

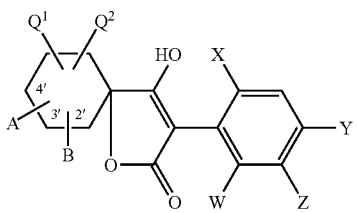

in which
A, B, $Q^1$, $Q^2$, W, X, Y and Z are as defined above,
are obtained when
compounds of the formula (III)

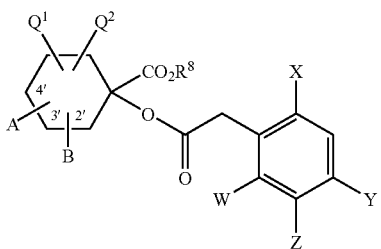

in which
A, B, $Q^1$, $Q^2$, W, X, Y, Z and $R^8$ are as defined above,
are condensed intramolecularly in the presence of a diluent and in the presence of a base.

Moreover, it has been found (C) that the compounds of the formulae (I-1-b) to (I-2-b) shown above in which $R^1$, A, B, $Q^1$, $Q^2$, W, X, Y and Z are as defined above are obtained when compounds of the formulae (I-1-a) to (I-2-a) shown above in which A, B, $Q^1$, $Q^2$, W, X, Y and Z are as defined above are in each case reacted α) with compounds of the formula (IV)

in which
$R^1$ is as defined above and
Hal represents halogen (in particular chlorine or bromine)
or
β) with carboxylic anhydrides of the formula (V)

in which
$R^1$ is as defined above,
if appropriate in the presence of a diluent and if appropriate in the presence of an acid binder;

(D) that the compounds of the formulae (I-1-c) to (I-2-c) shown above in which $R^2$, A, B, $Q^1$, $Q^2$, W, M, X, Y and Z are as defined above and L represents oxygen are obtained when compounds of the formulae (I-1-a) to (I-2-a) shown above in which A, B, $Q^1$, $Q^2$, W, X, Y and Z are as defined above are in each case reacted
with chloroformic esters or chloroformic thioesters of the formula (VI)

in which
$R^2$ and M are as defined above,
if appropriate in the presence of a diluent and if appropriate in the presence of an acid binder;

(E) that compounds of the formulae (I-1-c) to (I-2-c) shown above in which $R^2$, A, B, $Q^1$, $Q^2$, W, M, X, Y and Z are as defined above and L represents sulphur are obtained when compounds of the formulae (I-1-a) to (I-2-a) shown above in which A, B, $Q^1$, $Q^2$, W, X, Y and Z are as defined above are in each case reacted
with chloromonothioformic esters or chlorodithioformic esters of the formula (VII)

in which
M and $R^2$ are as defined above,
if appropriate in the presence of a diluent and if appropriate in the presence of an acid binder, (F) that compounds of the formulae (I-1-d) to (I-2-d) shown above in which $R^3$, A, B, W, $Q^1$, $Q^2$, X, Y and Z are as defined above are obtained when compounds of the formulae (I-1-a) to (I-2-a) shown above in which A, B, $Q^1$, $Q^2$, W, X, Y and Z are as defined above are in each case reacted
with sulphonyl chlorides of the formula (VIII)

in which
$R^3$ is as defined above,
if appropriate in the presence of a diluent and if appropriate in the presence of an acid binder, (G) that compounds of the formulae (I-1-e) to (I-2-e) shown above in which L, $R^4$, $R^5$, A, B, $Q^1$, $Q^2$, W, X, Y and Z are as defined above are obtained when compounds of the formulae (I-1-a) to (I-2-a) shown above in which A, B, $Q^1$, $Q^2$, W, X, Y and Z are as defined above are in each case reacted
with phosphorus compounds of the formula (IX)

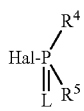

in which
L, $R^4$ and $R^5$ are as defined above and
Hal represents halogen (in particular chlorine or bromine), if appropriate in the presence of a diluent and if appropriate in the presence of an acid binder,
(H) that compounds of the formulae (I-1-f) to (I-2-f) shown above in which E, A, B, $Q^1$, $Q^2$, W, X, Y and Z are as defined above are obtained when compounds of the formulae (I-1-a) to (I-2-a) in which A, B, $Q^1$, $Q^2$, W, X, Y and Z are as defined above are in each case reacted
with metal compounds or amines of the formula (X) or (XI)

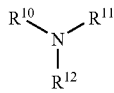

in which
Me represents a mono- or divalent metal (preferably an alkali metal or alkaline earth metal, such as lithium, sodium, potassium, magnesium or calcium),
t represents the number 1 or 2 and
$R^{10}$, $R^{11}$, $R^{12}$ independently of one another represent hydrogen or alkyl (preferably $C_1$-$C_8$-alkyl),
if appropriate in the presence of a diluent,
(I) that compounds of the formulae (I-1-g) to (I-2-g) shown above in which L, $R^6$, $R^7$, A, B, $Q^1$, $Q^2$, W, X, Y and Z are as defined above are obtained when compounds of the formulae (I-1-a) to (I-2-a) shown above in which A, B, $Q^1$, $Q^2$, W, X, Y and Z are as defined above are in each case
α) reacted with isocyanates or isothiocyanates of the formula (XII)

$$R^6\text{—}N\text{=}C\text{=}L \qquad (XII)$$

in which
$R^6$ and L are as defined above,
if appropriate in the presence of a diluent and if appropriate in the presence of a catalyst, or
β) reacted with carbamoyl chlorides or thiocarbamoyl chlorides of the formula (XIII)

in which
L, $R^6$ and $R^7$ are as defined above,
if appropriate in the presence of a diluent and if appropriate in the presence of an acid binder,
(J) that compounds of the formulae (I-1-a) to (I-1-g) and (I-2-a) to (I-2-g) shown above in which A, B, D, G, $Q^1$, $Q^2$, W, X, Y and Z are as defined above are obtained when compounds of the formula (XIV)

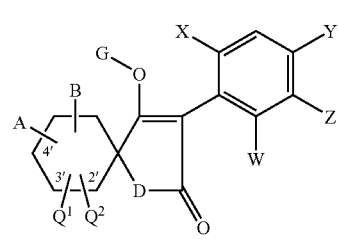

in which
D, G, $Q^1$, $Q^2$, W, X, Y and Z are as defined above,
and A, B and the carbon atom to which they are attached represent a

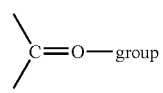

are reacted, for example, with diols of the formula (XV)

$$\text{HO-A-B—OH} \qquad (XV)$$

in which
A and B are as defined above,
if appropriate in the presence of a diluent, in the presence of an acidic catalyst and under dehydrating conditions.

The following compound of the formula (I-a) has been disclosed in 1994 in the context of the European Patent Examination of EP 596 298.

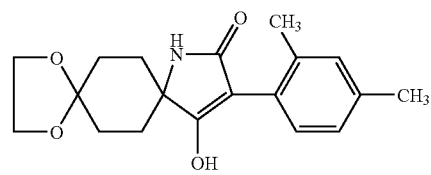

Ex. I-a-50

Furthermore, it has been found that the novel compounds of the formula (I) have good activity as pesticides, preferably as insecticides and/or acaricides and/or fungicides and/or herbicides, and are additionally frequently highly compatible with plants, in particular with crop plants.

Surprisingly, it has now also been found that certain substituted cyclic ketoenols, when employed together with the crop plant compatibility-improving compounds (safeners/antidotes) described later on, are extremely good at preventing damage to the crop plants and can be used with particular advantage as broad-spectrum combination products for the selective control of unwanted plants in crops of useful plants, such as, for example, in cereals, but also in maize, soy and rice.

The invention also provides selective herbicidal compositions comprising an effective amount of an active compound combination comprising, as components, (a') at least one compound of the formula (I) in which A, B, D, G, $Q^1$, $Q^2$, W, X, Y and Z are as defined above and (b') at least one crop plant compatibility-improving compound from the following group of compounds:

4-dichloroacetyl-1-oxa-4-azaspiro[4.5]decane (AD-67, MON-4660), 1-dichloroacetylhexahydro-3,3,8a-trimethylpyrrolo[1,2-a]pyrimidin-6(2H)-one (dicyclonon, BAS-145138), 4-dichloroacetyl-3,4-dihydro-3-methyl-2H-1,4-benzoxazine (benoxacor), 1-methylhexyl 5-chloroquinoline-8-oxy-acetate (cloquintocet-mexyl—cf. also related compounds in EP-A-86750, EP-A-94349, EP-A-191736, EP-A-492366), 3-(2-chlorobenzyl)-1-(1-methyl-1-phenylethyl)urea (cumyluron), α-(cyanomethoximino)phenylacetonitrile (cyometrinil), 2,4-dichlorophenoxyacetic acid (2,4-D), 4-(2,4-dichlorophenoxy)butyric acid (2,4-DB), 1-(1-methyl-1-phenylethyl)-3-(4-methylphenyl)urea (daimuron, dymron), 3,6-dichloro-2-methoxybenzoic acid (dicamba), S-1-methyl-1-phenylethyl piperidine-1-thiocarboxylate (dimepiperate), 2,2-dichloro-N-(2-oxo-2-(2-propenylamino) ethyl)-N-(2-propenyl)acetamide (DKA-24), 2,2-dichloro-N, N-di-2-propenylacetamide (dichlormid), 4,6-dichloro-2-phenylpyrimidine (fenclorim), ethyl 1-(2,4-dichlorophenyl)-5-trichloromethyl-1H-1,2,4-triazole-3-carboxylate (fenchlorazole-ethyl—cf. also related compounds in EP-A-174562 and EP-A-346620), phenylmethyl 2-chloro-4-trifluoromethylthiazole-5-carboxylate (flurazole), 4-chloro-N-(1,3-dioxolan-2-ylmethoxy)-α-trifluoroacetophenone oxime (fluxofenim), 3-dichloro-acetyl-5-(2-furanyl)-2,2-dimethyloxazolidine (furilazole, MON-13900), ethyl 4,5-dihydro-5,5-diphenyl-3-isoxazolecarboxylate (isoxadifen-ethyl—cf. also related compounds in WO-A-95/07897), 1-(ethoxycarbonyl)ethyl 3,6-dichloro-2-methoxybenzoate (lactidichlor), (4-chloro-o-tolyloxy)acetic acid (MCPA), 2-(4-chloro-o-tolyloxy)propionic acid (mecoprop), diethyl 1-(2,4-dichlorophenyl)-4,5-dihydro-5-methyl-1H-pyrazole-3,5-dicarboxylate (mefenpyr-diethyl—cf. also related compounds in WO-A-91/07874), 2-dichloromethyl-2-methyl-1,3-dioxolane (MG-191), 2-propenyl-1-oxa-4-azaspiro[4.5]decane-4-carbodithioate (MG-838), 1,8-naphthalic anhydride, α-(1, 3-dioxolan-2-ylmethoximino)phenylacetonitrile (oxabetrinil), 2,2-dichloro-N-(1,3-dioxolan-2-ylmethyl)-N-(2-propenyl)acetamide (PPG-1292), 3-dichloroacetyl-2,2-dimethyloxazolidine (R-28725), 3-dichloroacetyl-2,2,5-trimethyloxazolidine (R-29148), 4-(4-chloro-o-tolyl)butyric acid, 4-(4-chlorophenoxy)butyric acid, diphenylmethoxyacetic acid, methyl diphenylmethoxyacetate, ethyl diphenylmethoxyacetate, methyl 1-(2-chlorophenyl)-5-phenyl-1H-pyrazole-3-carboxylate, ethyl 1-(2,4-dichlorophenyl)-5-methyl-1H-pyrazole-3-carboxylate, ethyl 1-(2,4-dichlorophenyl)-5-isopropyl-1H-pyrazole-3-carboxylate, ethyl 1-(2,4-dichlorophenyl)-5-(1,1-dimethylethyl)-1H-pyrazole-3-carboxylate, ethyl 1-(2,4-dichlorophenyl)-5-phenyl-1H-pyrazole-3-carboxylate (cf. also related compounds in EP-A-269806 and EP-A-333131), ethyl 5-(2,4-dichlorobenzyl)-2-isoxazoline-3-carboxylate, ethyl 5-phenyl-2-isoxazoline-3-carboxylate, ethyl 5-(4-fluorophenyl)-5-phenyl-2-isoxazoline-3-carboxylate (cf. also related compounds in WO-A-91/08202), 1,3-dimethylbut-1-yl 5-chloroquinoline-8-oxyacetate, 4-allyloxybutyl 5-chloro-quinoline-8-oxyacetate, 1-allyloxyprop-2-yl 5-chloroquinoline-8-oxyacetate, methyl 5-chloroquinoxaline-8-oxyacetate, ethyl 5-chloroquinoxaline-8-oxyacetate, allyl 5-chloroquin-oxaline-8-oxyacetate, 2-oxoprop-1-yl 5-chloroquinoline-8-oxyacetate, diethyl 5-chloroquinoline-8-oxymalonate, diallyl 5-chloroquinoxaline-8-oxymalonate, diethyl 5-chloroquinoline-8-oxy-malonate (cf. also related compounds in EP-A-582198), 4-carboxychroman-4-ylacetic acid (AC-304415, cf. EP-A-613618), 4-chlorophenoxyacetic acid, 3,3'-dimethyl-4-methoxy-benzophenone, 1-bromo-4-chloromethylsulphonylbenzene, 1-[4-(N-2-methoxybenzoylsulphamoyl)phenyl]-3-methylurea (also known as N-(2-methoxybenzoyl)-4-[(methylaminocarbonyl)-amino]benzenesulphonamide), 1-[4-(N-2-methoxybenzoylsulphamoyl)phenyl]-3,3-dimethylurea, 1-[4-(N-4,5-dimethylbenzoylsulphamoyl)phenyl]-3-methylurea, 1-[4-(N-naphthylsulphamoyl)-phenyl]-3,3-dimethylurea, N-(2-methoxy-5-methylbenzoyl)-4-(cyclopropylaminocarbonyl)-benzenesulphonamide, and/or one of the following compounds, defined by general formulae, of the general formula (IIa)

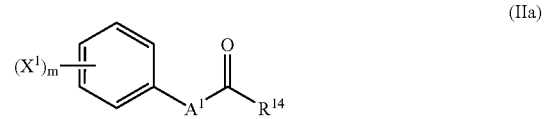

or of the general formula (IIb)

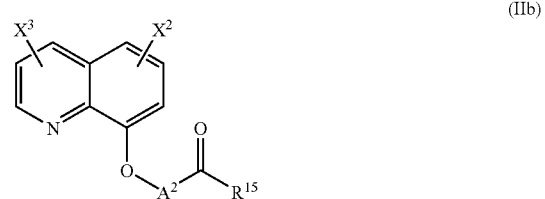

or of the formula (IIc)

where m represents a number 0, 1, 2, 3, 4 or 5, $A^1$ represents one of the divalent heterocyclic groupings shown below

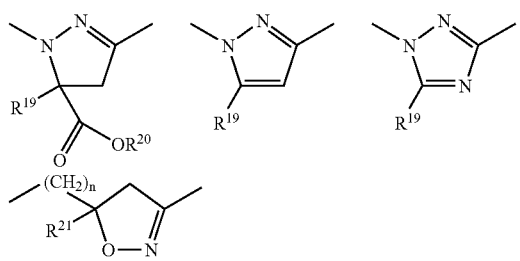

n represents a number 0, 1, 2, 3, 4 or 5,

A² represents optionally C₁-C₄-alkyl- and/or C₁-C₄-alkoxy-carbonyl- and/or C₁-C₄-alkenyloxy-carbonyl-substituted alkanediyl having 1 or 2 carbon atoms, R¹⁴ represents hydroxyl, mercapto, amino, C₁-C₆-alkoxy, C₁-C₆-alkylthio, C₁-C₆-alkylamino or di(C₁-C₄-alkyl)-amino, R¹⁵ represents hydroxyl, mercapto, amino, C₁-C₇-alkoxy, C₁-C₆-alkylthio, C₁-C₆-alkenyloxy, C₁-C₆-alkenyloxy-C₁-C₆-alkoxy, C₁-C₆-alkylamino or di(C₁-C₄-alkyl)-amino, R¹⁶ represents optionally fluorine-, chlorine- and/or bromine-substituted C₁-C₄-alkyl, R¹⁷ represents hydrogen, in each case optionally fluorine-, chlorine- and/or bromine-substituted C₁-C₆-alkyl, C₂-C₆-alkenyl or C₂-C₆-alkynyl, C₁-C₄-alkoxy-C₁-C₄-alkyl, dioxolanyl-C₁-C₄-alkyl, furyl, furyl-C₁-C₄-alkyl, thienyl, thiazolyl, piperidinyl, or optionally fluorine-, chlorine- and/or bromine- or C₁-C₄-alkyl-substituted phenyl, R¹⁸ represents hydrogen, in each case optionally fluorine-, chlorine- and/or bromine-substituted C₁-C₆-alkyl, C₂-C₆-alkenyl or C₂-C₆-alkynyl, C₁-C₄-alkoxy-C₁-C₄-alkyl, dioxolanyl-C₁-C₄-alkyl, furyl, furyl-C₁-C₄-alkyl, thienyl, thiazolyl, piperidinyl, or optionally fluorine-, chlorine- and/or bromine- or C₁-C₄-alkyl-substituted phenyl, R¹⁷ and R¹⁸ also together represent C₃-C₆-alkanediyl or C₂-C₅-oxaalkanediyl, each of which is optionally substituted by C₁-C₄-alkyl, phenyl, furyl, a fused benzene ring or by two substituents which, together with the C atom to which they are attached, form a 5- or 6-membered carbocycle, R¹⁹ represents hydrogen, cyano, halogen, or represents in each case optionally fluorine-, chlorine- and/or bromine-substituted C₁-C₄-alkyl, C₃-C₆-cycloalkyl or phenyl, R²⁰ represents hydrogen, in each case optionally hydroxyl-, cyano-, halogen- or C₁-C₄-alkoxy-substituted C₁-C₆-alkyl, C₃-C₆-cycloalkyl or tri-(C₁-C₄-alkyl)-silyl, R²¹ represents hydrogen, cyano, halogen, or represents in each case optionally fluorine-, chlorine- and/or bromine-substituted C₁-C₄-alkyl, C₃-C₆-cycloalkyl or phenyl, X¹ represents nitro, cyano, halogen, C₁-C₄-alkyl, C₁-C₄-haloalkyl, C₁-C₄-alkoxy or C₁-C₄-haloalkoxy, X² represents hydrogen, cyano, nitro, halogen, C₁-C₄-alkyl, C₁-C₄-haloalkyl, C₁-C₄-alkoxy or C₁-C₄-haloalkoxy, X³ represents hydrogen, cyano, nitro, halogen, C₁-C₄-alkyl, C₁-C₄-haloalkyl, C₁-C₄-alkoxy or C₁-C₄-haloalkoxy, and/or the following compounds, defined by general formulae, of the general formula (IId)

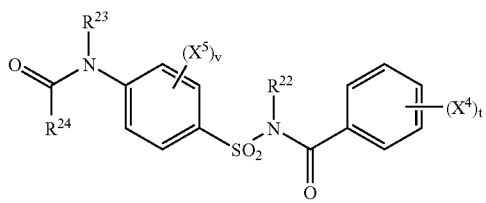

(IId)

or of the general formula (IIe)

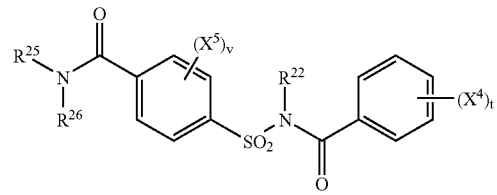

(IIe)

where t represents a number between 0 and 5, v represents a number between 0 and 5, R²² represents hydrogen or C₁-C₄-alkyl, R²³ represents hydrogen or C₁-C₄-alkyl, R²⁴ represents hydrogen, in each case optionally cyano-, halogen- or C₁-C₄-alkoxy-substituted C₁-C₆-alkyl, C₁-C₆-alkoxy, C₁-C₆-alkylthio, C₁-C₆-alkylamino or di(C₁-C₄-alkyl)-amino, or in each case optionally cyano-, halogen- or C₁-C₄-alkyl-substituted C₃-C₆-cycloalkyl, C₃-C₆-cycloalkyloxy, C₃-C₆-cycloalkylthio or C₃-C₆-cycloalkylamino, R²⁵ represents hydrogen, optionally cyano-, hydroxyl-, halogen- or C₁-C₄-alkoxy-substituted C₁-C₆-alkyl, in each case optionally cyano- or halogen-substituted C₃-C₆-alkenyl or C₃-C₆-alkynyl, or optionally cyano-, halogen- or C₁-C₄-alkyl-substituted C₃-C₆-cycloalkyl, R²⁶ represents hydrogen, optionally cyano-, hydroxyl-, halogen- or C₁-C₄-alkoxy-substituted C₁-C₆-alkyl, in each case optionally cyano- or halogen-substituted C₃-C₆-alkenyl or C₃-C₆-alkynyl, optionally cyano-, halogen- or C₁-C₄-alkyl-substituted C₃-C₆-cycloalkyl, or optionally nitro-, cyano-, halogen-, C₁-C₄-alkyl-, C₁-C₄-haloalkyl-, C₁-C₄-alkoxy- or C₁-C₄-haloalkoxy-substituted phenyl, or together with R²⁵ represents in each case optionally C₁-C₄-alkyl-substituted C₂-C₆-alkanediyl or C₂-C₅-oxaalkanediyl, X⁴ represents nitro, cyano, carboxyl, carbamoyl, formyl, sulphamoyl, hydroxyl, amino, halogen, C₁-C₄-alkyl, C₁-C₄-haloalkyl, C₁-C₄-alkoxy or C₁-C₄-haloalkoxy, and X⁵ represents nitro, cyano, carboxyl, carbamoyl, formyl, sulphamoyl, hydroxyl, amino, halogen, C₁-C₄-alkyl, C₁-C₄-haloalkyl, C₁-C₄-alkoxy or C₁-C₄-haloalkoxy.

The formula (I) provides a general definition of the compounds according to the invention. Preferred substituents or ranges of the radicals listed in the formulae given above and below are illustrated below:

W preferably represents hydrogen, C₁-C₆-alkyl, C₂-C₆-alkenyl, C₂-C₆-alkynyl, halogen, C₁-C₆-alkoxy, C₁-C₄-haloalkyl, C₁-C₄-haloalkoxy or cyano, X preferably represents halogen, C₁-C₆-alkyl, C₂-C₆-alkenyl, C₂-C₆-alkynyl, C₁-C₆-haloalkyl, C₁-C₆-alkoxy, C₃-C₆-alkenyloxy, C₁-C₆-alkylthio, C₁-C₆-alkylsulphinyl, C₁-C₆-alkylsulphonyl, C₁-C₆-haloalkoxy, C₃-C₆-haloalkenyloxy, nitro or cyano, Y and Z independently of one another preferably represent hydrogen, halogen, C₁-C₆-alkyl, C₂-C₆-alkenyl, C₂-C₆-alkynyl, C₁-C₆-alkoxy, C₁-C₆-haloalkyl, C₁-C₆-haloalkoxy, cyano, C₂-C₆-alkenyl, C₂-C₆-alkynyl or one of the (het)aryl radicals

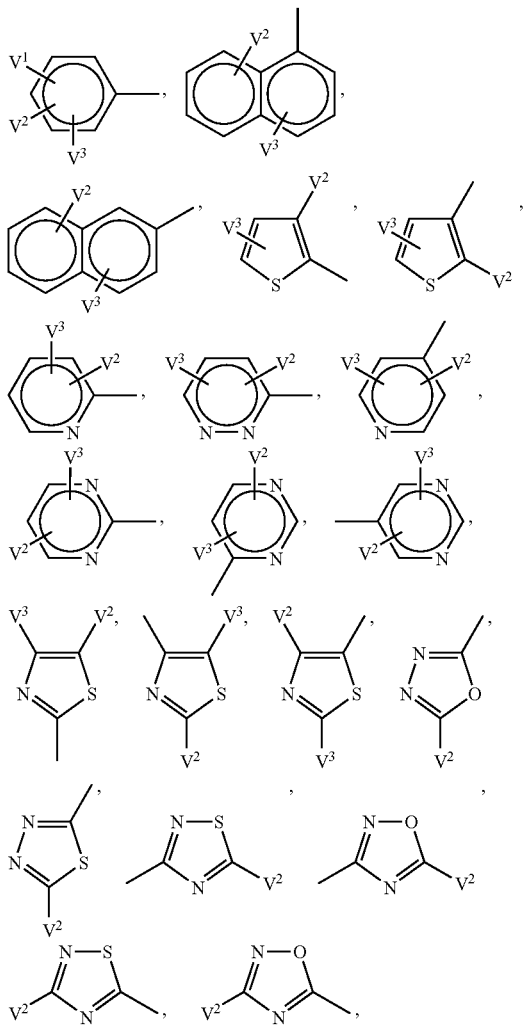

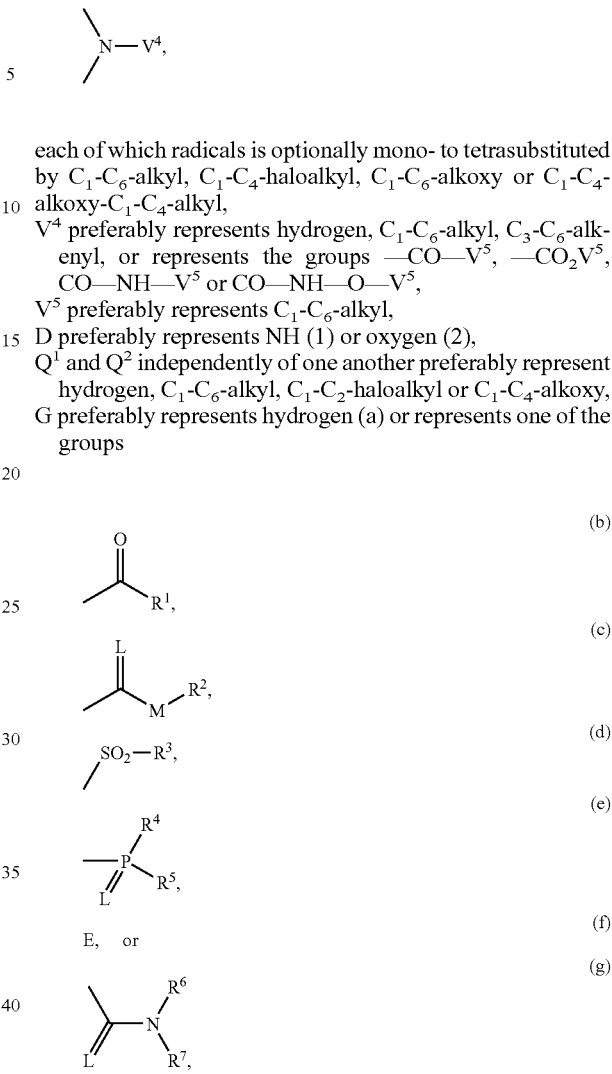

where in the case of (het)aryl only one of the radicals Y or Z may represent (het)aryl, $V^1$ preferably represents hydrogen, halogen, $C_1$-$C_{12}$-alkyl, $C_1$-$C_6$-alkoxy, $C_1$-$C_6$-alkylthio, $C_1$-$C_6$-alkylsulphinyl, $C_1$-$C_6$-alkylsulphonyl, $C_1$-$C_4$-haloalkyl, $C_1$-$C_4$-haloalkoxy, nitro, cyano or represents phenyl, phenoxy, phenoxy-$C_1$-$C_4$-alkyl, phenyl-$C_1$-$C_4$-alkoxy, phenylthio-$C_1$-$C_4$-alkyl or phenyl-$C_1$-$C_4$-alkylthio, each of which is optionally mono- or polysubstituted by halogen, $C_1$-$C_6$-alkyl, $C_1$-$C_6$-alkoxy, $C_1$-$C_4$-haloalkyl, $C_1$-$C_4$-haloalkoxy, nitro or cyano, $V^2$ and $V^3$ independently of one another preferably represent hydrogen, halogen, $C_1$-$C_6$-alkyl, $C_1$-$C_6$-alkoxy, $C_1$-$C_4$-haloalkyl or $C_1$-$C_4$-haloalkoxy, with the proviso that at least one of the radicals W or Z has to be different from hydrogen if X and Y represent methyl, A and B and the carbon atom to which they are attached preferably represent five- to seven-membered ketal, thioketal, or dithioketal which may optionally be interrupted by a further oxygen atom, sulphur atom or by the group each of which radicals is optionally mono- to tetrasubstituted by $C_1$-$C_6$-alkyl, $C_1$-$C_4$-haloalkyl, $C_1$-$C_6$-alkoxy or $C_1$-$C_4$-alkoxy-$C_1$-$C_4$-alkyl, $V^4$ preferably represents hydrogen, $C_1$-$C_6$-alkyl, $C_3$-$C_6$-alkenyl, or represents the groups —CO—$V^5$, —CO$_2$$V^5$, CO—NH—$V^5$ or CO—NH—O—$V^5$, $V^5$ preferably represents $C_1$-$C_6$-alkyl, D preferably represents NH (1) or oxygen (2), $Q^1$ and $Q^2$ independently of one another preferably represent hydrogen, $C_1$-$C_6$-alkyl, $C_1$-$C_2$-haloalkyl or $C_1$-$C_4$-alkoxy, G preferably represents hydrogen (a) or represents one of the groups in which E represents a metal ion or an ammonium ion, L represents oxygen or sulphur and M represents oxygen or sulphur, $R^1$ preferably represents in each case optionally halogen- or cyano-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl or poly-$C_1$-$C_8$-alkoxy-$C_1$-$C_8$-alkyl or represents optionally halogen-, $C_1$-$C_6$-alkyl- or $C_1$-$C_6$-alkoxy-substituted $C_3$-$C_8$-cycloalkyl in which optionally one or two not directly adjacent methylene groups are replaced by oxygen and/or sulphur, represents optionally halogen-, cyano-, nitro-, $C_1$-$C_6$-alkyl-, $C_1$-$C_6$-alkoxy-, $C_1$-$C_6$-haloalkyl-, $C_1$-$C_6$-haloalkoxy-, $C_1$-$C_6$-alkylthio- or $C_1$-$C_6$-alkylsulphonyl-substituted phenyl, represents optionally halogen-, nitro-, cyano-, $C_1$-$C_6$-alkyl-, $C_1$-$C_6$-alkoxy-, $C_1$-$C_6$-haloalkyl- or $C_1$-$C_6$-haloalkoxy-substituted phenyl-$C_1$-$C_6$-alkyl, represents optionally halogen- or $C_1$-$C_6$-alkyl-substituted 5- or 6-membered hetaryl having one or two heteroatoms from the group consisting of oxygen, sulphur and nitrogen, represents optionally halogen- or $C_1$-$C_6$-alkyl-substituted phenoxy-$C_1$-$C_6$-alkyl or represents optionally halogen-, amino- or $C_1$-$C_6$-alkyl-substituted 5- or 6-membered hetaryloxy-$C_1$-$C_6$-alkyl having one or two heteroatoms from the group consisting of oxygen, sulphur and nitrogen, $R^2$ preferably represents in each case optionally halogen- or cyano-substituted $C_1$-$C_{20}$-alkyl, $C_2$-$C_{20}$-alkenyl, $C_1$-$C_8$-alkoxy-$C_2$-$C_8$-alkyl or poly-$C_1$-$C_8$-alkoxy-$C_2$-$C_8$-alkyl, represents optionally halogen-, $C_1$-$C_6$-alkyl- or $C_1$-$C_6$-alkoxy-substituted $C_3$-$C_8$-cycloalkyl or represents in each case optionally halogen-, cyano-, nitro-, $C_1$-$C_6$-alkyl-, $C_1$-$C_6$-alkoxy-, $C_1$-$C_6$-haloalkyl- or $C_1$-$C_6$-haloalkoxy-substituted phenyl or benzyl, $R^3$ preferably represents optionally halogen-substituted $C_1$-$C_8$-alkyl or in each case optionally halogen-, $C_1$-$C_6$-alkyl-, $C_1$-$C_6$-alkoxy-, $C_1$-$C_4$-haloalkyl-, $C_1$-$C_4$-haloalkoxy-, cyano- or nitro-substituted phenyl or benzyl, $R^4$ and $R^5$ independently of one another preferably represent in each case optionally halogen-substituted $C_1$-$C_8$-alkyl, $C_1$-$C_8$-alkoxy, $C_1$-$C_8$-alkylamino, di($C_1$-$C_8$-alkyl)amino, $C_1$-$C_8$-alkylthio or $C_3$-$C_8$-alkenylthio or represent in each case optionally halogen-, nitro-, cyano-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkyl- or $C_1$-$C_4$-haloalkyl-substituted phenyl, phenoxy or phenylthio, $R^6$ and $R^7$ independently of one another preferably represent hydrogen, represent in each case optionally halogen- or cyano-substituted $C_1$-$C_8$-alkyl, $C_3$-$C_8$-cycloalkyl, $C_1$-$C_8$-alkoxy, $C_3$-$C_8$-alkenyl or $C_1$-$C_8$-alkoxy-$C_2$-$C_8$-alkyl, represent in each case optionally halogen-, $C_1$-$C_8$-alkyl-, $C_1$-$C_8$-haloalkyl- or $C_1$-$C_8$-alkoxy-substituted phenyl or benzyl or together represent an optionally $C_1$-$C_6$-alkyl-substituted $C_3$-$C_6$-alkylene radical in which optionally one methylene group is replaced by oxygen or sulphur.

In the radical definitions mentioned as being preferred, halogen represents fluorine, chlorine, bromine and iodine, in particular fluorine, chlorine and bromine.

W particularly preferably represents hydrogen, chlorine, bromine, $C_1$-$C_4$-alkyl, $C_2$-$C_4$-alkenyl, $C_2$-$C_4$-alkynyl, $C_1$-$C_4$-alkoxy, $C_1$-$C_2$-haloalkyl or $C_1$-$C_2$-haloalkoxy, X particularly preferably represents chlorine, bromine, $C_1$-$C_4$-alkyl, $C_2$-$C_4$-alkenyl, $C_2$-$C_4$-alkynyl, $C_1$-$C_4$-alkoxy, $C_1$-$C_4$-haloalkyl, $C_1$-$C_4$-haloalkoxy or cyano, Y and Z independently of one another particularly preferably represent hydrogen, fluorine, chlorine, bromine, $C_1$-$C_4$-alkyl, $C_2$-$C_4$-alkenyl, $C_2$-$C_4$-alkynyl, $C_1$-$C_6$-alkoxy, $C_1$-$C_4$-haloalkyl, $C_1$-$C_4$-haloalkoxy, cyano, $C_2$-$C_4$-alkenyl, $C_2$-$C_4$-alkynyl or represent one of the (het)aryl radicals

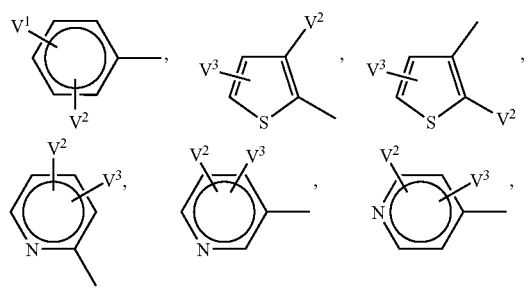

-continued

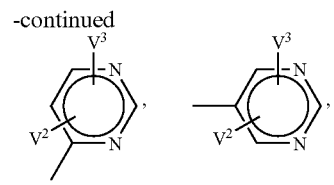

where in the case of (het)aryl only one of the radicals Y or Z may represent (het)aryl, $V^1$ particularly preferably represents hydrogen, fluorine, chlorine, bromine, $C_1$-$C_6$-alkyl, $C_1$-$C_4$-alkoxy, $C_1$-$C_2$-haloalkyl, $C_1$-$C_2$-haloalkoxy, nitro, cyano or represents phenyl which is optionally mono- or disubstituted by fluorine, chlorine, bromine, $C_1$-$C_4$-alkyl, $C_1$-$C_4$-alkoxy, $C_1$-$C_2$-haloalkyl, $C_1$-$C_2$-haloalkoxy, nitro or cyano, $V^2$ and $V^3$ independently of one another particularly preferably represent hydrogen, fluorine, chlorine, bromine, $C_1$-$C_4$-alkyl, $C_1$-$C_4$-alkoxy, $C_1$-$C_2$-haloalkyl or $C_1$-$C_2$-haloalkoxy, with the proviso that at least one of the radicals W or Z has to be different from hydrogen if X and Y represent methyl, A and B and the carbon atom to which they are attached particularly preferably represent a five-, six- or seven-membered ketal which may optionally be interrupted by a further oxygen atom and which is optionally mono- to trisubstituted by $C_1$-$C_4$-alkyl, $C_1$-$C_3$-haloalkyl, $C_1$-$C_4$-alkoxy or $C_1$-$C_4$-alkoxy-$C_1$-$C_2$-alkyl, D particularly preferably represents NH (1) or oxygen (2), $Q^1$ and $Q^2$ independently of one another particularly preferably represent hydrogen, methyl, ethyl, trifluoromethyl, methoxy or ethoxy, G particularly preferably represents hydrogen (a) or represents one of the groups

(b)

(c)

(d)

(e)

(f)
E, or
(g)

in which

E represents a metal ion or an ammonium ion,

L represents oxygen or sulphur and

M represents oxygen or sulphur, $R^1$ particularly preferably represents $C_1$-$C_{16}$-alkyl, $C_2$-$C_{16}$-alkenyl, $C_1$-$C_6$-alkoxy-$C_1$-$C_4$-alkyl, $C_1$-$C_6$-alkylthio-$C_1$-

$C_4$-alkyl or poly-$C_1$-$C_6$-alkoxy-$C_1$-$C_4$-alkyl, each of which is optionally mono- to trisubstituted by fluorine or chlorine, or represents $C_3$-$C_7$-cycloalkyl which is optionally mono- or disubstituted by fluorine, chlorine, $C_1$-$C_5$-alkyl or $C_1$-$C_5$-alkoxy and in which optionally one or two not directly adjacent methylene groups are replaced by oxygen and/or sulphur, represents phenyl which is optionally mono- to trisubstituted by fluorine, chlorine, bromine, cyano, nitro, $C_1$-$C_4$-alkyl, $C_1$-$C_4$-alkoxy, $C_1$-$C_3$-haloalkyl, $C_1$-$C_3$-haloalkoxy, $C_1$-$C_4$-alkylthio or $C_1$-$C_4$-alkylsulphonyl, represents phenyl-$C_1$-$C_4$-alkyl which is optionally mono- or disubstituted by fluorine, chlorine, bromine, $C_1$-$C_4$-alkyl, $C_1$-$C_4$-alkoxy, $C_1$-$C_3$-haloalkyl or $C_1$-$C_3$-haloalkoxy, represents pyrazolyl, thiazolyl, pyridyl, pyrimidyl, furanyl or thienyl, each of which is optionally mono- or disubstituted by fluorine, chlorine, bromine or $C_1$-$C_4$-alkyl, represents phenoxy-$C_1$-$C_5$-alkyl which is optionally mono- or disubstituted by fluorine, chlorine, bromine or $C_1$-$C_4$-alkyl or represents pyridyloxy-$C_1$-$C_5$-alkyl, pyrimidyloxy-$C_1$-$C_5$-alkyl or thiazolyloxy-$C_1$-$C_5$-alkyl, each of which is optionally mono- or disubstituted by fluorine, chlorine, bromine, amino or $C_1$-$C_4$-alkyl, $R^2$ particularly preferably represents $C_1$-$C_{16}$-alkyl, $C_2$-$C_{16}$-alkenyl, $C_1$-$C_6$-alkoxy-$C_2$-$C_6$-alkyl or poly-$C_1$-$C_6$-alkoxy-$C_2$-$C_6$-alkyl, each of which is optionally mono- to trisubstituted by fluorine or chlorine, represents $C_3$-$C_7$-cycloalkyl which is optionally mono- or disubstituted by fluorine, chlorine, $C_1$-$C_4$-alkyl or $C_1$-$C_4$-alkoxy or represents phenyl or benzyl, each of which is optionally mono- to trisubstituted by fluorine, chlorine, bromine, cyano, nitro, $C_1$-$C_4$-alkyl, $C_1$-$C_3$-alkoxy, $C_1$-$C_3$-haloalkyl or $C_1$-$C_3$-haloalkoxy, $R^3$ particularly preferably represents $C_1$-$C_6$-alkyl which is optionally mono- to trisubstituted by fluorine or chlorine or represents phenyl or benzyl, each of which is optionally mono- or disubstituted by fluorine, chlorine, bromine, $C_1$-$C_4$-alkyl, $C_1$-$C_4$-alkoxy, $C_1$-$C_2$-haloalkoxy, $C_1$-$C_2$-haloalkyl, cyano or nitro, $R^4$ and $R^5$ independently of one another particularly preferably represent $C_1$-$C_6$-alkyl, $C_1$-$C_6$-alkoxy, $C_1$-$C_6$-alkylamino, di($C_1$-$C_6$-alkyl)amino, $C_1$-$C_6$-alkylthio or $C_3$-$C_4$-alkenylthio, each of which is optionally mono- to trisubstituted by fluorine or chlorine, or represent phenyl, phenoxy or phenylthio, each of which is optionally mono- or disubstituted by fluorine, chlorine, bromine, nitro, cyano, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkyl or $C_1$-$C_3$-haloalkyl, $R^6$ and $R^7$ independently of one another particularly preferably represent hydrogen, represent $C_1$-$C_6$-alkyl, $C_3$-$C_6$-cycloalkyl, $C_1$-$C_6$-alkoxy, $C_3$-$C_6$-alkenyl or $C_1$-$C_6$-alkoxy-$C_2$-$C_6$-alkyl, each of which is optionally mono- to trisubstituted by fluorine or chlorine, represent phenyl or benzyl, each of which is optionally mono- to trisubstituted by fluorine, chlorine, bromine, $C_1$-$C_5$-haloalkyl, $C_1$-$C_5$-alkyl or $C_1$-$C_5$-alkoxy, or together represent an optionally $C_1$-$C_4$-alkyl-substituted $C_3$-$C_6$-alkylene radical in which optionally one methylene group is replaced by oxygen or sulphur.

In the radical definitions mentioned as being particularly preferred, halogen represents fluorine, chlorine and bromine, in particular fluorine and chlorine.

W very particularly preferably represents hydrogen, chlorine, bromine, methyl, ethyl, vinyl, ethynyl, propynyl, methoxy, ethoxy or trifluoromethyl, X very particularly preferably represents chlorine, bromine, methyl, ethyl, propyl, isopropyl, vinyl, ethynyl, propynyl, methoxy, ethoxy, trifluoromethyl, difluoromethoxy, trifluoromethoxy or cyano, Y and Z independently of one another very particularly preferably represent hydrogen, fluorine, chlorine, bromine, methyl, ethyl, vinyl, ethynyl, propynyl, methoxy, trifluoromethyl, trifluoromethoxy, cyano or a phenyl radical

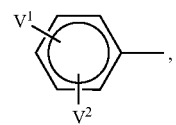

where in the case of phenyl only one of the radicals Y or Z may represent phenyl, $V^1$ very particularly preferably represents hydrogen, fluorine, chlorine, bromine, methyl, ethyl, n-propyl, isopropyl, tert-butyl, methoxy, ethoxy, n-propoxy, isopropoxy, trifluoromethyl or trifluoromethoxy, $V^2$ very particularly preferably represents hydrogen, fluorine, chlorine, methyl, ethyl, n-propyl, isopropyl, methoxy, ethoxy or trifluoromethyl, with the proviso that at least one of the radicals W or Z has to be different from hydrogen if X and Y represent methyl, A and B and the carbon atom to which they are attached very particularly preferably represent a five-, six- or seven-membered ketal which may optionally be interrupted by a further oxygen atom and which is optionally mono- or disubstituted by methyl, ethyl, propyl, trifluoromethyl, monochloromethyl, methoxy, ethoxy, methoxymethyl or ethoxymethyl, D very particularly preferably represents NH (1) or oxygen (2), $Q^1$ and $Q^2$ very particularly preferably represent hydrogen, G very particularly preferably represents hydrogen (a) or represents one of the groups

(b)

(c)

(d)

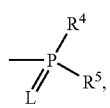
(e)

E, or
(f)

-continued

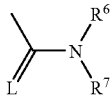
(g)

in which

E represents a metal ion or an ammonium ion,

L represents oxygen or sulphur and

M represents oxygen or sulphur, $R^1$ very particularly preferably represents $C_1$-$C_{10}$-alkyl, $C_2$-$C_{10}$-alkenyl, $C_1$-$C_4$-alkoxy-$C_1$-$C_2$-alkyl, $C_1$-$C_4$-alkylthio-$C_1$-$C_2$-alkyl, each of which is optionally mono- to trisubstituted by fluorine or chlorine, or represents $C_3$-$C_6$-cycloalkyl which is optionally monosubstituted by fluorine, chlorine, methyl, ethyl or methoxy, represents phenyl which is optionally mono- or disubstituted by fluorine, chlorine, bromine, cyano, nitro, methyl, ethyl, n-propyl, isopropyl, methoxy, ethoxy, trifluoromethyl or trifluoromethoxy, represents furanyl, thienyl or pyridyl, each of which is optionally monosubstituted by chlorine, bromine or methyl, $R^2$ very particularly preferably represents $C_1$-$C_{10}$-alkyl, $C_2$-$C_{10}$-alkenyl or $C_1$-$C_4$-alkoxy-$C_2$-$C_4$-alkyl, each of which is optionally mono- to trisubstituted by fluorine or chlorine, represents cyclopentyl or cyclohexyl, or represents phenyl or benzyl, each of which is optionally mono- or disubstituted by fluorine, chlorine, cyano, nitro, methyl, ethyl, methoxy, trifluoromethyl or trifluoromethoxy, $R^3$ very particularly preferably represents methyl, ethyl, propyl or isopropyl, each of which is optionally mono- to trisubstituted by fluorine or chlorine, or represents phenyl which is optionally monosubstituted by fluorine, chlorine, bromine, methyl, ethyl, isopropyl, tert-butyl, methoxy, ethoxy, isopropoxy, trifluoromethyl, trifluoromethoxy, cyano or nitro, $R^4$ and $R^5$ independently of one another very particularly preferably represent $C_1$-$C_4$-alkoxy or $C_1$-$C_4$-alkylthio or represent phenyl, phenoxy or phenylthio, each of which is optionally monosubstituted by fluorine, chlorine, bromine, nitro, cyano, methyl, methoxy, trifluoromethyl or trifluoromethoxy, $R^6$ and $R^7$ independently of one another very particularly preferably represent hydrogen, represent $C_1$-$C_4$-alkyl, $C_3$-$C_6$-cycloalkyl, $C_1$-$C_4$-alkoxy, $C_3$-$C_4$-alkenyl or $C_1$-$C_4$-alkoxy-$C_2$-$C_4$-alkyl, represent phenyl which is optionally mono- or disubstituted by fluorine, chlorine, bromine, methyl, methoxy or trifluoromethyl, or together represent a $C_5$-$C_6$-alkylene radical in which optionally one methylene group is replaced by oxygen or sulphur.

W especially preferably represents hydrogen, chlorine, bromine, methyl, ethyl or methoxy, X especially preferably represents chlorine, bromine, methyl, ethyl or methoxy, Y and Z independently of one another especially preferably represent hydrogen, chlorine, bromine, methyl or represent the radical

where in this case only one of the radicals Y or Z may represent

with the proviso that at least one of the radicals W or Z has to be different from hydrogen if X and Y represent methyl, A and B and the carbon atom to which they are attached especially preferably represent a five- or six-membered ketal which is optionally mono- or disubstituted by methyl, ethyl, propyl, monochloromethyl or methoxymethyl, D especially preferably represents NH (1) or oxygen (2), $Q^1$ and $Q^2$ especially preferably represent hydrogen, G especially preferably represents hydrogen (a) or represents one of the groups

(b)

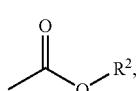
(c)

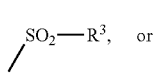
(d)

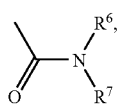
(g)

$R^1$ especially preferably represents $C_1$-$C_{10}$-alkyl, $C_1$-$C_4$-alkoxy-$C_1$-$C_2$-alkyl, $C_3$-$C_6$-cycloalkyl, represents phenyl which is optionally monosubstituted by chlorine, or represents thienyl, $R^2$ especially preferably represents $C_1$-$C_{10}$-alkyl, $C_2$-$C_{10}$-alkenyl or benzyl, $R^3$ especially preferably represents methyl, $R^6$ and $R^7$ together especially preferably represent a $C_5$-$C_6$-alkylene radical in which optionally one methylene group is replaced by oxygen or sulphur.

General or preferred radical definitions or illustrations given above can be combined with one another as desired, i.e. including combinations between the respective ranges and preferred ranges. They apply both to the end products and, correspondingly, to precursors and intermediates.

Preference according to the invention is given to the compounds of the formula (I) which contain a combination of the meanings given above as being preferred (preferable).

Particular preference according to the invention is given to the compounds of the formula (I) which contain a combination of the meanings given above as being particularly preferred.

Very particular preference according to the invention is given to the compounds of the formula (I) which contain a combination of the meanings given above as being very particularly preferred.

Special preference according to the invention is given to the compounds of the formula (I) which contain a combination of the meanings given above as being especially preferred.

Emphasis is given to compounds of the formula (I) in which G represents hydrogen.

In the case of the compounds of the formula (I-1), the phenyl ring is, with emphasis, substituted 3 times, resulting in the following substitution patterns: 2,4,6-, 2,4,5- or 2,5,6-substitution. Moreover, in the case of the compounds of the formula (I-1), the phenyl ring is, with emphasis, substituted 4 times, resulting in the following substitution pattern: 2,4,5,6-substitution. In the case of the compounds of the formula (I-1), the phenyl ring is, with emphasis, also substituted 2 times (2,5-position). In the case of the compounds of the formula (I-1), the phenyl ring is, with emphasis, also mono-substituted (ortho position). The other substituents W, X, Y, Z, G, A, B, $Q^1$ and $Q^2$ are as defined in the text.

Moreover, in the case of the compounds of the formula (I-1) in which the phenyl ring is substituted in the 2,4-position, the substituent G represents, with emphasis, the group (b), but also the group (c) or (d) or (e) or (f) or (g). In this case, G represents especially the groups (a), (b) or (c). The other substituents W, X, Y, Z, A, B, $Q^1$ and $Q^2$ are as defined in the text. Furthermore, in the case of the compounds of the formula (I-1) in which the phenyl ring is substituted in the 2,4-position, the substituents A and B are, with emphasis, in the 3'-position on the spirocycle. Furthermore, in the case of the compounds of the formula (I-1) in which the phenyl ring is substituted in the 2,4-position, the substituents A and B are, with emphasis, in the 4'-position on the spirocycle.

Saturated or unsaturated hydrocarbon radicals, such as alkyl, alkanediyl or alkenyl, may in each case be straight-chain or branched as far as this is possible, including in combination with heteroatoms, such as, for example, in alkoxy.

Unless indicated otherwise, optionally substituted radicals may be mono- or polysubstituted, where in the case of polysubstitution the substituents may be identical or different.

In addition to the compounds mentioned in the Preparation Examples, the following compounds of the formula (I-1-a) may be specifically mentioned:

TABLE 1

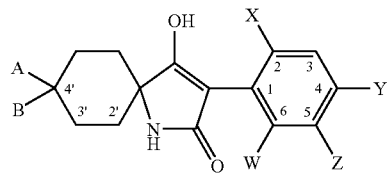

(I-1-a)

| A-B | X | W | Y | Z |
|---|---|---|---|---|
| —O—(CH$_2$)$_2$—O— | CH$_3$ | H | H | H |
| —O—(CH$_2$)$_2$—O— | Br | H | H | H |
| —O—(CH$_2$)$_2$—O— | Cl | H | H | H |
| —O—(CH$_2$)$_2$—O— | CF$_3$ | H | H | H |
| —O—(CH$_2$)$_2$—O— | OCH$_3$ | H | H | H |
| —O—(CH$_2$)$_2$—O— | Br | H | Cl | H |
| —O—(CH$_2$)$_2$—O— | Cl | H | Br | H |
| —O—(CH$_2$)$_2$—O— | Cl | H | Cl | H |

TABLE 1-continued (I-1-a)

| A-B | X | W | Y | Z |
|---|---|---|---|---|
| —O—(CH$_2$)$_2$—O— | Cl | H | CH$_3$ | H |
| —O—(CH$_2$)$_2$—O— | CH$_3$ | H | Cl | H |
| —O—(CH$_2$)$_2$—O— | Cl | Cl | H | H |
| —O—(CH$_2$)$_2$—O— | Cl | OCH$_3$ | H | H |
| —O—(CH$_2$)$_2$—O— | Cl | CH$_3$ | H | H |
| —O—(CH$_2$)$_2$—O— | Cl | OC$_2$H$_5$ | H | H |
| —O—(CH$_2$)$_2$—O— | OCH$_3$ | OCH$_3$ | H | H |
| —O—(CH$_2$)$_2$—O— | CH$_3$ | CH$_3$ | H | H |
| —O—(CH$_2$)$_2$—O— | C$_2$H$_5$ | CH$_3$ | H | H |
| —O—(CH$_2$)$_2$—O— | C$_2$H$_5$ | C$_2$H$_5$ | H | H |
| —O—(CH$_2$)$_2$—O— | Br | CH$_3$ | Br | H |
| —O—(CH$_2$)$_2$—O— | Cl | CH$_3$ | Cl | H |
| —O—(CH$_2$)$_2$—O— | CH$_3$ | Br | CH$_3$ | H |
| —O—(CH$_2$)$_2$—O— | CH$_3$ | Cl | CH$_3$ | H |
| —O—(CH$_2$)$_2$—O— | OCH$_3$ | CH$_3$ | CH$_3$ | H |
| —O—(CH$_2$)$_2$—O— | OC$_2$H$_5$ | CH$_3$ | CH$_3$ | H |
| —O—(CH$_2$)$_2$—O— | OC$_3$H$_7$ | CH$_3$ | CH$_3$ | H |
| —O—(CH$_2$)$_2$—O— | CH$_3$ | CH$_3$ | CH$_3$ | H |
| —O—(CH$_2$)$_2$—O— | Br | Br | CH$_3$ | H |
| —O—(CH$_2$)$_2$—O— | Cl | Cl | CH$_3$ | H |
| —O—(CH$_2$)$_2$—O— | CH$_3$ | CH$_3$ | Br | H |
| —O—(CH$_2$)$_2$—O— | OCH$_3$ | C$_2$H$_5$ | CH$_3$ | H |
| —O—(CH$_2$)$_2$—O— | OC$_2$H$_5$ | C$_2$H$_5$ | CH$_3$ | H |
| —O—(CH$_2$)$_2$—O— | CH$_3$ | CH$_3$ | OCH$_3$ | H |
| —O—(CH$_2$)$_2$—O— | Br | Cl | CH$_3$ | H |
| —O—(CH$_2$)$_2$—O— | Br | CH$_3$ | Cl | H |
| —O—(CH$_2$)$_2$—O— | Cl | CH$_3$ | Br | H |
| —O—(CH$_2$)$_2$—O— | CH$_3$ | CH$_3$ | Cl | H |
| —O—(CH$_2$)$_2$—O— | C$_2$H$_5$ | CH$_3$ | CH$_3$ | H |
| —O—(CH$_2$)$_2$—O— | C$_2$H$_5$ | C$_2$H$_5$ | CH$_3$ | H |
| —O—(CH$_2$)$_2$—O— | C$_2$H$_5$ | CH$_3$ | C$_2$H$_5$ | H |
| —O—(CH$_2$)$_2$—O— | C$_2$H$_5$ | C$_2$H$_5$ | C$_2$H$_5$ | H |
| —O—(CH$_2$)$_2$—O— | C$_2$H$_5$ | CH$_3$ | Cl | H |
| —O—(CH$_2$)$_2$—O— | C$_2$H$_5$ | C$_2$H$_5$ | Cl | H |
| —O—(CH$_2$)$_2$—O— | C$_2$H$_5$ | CH$_3$ | Br | H |
| —O—(CH$_2$)$_2$—O— | C$_2$H$_5$ | C$_2$H$_5$ | Br | H |
| —O—(CH$_2$)$_2$—O— | C$_2$H$_5$ | Cl | CH$_3$ | H |
| —O—(CH$_2$)$_2$—O— | C$_2$H$_5$ | Br | CH$_3$ | H |
| —O—(CH$_2$)$_2$—O— | C$_2$H$_5$ | Cl | Cl | H |
| —O—(CH$_2$)$_2$—O— | C$_2$H$_5$ | Br | Br | H |
| —O—(CH$_2$)$_2$—O— | C$_2$H$_5$ | Cl | Br | H |
| —O—(CH$_2$)$_2$—O— | C$_2$H$_5$ | Br | Cl | H |
| —O—(CH$_2$)$_2$—O— | OCH$_3$ | CH$_3$ | Cl | H |
| —O—(CH$_2$)$_2$—O— | OCH$_3$ | C$_2$H$_5$ | Cl | H |
| —O—(CH$_2$)$_2$—O— | OC$_2$H$_5$ | CH$_3$ | Cl | H |
| —O—(CH$_2$)$_2$—O— | OC$_2$H$_5$ | C$_2$H$_5$ | Cl | H |
| —O—(CH$_2$)$_2$—O— | Cl | OCH$_3$ | CH$_3$ | H |
| —O—(CH$_2$)$_2$—O— | Cl | OC$_2$H$_5$ | CH$_3$ | H |
| —O—(CH$_2$)$_2$—O— | CH$_3$ | CH$_3$ | Cl | H |
| —O—(CH$_2$)$_2$—O— | Cl | H | Cl | Cl |
| —O—(CH$_2$)$_2$—O— | CH$_3$ | H | CH$_3$ | CH$_3$ |
| —O—(CH$_2$)$_2$—O— | CH$_3$ | H | Cl | CH$_3$ |
| —O—(CH$_2$)$_2$—O— | Br | H | Cl | CH$_3$ |
| —O—(CH$_2$)$_2$—O— | Br | H | CH$_3$ | CH$_3$ |
| —O—(CH$_2$)$_2$—O— | Cl | H | Br | CH$_3$ |
| —O—(CH$_2$)$_2$—O— | Cl | H | Cl | CH$_3$ |
| —O—(CH$_2$)$_2$—O— | CH$_3$ | H | Br | CH$_3$ |
| —O—(CH$_2$)$_2$—O— | Cl | H | CH$_3$ | Cl |
| —O—(CH$_2$)$_2$—O— | CH$_3$ | H | H | CH$_3$ |
| —O—(CH$_2$)$_2$—O— | Cl | H | H | CH$_3$ |
| —O—(CH$_2$)$_2$—O— | Br | H | H | CH$_3$ |
| —O—(CH$_2$)$_2$—O— | CH$_3$ | H | H | Cl |
| —O—(CH$_2$)$_2$—O— | CH$_3$ | H | H | Br |
| —O—(CH$_2$)$_2$—O— | CH$_3$ | CH$_3$ | CH$_3$ | CH$_3$ |
| —O—(CH$_2$)$_2$—O— | CH$_3$ | CH$_3$ | CH$_3$ | F |
| —O—(CH$_2$)$_2$—O— | CH$_3$ | CH$_3$ | CH$_3$ | Cl |

TABLE 1-continued (I-1-a)

A structure showing a spiro compound with OH, substituents A, B on cyclohexane ring (positions 4', 3', 2', 1') and a phenyl ring with positions 1-6 bearing X (position 3), Y (position 4), Z (position 5), W (position 6), and an NH-C(=O) lactam.

| A-B | X | W | Y | Z |
|---|---|---|---|---|
| —O—(CH$_2$)$_2$—O— | CH$_3$ | CH$_3$ | CH$_3$ | Br |
| —O—(CH$_2$)$_2$—O— | CH$_3$ | CH$_3$ | H | Cl |
| —O—(CH$_2$)$_2$—O— | CH$_3$ | CH$_3$ | H | Br |
| —O—(CH$_2$)$_2$—O— | Cl | Cl | H | Br |
| —O—(CH$_2$)$_2$—O— | CH$_3$ | CH$_3$ | 4-Cl—C$_6$H$_4$ | H |
| —O—(CH$_2$)$_2$—O— | C$_2$H$_5$ | CH$_3$ | 4-Cl—C$_6$H$_4$ | H |
| —O—(CH$_2$)$_2$—O— | C$_2$H$_5$ | C$_2$H$_5$ | 4-Cl—C$_6$H$_4$ | H |
| —O—(CH$_2$)$_2$—O— | Cl | CH$_3$ | 4-Cl—C$_6$H$_4$ | H |
| —O—(CH$_2$)$_2$—O— | Cl | C$_2$H$_5$ | 4-Cl—C$_6$H$_4$ | H |
| —O—(CH$_2$)$_2$—O— | CH$_3$ | H | H | 4-Cl—C$_6$H$_4$ |
| —O—(CH$_2$)$_2$—O— | CH$_3$ | CH$_3$ | H | 4-Cl—C$_6$H$_4$ |
| —O—(CH$_2$)$_2$—O— | CH$_3$ | H | CH$_3$ | 4-Cl—C$_6$H$_4$ |
| —O—(CH$_2$)$_2$—O— | CH$_3$ | CH$_3$ | CH$_3$ | 4-Cl—C$_6$H$_4$ |
| —O—(CH$_2$)$_2$—O— | Cl | H | H | 4-Cl—C$_6$H$_4$ |
| —O—(CH$_2$)$_2$—O— | I | H | H | H |
| —O—(CH$_2$)$_2$—O— | I | H | CH$_3$ | H |
| —O—(CH$_2$)$_2$—O— | I | CH$_3$ | H | H |
| —O—(CH$_2$)$_2$—O— | I | C$_2$H$_5$ | H | H |
| —O—(CH$_2$)$_2$—O— | CH$_3$ | H | H | I |
| —O—(CH$_2$)$_2$—O— | CH$_3$ | H | CH$_3$ | I |
| —O—(CH$_2$)$_2$—O— | I | CH$_3$ | CH$_3$ | H |
| —O—(CH$_2$)$_2$—O— | I | C$_2$H$_5$ | CH$_3$ | H |
| —O—(CH$_2$)$_2$—O— | I | CH$_3$ | Cl | H |
| —O—(CH$_2$)$_2$—O— | I | C$_2$H$_5$ | Cl | H |
| —O—(CH$_2$)$_2$—O— | I | Cl | CH$_3$ | H |
| —O—(CH$_2$)$_2$—O— | I | H | CH$_3$ | CH$_3$ |
| —O—(CH$_2$)$_2$—O— | CH$_3$ | H | I | H |
| —O—(CH$_2$)$_2$—O— | C$_2$H$_5$ | H | I | H |
| —O—(CH$_2$)$_2$—O— | CH$_3$ | CH$_3$ | I | H |
| —O—(CH$_2$)$_2$—O— | C$_2$H$_5$ | CH$_3$ | I | H |
| —O—(CH$_2$)$_2$—O— | C$_2$H$_5$ | C$_2$H$_5$ | I | H |
| —O—(CH$_2$)$_2$—O— | Cl | CH$_3$ | I | H |
| —O—(CH$_2$)$_2$—O— | Cl | C$_2$H$_5$ | I | H |
| —O—(CH$_2$)$_2$—O— | CH$_3$ | H | I | CH$_3$ |
| —O—(CH$_2$)$_2$—O— | CH$_3$ | CH$_3$ | H | I |
| —O—(CH$_2$)$_2$—O— | I | H | H | CH$_3$ |
| —O—(CH$_2$)$_2$—O— | C$_2$H$_5$ | H | H | H |

Table 2: W, X, Y and Z as Stated in Table 1

A-B=4'-O—CH$_2$—CHCH$_3$—O—

Table 3: W, X, Y and Z as Stated in Table 1

A-B=4'-O—CHCH$_3$—CHCH$_3$—O—

Table 4: W, X, Y and Z as Stated in Table 1

A-B=4'-O—(CH$_2$)$_3$—O—

Table 5: W, X, Y and Z as Stated in Table 1

A-B=4'-O—CHCH$_3$—(CH$_2$)$_2$—O—

Table 6: W, X, Y and Z as Stated in Table 1

A-B=4'-O—CHCH$_3$—CH$_2$—CHCH$_3$—O—

Table 7: W, X, Y and Z as Stated in Table 1

A-B=-4'O—CH$_2$—C(CH$_3$)$_2$—CH$_2$—O—

TABLE 8

W, X, Y and Z as stated in Table 1

A-B = 4'-O—CH$_2$—CH—CH$_2$—O—CH$_3$
               |
               O—

Table 9: W, X, Y and Z as Stated in Table 1

A-B=3'-O—(CH$_2$)$_2$—O—

Table 10: W, X, Y and Z as Stated in Table 1

A-B=3'-O—CH$_2$—CHCH$_3$—O—

Table 11: W, X, Y and Z as Stated in Table 1

A-B=3'-O—CHCH$_3$—CHCH$_3$—O—

Table 12: W, X, Y and Z as Stated in Table 1

A-B=3'-O—(CH$_2$)$_3$—O—

Table 13: W, X, Y and Z as Stated in Table 1

A-B=3'-O—CHCH$_3$—(CH$_2$)$_2$—O—

Table 14: W, X, Y and Z as Stated in Table 1

A-B=3'-O—CHCH$_3$—CH$_2$—CHCH$_3$—O—

Table 15: W, X, Y and Z as Stated in Table 1

A-B=3'-O—CH$_2$—C(CH$_3$)$_2$—CH$_2$—O—

TABLE 16

W, X, Y and Z as stated in Table 1

A-B = 3'-O—CH$_2$—CH—CH$_2$—O—CH$_3$
               |
               O—

In addition to the compounds mentioned in the Preparation Examples, the following compounds of the formula (I-2-a) may be specifically mentioned:

TABLE 17

(I-2-a)

Structure showing a spiro compound with OH and a lactone (O—C=O) linked to a phenyl ring bearing X, Y, Z, W substituents.

| A-B | X | W | Y | Z |
|---|---|---|---|---|
| —O—(CH$_2$)$_2$—O— | CH$_3$ | H | H | H |
| —O—(CH$_2$)$_2$—O— | Br | H | H | H |
| —O—(CH$_2$)$_2$—O— | Cl | H | H | H |
| —O—(CH$_2$)$_2$—O— | CF$_3$ | H | H | H |
| —O—(CH$_2$)$_2$—O— | OCH$_3$ | H | H | H |
| —O—(CH$_2$)$_2$—O— | Br | H | Cl | H |
| —O—(CH$_2$)$_2$—O— | Cl | H | Br | H |
| —O—(CH$_2$)$_2$—O— | Cl | H | Cl | H |
| —O—(CH$_2$)$_2$—O— | Cl | H | CH$_3$ | H |
| —O—(CH$_2$)$_2$—O— | CH$_3$ | H | Cl | H |
| —O—(CH$_2$)$_2$—O— | Cl | Cl | H | H |
| —O—(CH$_2$)$_2$—O— | Cl | OCH$_3$ | H | H |
| —O—(CH$_2$)$_2$—O— | Cl | CH$_3$ | H | H |

TABLE 17-continued (I-2-a)

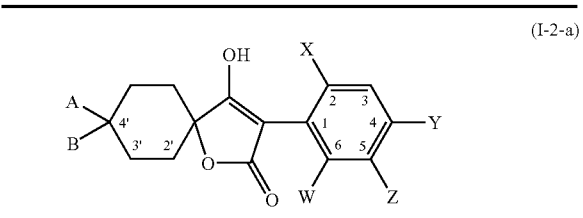

| A-B | X | W | Y | Z |
|---|---|---|---|---|
| —O—(CH$_2$)$_2$—O— | Cl | OC$_2$H$_5$ | H | H |
| —O—(CH$_2$)$_2$—O— | OCH$_3$ | OCH$_3$ | H | H |
| —O—(CH$_2$)$_2$—O— | CH$_3$ | CH$_3$ | H | H |
| —O—(CH$_2$)$_2$—O— | C$_2$H$_5$ | CH$_3$ | H | H |
| —O—(CH$_2$)$_2$—O— | C$_2$H$_5$ | C$_2$H$_5$ | H | H |
| —O—(CH$_2$)$_2$—O— | Br | CH$_3$ | Br | H |
| —O—(CH$_2$)$_2$—O— | Cl | CH$_3$ | Cl | H |
| —O—(CH$_2$)$_2$—O— | CH$_3$ | Br | CH$_3$ | H |
| —O—(CH$_2$)$_2$—O— | CH$_3$ | Cl | CH$_3$ | H |
| —O—(CH$_2$)$_2$—O— | OCH$_3$ | CH$_3$ | CH$_3$ | H |
| —O—(CH$_2$)$_2$—O— | OC$_2$H$_5$ | CH$_3$ | CH$_3$ | H |
| —O—(CH$_2$)$_2$—O— | OC$_3$H$_7$ | CH$_3$ | CH$_3$ | H |
| —O—(CH$_2$)$_2$—O— | CH$_3$ | CH$_3$ | CH$_3$ | H |
| —O—(CH$_2$)$_2$—O— | Br | Br | CH$_3$ | H |
| —O—(CH$_2$)$_2$—O— | Cl | Cl | CH$_3$ | H |
| —O—(CH$_2$)$_2$—O— | CH$_3$ | CH$_3$ | Br | H |
| —O—(CH$_2$)$_2$—O— | CH$_3$ | CH$_3$ | Br | H |
| —O—(CH$_2$)$_2$—O— | OCH$_3$ | C$_2$H$_5$ | CH$_3$ | H |
| —O—(CH$_2$)$_2$—O— | OC$_2$H$_5$ | C$_2$H$_5$ | CH$_3$ | H |
| —O—(CH$_2$)$_2$—O— | CH$_3$ | CH$_3$ | OCH$_3$ | H |
| —O—(CH$_2$)$_2$—O— | Br | Cl | CH$_3$ | H |
| —O—(CH$_2$)$_2$—O— | Br | CH$_3$ | Cl | H |
| —O—(CH$_2$)$_2$—O— | Cl | CH$_3$ | Br | H |
| —O—(CH$_2$)$_2$—O— | CH$_3$ | CH$_3$ | Cl | H |
| —O—(CH$_2$)$_2$—O— | C$_2$H$_5$ | CH$_3$ | CH$_3$ | H |
| —O—(CH$_2$)$_2$—O— | C$_2$H$_5$ | C$_2$H$_5$ | CH$_3$ | H |
| —O—(CH$_2$)$_2$—O— | C$_2$H$_5$ | C$_2$H$_5$ | C$_2$H$_5$ | H |
| —O—(CH$_2$)$_2$—O— | C$_2$H$_5$ | CH$_3$ | Cl | H |
| —O—(CH$_2$)$_2$—O— | C$_2$H$_5$ | C$_2$H$_5$ | Cl | H |
| —O—(CH$_2$)$_2$—O— | C$_2$H$_5$ | CH$_3$ | Br | H |
| —O—(CH$_2$)$_2$—O— | C$_2$H$_5$ | C$_2$H$_5$ | Br | H |
| —O—(CH$_2$)$_2$—O— | C$_2$H$_5$ | Cl | CH$_3$ | H |
| —O—(CH$_2$)$_2$—O— | C$_2$H$_5$ | Br | CH$_3$ | H |
| —O—(CH$_2$)$_2$—O— | C$_2$H$_5$ | Cl | Cl | H |
| —O—(CH$_2$)$_2$—O— | C$_2$H$_5$ | Br | Br | H |
| —O—(CH$_2$)$_2$—O— | C$_2$H$_5$ | Cl | Br | H |
| —O—(CH$_2$)$_2$—O— | C$_2$H$_5$ | Br | Cl | H |
| —O—(CH$_2$)$_2$—O— | OCH$_3$ | CH$_3$ | Cl | H |
| —O—(CH$_2$)$_2$—O— | OCH$_3$ | C$_2$H$_5$ | Cl | H |
| —O—(CH$_2$)$_2$—O— | OC$_2$H$_5$ | CH$_3$ | Cl | H |
| —O—(CH$_2$)$_2$—O— | OC$_2$H$_5$ | C$_2$H$_5$ | Cl | H |
| —O—(CH$_2$)$_2$—O— | Cl | OCH$_3$ | CH$_3$ | H |
| —O—(CH$_2$)$_2$—O— | Cl | OC$_2$H$_5$ | CH$_3$ | H |
| —O—(CH$_2$)$_2$—O— | CH$_3$ | CH$_3$ | Cl | H |
| —O—(CH$_2$)$_2$—O— | Cl | H | Cl | Cl |
| —O—(CH$_2$)$_2$—O— | CH$_3$ | H | CH$_3$ | CH$_3$ |
| —O—(CH$_2$)$_2$—O— | CH$_3$ | H | Cl | CH$_3$ |
| —O—(CH$_2$)$_2$—O— | Br | H | Cl | CH$_3$ |
| —O—(CH$_2$)$_2$—O— | Br | H | CH$_3$ | CH$_3$ |
| —O—(CH$_2$)$_2$—O— | Cl | H | Br | CH$_3$ |
| —O—(CH$_2$)$_2$—O— | Cl | H | Cl | CH$_3$ |
| —O—(CH$_2$)$_2$—O— | CH$_3$ | H | Br | CH$_3$ |
| —O—(CH$_2$)$_2$—O— | Cl | H | CH$_3$ | Cl |
| —O—(CH$_2$)$_2$—O— | CH$_3$ | H | H | CH$_3$ |
| —O—(CH$_2$)$_2$—O— | Br | H | H | CH$_3$ |
| —O—(CH$_2$)$_2$—O— | CH$_3$ | H | H | Cl |
| —O—(CH$_2$)$_2$—O— | CH$_3$ | H | H | Br |
| —O—(CH$_2$)$_2$—O— | CH$_3$ | CH$_3$ | CH$_3$ | CH$_3$ |
| —O—(CH$_2$)$_2$—O— | CH$_3$ | CH$_3$ | CH$_3$ | F |
| —O—(CH$_2$)$_2$—O— | CH$_3$ | CH$_3$ | CH$_3$ | Cl |
| —O—(CH$_2$)$_2$—O— | CH$_3$ | CH$_3$ | CH$_3$ | Br |
| —O—(CH$_2$)$_2$—O— | CH$_3$ | CH$_3$ | H | Cl |
| —O—(CH$_2$)$_2$—O— | CH$_3$ | CH$_3$ | H | Br |
| —O—(CH$_2$)$_2$—O— | Cl | Cl | H | Br |

TABLE 17-continued (I-2-a)

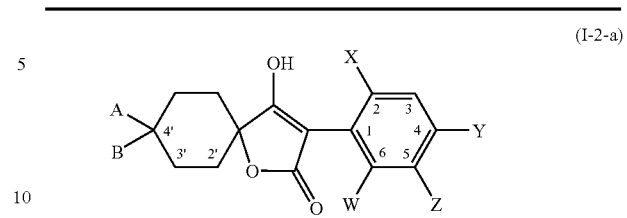

| A-B | X | W | Y | Z |
|---|---|---|---|---|
| —O—(CH$_2$)$_2$—O— | CH$_3$ | CH$_3$ | 4-Cl—C$_6$H$_4$ | H |
| —O—(CH$_2$)$_2$—O— | C$_2$H$_5$ | CH$_3$ | 4-Cl—C$_6$H$_4$ | H |
| —O—(CH$_2$)$_2$—O— | C$_2$H$_5$ | C$_2$H$_5$ | 4-Cl—C$_6$H$_4$ | H |
| —O—(CH$_2$)$_2$—O— | Cl | CH$_3$ | 4-Cl—C$_6$H$_4$ | H |
| —O—(CH$_2$)$_2$—O— | Cl | C$_2$H$_5$ | 4-Cl—C$_6$H$_4$ | H |
| —O—(CH$_2$)$_2$—O— | CH$_3$ | H | H | 4-Cl—C$_6$H$_4$ |
| —O—(CH$_2$)$_2$—O— | CH$_3$ | CH$_3$ | H | 4-Cl—C$_6$H$_4$ |
| —O—(CH$_2$)$_2$—O— | CH$_3$ | H | CH$_3$ | 4-Cl—C$_6$H$_4$ |
| —O—(CH$_2$)$_2$—O— | CH$_3$ | CH$_3$ | CH$_3$ | 4-Cl—C$_6$H$_4$ |
| —O—(CH$_2$)$_2$—O— | Cl | H | H | 4-Cl—C$_6$H$_4$ |
| —O—(CH$_2$)$_2$—O— | I | H | H | H |
| —O—(CH$_2$)$_2$—O— | I | H | CH$_3$ | H |
| —O—(CH$_2$)$_2$—O— | I | CH$_3$ | H | H |
| —O—(CH$_2$)$_2$—O— | I | C$_2$H$_5$ | H | H |
| —O—(CH$_2$)$_2$—O— | CH$_3$ | H | H | I |
| —O—(CH$_2$)$_2$—O— | CH$_3$ | H | CH$_3$ | I |
| —O—(CH$_2$)$_2$—O— | I | CH$_3$ | CH$_3$ | H |
| —O—(CH$_2$)$_2$—O— | I | C$_2$H$_5$ | CH$_3$ | H |
| —O—(CH$_2$)$_2$—O— | I | CH$_3$ | Cl | H |
| —O—(CH$_2$)$_2$—O— | I | C$_2$H$_5$ | Cl | H |
| —O—(CH$_2$)$_2$—O— | I | Cl | CH$_3$ | H |
| —O—(CH$_2$)$_2$—O— | I | H | CH$_3$ | CH$_3$ |
| —O—(CH$_2$)$_2$—O— | CH$_3$ | H | I | H |
| —O—(CH$_2$)$_2$—O— | C$_2$H$_5$ | H | I | H |
| —O—(CH$_2$)$_2$—O— | CH$_3$ | CH$_3$ | I | H |
| —O—(CH$_2$)$_2$—O— | C$_2$H$_5$ | CH$_3$ | I | H |
| —O—(CH$_2$)$_2$—O— | C$_2$H$_5$ | C$_2$H$_5$ | I | H |
| —O—(CH$_2$)$_2$—O— | Cl | CH$_3$ | I | H |
| —O—(CH$_2$)$_2$—O— | Cl | C$_2$H$_5$ | I | H |
| —O—(CH$_2$)$_2$—O— | CH$_3$ | H | I | CH$_3$ |
| —O—(CH$_2$)$_2$—O— | CH$_3$ | CH$_3$ | H | I |
| —O—(CH$_2$)$_2$—O— | I | H | H | CH$_3$ |

Table 18: W, X, Y and Z as Stated in Table 17

A-B=4'-O—CH$_2$—CHCH$_3$—O—

Table 19: W, X, Y and Z as Stated in Table 17

A-B=4'-O—CHCH$_3$—CHCH$_3$—O—

Table 20: W, X, Y and Z as Stated in Table 17

A-B=4'-O—(CH$_2$)$_3$—O—

Table 21: W, X, Y and Z as Stated in Table 17

A-B=4'-O—CHCH$_3$—(CH$_2$)$_2$—O—

Table 22: W, X, Y and Z as Stated in Table 17

A-B=4'-O—CHCH$_3$—CH$_2$—CHCH$_3$—O—

Table 23: W, X, Y and Z as Stated in Table 17

A-B=4'-O—CH$_2$—C(CH$_3$)$_2$—CH$_2$—O—

TABLE 24

W, X, Y and Z as stated in Table 17

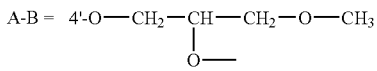

Table 25: W, X, Y and Z as Stated in Table 17

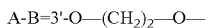

Table 26: W, X, Y and Z as Stated in Table 17

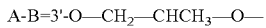

Table 27: W, X, Y and Z as Stated in Table 17

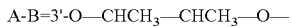

Table 28: W, X, Y and Z as Stated in Table 17

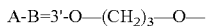

Table 29: W, X, Y and Z as Stated in Table 17

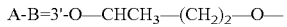

Table 30: W, X, Y and Z as Stated in Table 17

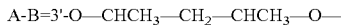

Table 31: W, X, Y and Z as Stated in Table 17

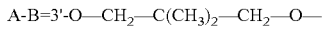

TABLE 32

W, X, Y and Z as stated in Table 17

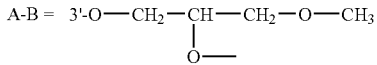

Preferred definitions of the groups listed above in connection with the crop plant compatibility-improving compounds ("herbicide safeners") of the formulae (IIa), (IIb), (IIc), (IId) and (IIe) are defined below.

m preferably represents the numbers 0, 1, 2, 3 or 4.

$A^1$ preferably represents one of the divalent heterocyclic groupings shown below

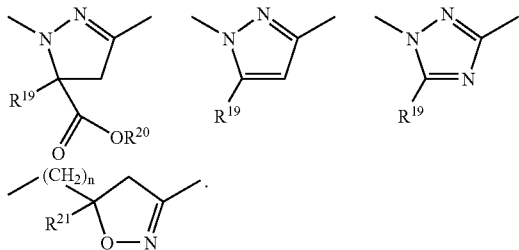

n preferably represents the numbers 0, 1, 2, 3 or 4.

$A^2$ preferably represents in each case optionally methyl-, ethyl-, methoxycarbonyl- or ethoxycarbonyl- or allyloxycarbonyl-substituted methylene or ethylene.

$R^{14}$ preferably represents hydroxyl, mercapto, amino, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino.

$R^{15}$ preferably represents hydroxyl, mercapto, amino, methoxy, ethoxy, n- or i-propoxy, n-, i-, s- or t-butoxy, 1-methylhexyloxy, allyloxy, 1-allyloxymethylethoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino.

$R^{16}$ preferably represents in each case optionally fluorine-, chlorine-, and/or bromine-substituted methyl, ethyl, n- or i-propyl.

$R^{17}$ preferably represents hydrogen, in each case optionally fluorine- and/or chlorine-substituted methyl, ethyl, n- or i-propyl, n-, i-, s- or t-butyl, propenyl, butenyl, propynyl or butynyl, methoxymethyl, ethoxymethyl, methoxyethyl, ethoxyethyl, dioxolanylmethyl, furyl, furyl-methyl, thienyl, thiazolyl, piperidinyl, or optionally fluorine-, chlorine-, methyl-, ethyl-, n- or i-propyl-, n-, i-, s- or t-butyl-substituted phenyl.

$R^{18}$ preferably represents hydrogen, in each case optionally fluorine- and/or chlorine-substituted methyl, ethyl, n- or i-propyl, n-, i-, s- or t-butyl, propenyl, butenyl, propynyl or butynyl, methoxymethyl, ethoxymethyl, methoxyethyl, ethoxyethyl, dioxolanylmethyl, furyl, furyl-methyl, thienyl, thiazolyl, piperidinyl, or optionally fluorine-, chlorine-, methyl-, ethyl-, n- or i-propyl-, n-, i-, s- or t-butyl-substituted phenyl, or together with $R^{17}$ represents one of the radicals —CH$_2$—O—CH$_2$—CH$_2$— and —CH$_2$—CH$_2$—O—CH$_2$—CH$_2$— which are optionally substituted by methyl, ethyl, furyl, phenyl, a fused benzene ring or by two substituents which, together with the C atom to which they are attached, form a 5- or 6-membered carbocycle.

$R^{19}$ preferably represents hydrogen, cyano, fluorine, chlorine, bromine, or represents in each case optionally fluorine-, chlorine- and/or bromine-substituted methyl, ethyl, n- or i-propyl, cyclo-propyl, cyclobutyl, cyclopentyl, cyclohexyl or phenyl.

$R^{20}$ preferably represents hydrogen, optionally hydroxyl-, cyano-, fluorine-, chlorine-, methoxy-, ethoxy-, n- or i-propoxy-substituted methyl, ethyl, n- or i-propyl, n-, i-, s- or t-butyl.

$R^{21}$ preferably represents hydrogen, cyano, fluorine, chlorine, bromine, or represents in each case optionally fluorine-, chlorine- and/or bromine-substituted methyl, ethyl, n- or i-propyl, n-, i-, s- or t-butyl, cyclopropyl, cyclobutyl, cyclopentyl, cyclohexyl or phenyl.

$X^1$ preferably represents nitro, cyano, fluorine, chlorine, bromine, methyl, ethyl, n- or i-propyl, n-, i-, s- or t-butyl, difluoromethyl, dichloromethyl, trifluoromethyl, trichloromethyl, chloro-difluoromethyl, fluorodichloromethyl, methoxy, ethoxy, n- or i-propoxy, difluoromethoxy or trifluoromethoxy.

$X^2$ preferably represents hydrogen, nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoro-methoxy or trifluoromethoxy.

$X^3$ preferably represents hydrogen, nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoro-methoxy or trifluoromethoxy.

t preferably represents the numbers 0, 1, 2, 3 or 4.

v preferably represents the numbers 0, 1, 2, or 3.

$R^{22}$ preferably represents hydrogen, methyl, ethyl, n- or i-propyl.

$R^{23}$ preferably represents hydrogen, methyl, ethyl, n- or i-propyl.

R²⁴ preferably represents hydrogen, in each case optionally cyano-, fluorine-, chlorine-, methoxy-, ethoxy-, n- or i-propoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino, or in each case optionally cyano-, fluorine-, chlorine-, bromine-, methyl-, ethyl-, n- or i-propyl-substituted cyclopropyl, cyclobutyl, cyclo-pentyl, cyclohexyl, cyclopropyloxy, cyclobutyloxy, cyclopentyloxy, cyclohexyloxy, cyclo-propylthio, cyclobutylthio, cyclopentylthio, cyclohexylthio, cyclopropylamino, cyclobutyl-amino, cyclopentylamino or cyclohexylamino.

R²⁵ preferably represents hydrogen, in each case optionally cyano-, hydroxyl-, fluorine-, chlorine-, methoxy-, ethoxy-, n- or i-propoxy-substituted methyl, ethyl, n- or i-propyl, n-, i- or s-butyl, in each case optionally cyano-, fluorine-, chlorine- or bromine-substituted propenyl, butenyl, propynyl or butynyl, or in each case optionally cyano-, fluorine-, chlorine-, bromine-, methyl-, ethyl-, n- or i-propyl-substituted cyclopropyl, cyclobutyl, cyclopentyl or cyclohexyl.

R²⁶ preferably represents hydrogen, in each case optionally cyano-, hydroxyl-, fluorine-, chlorine-, methoxy-, ethoxy-, n- or i-propoxy-substituted methyl, ethyl, n- or i-propyl, n-, i- or s-butyl, in each case optionally cyano-, fluorine-, chlorine- or bromine-substituted propenyl, butenyl, propynyl or butynyl, in each case optionally cyano-, fluorine-, chlorine-, bromine-, methyl-, ethyl-, n- or i-propyl-substituted cyclopropyl, cyclobutyl, cyclopentyl or cyclohexyl, or optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenyl, or together with R²⁵ represents in each case optionally methyl- or ethyl-substituted butane-1,4-diyl (trimethylene), pentane-1,5-diyl, 1-oxabutane-1,4-diyl or 3-oxapentane-1,5-diyl.

X⁴ preferably represents nitro, cyano, carboxyl, carbamoyl, formyl, sulphamoyl, hydroxyl, amino, fluorine, chlorine, bromine, methyl, ethyl, n- or i-propyl, n-, i-, s- or t-butyl, trifluoro-methyl, methoxy, ethoxy, n- or i-propoxy, difluoromethoxy or trifluoromethoxy.

X⁵ preferably represents nitro, cyano, carboxyl, carbamoyl, formyl, sulphamoyl, hydroxyl, amino, fluorine, chlorine, bromine, methyl, ethyl, n- or i-propyl, n-, i-, s- or t-butyl, trifluoro-methyl, methoxy, ethoxy, n- or i-propoxy, difluoromethoxy or trifluoromethoxy.

Examples of the compounds of the formula (IIa) which are very particularly preferred as herbicide safeners according to the invention are listed in the table below.

TABLE

Examples of the compounds of the formula (IIa)

(IIa)

| Example No. | (Positions) $(X^1)_m$ | $A^1$ | $R^{14}$ |
|---|---|---|---|
| IIa-1 | (2) Cl, (4) Cl | (pyrazoline with H₃C, C(O)OCH₃) | OCH₃ |
| IIa-2 | (2) Cl, (4) Cl | (pyrazoline with H₃C, C(O)OC₂H₅) | OCH₃ |
| IIa-3 | (2) Cl, (4) Cl | (pyrazoline with H₃C, C(O)OCH₃) | OC₂H₅ |
| IIa-4 | (2) Cl, (4) Cl | (pyrazoline with H₃C, C(O)OC₂H₅) | OC₂H₅ |
| IIa-5 | (2) Cl | (pyrazole with phenyl) | OCH₃ |
| IIa-6 | (2) Cl, (4) Cl | (pyrazole with phenyl) | OCH₃ |
| IIa-7 | (2) F | (pyrazole with phenyl) | OCH₃ |
| IIa-8 | (2) F | (pyrazole with 2-Cl-phenyl) | OCH₃ |

TABLE-continued

Examples of the compounds of the formula (IIa)

(IIa)

| Example No. | (Positions) $(X^1)_m$ | $A^1$ | $R^{14}$ |
|---|---|---|---|
| IIa-9 | (2) Cl, (4) Cl | [triazole with Cl₃C substituent] | $OC_2H_5$ |
| IIa-10 | (2) Cl, (4) $CF_3$ | [pyrazole with phenyl] | $OCH_3$ |
| IIa-11 | (2) Cl | [pyrazole with 2-F-phenyl] | $OCH_3$ |
| IIa-12 | — | [isoxazoline with phenyl] | $OC_2H_5$ |
| IIa-13 | (2) Cl, (4) Cl | [pyrazole with H₃C] | $OC_2H_5$ |
| IIa-14 | (2) Cl, (4) Cl | [pyrazole with $C_3H_7$-i] | $OC_2H_5$ |
| IIa-15 | (2) Cl, (4) Cl | [pyrazole with $C_4H_9$-t] | $OC_2H_5$ |
| IIa-16 | (2) Cl, (4) Cl | [isoxazoline with CH₂] | $OC_2H_5$ |
| IIa-17 | (2) Cl, (4) Cl | [isoxazoline] | $OC_2H_5$ |
| IIa-18 | — | [isoxazoline with phenyl] | OH |

Examples of the compounds of the formula (IIb) which are very particularly preferred as herbicide safeners according to the invention are listed in the table below.

(IIb)

TABLE

Examples of the compounds of the formula (IIb)

| Example No. | (Position) $X^2$ | (Position) $X^3$ | $A^2$ | $R^{15}$ |
|---|---|---|---|---|
| IIb-1 | (5) Cl | — | $CH_2$ | OH |
| IIb-2 | (5) Cl | — | $CH_2$ | $OCH_3$ |
| IIb-3 | (5) Cl | — | $CH_2$ | $OC_2H_5$ |
| IIb-4 | (5) Cl | — | $CH_2$ | $OC_3H_7$-n |
| IIb-5 | (5) Cl | — | $CH_2$ | $OC_3H_7$-i |
| IIb-6 | (5) Cl | — | $CH_2$ | $OC_4H_9$-n |
| IIb-7 | (5) Cl | — | $CH_2$ | $OCH(CH_3)C_5H_{11}$-n |
| IIb-8 | (5) Cl | (2) F | $CH_2$ | OH |
| IIb-9 | (5) Cl | (2) Cl | $CH_2$ | OH |
| IIb-10 | (5) Cl | — | $CH_2$ | $OCH_2CH=CH_2$ |
| IIb-11 | (5) Cl | — | $CH_2$ | $OC_4H_9$-i |

TABLE-continued
Examples of the compounds of the formula (IIb)

| Example No. | (Position) X² | (Position) X³ | A² | R¹⁵ |
|---|---|---|---|---|
| IIb-12 | (5) Cl | — | $CH_2$ | (structure with $CH_2=CH-CH_2-O-CH_2-CH(O-)-CH_3$ ether group) |
| IIb-13 | (5) Cl | — | $CH_2$ | $OCH_2CH=CH_2$ (with propenyl ester substituent) |
| IIb-14 | (5) Cl | — | $C_2H_5$ | $OC_2H_5$ (with ethyl ester substituent) |
| IIb-15 | (5) Cl | — | $CH_3$ | $OCH_3$ (with methyl ester substituent) |

Examples of the compounds of the formula (IIc) which are very particularly preferred as herbicide safeners according to the invention are listed in the table below.

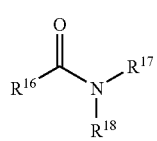

(IIc)

TABLE
Examples of the compounds of the formula (IIc)

| Example No. | R¹⁶ | N(R¹⁷,R¹⁸) |
|---|---|---|
| IIc-1 | $CHCl_2$ | $N(CH_2CH=CH_2)_2$ |
| IIc-2 | $CHCl_2$ | 2,2-dimethyl-3-methyl-oxazolidine |
| IIc-3 | $CHCl_2$ | 2,2-dimethyl-3-methyl-5-methyl-oxazolidine |
| IIc-4 | $CHCl_2$ | 3-methyl-1-oxa-4-azaspiro[4.5]decane |
| IIc-5 | $CHCl_2$ | 2,2-dimethyl-3-methyl-5-phenyl-oxazolidine |
| IIc-6 | $CHCl_2$ | 4-methyl-3-methyl-3,4-dihydro-2H-benzo[1,4]oxazine |
| IIc-7 | $CHCl_2$ | 2,2-dimethyl-3-methyl-5-(furan-2-yl)-oxazolidine |

Examples of the compounds of the formula (IId) which are very particularly preferred as herbicide safeners according to the invention are listed in the table below.

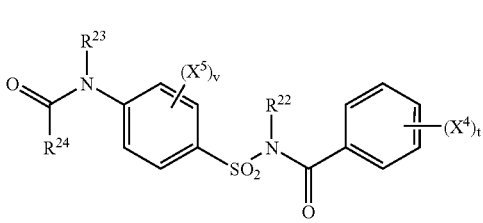

(IId)

TABLE

Examples of the compounds of the formula (IId)

| Example No. | $R^{22}$ | $R^{23}$ | $R^{24}$ | (Positions) $(X^4)_t$ | (Positions) $(X^5)_v$ |
|---|---|---|---|---|---|
| IId-1 | H | H | $CH_3$ | (2) $OCH_3$ | — |
| IId-2 | H | H | $C_2H_5$ | (2) $OCH_3$ | — |
| IId-3 | H | H | $C_3H_7$-n | (2) $OCH_3$ | — |
| IId-4 | H | H | $C_3H_7$-i | (2) $OCH_3$ | — |
| IId-5 | H | H | cyclopropyl | (2) $OCH_3$ | — |
| IId-6 | H | H | $CH_3$ | (2) $OCH_3$ (5) $CH_3$ | — |
| IId-7 | H | H | $C_2H_5$ | (2) $OCH_3$ (5) $CH_3$ | — |
| IId-8 | H | H | $C_3H_7$-n | (2) $OCH_3$ (5) $CH_3$ | — |
| IId-9 | H | H | $C_3H_7$-i | (2) $OCH_3$ (5) $CH_3$ | — |
| IId-10 | H | H | cyclopropyl | (2) $OCH_3$ (5) $CH_3$ | — |
| IId-11 | H | H | $OCH_3$ | (2) $OCH_3$ (5) $CH_3$ | — |
| IId-12 | H | H | $OC_2H_5$ | (2) $OCH_3$ (5) $CH_3$ | — |
| IId-13 | H | H | $OC_3H_7$-i | (2) $OCH_3$ (5) $CH_3$ | — |
| IId-14 | H | H | $SCH_3$ | (2) $OCH_3$ (5) $CH_3$ | — |
| IId-15 | H | H | $SC_2H_5$ | (2) $OCH_3$ (5) $CH_3$ | — |
| IId-16 | H | H | $SC_3H_7$-i | (2) $OCH_3$ (5) $CH_3$ | — |
| IId-17 | H | H | $NHCH_3$ | (2) $OCH_3$ (5) $CH_3$ | — |
| IId-18 | H | H | $NHC_2H_5$ | (2) $OCH_3$ (5) $CH_3$ | — |
| IId-19 | H | H | $NHC_3H_7$-i | (2) $OCH_3$ (5) $CH_3$ | — |
| IId-20 | H | H | NH-cyclopropyl | (2) $OCH_3$ (5) $CH_3$ | — |
| IId-21 | H | H | $NHCH_3$ | (2) $OCH_3$ | — |
| IId-22 | H | H | $NHC_3H_7$-i | (2) $OCH_3$ | — |
| IId-23 | H | H | $N(CH_3)_2$ | (2) $OCH_3$ | — |
| IId-24 | H | H | $N(CH_3)_2$ | (3) $CH_3$ (4) $CH_3$ | — |
| IId-25 | H | H | $CH_2$—O—$CH_3$ | (2) $OCH_3$ | — |

Examples of the compounds of the formula (IIe) which are very particularly preferred as herbicide safeners according to the invention are listed in the table below.

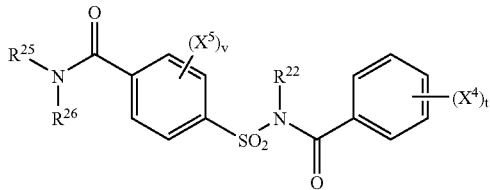

(IIe)

TABLE

Examples of the compounds of the formula (IIe)

| Example No. | $R^{22}$ | $R^{25}$ | $R^{26}$ | (Positions) $(X^4)_t$ | (Positions) $(X^5)_v$ |
|---|---|---|---|---|---|
| IIe-1 | H | H | $CH_3$ | (2) $OCH_3$ | — |
| IIe-2 | H | H | $C_2H_5$ | (2) $OCH_3$ | — |
| IIe-3 | H | H | $C_3H_7$-n | (2) $OCH_3$ | — |
| IIe-4 | H | H | $C_3H_7$-i | (2) $OCH_3$ | — |
| IIe-5 | H | H | cyclopropyl | (2) $OCH_3$ | — |
| IIe-6 | H | $CH_3$ | $CH_3$ | (2) $OCH_3$ | — |
| IIe-7 | H | H | $CH_3$ | (2) $OCH_3$ (5) $CH_3$ | — |
| IIe-8 | H | H | $C_2H_5$ | (2) $OCH_3$ (5) $CH_3$ | — |
| IIe-9 | H | H | $C_3H_7$-n | (2) $OCH_3$ (5) $CH_3$ | — |
| IIe-10 | H | H | $C_3H_7$-i | (2) $OCH_3$ (5) $CH_3$ | — |
| IIe-11 | H | H | cyclopropyl | (2) $OCH_3$ (5) $CH_3$ | — |
| IIe-12 | H | $CH_3$ | $CH_3$ | (2) $OCH_3$ (5) $CH_3$ | — |

Most preferred as crop plant compatibility-improving compound [component (b')] are cloquintocet-mexyl, fenchlorazole-ethyl, isoxadifen-ethyl, mefenpyr-diethyl, furilazole, fenclorim, cumyluron, dymron, dimepiperate and the compounds IIe-5 and IIe-11, and particular emphasis is given to cloquintocet-mexyl and mefenpyr-diethyl.

The compounds of the general formula (IIa) to be used as safeners according to the invention are known and/or can be prepared by processes known per se (cf. WO-A-91/07874, WO-A-95/07897).

The compounds of the general formula (IIb) to be used as safeners according to the invention are known and/or can be prepared by processes known per se (cf. EP-A-191736).

The compounds of the general formula (IIc) to be used as safeners according to the invention are known and/or can be prepared by processes known per se (cf. DE-A-2218097, DE-A-2350547).

The compounds of the general formula (IId) to be used as safeners according to the invention are known and/or can be prepared by processes known per se (cf. DE-A-19621522/ U.S. Pat. No. 6,235,680).

The compounds of the general formula (IIe) to be used as safeners according to the invention are known and can be prepared by processes known per se (cf. WO-A-99/66795/ U.S. Pat. No. 6,251,827).

Examples of the selective herbicidal combinations according to the invention comprising in each case one active compound of the formula (I) and one of the safeners defined above are listed in the table below.

TABLE

Examples of the combinations according to the invention

| Active compounds of the formula (I) | Safeners |
|---|---|
| I-1-a | cloquintocet-mexyl |
| I-1-a | fenchlorazole-ethyl |
| I-1-a | isoxadifen-ethyl |
| I-1-a | mefenpyr-diethyl |
| I-1-a | furilazole |
| I-1-a | fenclorim |
| I-1-a | cumyluron |
| I-1-a | daimuron/dymron |
| I-1-a | dimepiperate |
| I-1-a | IIe-11 |
| I-1-a | IIe-5 |
| I-1-b | cloquintocet-mexyl |
| I-1-b | fenchlorazole-ethyl |
| I-1-b | isoxadifen-ethyl |
| I-1-b | mefenpyr-diethyl |
| I-1-b | furilazole |
| I-1-b | fenclorim |
| I-1-b | cumyluron |
| I-1-b | daimuron/dymron |
| I-1-b | dimepiperate |
| I-1-b | IIe-11 |
| I-1-b | IIe-5 |
| I-1-c | cloquintocet-mexyl |
| I-1-c | fenchlorazole-ethyl |
| I-1-c | isoxadifen-ethyl |
| I-1-c | mefenpyr-diethyl |
| I-1-c | furilazole |
| I-1-c | fenclorim |
| I-1-c | cumyluron |
| I-1-c | daimuron/dymron |
| I-1-c | dimepiperate |
| I-1-c | IIe-5 |
| I-1-c | IIe-11 |
| I-1-d | cloquintocet-mexyl |
| I-1-d | fenchlorazole-ethyl |
| I-1-d | isoxadifen-ethyl |
| I-1-d | mefenpyr-diethyl |
| I-1-d | furilazole |
| I-1-d | fenclorim |
| I-1-d | cumyluron |
| I-1-d | daimuron/dymron |
| I-1-d | dimepiperate |
| I-1-d | IIe-11 |
| I-1-d | IIe-5 |
| I-1-e | cloquintocet-mexyl |
| I-1-e | fenchlorazole-ethyl |
| I-1-e | isoxadifen-ethyl |
| I-1-e | mefenpyr-diethyl |
| I-1-e | furilazole |
| I-1-e | fenclorim |
| I-1-e | cumyluron |
| I-1-e | daimuron/dymron |
| I-1-e | dimepiperate |
| I-1-e | IIe-5 |
| I-1-e | IIe-11 |
| I-1-f | cloquintocet-mexyl |
| I-1-f | fenchlorazole-ethyl |
| I-1-f | isoxadifen-ethyl |
| I-1-f | mefenpyr-diethyl |
| I-1-f | furilazole |
| I-1-f | fenclorim |
| I-1-f | cumyluron |
| I-1-f | daimuron/dymron |
| I-1-f | dimepiperate |
| I-1-f | IIe-5 |
| I-1-f | IIe-11 |
| I-1-g | cloquintocet-mexyl |
| I-1-g | fenchlorazole-ethyl |
| I-1-g | isoxadifen-ethyl |
| I-1-g | mefenpyr-diethyl |
| I-1-g | furilazole |
| I-1-g | fenclorim |
| I-1-g | cumyluron |
| I-1-g | daimuron/dymron |
| I-1-g | dimepiperate |
| I-1-g | IIe-5 |
| I-1-g | IIe-11 |
| I-2-a | cloquintocet-mexyl |
| I-2-a | fenchlorazole-ethyl |
| I-2-a | isoxadifen-ethyl |
| I-2-a | mefenpyr-diethyl |
| I-2-a | furilazole |
| I-2-a | fenclorim |
| I-2-a | cumyluron |
| I-2-a | daimuron/dymron |
| I-2-a | dimepiperate |
| I-2-a | IIe-5 |
| I-2-a | IIe-11 |
| I-2-b | cloquintocet-mexyl |
| I-2-b | fenchlorazole-ethyl |
| I-2-b | isoxadifen-ethyl |
| I-2-b | mefenpyr-diethyl |
| I-2-b | furilazole |
| I-2-b | fenclorim |
| I-2-b | cumyluron |
| I-2-b | daimuron/dymron |
| I-2-b | dimepiperate |
| I-2-b | IIe-5 |
| I-2-b | IIe-11 |
| I-2-c | cloquintocet-mexyl |
| I-2-c | fenchlorazole-ethyl |
| I-2-c | isoxadifen-ethyl |
| I-2-c | mefenpyr-diethyl |
| I-2-c | furilazole |
| I-2-c | fenclorim |
| I-2-c | cumyluron |
| I-2-c | daimuron/dymron |
| I-2-c | dimepiperate |
| I-2-c | IIe-5 |
| I-2-c | IIe-11 |
| I-2-d | cloquintocet-mexyl |
| I-2-d | fenchlorazole-ethyl |
| I-2-d | isoxadifen-ethyl |
| I-2-d | mefenpyr-diethyl |
| I-2-d | furilazole |
| I-2-d | fenclorim |
| I-2-d | cumyluron |
| I-2-d | daimuron/dymron |
| I-2-d | dimepiperate |
| I-2-d | IIe-5 |
| I-2-d | IIe-11 |
| I-2-e | cloquintocet-mexyl |
| I-2-e | fenchlorazole-ethyl |
| I-2-e | isoxadifen-ethyl |
| I-2-e | mefenpyr-diethyl |
| I-2-e | furilazole |
| I-2-e | fenclorim |
| I-2-e | cumyluron |
| I-2-e | daimuron/dymron |
| I-2-e | dimepiperate |
| I-2-e | IIe-5 |
| I-2-e | IIe-11 |
| I-2-f | cloquintocet-mexyl |
| I-2-f | fenchlorazole-ethyl |
| I-2-f | isoxadifen-ethyl |
| I-2-f | mefenpyr-diethyl |
| I-2-f | furilazole |
| I-2-f | fenclorim |
| I-2-f | cumyluron |
| I-2-f | daimuron/dymron |
| I-2-f | dimepiperate |
| I-2-f | IIe-5 |
| I-2-f | IIe-11 |

TABLE-continued

Examples of the combinations according to the invention

| Active compounds of the formula (I) | Safeners |
|---|---|
| I-2-g | cloquintocet-mexyl |
| I-2-g | fenchlorazole-ethyl |
| I-2-g | isoxadifen-ethyl |
| I-2-g | mefenpyr-diethyl |
| I-2-g | furilazole |
| I-2-g | fenclorim |
| I-2-g | cumyluron |
| I-2-g | daimuron/dymron |
| I-2-g | dimepiperate |
| I-2-g | IIe-5 |
| I-2-g | IIe-11 |

It has now surprisingly been found that the above-defined active-compound combinations of compounds of the general formula (I) and safeners (antidotes) from the group (b') set out above combine very good useful plant tolerance with a high herbicidal activity and can be used in various crops, in particular in cereals (especially wheat), but also in soya, potatoes, maize and rice, for selective weed control.

In this context it is considered surprising that, from a multiplicity of known safeners or antidotes capable of antagonizing the damaging effect of a herbicide on the crop plants, it is specifically the compounds of group (b') set out above which are suitable for compensating—almost completely—the damaging effect of substituted cyclic ketoenols on the crop plants, without at the same time having any critical adverse effect on the herbicidal activity against the weeds.

Emphasis may be given here to the particularly advantageous effect of the particularly preferred and most preferred combination partners from group (b'), particularly with regard to the gentle treatment of cereal plants, such as wheat, barley and rye, for example, but also maize and rice, as crop plants.

Using, for example, according to process (A) ethyl N-[(4-chloro-2,6-dimethyl)phenylacetyl]-1-amino-4,4'-propylene-dioxycyclohexanecarboxylate as starting material, the course of the process according to the invention can be represented by the reaction scheme below:

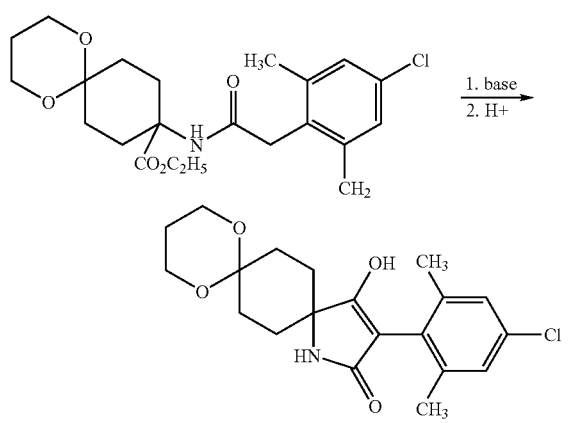

Using, for example, according to process (B) ethyl O-[(2-chloro-6-methyl)phenylacetyl]-1-hydroxy-4,4'-ethylene-dioxycyclohexanecarboxylate, the course of the process according to the invention can be represented by the reaction scheme below:

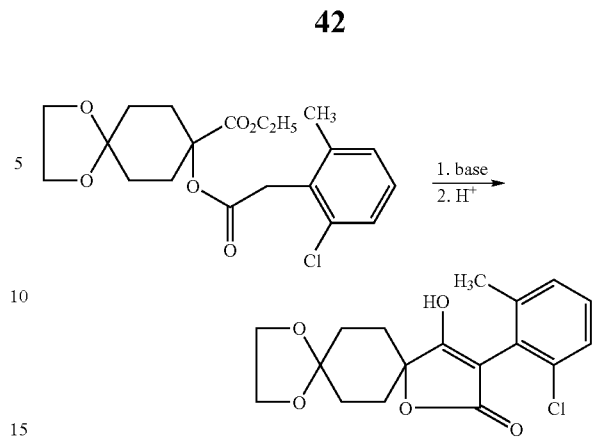

Using, for example, according to process (Cα) 8,8'-ethyl-enedioxy-3-[(4-chloro-2,6-dimethyl)phenyl]-1-azaspiro[4,5]decane-2,4-dione and pivaloyl chloride as starting materials, the course of the process according to the invention can be represented by the reaction scheme below:

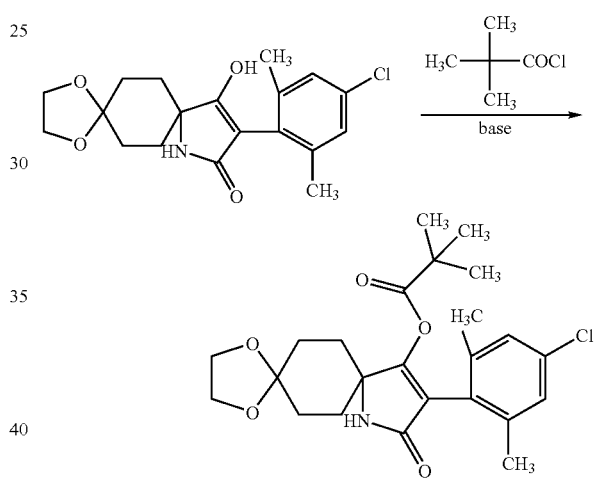

Using, for example, according to process (C) (variant B) 8,8'-propylenedioxy-3-[(2,4-dichloro)phenyl]-1-oxaspiro-[4,5]-decane-2,4-dione and acetic anhydride as starting materials, the course of the process according to the invention can be represented by the reaction scheme below:

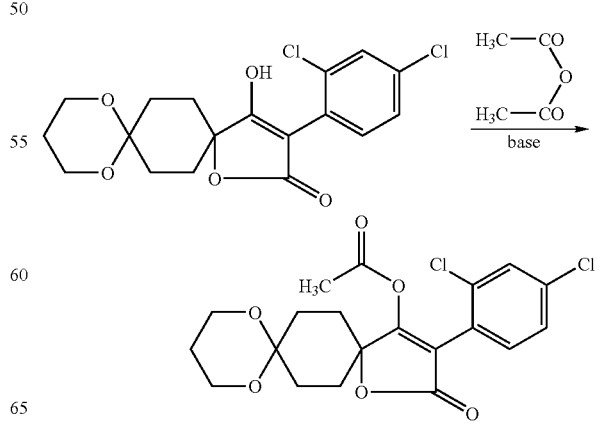

Using, for example, according to process (D) 8,8'-propylenedioxy-3-[(2,4-dichloro-6-methyl)phenyl]-1-azaspiro[4,5]decane-2,4-dione and ethyl chloroformate as starting materials, the course of the process according to the invention can be represented by the reaction scheme below:

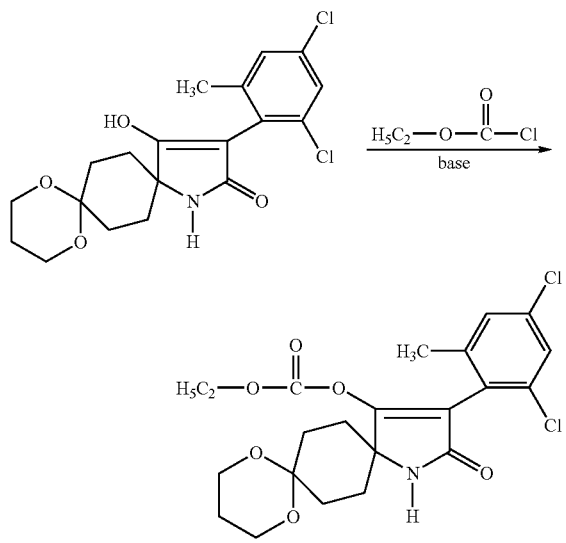

Using, for example, according to process (E) 8,8'-ethylenedioxy-3-[(2,4,6-trimethyl)phenyl]-1-oxaspiro[4,5]decane-2,4-dione and methyl chloromonothioformate as starting materials, the course of the reaction can be represented as follows:

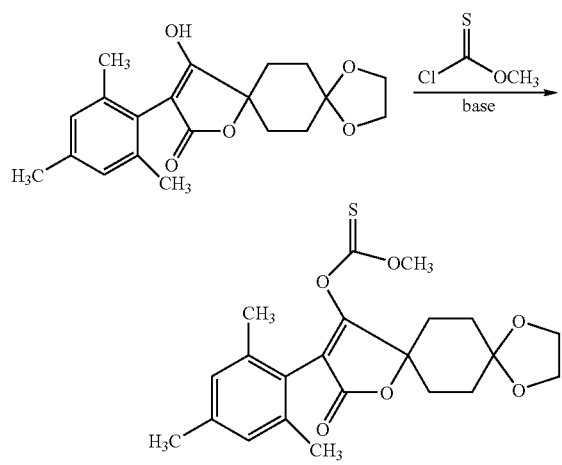

Using, for example, according to process (F) 8,8'-propylenedioxy-3-[(2,4,6-trimethyl)phenyl]-1-azaspiro[4,5]decane-2,4-dione and methanesulphonyl chloride as starting materials, the course of the reaction can be represented by the reaction scheme below:

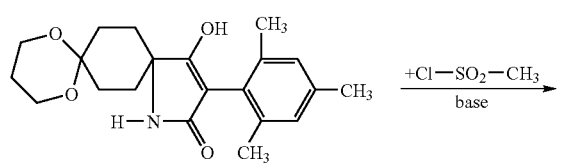

-continued

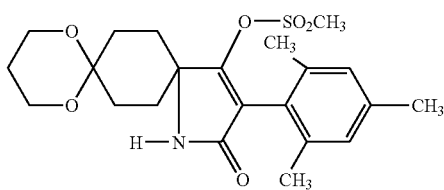

Using, for example, according to process (G) 8,8'-propylenedioxy-3-[(2,4-dichloro-6-methyl)phenyl]-1-oxaspiro[4,5]decane-2,4-dione and 2,2,2-trifluoroethyl methanethiophosphonyl chloride as starting materials, the course of the reaction can be represented by the reaction scheme below:

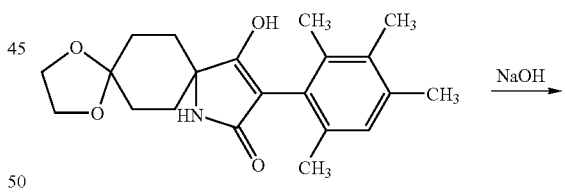

Using, for example, according to process (H) 8,8'-ethylenedioxy-3-[(2,3,4,6-tetramethyl)phenyl]-1-azaspiro[4,5]decane-2,4-dione and NaOH as components, the course of the process according to the invention can be represented by the reaction scheme below:

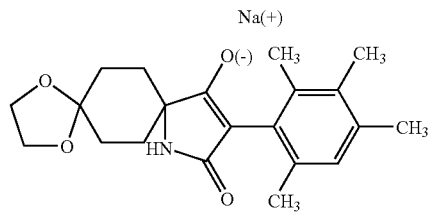

Using, for example, according to process (I) (variant α) 8,8'-ethylenedioxy-3-[(2,4,5-trimethyl)phenyl]-1-oxaspiro[4,5]decane-2,4-dione and ethyl isocyanate as starting materials, the course of the reaction can be represented by the reaction scheme below:

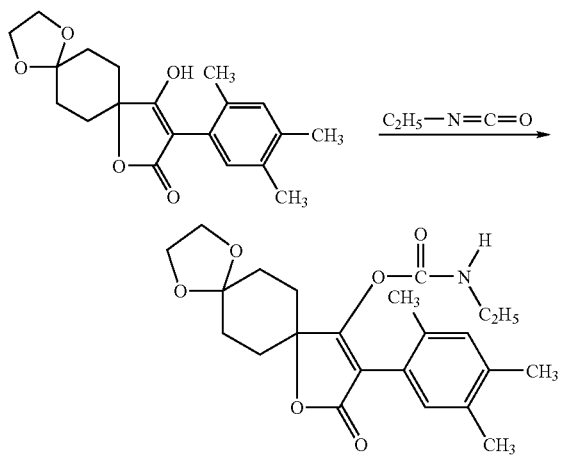

Using, for example, according to process (I) (variant β) 8,8'-ethylenedioxy-3-[(2,4,6-trimethyl)phenyl]-1-azaspiro[4,5]decane-2,4-dione and dimethylcarbamoyl chloride as starting materials, the course of the reaction can be represented by the scheme below:

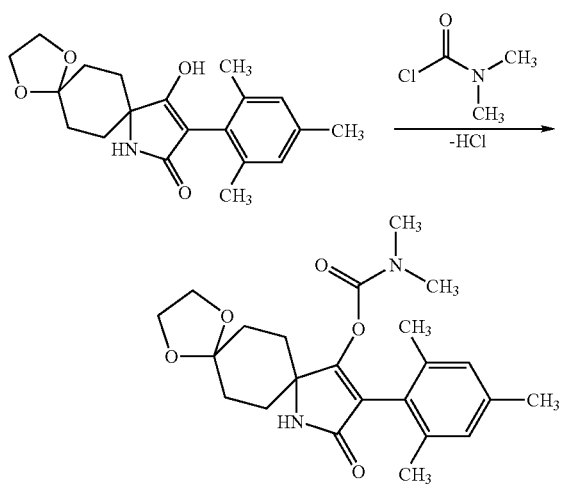

The compounds, required as starting materials in the process (A) according to the invention, of the formula (II)

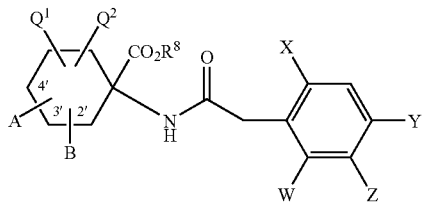

(II)

in which

A, B, $Q^1$, $Q^2$, W, X, Y, Z and $R^8$ are as defined above are novel.

The acylamino acid esters of the formula (II) are obtained, for example, when amino acid derivatives of the formula (XVI)

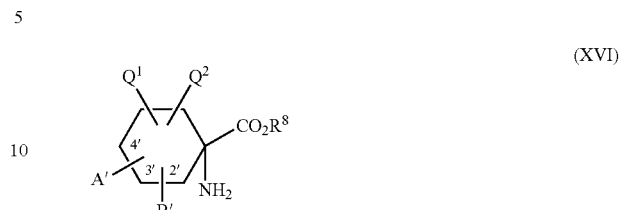

(XVI)

in which

A, B, $Q^1$ and $Q^2$ and $R^8$ are as defined above are acylated with substituted phenylacetic acid derivatives of the formula (XVII)

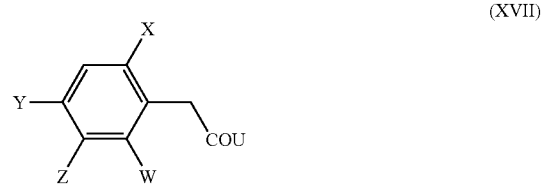

(XVII)

in which

W, X, Y and Z are as defined above and

U represents a leaving group introduced by reagents for activating carboxylic acids, such as carbonyldiimidazole, carbodiimides (such as, for example, dicyclohexylcarbodiimide), phosphorylating agents (such as, for example, $POCl_3$, BOP—Cl), halogenating agents, such as, for example, thionyl chloride, oxalyl chloride, phosgene or chloroformic esters (Chem. Reviews 52, 237-416 (1953); Bhattacharya, Indian J. Chem. 6, 341-5, 1968)

or when acylamino acids of the formula (XVIII)

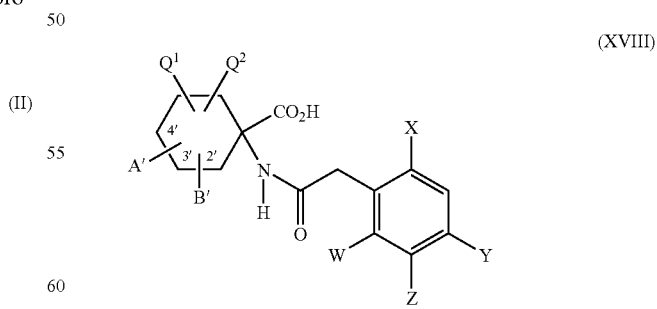

(XVIII)

in which

A, B, $Q^1$, $Q^2$, W, X, Y and Z are as defined above, are esterified (Chem. Ind. (London) 1568 (1968)).

The compounds of the formula (XVIII)

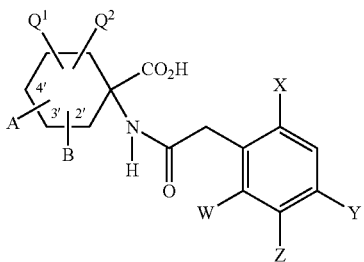
(XVIII)

in which

A, B, $Q^1$, $Q^2$, W, X, Y and Z are as defined above, are novel.

The compounds of the formula (XVIII) are obtained, for example, when 1-aminocyclohexane-carboxylic acids of the formula (XIX)

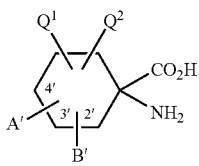
(XIX)

in which

A, B, $Q^1$ and $Q^2$ are as defined above are acylated with substituted phenylacetic acid derivatives of the formula (XVII)

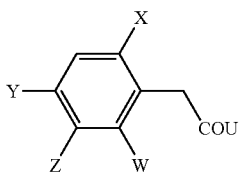
(XVII)

in which

U, W, X, Y and Z are as defined above, for example according to Schotten-Baumann (Organikum, VEB Deutscher Verlag der Wissenschaften, Berlin 1977, p. 505).

Some of the compounds of the formula (XVII) are known, and/or they can be prepared by the known processes described in the laid-open publications cited at the outset.

Some of the compounds of the formulae (XVI) and (XIX) are novel, and they can be prepared by known processes (see, for example, Compagnon, Ann. Chim. (Paris) [14] 5, pp. 11-22, 23-27 (1970), L. Munday, J. Chem. Soc. 4372 (1961); J. T. Eward, C. Jitrangeri, Can. J. Chem. 53, 3339 (1975)).

Furthermore, the starting materials, used in the above process (A), of the formula (II)

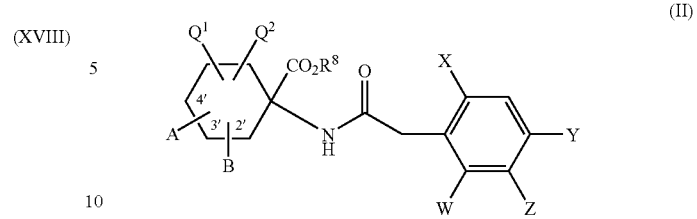
(II)

in which

A, B, $Q^1$, $Q^2$, W, X, Y, Z and $R^8$ are as defined above, can be prepared by reacting 1-aminocyclohexanecarbonitriles of the formula (XX)

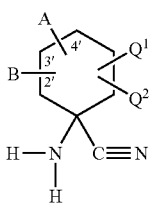
(XX)

in which

A, B, $Q^1$ and $Q^2$ are as defined above, with substituted phenylacetic acid derivatives of the formula (XVII)

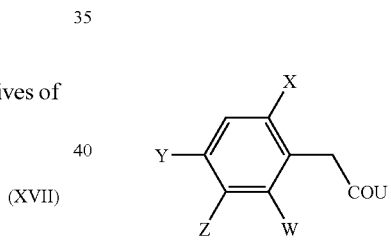
(XVII)

in which

U, W, X, Y and Z are as defined above, to give compounds of the formula (XXI)

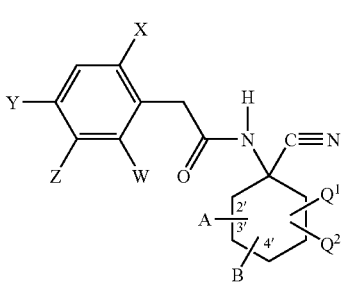
(XXI)

in which

A, B, $Q^1$, $Q^2$, W, X, Y and Z are as defined above, and then subjecting these to an acidic alcoholysis.

The compounds of the formula (XXI) are likewise novel. Some of the compounds of the formula (XX) are novel and can be prepared, for example, as described in EP-A-595 130.

The compounds, required as starting materials in the process (B) according to the invention, of the formula (III)

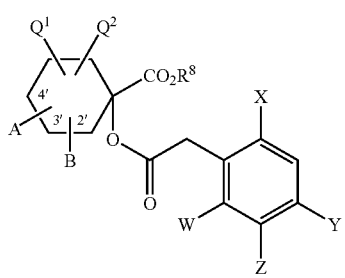

(III)

in which

A, B, $Q^1$, $Q^2$, W, X, Y, Z and $R^8$ are as defined above, are novel.

They can be prepared in a simple manner by methods known in principle.

The compounds of the formula (III) obtained, for example, when 1-hydroxycyclohexanecarboxylic esters of the formula (XXII)

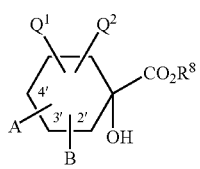

(XXII)

in which

A, B, $Q^1$, $Q^2$ and $R^8$ are as defined above, are acylated with substituted phenylacetic acid derivatives of the formula (XVII)

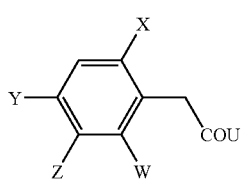

(XVII)

in which

U, W, X, Y and Z are as defined above, (Chem. Reviews 52, 237-416 (1953)).

The 1-hydroxy-3-alkoxycyclohexylcarboxylic esters of the formula (XXII) are novel. They are obtained, for example, when substituted 1-hydroxy-4,4'-alkylidenyldioxycyclohexanecarbonitriles are reacted with alcohols in the presence of acids, for example according to Pinner, and the 1-hydroxy-4-oxocyclohexanecarboxylic esters formed, which are known from WO 99/16748 (Ex. XXI-1), are re-ketalized with diols.

The cyanohydrin is obtained, for example, by reacting 4,4'-alkylidenyldioxycyclohexan-1-ones with hydrocyanic acid (see WO 99/16748).

The acid halides of the formula (IV), carboxylic anhydrides of the formula (V), chloroformic esters or chloroformic thioesters of the formula (VI), chloromonothioformic esters or chlorodithioformic esters of the formula (VII), sulphonyl chlorides of the formula (VIII), phosphorus compounds of the formula (IX) and metal hydroxides, metal alkoxides or amines of the formulae (X) and (XI) and isocyanates of the formula (XII) and carbamoyl chlorides of the formula (XIII) and diols of the formula (XV) furthermore required as starting materials for carrying out the processes (C), (D), (E), (F), (G), (H), (I) and (J) according to the invention are generally known compounds of organic or inorganic chemistry. Some of the compounds of the formula (XIV) are known from WO 99/16748.

Additionally, the compounds of the formula (XVII) are known from the patent applications cited at the outset, and/or they can be prepared by the methods given therein.

The process (A) is characterized in that compounds of the formula (II) in which A, B, $Q^1$, $Q^2$, W, X, Y, Z and $R^8$ are as defined above are subjected to an intramolecular condensation in the presence of a diluent and in the presence of a base.

Suitable diluents for use in the process (A) according to the invention are all organic solvents which are inert towards the reaction participants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methylpyrrolidone, and also alcohols such as methanol, ethanol, propanol, isopropanol, butanol, isobutanol and tert-butanol.

Suitable bases (deprotonating agents) for carrying out the process (A) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase-transfer catalysts, such as, for example, triethyl-benzylammonium chloride, tetrabutylammonium bromide, Adogen 464 (=methyltrialkyl($C_8$-$C_{10}$)ammonium chloride) or TDA 1 (=tris(methoxyethoxyethyl)amine). It is furthermore possible to use alkali metals, such as sodium or potassium. Alkali metal or alkaline earth metal amides and hydrides, such as sodium amide, sodium hydride and calcium hydride, and additionally also alkali metal alkoxides, such as sodium methoxide, sodium ethoxide and potassium tert-butoxide, can be employed, too.

When carrying out the process (A) according to the invention, the reaction temperature can be varied within a relatively wide range. In general, the process is carried out at temperatures between −75° C. and 200° C., preferably between −50° C. and 150° C.

The process (A) according to the invention is generally carried out under atmospheric pressure.

When carrying out the process (A) according to the invention, the reaction component of the formula (II) and the deprotonating base are generally employed in equimolar to about doubly equimolar amounts. However, it is also possible to use a relatively large excess (up to 3 mol) of one component or the other.

The process (B) is characterized in that compounds of the formula (III) in which A, B, $Q^1$, $Q^2$, W, X, Y, Z and $R^8$ are as defined above are condensed intramolecularly in the presence of a diluent and in the presence of a base.

Suitable diluents for use in the process (B) according to the invention are all organic solvents which are inert towards the reaction participants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methylpyrrolidone. It is furthermore possible to use alcohols, such as methanol, ethanol, propanol, isopropanol, butanol, isobutanol and tert-butanol.

Suitable bases (deprotonating agents) for carrying out the process (B) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase-transfer catalysts, such as, for example, triethyl-benzylammonium chloride, tetrabutylammonium bromide, Adogen 464 (=methyltrialkyl($C_8$-$C_{10}$)ammonium chloride) or TDA 1 (=tris(methoxyethoxyethyl)amine). It is furthermore possible to use alkali metals, such as sodium or potassium. Alkali metal or alkaline earth metal amides and hydrides, such as sodium amide, sodium hydride and calcium hydride, and additionally also alkali metal alkoxides, such as sodium methoxide, sodium ethoxide and potassium tert-butoxide, can be employed, too.

When carrying out the process (B) according to the invention, the reaction temperature can be varied within a relatively wide range. In general, the process is carried out at temperatures between −75° C. and 200° C., preferably between −50° C. and 150° C.

The process (B) according to the invention is generally carried out under atmospheric pressure.

When carrying out the process (B) according to the invention, the reaction component of the formula (II) and the deprotonating base are generally employed in equimolar to about doubly equimolar amounts. However, it is also possible to use a relatively large excess (up to 3 mol) of one component or the other.

The process ($C_\alpha$) is characterized in that compounds of the formulae (I-1-a) to (I-2-a) are in each case reacted with carbonyl halides of the formula (IV), if appropriate in the presence of a diluent and if appropriate in the presence of an acid binder.

Suitable diluents for the process ($C_\alpha$) according to the invention are all solvents which are inert towards the acid halides. Preference is given to using hydrocarbons, such as benzine, benzene, toluene, xylene and tetralin; furthermore halogenated hydrocarbons, such as methylene chloride, chloroform, carbon tetrachloride, chlorobenzene and o-dichlorobenzene, moreover ketones, such as acetone and methylisopropyl ketone, furthermore ethers, such as diethyl ether, tetrahydrofuran and dioxane, additionally carboxylic esters, such as ethyl acetate, and also strongly polar solvents, such as dimethylformamide, dimethyl sulphoxide and sulpholane. The hydrolytic stability of the acid halide permitting, the reaction may also be carried out in the presence of water.

Suitable acid binders for the reaction according to the process ($C_\alpha$) according to the invention are all customary acid acceptors. Preference is given to using tertiary amines, such as triethylamine, pyridine, diazabicyclooctane (DABCO), diazabicycloundecene (DBU), diazabicyclononene (DBN), Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

The reaction temperature in the process ($C_\alpha$) according to the invention can be varied within a relatively wide range. In general, the process is carried out at temperatures between −20° C. and +150° C., preferably between 0° C. and 100° C.

When carrying out the process ($C_\alpha$) according to the invention, the starting materials of the formulae (I-1-a) to (I-2-a) and the carbonyl halide of the formula (IV) are generally each used in approximately equivalent amounts. However, it is also possible to employ a relatively large excess (up to 5 mol) of the carbonyl halide. Work-up is carried out by customary methods.

The process ($C_\beta$) is characterized in that compounds of the formulae (I-1-a) to (I-2-a) are in each case reacted with carboxylic anhydrides of the formula (V), if appropriate in the presence of a diluent and if appropriate in the presence of an acid binder.

Suitable diluents for use in the process ($C_\beta$) according to the invention are preferably those diluents which are also preferred when using acid halides. Besides, it is also possible for excess carboxylic anhydride to act simultaneously as diluent.

Suitable acid binders for the process ($C_\beta$), which are added, if appropriate, are preferably those acid binders which are also preferred when using acid halides.

The reaction temperature in the process ($C_\beta$) according to the invention can be varied within a relatively wide range. In general, the process is carried out at temperatures between −20° C. and +150° C., preferably between 0° C. and 100° C.

When carrying out the process ($C_\beta$) according to the invention, the starting materials of the formulae (I-1-a) to (I-2-a) and the carboxylic anhydride of the formula (V) are generally each employed in approximately equivalent amounts. However, it is also possible to use a relatively large excess (up to 5 mol) of the carboxylic anhydride. Work-up is carried out by customary methods.

In general, diluent and excess carboxylic anhydride and the carboxylic acid formed are removed by distillation or by washing with an organic solvent or with water.

The process (D) is characterized in that compounds of the formulae (I-1-a) to (I-2-a) are in each case reacted with chloroformic esters or chloroformic thioesters of the formula (VI), if appropriate in the presence of a diluent and if appropriate in the presence of an acid binder.

Suitable acid binders for the process (D) according to the invention are all customary acid acceptors. Preference is given to using tertiary amines, such as triethylamine, pyridine, DABCO, DBU, DBN, Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

Suitable diluents for use in the process (D) according to the invention are all solvents which are inert towards the chloroformic esters or chloroformic thioesters. Preference is given to using hydrocarbons, such as benzine, benzene, toluene, xylene and tetralin; furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, moreover nitriles, such as acetonitrile, and also strongly polar solvents, such as dimethylformamide, dimethyl sulphoxide and sulpholane.

When carrying out the process (D) according to the invention, the reaction temperature can be varied within a relatively wide range. In general, the reaction temperature is between −20° C. and +100° C., preferably between 0° C. and 50° C.

Process (D) according to the invention is generally carried out under atmospheric pressure.

When carrying out the process (D) according to the invention, the starting materials of the formulae (I-1-a) to (I-2-a) and the appropriate chloroformic ester or chloroformic thioester of the formula (VI) are generally each employed in approximately equivalent amounts. However, it is also possible to use a relatively large excess (up to 2 mol) of one component or the other. Work-up is carried out by customary methods. In general, precipitated salts are removed and the reaction mixture that remains is concentrated by removing the diluent under reduced pressure.

The process (E) according to the invention is characterized in that compounds of the formulae (I-1-a) to (I-2-a) are in each case reacted with compounds of the formula (VII) in the presence of a diluent and, if appropriate, in the presence of an acid binder.

In the preparation process (E), about 1 mol of chloromonothioformic ester or chlorodithioformic ester of the formula (VU) is employed per mole of starting material of the formulae (I-1-a) to (I-2-a), at from 0 to 120° C., preferably from 20 to 60° C.

Suitable diluents which are added, if appropriate, are all inert polar organic solvents, such as ethers, amides, sulphones, sulphoxides, and also halogenated alkanes.

Preference is given to using dimethyl sulphoxide, tetrahydrofuran, dimethylformamide, ethyl acetate or methylene chloride.

If, in a preferred embodiment, the enolate salt of the compounds (I-1-a) to (I-2-a) is prepared by adding strong deprotonating agents, such as, for example, sodium hydride or potassium tert-butoxide, the further addition of acid binders may be dispensed with.

Suitable bases for use in the process (E) are all customary proton acceptors. Preference is given to using alkali metal hydrides, alkali metal alkoxides, alkali metal or alkaline earth metal carbonates or bicarbonates or nitrogen bases. Sodium hydride, sodium methoxide, sodium hydroxide, calcium hydroxide, potassium carbonate, sodium bicarbonate, triethylamine, dibenzylamine, diisopropylamine, pyridine, quinoline diazabicyclooctane (DABCO), diazabicyclononene (DBN) and diazabicycloundecene (DBU) may be mentioned by way of example.

The reaction can be carried out at atmospheric pressure or under elevated pressure and is preferably carried out at atmospheric pressure. Work-up is carried out by customary methods.

The process (F) according to the invention is characterized in that compounds of the formulae (I-1-a) to (I-2-a) are in each case reacted with sulphonyl chlorides of the formula (VIII), if appropriate in the presence of a diluent and if appropriate in the presence of an acid binder.

In the preparation process (F), about 1 mol of sulphonyl chloride of the formula (VI) is reacted per mole of starting material of the formulae (I-1-a) to (I-2-a), at from −20 to 150° C., preferably from 0 to 70° C.

The process (F) is preferably carried out in the presence of a diluent.

Suitable diluents are all inert polar organic solvents, such as ethers, amides, ketones, carboxylic esters, nitriles, sulphones, sulphoxides or halogenated hydrocarbons, such as methylene chloride.

Preference is given to using dimethyl sulphoxide, tetrahydrofuran, dimethylformamide, ethyl acetate, methylene chloride.

If, in a preferred embodiment, the enolate salt of the compounds (I-1-a) to (I-2-a) is prepared by adding strong deprotonating agents (such as, for example, sodium hydride or potassium tert-butoxide), the further addition of acid binders may be dispensed with.

If acid binders are used, these may be customary inorganic or organic bases, for example sodium hydride, sodium carbonate, potassium carbonate, pyridine and triethylamine.

The reaction can be carried out at atmospheric pressure or under elevated pressure and is preferably carried out at atmospheric pressure. Work-up is carried out by customary methods.

The process (G) according to the invention is characterized in that compounds of the formulae (I-1-a) to (I-2-a) are in each case reacted with phosphorus compounds of the formula (IX), if appropriate in the presence of a diluent and if appropriate in the presence of an acid binder.

In the preparation process (G), to obtain compounds of the formulae (I-1-e) to (I-2-e), from 1 to 2, preferably from 1 to 1.3, mol of the phosphorus compound of the formula (IX) are employed per mole of the compounds (I-1-a) to (I-2-a), at temperatures between −40° C. and 150° C., preferably between −10 and 110° C.

The process (G) is preferably carried out in the presence of a diluent.

Suitable diluents are all inert polar organic solvents, such as ethers, carboxylic esters, halogenated hydrocarbons, ketones, amides, nitriles, sulphones, sulphoxides, etc.

Preference is given to using acetonitrile, dimethyl sulphoxide, tetrahydrofuran, dimethyl-formamide, methylene chloride.

Suitable acid binders, which are added, if appropriate, are customary inorganic or organic bases, such as hydroxides, carbonates or amines. Sodium hydroxide, sodium carbonate, potassium carbonate, pyridine and triethylamine may be mentioned by way of example.

The reaction can be carried out at atmospheric pressure or under elevated pressure and is preferably carried out at atmospheric pressure. Work-up is carried out by customary methods of organic chemistry. The end products are preferably purified by crystallization, chromatographic purification or "incipient distillation", i.e. removal of the volatile components under reduced pressure.

The process (H) is characterized in that compounds of the formulae (I-1-a) to (I-2-a) are in each case reacted with metal hydroxides or metal alkoxides of the formula (X) or amines of the formula (XI), if appropriate in the presence of a diluent.

Suitable diluents for use in the process (H) according to the invention are, preferably, ethers, such as tetrahydrofuran, dioxane, diethyl ether, or else alcohols, such as methanol, ethanol, isopropanol, and also water. The process (H) according to the invention is generally carried out under atmospheric pressure. The reaction temperature is generally between −20° C. and 100° C., preferably between 0° C. and 50° C.

The process (I) according to the invention is characterized in that compounds of the formulae (I-1-a) to (I-2-a) are in each case reacted with (Iα) compounds of the formula (XII), if appropriate in the presence of a diluent and if appropriate in the presence of a catalyst, or (Iβ) with compounds of the formula (XIII), if appropriate in the presence of a diluent and if appropriate in the presence of an acid binder.

In the preparation process (Iα), about 1 mol of isocyanate of the formula (XII) is employed per mole of starting material of the formulae (I-1-a) to (I-2-a) at from 0 to 100° C., preferably from 20 to 50° C.

The process (Iα) is preferably carried out in the presence of a diluent.

Suitable diluents are all inert organic solvents, such as aromatic hydrocarbons, halogenated hydrocarbons, ethers, amides, nitriles, sulphones or sulphoxides.

If appropriate, catalysts may be added to promote the reaction. Suitable for use as catalysts are, very advantageously, organotin compounds, such as, for example, dibutyltin dilaurate.

The reaction is preferably carried out at atmospheric pressure.

In the preparation process (Iβ), about 1 mol of carbamoyl chloride of the formula (XIII) is employed per mole of starting material of the formulae (I-1-a) to (I-2-a), at from 0 to 150° C., preferably from 20 to 70° C.

Suitable diluents which are added, if appropriate, are all inert polar organic solvents, such as ethers, carboxylic esters, nitriles, ketones, amides, sulphones, sulphoxides or halogenated hydrocarbons.

Preference is given to using dimethyl sulphoxide, tetrahydrofuran, dimethylformamide or methylene chloride.

If, in a preferred embodiment, the enolate salt of the compound (I-1-a) to (I-2-a) is prepared by adding strong deprotonating agents (such as, for example, sodium hydride or potassium tert-butoxide), the further addition of acid binders may be dispensed with.

If acid binders are used, these may be customary inorganic or organic bases, for example sodium hydroxide, sodium carbonate, potassium carbonate, triethylamine or pyridine.

The reaction can be carried out at atmospheric pressure or under elevated pressure and is preferably carried out at atmospheric pressure. Work-up is carried out by customary methods.

In the preparation process (J), up to 50 mol of diol of the formula (XVI), preferably from 1 to 10 mol, are employed per mole of the starting materials (I-1-a) to (I-1-g) or (I-2-a) to (I-2-g), at from −50 to 250° C., preferably from 0 to 150° C.

Suitable diluents are all inert organic solvents, such as aromatic hydrocarbons, halogenated hydrocarbons, ethers, esters, amides, nitriles, sulphones or sulphoxides.

If appropriate, catalysts may be added to promote the reaction. Suitable for use as catalysts are, very advantageously, acids, such as, for example, p-toluenesulphonic acid, concentrated sulphuric acid, and also Lewis acids, such as, for example, boron trifluoride etherate.

The reaction is preferably carried out at atmospheric pressure.

The dehydrating conditions can be achieved both by azeotropic removal of the water and by adding suitable dehydrating agents, such as, for example, orthoformates, dimethoxypropane and also molecular sieves.

Work-up is carried out by customary methods.

The active compounds/active compound combinations, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as plant protection agents. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnostema consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Stemechus* spp., *Symphyletes* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus*.

From the order of the *Dermaptera*, for example, *Forficula auricularia*.

From the order of the Diplopoda, for example, *Blaniulus guttulatus*.

From the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa*.

From the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale, Ancylostoma ceylanicum, Acylostoma braziliensis, Ancylostoma* spp., *Ascaris lubricoides, Ascaris* spp., *Bru-*

*gia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., Loa Loa, *Nematodirus* spp., *Oesophagostomum* spp., *Opisthorchis* spp., *Onchocerca volvulus, Ostertagia* spp., *Paragonimus* spp., *Schistosomen* spp, *Strongyloides fuellebomi, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti*.

It is furthermore possible to control Protozoa, such as Eimeria.

From the order of the Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii*.

From the order of the Hymenoptera, for example, *Diprion* spp., *Hoplocampa* spp., *Lasius* spp., *Monomorium pharaonis, Vespa* spp.

From the order of the Isopoda, for example, *Armadillidium vulgare, Oniscus asellus, Porcellio scaber*.

From the order of the *Isoptera*, for example, *Reticulitermes* spp.

From the order of the *Lepidoptera*, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Chematobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.

From the order of the Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria*.

From the order of the Siphonaptera, for example, *Ceratophyllus* spp., *Xenopsylla cheopis*.

From the order of the Symphyla, for example, *Scutigerella immaculata*.

From the order of the Thysanoptera, for example, *Baliothrips biformis, Enneothrips flavens, Frankliniella* spp., *Heliothrips* spp., *Hercinothrips femoralis, Rhipiphorothrips cruentatus, Scirtothrips* spp., *Taeniothrips cardamoni, Thrips* spp.

From the order of the Thysanura, for example, *Lepisma saccharina*.

The phytoparasitic nematodes include, for example, *Aphelenchoides* spp., *Bursaphelenchus* spp., *Ditylenchus dipsaci, Globodera* spp., *Heterodera* spp., *Longidorus* spp., *Meloidogyne* spp., *Pratylenchus* spp., *Radopholus similis, Trichodorus* spp., *Tylenchulus semipenetrans, Xiphinema* spp.

If appropriate, the compounds/active compound combinations according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (Mycoplasma-like organisms) and RLO (*Rickettsia*-like organisms). If appropriate, they can also be employed as intermediates or precursors for the synthesis of other active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds/active compound combinations is carried out directly or by allowing the compounds to act on the surroundings, habitat or storage space by the customary treatment methods, for example by immersion, spraying, evaporation, fogging, scattering, painting on, injection and, in the case of propagation material, in particular in the case of seeds, also by applying one or more coats.

The active compounds/active compound combinations can be converted to the customary formulations, such as solutions, emulsions, wettable powders, water- and oil-based suspensions, powders, dusts, pastes, soluble powders, soluble granules, granules for broadcasting, suspension-emulsion concentrates, natural materials impregnated with active compound, synthetic materials impregnated with active compound, fertilizers and microencapsulations in polymeric substances.

These formulations are produced in a known manner, for example by mixing the active compounds/active compound combinations with extenders, that is liquid solvents and/or solid carriers, optionally with the use of surfactants, that is emulsifiers and/or dispersants and/or foam-formers.

If the extender used is water, it is also possible to use organic solvents, for example, as auxiliary solvents. Suitable liquid solvents are essentially aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, as well as their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are:

for example ammonium salts and ground natural minerals such as kaolins, clays, talc, chalk, quartz, attapulgite, montmorillonite or diatomaceous earth, and ground synthetic minerals such as highly disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignosulphite waste liquors and methylcellulose.

Tackifiers such as carboxymethylcellulose and natural and synthetic polymers in the form of powders, granules or lattices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

The formulations generally comprise between 0.1 and 95% by weight of active compound, preferably between 0.5 and 90%.

The active compound/active compound combinations according to the invention can be present in their commercially available formulations, as well as in the use forms prepared from these formulations, in a mixture with other active compounds such as insecticides, attractants, sterilizers, bactericides, acaricides, nematicides, fungicides, growth-regulating substances, herbicides, safeners, fertilizers or semiochemicals.

Compounds which are suitable as mixing partners are, for example, the following:

Fungicides:

2-phenylphenol; 8-hydroxyquinoline sulphate; acibenzolar-S-methyl; aldimorph; amidoflumet; ampropylfos; ampropylfos-potassium; andoprim; anilazine; azaconazole; azoxystrobin; benalaxyl; benodanil; benomyl; benthiavalicarb-isopropyl; benzamacril; benzamacril-isobutyl; bilanafos; binapacryl; biphenyl; bitertanol; blasticidin-S; bromuconazole; bupirimate; buthiobate; butylamine; calcium polysulphide; capsimycin; captafol; captan; carbendazim; carboxin; carpropamid; carvone; chinomethionat; chlobenthiazone; chlorfenazole; chloroneb; chlorothalonil; chlozolinate; clozylacon; cyazofamid; cyflufenamid; cymoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulfamide; flutolanil; flutriafol; folpet; fosetyl-Al; fosetyl-sodium; fuberidazole; furalaxyl; furametpyr; furcarbanil; furmecyclox; guazatine; hexachlorobenzene; hexaconazole; hymexazole; imazalil; imibenconazole; iminoctadine triacetate; iminoctadine tris(albesilate); iodocarb; ipconazole; iprobenfos; iprodione; iprovalicarb; irumamycin; isoprothiolane; isovaledione; kasugamycin; kresoxim-methyl; mancozeb; maneb; meferimzone; mepanipyrim; mepronil; metalaxyl; metalaxyl-M; metconazole; methasulfocarb; methfuroxam; metiram; metominostrobin; metsulfovax; mildiomycin; myclobutanil; myclozolin; natamycin; nicobifen; nitrothal-isopropyl; noviflumuron; nuarimol; ofurace; orysastrobin; oxadixyl; oxolinic acid; oxpoconazole; oxycarboxin; oxyfenthiin; paclobutrazole; pefurazoate; penconazole; pencycuron; phosdiphen; phthalide; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolenitrine; quinconazole; quinoxyfen; quintozene; simeconazole; spiroxamine; sulphur; tebuconazole; tecloftalam; tecnazene; tetcyclacis; tetraconazole; thiabendazole; thicyofen; thifluzamide; thiophanate-methyl; thiram; tioxymid; tolclofos-methyl; tolylfluanid; triadimefon; triadimenol; triazbutil; triazoxide; tricyclamide; tricyclazole; tridemorph; trifloxystrobin; triflumizole; triforine; triticonazole; uniconazole; validamycin A; vinclozolin; zineb; ziram; zoxamide; (2S)—N-[2-[4-[[3-(4-chlorophenyl)-2-propynyl]oxy]-3-methoxyphenyl]ethyl]-3-methyl-2-[(methylsulphonyl)amino]butanamide; 1-(1-naphthalenyl)-1H-pyrrole-2,5-dione; 2,3,5,6-tetrachloro-4-(methylsulphonyl)pyridine; 2-amino-4-methyl-N-phenyl-5-thiazolecarboxamide; 2-chloro-N-(2,3-dihydro-1,1,3-trimethyl-1H-inden-4-yl)-3-pyridinecarboxamide; 3,4,5-trichloro-2,6-pyridinedicarbonitrile; actinovate; cis-1-(4-chlorophenyl)-2-(1H-1,2,4-triazol-1-yl)cycloheptanol; methyl 1-(2,3-dihydro-2,2-dimethyl-1H-inden-1-yl)-1H-imidazole-5-carboxylate; monopotassium carbonate; N-(6-methoxy-3-pyridinyl)cyclopropanecarboxamide; N-butyl-8-(1,1-dimethylethyl)-1-oxaspiro[4.5]decane-3-amine; sodium tetrathiocarbonate; and copper salts and preparations, such as Bordeaux mixture; copper hydroxide; copper naphthenate; copper oxychloride; copper sulphate; cufraneb; cuprous oxide; mancopper; oxine-copper.

Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:

1. Acetylcholine Esterase (AChE) Inhibitors 1.1 Carbamates,
for example alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb, triazamate 1.2 Organophosphates,
for example acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methylsulphon, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methi-dathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion 2. Sodium Channel Modulators/Voltage-Gated Sodium Channel Blockers 2.1 Pyrethroids,
for example acrinathrin, allethrin (d-cis-trans, d-trans), beta-cyfluthrin, bifenthrin, bioallethrin, bioallethrin-S cyclopentyl isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, deltamethrin, empenthrin (1R isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R trans-isomer), prallethrin, profluthrin, protrifenbute, pyresmethrin, resmethrin, RU 15525, silafluofen, tau-fluvalinate, tefluthrin, terallethrin, tetramethrin (1R isomer), tralomethrin, transfluthrin, ZXI 8901, pyrethrins (pyrethrum) DDT 2.2 Oxadiazines,
for example indoxacarb 2.3 Semicarbazones,
for example metaflumizone (BAS 3201)

Acetylcholine Receptor Agonists-Antagonists 3.1 Chloronicotinyls,
for example acetamiprid, clothianidin, dinotefuran, imidacloprid, nitenpyram, nithiazine, thiacloprid, thiamethoxam 3.2 Nicotine, Bensultap, Cartap Acetylcholine Receptor Modulators 4.1 Spinosyns,
for example spinosad
GABA-Gated Chloride Channel Antagonists 5.1 Cyclodiene Organochlorines,
for example camphechlor, chlordane, endosulfan, gamma-HCH, HCH, heptachlor, lindane, methoxychlor 5.2 Fiproles,
for example acetoprole, ethiprole, fipronil, pyrafluprole, pyripole, vaniliprole Chloride Channel Activators 6.1 Mectins,
for example avermectin, emamectin, emamectin-benzoate, ivermectin, milbemycin Juvenile Hormone Mimetics,
for example diofenolan, epofenonane, fenoxycarb, hydroprene, kinoprene, methoprene, pyriproxifen, triprene Ecdyson Agonists/Disruptors 8.1 Diacylhydrazines,
for example chromafenozide, halofenozide, methoxyfenozide, tebufenozide Chitin Biosynthesis Inhibitors 9.1 Benzoylureas,
for example bistrifluron, chlofluazuron, diflubenzuron, fluazuron, flucycloxuron, flufenoxuron, hexaflumuron, lufenuron, novaluron, noviflumuron, penfluoron, teflubenzuron, triflumuron 9.2 Buprofezin 9.3 Cyromazine Oxidative Phosphorylation Inhibitors, ATP Disruptors 10.1 Diafenthiuron 10.2 Organotins,
for example azocyclotin, cyhexatin, fenbutatin-oxide Oxidative Phosphorylation Decouplers Acting by Interrupting the H-Proton Gradient 11.1 Pyrroles,
for example chlorfenapyr 11.2 Dinitrophenols,
for example binapacyrl, dinobuton, dinocap, DNOC Electron Transport Inhibitors 12.1 Site-I Electron Transport Inhibitors
from the group of the
METIs,
for example fenazaquin, fenpyroximate, pyrimidifen, pyridaben, tebufenpyrad, tolfenpyrad and also
Hydramethylnon
Dicofol 12.2 Site-II Electron Transport Inhibitors
Rotenone 12.3 Site-III Electron Transport Inhibitors
Acequinocyl, fluacrypyrim Microbial Disruptors of the Insect Gut Membrane
*Bacillus thuringiensis* strains Fat Biosynthesis Inhibitors 14.1 Tetronic Acids,
for example spirodiclofen, spiromesifen 14.2 Tetramic Acids,
for example spirotetramat Carboxamides,
for example flonicamid Octopaminergic Agonists,
for example amitraz Inhibitors of Magnesium-Stimulated ATPase,
propargite Ryanodine Receptor Effectors 18.1 Benzoic Acid Dicarboxamides,
for example flubendiamide 18.2 Anthranilamides, for Example DPX E2 Y45

Nereistoxin Analogues,
for example thiocyclam hydrogen oxalate, thiosultap-sodium Biologicals, Hormones or Pheromones,
azadirachtin, *Bacillus* spec., *Beauveria* spec., codlemone, *Metarrhizium* spec., *Paecilomyces* spec., thuringiensin, *Verticillium* spec.

Active Compounds with Unknown or Unspecific Mechanisms of Action 21.1 Fumigants,
for example aluminium phosphide, methyl bromide, sulphuryl fluoride 21.2 Antifeedants,
for example cryolite, flonicamid, pymetrozine 21.3 Mite Growth Inhibitors,
for example clofentezine, etoxazole, hexythiazox 21.4 Amidoflumet, benclothiaz, benzoximate, bifenazate, bromopropylate, buprofezin, chino-methionat, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyridalyl, sulfluramid, tetradifon, tetrasul, triarathene, verbutin A mixture with other known active compounds, such as herbicides, fertilizers, growth regulators, safeners, semiochemicals, or else with agents which improve plant properties is also possible.

When used as insecticides in their commercially available formulations and in the use forms prepared with these formulations, the active compounds/active compound combinations according to the invention can furthermore be present in the form of a mixture with synergists. Synergists are compounds by which the activity of the active compounds is increased without it being necessary for the synergist added to be active itself.

When used as insecticides in their commercially available formulations and in the use forms prepared with these formulations, the active compounds/active compound combinations according to the invention can furthermore be present in the form of a mixture with inhibitors which reduce the degradation of the active compound after application in the habitat of the plant, on the surface of parts of plants or in plant tissues.

The active compound content of the use forms prepared from the commercially available formulations can vary within broad ranges. The active compound concentration of the use forms can be from 0.00000001 up to 95% by weight of active compound and is preferably between 0.00001 and 1% by weight.

Application is in a customary manner adapted to suit the use forms.

As already mentioned above, it is possible to treat all plants and their parts in accordance with the invention. In a preferred embodiment, wild plant species or plant varieties and plant cultivars which have been obtained by traditional biological breeding methods, such as hybridization or protoplast fusion, and the parts of these varieties and cultivars are treated. In a further preferred embodiment, transgenic plants and plant cultivars which have been obtained by recombinant methods, if appropriate in combination with conventional methods (genetically modified organisms), and their parts are treated. The term "parts" or "parts of plants" or "plant parts" has been explained above.

Plants which are treated particularly preferably in accordance with the invention are those of the plant cultivars which are in each case commercially available or in use. Plant cultivars are understood as meaning plants with new traits which have been bred either by conventional breeding, by mutagenesis or by recombinant DNA techniques. They may take the form of cultivars, biotypes and genotypes.

Depending on the plant species or plant cultivars, their location and growth conditions (soils, climate, vegetation period, nutrition), the treatment according to the invention may also result in superadditive ("synergistic") effects. Thus, for example, reduced application rates and/or a widened activity spectrum and/or an increase in the activity of the substances and compositions which can be used in accordance with the invention, better plant growth, increased tolerance to high or low temperatures, increased tolerance to drought or to salinity in the water or soil, increased flowering performance, facilitated harvesting, accelerated maturation, higher yields, higher quality and/or better nutritional value of the harvested products, better storage characteristics and/or processability of the harvested products are possible which exceed the effects which were actually to be expected.

The preferred transgenic plants or plant cultivars (those obtained by recombinant methods) to be treated in accordance with the invention include all those plants which, owing to the process of recombinant modification, were given genetic material which confers particular, advantageous, valuable traits to these plants. Examples of such properties are better plant growth, increased tolerance to high or low temperatures, increased tolerance to drought or to salinity in the water or soil, increased flowering performance, facilitated harvesting, accelerated maturation, higher yields, higher quality and/or higher nutritional value of the harvested products, better storage characteristics and/or better processability of the harvested products. Further examples of such traits, examples which must be mentioned especially, are better defense of the plants against animal and microbial pests, such as against insects, mites, phytopathogenic fungi, bacteria and/or viruses and an increased tolerance of the plants to certain herbicidal active compounds. Examples of transgenic plants which may be mentioned are the important crop plants, such as cereals (wheat, rice), maize, soybeans, potato, sugar beet, tomatoes, peas and other vegetable varieties, cotton, tobacco, oilseed rape and fruit plants (with the fruits apples, pears, citrus fruits and grapes), with particular emphasis on maize, soybeans, potatoes, cotton, tobacco, and oilseed rape. Traits which are especially emphasized are the increased defense of the plants against insects, arachnids, nematodes and slugs and snails, owing to toxins being formed in the plants, in particular toxins which are generated in the plants by the genetic material of *Bacillus thuringiensis* (for example by the genes CryIA(a), CryIA(b), CryIA(c), CryIIA, CryIIIA, CryIIIB2, Cry9c Cry2Ab, Cry3Bb and CryIF and their combinations; hereinbelow "Bt plants"). Other traits which are particularly emphasized are the increased defense of plants against fungi, bacteria and viruses by the systemic acquired resistance (SAR), systemins, phytoalexins, elicitors and resistance genes and correspondingly expressed proteins and toxins. Other traits which are especially emphasized are the increased tolerance of the plants to certain herbicidal active compounds, for example imidazolinones, sulphonylureas, glyphosate or phosphinotricin (for example "PAT" gene). The genes which confer the desired traits in each case may also be present in the transgenic plants in combination with one another. Examples of "Bt plants" which may be mentioned are maize cultivars, cotton cultivars, soybean cultivars and potato cultivars which are commercially available under the trade names YELD GARD® (for example maize, cotton, soybeans), KnockOut® (for example maize), StarLink® (for example maize), Bollgard® (cotton), Nucotn® (cotton) and NewLeaf® (potato). Examples of herbicide-tolerant plants which may be mentioned are maize cultivars, cotton cultivars and soybean cultivars which are commercially available under the trade names Roundup Ready® (tolerance to glyphosate, for example maize, cotton, soybean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned also include the varieties commercially available under the name Clearfield® (for example maize). Naturally, these statements also apply to plant cultivars having these genetic traits or genetic traits still to be developed, which plant cultivars will be developed and/or marketed in the future.

The plants listed can be treated particularly advantageously according to the invention with the compounds of the general formula I or the active compound mixtures according to the invention. The preferred ranges stated above for the active compounds and mixtures also apply to the treatment of these plants. Particular emphasis may be given to the treatment of plants with the compounds or mixtures specifically mentioned in the present text.

The active compounds/active compound combinations according to the invention are not only active against plant, hygiene and stored-product pests, but also, in the veterinary medicine sector, against animal parasites (ectoparasites and endoparasites), such as ixodid ticks, argasid ticks, scab mites, trombi-culid mites, flies (stinging and sucking), parasitic fly larvae, lice, hair lice, bird lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the sub-orders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order of the Diptera and the sub-orders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example, *Pulex* spp., *Ctenocephalides* spp., *Xenopyslla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example, *Blatta orientalis, Periplaneta americana, Blattela germanica* and *Supella* spp.

From the sub-class of the Acaria (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The active compounds/active compound combinations of the formula (I) according to the invention are also suitable for controlling arthropods which attack agricultural livestock, such as, for example, cattle, sheep, goats, horses, pigs, donkeys, camels, buffaloes, rabbits, chickens, turkeys, ducks, geese, honeybees, other domestic animals, such as, for example, dogs, cats, cage birds, aquarium fish, and so-called experimental animals, such as, for example, hamsters, guinea-pigs, rats and mice. By combating these arthropods, it is intended to reduce deaths and decreased performances (in meat, milk, wool, hides, eggs, honey and the like), so that more economical and simpler animal keeping is made possible by using the active compounds according to the invention.

In the veterinary sector, the active compounds/active compound combinations according to the invention are used in a known manner by enteral administration, for example in the form of tablets, capsules, drinks, drenches, granules, pastes, boli, the feed-through method, suppositories, by parenteral administration, such as, for example, by means of injections (intramuscular, subcutaneous, intravenous, intraperitoneal and the like), implants, by nasal application, by dermal administration, for example in the form of dipping or bathing, spraying, pouring-on and spotting-on, washing, dusting, and with the aid of shaped articles which comprise active compound, such as collars, ear tags, tail marks, limb bands, halters, marking devices and the like.

When administered to livestock, poultry, domestic animals and the like, the active compounds of the formula (I) can be used as formulations (for example powders, emulsions, flowables) which comprise the active compounds in an amount of 1 to 80% by weight, either directly or after dilution by a factor of 100 to 10 000, or they may be used in the form of a chemical bath.

Furthermore, it has been found that the compounds/active compound combinations according to the invention have a potent insecticidal action against insects which destroy industrial materials.

The following insects may be mentioned by way of example and as being preferred, but without any limitation:

Beetles, such as *Hylotrupes bajulus, Chlorophorus pilosis, Anobium punctatum, Xestobium rufovillosum, Ptilinus pecticomis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec., *Dinoderus minutus.*

Dermapterans, such as *Sirex juvencus, Urocerus gigas, Urocerus gigas taignus, Urocerus augur.*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristletails, such as *Lepisma saccharina.*

Industrial materials are to be understood as meaning, in the present context, non-live materials, such as, preferably, synthetic materials, glues, sizes, paper and board, leather, wood and timber products, and paint.

The materials to be very particularly preferably protected against attack by insects are wood and timber products.

Wood and timber products which can be protected by the composition according to the invention or mixtures comprising such a composition are to be understood as meaning, for example:

construction timber, wooden beams, railway sleepers, bridge components, jetties, wooden vehicles, boxes, pallets, containers, telephone poles, wood cladding, windows and doors made of wood, plywood, particle board, joiner's articles, or wood products which, quite generally, are used in the construction of houses or in joinery.

The active compounds can be used as such, in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if appropriate desiccants and UV stabilizers and, if appropriate, colorants and pigments and other processing auxiliaries.

The insecticidal compositions or concentrates used for the protection of wood and wooden materials comprise the active compound according to the invention in a concentration of 0.0001 to 95% by weight, in particular 0.001 to 60% by weight.

The amount of the compositions or concentrates employed depends on the species and the occurrence of the insects and on the medium. The optimum rate of application can be determined upon use in each case by a test series. However, in general, it suffices to employ 0.0001 to 20% by weight, preferably 0.001 to 10% by weight, of the active compound, based on the material to be protected.

The solvent and/or diluent used is an organochemical solvent or solvent mixture and/or an oily or oil-type organochemical solvent or solvent mixture of low volatility and/or a polar organochemical solvent or solvent mixture and/or water and, if appropriate, an emulsifier and/or wetting agent.

Organochemical solvents which are preferably employed are oily or oil-type solvents having an evaporation number of above 35 and a flashpoint of above 30° C., preferably above 45° C. Substances which are used as such oily and oil-type solvents which have low volatility and are insoluble in water are suitable mineral oils or their aromatic fractions, or mineral-oil-containing solvent mixtures, preferably white spirit, petroleum and/or alkylbenzene.

Substances which are advantageously used are mineral oils with a boiling range of 170 to 220° C., white spirit with a boiling range of 170 to 220° C., spindle oil with a boiling range of 250 to 350° C., petroleum or aromatics of boiling range 160 to 280° C., essence of terpentine and the like.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene, are used.

The organic oily or oil-type solvents of low volatility having an evaporation number of above 35 and a flashpoint of above 30° C., preferably above 45° C., can be partially replaced by organochemical solvents of high or medium volatility, with the proviso that the solvent mixture also has an evaporation number of above 35 and a flashpoint of above 30° C., preferably above 45° C., and that the insecticide/fungicide mixture is soluble or emulsifiable in this solvent mixture.

In a preferred embodiment, part of the organochemical solvent or solvent mixture or an aliphatic polar organochemical solvent or solvent mixture is replaced. Substances which are preferably used are aliphatic organochemical solvents having hydroxyl and/or ester and/or ether groups, such as, for example, glycol ethers, esters and the like.

The organochemical binders used within the scope of the present invention are the synthetic resins and/or binding drying oils which are known per se and can be diluted with water and/or are soluble or dispersible or emulsifiable in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin, such as indene/cumarone resin, silicone resin, drying vegetable and/or drying oils and/or physically drying binders based on a natural and/or synthetic resin.

The synthetic resin used as the binder can be employed in the form of an emulsion, dispersion or solution. Up to 10% by weight of bitumen or bituminous substances can also be used as binders. In addition, colorants, pigments, water repellents, odour-masking substances and inhibitors or anticorrosives known per se and the like can also be employed.

The composition or the concentrate preferably comprises, in accordance with the invention, at least one alkyd resin or modified alkyd resin and/or a drying vegetable oil as the organochemical binder. Preferably used according to the invention are alkyd resins with an oil content of over 45% by weight, preferably 50 to 68% by weight.

All or some of the abovementioned binder can be replaced by a fixative (mixture) or a plasticizer (mixture). These additives are intended to prevent volatilization of the active compounds and crystallization or precipitation. They preferably replace 0.01 to 30% of the binder (based on 100% of binder employed).

The plasticizers are from the chemical classes of the phthalic esters, such as dibutyl phthalate, dioctyl phthalate or benzyl butyl phthalate, the phosphoric esters, such as tributyl phosphate, the adipic esters, such as di(2-ethylhexyl)adipate, the stearates, such as butyl stearate or amyl stearate, the oleates, such as butyl oleate, the glycerol ethers or relatively high-molecular-weight glycol ethers, glycerol esters and p-toluenesulphonic esters.

Fixatives are chemically based on polyvinyl alkyl ethers, such as, for example, polyvinyl methyl ether, or ketones, such as benzophenone or ethylenebenzophenone.

Particularly suitable as a solvent or diluent is also water, if appropriate as a mixture with one or more of the abovementioned organochemical solvents or diluents, emulsifiers and dispersants.

Particularly effective protection of wood is achieved by large-scale industrial impregnation processes, for example vacuum, double-vacuum or pressure processes.

If appropriate, the ready-to-use compositions can additionally comprise other insecticides and, if appropriate, additionally one or more fungicides.

Suitable additional components which may be admixed are, preferably, the insecticides and fungicides mentioned in WO 94/29 268. The compounds mentioned in that document are expressly part of the present application.

Very particularly preferred components which may be admixed are insecticides, such as chlorpyriphos, phoxim, silafluofin, alphamethrin, cyfluthrin, cypermethrin, deltamethrin, permethrin, imidacloprid, NI-25, flufenoxuron, hexaflumuron, transfluthrin, thiacloprid, methoxyphenoxid, triflumuron, chlothianidin, spinosad, tefluthrin, and fungicides, such as epoxyconazole, hexaconazole, azaconazole, propiconazole, tebuconazole, cyproconazole, metconazole, imazalil, dichlorfluanid, tolylfluanid, 3-iodo-2-propynylbutyl carbamate, N-octyl-isothiazolin-3-one and 4,5-dichloro-N-octylisothiazolin-3-one.

The compounds according to the invention can at the same time be employed for protecting objects which come into contact with saltwater or brackish water, in particular hulls, screens, nets, buildings, moorings and signalling systems, against fouling.

Fouling by sessile Oligochaeta, such as Serpulidae, and by shells and species from the Ledamorpha group (goose barnacles), such as various Lepas and Scalpellum species, or by species from the Balanomorpha group (acorn barnacles), such as Balanus or Pollicipes species, increases the frictional drag of ships and, as a consequence, leads to a marked increase in operation costs owing to higher energy consumption and additionally frequent residence in the dry dock.

Apart from fouling by algae, for example *Ectocarpus* sp. and *Ceramium* sp., fouling by sessile Entomostraka groups, which come under the generic term Cirripedia (cirriped crustaceans), is of particular importance.

Surprisingly, it has now been found that the compounds according to the invention, alone or in combination with other active compounds, have an outstanding antifouling action.

Using the compounds according to the invention, alone or in combination with other active compounds, allows the use of heavy metals such as, for example, in bis(trialkyltin)sulphides, tri-n-butyltin laurate, tri-n-butyltin chloride, copper (I) oxide, triethyltin chloride, tri-n-butyl-(2-phenyl-4-chlorophenoxy)tin, tributyltin oxide, molybdenum disulphide, antimony oxide, polymeric butyl titanate, phenyl(bispyridine)bismuth chloride, tri-n-butyltin fluoride, manganese ethylenebisthio-carbamate, zinc dimethyldithiocarbamate, zinc ethylenebisthiocarbamate, zinc salts and copper salts of 2-pyridinethiol 1-oxide, bisdimethyldithiocarbamoylzinc ethylenebisthiocarbamate, zinc oxide, copper(I) ethylenebisdithiocarbamate, copper thiocyanate, copper naphthenate and tri-butyltin halides to be dispensed with, or the concentration of these compounds to be substantially reduced.

If appropriate, the ready-to-use antifouling paints can additionally comprise other active compounds, preferably algicides, fungicides, herbicides, molluscicides, or other antifouling active compounds.

Preferably suitable components in combination with the antifouling compositions according to the invention are:

algicides such as 2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;

fungicides such as benzo[b]thiophenecarboxylic acid cyclohexylamide S,S-dioxide, dichlofluanid, fluorfolpet, 3-iodo-2-propinyl butylcarbamate, tolylfluanid and azoles such as azaconazole, cyproconazole, epoxyconazole, hexaconazole, metconazole, propiconazole and tebuconazole;

molluscicides such as fentin acetate, metaldehyde, methiocarb, niclosamid, thiodicarb and trimethacarb; Fe chelates; or conventional antifouling active compounds such as 4,5-dichloro-2-octyl-4-isothiazolin-3-one, diiodomethylparatryl sulphone, 2-(N,N-dimethyl-thiocarbamoylthio)-5-nitrothiazyl, potassium, copper, sodium and zinc salts of 2-pyridinethiol 1-oxide, pyridine-triphenylborane, tetrabutyldistannoxane, 2,3,5,6-tetrachloro-4-(methylsulphonyl)-pyridine, 2,4,5,6-tetrachloroisophthalonitrile, tetramethylthiuram disulphide and 2,4,6-trichlorophenylmaleimide.

The antifouling compositions used comprise the active compound according to the invention of the compounds according to the invention in a concentration of 0.001 to 50% by weight, in particular 0.01 to 20% by weight.

Moreover, the antifouling compositions according to the invention comprise the customary components such as, for example, those described in Ungerer, *Chem. Ind.* 1985, 37, 730-732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in saltwater. Paints may furthermore comprise materials such as rosin to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compounds are also suitable for controlling animal pests, in particular insects, arachnids and mites, which are found in enclosed spaces such as, for example, dwellings, factory halls, offices, vehicle cabins and the like. They can be employed in domestic insecticide products for controlling these pests alone or in combination with other active compounds and auxiliaries. They are active against sensitive and resistant species and against all development stages. These pests include:

From the order of the Scorpionidea, for example, *Buthus occitanus*.

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, Aviculariidae, Araneidae.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Phthirus pubis*.

From the order of the Heteroptera, for example, *Cimex hemipterus, Cimex lectularius, Rhodinus prolixus, Triatoma infestans*.

They are used in the household insecticides sector alone or in combination with other suitable active compounds such as phosphoric esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

The active compounds/active compound combinations according to the invention can also be used as defoliants, desiccants, haulm killers and, in particular, as weed killers. Weeds in the broadest sense are understood as meaning all plants which grow at locations where they are undesired. Whether the substances according to the invention act as nonselective or selective herbicides depends essentially on the application rate.

The active compounds/active compound combinations according to the invention can be used, for example, in the following plants:

Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium*.

Dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia*.

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum*.

Monocotyledonous crops of the genera: *Allium, Ananas, Asparagus, Avena, Hordeum, Oryza, Panicum, Saccharum, Secale, Sorghum, Triticale, Triticum, Zea*.

However, the use of the active compounds/active compound combinations according to the invention is in no way restricted to these genera, but extends in the same manner to other plants.

Depending on the concentration, the active compounds/active compound combinations according to the invention are suitable for the nonselective weed control on, for example, industrial terrains and railway tracks and on paths and locations with and without trees. Likewise the active compounds according to the invention can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantations and hop fields, on lawns, turf and pastureland, and for the selective control of weeds in annual crops.

The compounds of the formula (I)/active compound combinations according to the invention have strong herbicidal activity and a broad activity spectrum when used on the soil and on aerial plant parts. To a certain extent, they are also suitable for the selective control of monocotyledonous and dicotyledonous weeds in monocotyledonous and dicotyledonous crops, both pre- and post-emergence.

At certain concentrations or application rates, the active compounds/active compound combinations according to the invention can also be employed for controlling animal pests and fungal or bacterial plant diseases. If appropriate, they can also be used as intermediates or precursors for the synthesis of other active compounds.

The active compounds/active compound combinations can be converted into the customary formulations, such as solutions, emulsions, wettable powders, suspensions, powders, dusting agents, pastes, soluble powders, granules, suspoemulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If the extender used is water, it is also possible to use, for example, organic solvents as auxiliary solvents. Suitable liquid solvents are essentially: aromatics, such as xylene, toluene or alkylnaph-thalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates, suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Tackifiers such as carboxymethylcellulose and natural and synthetic polymers in the form of powders, granules or lattices, such as gum arabic, polyvinyl alcohol and polyvinyl acetate, and also natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic colorants, such as alizarin colorants, azo colorants and metal phthalo-cyanine colorants, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds/active compound combinations according to the invention, as such or in their formulations, can also be used for weed control purposes as a mixture with known herbicides and/or with substances which improve crop plant tolerance ("safeners"), ready mixes or tank mixes being possible. Mixtures with herbicide products which contain one or more known herbicides and a safener are hence also possible.

Herbicides which are suitable for the mixtures are known herbicides, for example acetochlor, acifluorfen (-sodium), aclonifen, alachlor, alloxydim (-sodium), ametryne, amicarb-azone, amidochlor, amidosulfuron, aminopyralid, anilofos, asulam, atrazine, azafenidin, azimsulfuron, beflubutamid, benazolin (-ethyl), benfuresate, bensulfuron (-methyl), bentazone, bencarbazone, benzfendizone, benzobicyclon, benzofenap, benzoylprop (-ethyl), bialaphos, bifenox, bispyribac (-sodium), bromobutide, bromofenoxim, bromoxynil, butachlor, butafenacil (-allyl), butroxydim, butylate, cafenstrole, caloxydim, carbetamide, carfentrazone (-ethyl), chlomethoxyfen, chloramben, chloridazon, chlorimuron (-ethyl), chlomitrofen, chlorsulfuron, chlortoluron, cinidon (-ethyl), cinmethylin, cinosulfuron, clefoxydim, clethodim, clodinafop (-propargyl), clomazone, clomeprop, clopyralid, clopyrasulfuron (-methyl), cloransulam (-methyl), cumyluron, cyan-azine, cybutryne, cycloate, cyclosulfamuron, cycloxydim, cyhalofop (-butyl), 2,4-D, 2,4-DB, desmedipham, diallate, dicamba, dichlorprop (-P), diclofop (-methyl), diclosulam, diethatyl (-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulfuron (-methyl), ethofumesate, ethoxyfen, ethoxysulfuron, etobenzanid, fenoxaprop (-P-ethyl), fentrazamide, flamprop (-isopropyl, -iso-propyl-L, -methyl), flazasulfuron, florasulam, fluazifop (-P-butyl), fluazolate, flucarbazone (-sodium), flufenacet, flumetsulam, flumiclorac (-pentyl), flumioxazin, flumipropyn, flumetsulam, fluometuron, fluorochloridone, fluoroglycofen (-ethyl), flupoxam, flupropacil, flurpyrsulfuron (-methyl, -sodium), flurenol (-butyl), fluridone, fluoroxypyr (-butoxypropyl, -meptyl), flurprimidol, flurtamone, fluthiacet (-methyl), fluthiamide, fomesafen, foramsulfuron, glufosinate (-ammonium), glyphosate (-isopropylammonium), halosafen, haloxyfop (-ethoxyethyl, -P-methyl), hexazinone, HOK-201, imazamethabenz (-methyl), imazamethapyr, imazamox, imazapic, imazapyr, imazaquin, imazethapyr, imazosulfuron, iodosulfuron (-methyl, -sodium), ioxynil, isopropalin, isoproturon, isouron, isoxaben, isoxachlortole, isoxaflutole, isoxapyrifop, KIH 485, lactofen, lenacil, linuron, MCPA, mecoprop, mefenacet, mesosulfuron, mesotrione, metamifop, metamitron, metazachlor, methabenzthiazuron, metobenzuron, metobromuron, (alpha-) metolachlor, metosulam, metoxuron, metribuzin, metsulfuron (-methyl), molinate, monolinuron, naproanilide, napropamide, neburon, nicosulfuron, norflurazon, orbencarb, orthosulfamuron, oryzalin, oxadiargyl, oxadiazon, oxasulfuron, oxaziclomefone, oxyfluorfen, paraquat, pelargonic acid, pendimethalin, pendralin, penoxsulam, pentoxazone, phenmedipham, picolinafen, pinoxaden, piperophos, pretilachlor, primisulfuron (-methyl), profluazol, prometryn, propachlor, propanil, propaquizafop, propisochlor, propoxycarbazone (-sodium), propyzamide, prosulfocarb, prosulfuron, pyraflufen (-ethyl), pyrasulfotole, pyrazogyl, pyrazolate, pyrazosulfuron (-ethyl), pyrazoxyfen, pyribenzoxim, pyributicarb, pyridate, pyridatol, pyriftalide, pyriminobac (-methyl), pyrimisulfan, pyrithiobac (-sodium), quinchlorac, quinmerac, quinoclamine, quizalofop (-P-ethyl, -P-tefuryl), rimsulfuron, sethoxydim, simazine, simetryn, sulcotrione, sulfentrazone, sulfometuron (-methyl), sulfosate, sulfosulfuron, tebutam, tebuthiuron, tembotrione, tepraloxydim, terbuthylazine, terbutryn, thenylchlor, thiafluamide, thiazopyr, thidiazimin, thifensulfuron (-methyl), thiobencarb, tiocarbazil, topramezone, tralkoxydim, triallate, triasulfuron, tribenuron (-methyl), triclopyr, tridiphane, trifluralin, trifloxysulfuron, triflusulfuron (-methyl), tritosulfuron and

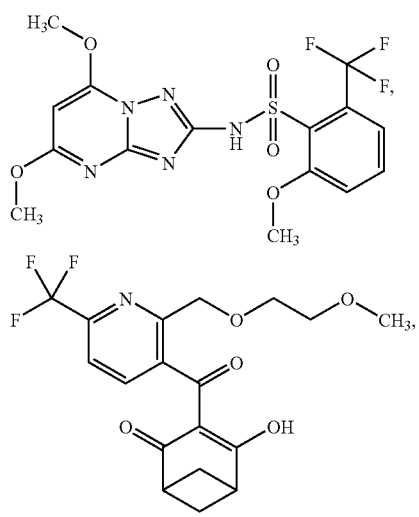

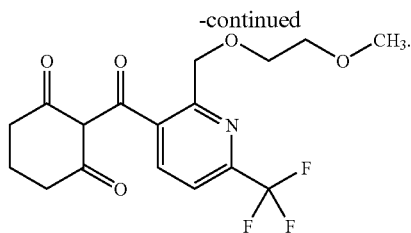

A mixture with other known active compounds, such as fungicides, insecticides, acaricides, nematicides, bird repellents, plant nutrients and soil conditioners, is also possible.

The active compounds/active compound combinations can be applied as such, in the form of their formulations or the use forms prepared therefrom by further dilution, such as ready-to-use solutions, suspensions, emulsions, powders, pastes and granules. They are applied in the customary manner, for example by pouring, spraying, atomizing, spreading.

The active compounds/active compound combinations according to the invention can be applied both before and after plant emergence. They can also be incorporated into the soil prior to planting.

The application rate of active compound can vary within a substantial range. Essentially, it depends on the nature of the desired effect. In general, the application rates are between 1 g and 10 kg of active compound per hectare of soil area, preferably between 5 g and 5 kg per ha.

The substances/active compound combinations according to the invention have potent microbicidal activity and can be employed for controlling unwanted microorganisms, such as fungi and bacteria, in crop protection and in the protection of materials.

Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

*Xanthomonas* species, such as, for example, *Xanthomonas campestris* pv. *oryzae;*

*Pseudomonas* species, such as, for example, *Pseudomonas syringae* pv. *lachrymans;*

*Erwinia* species, such as, for example, *Erwinia amylovora;*

*Pythium* species, such as, for example, *Pythium ultimum;*

*Phytophthora* species, such as, for example, *Phytophthora infestans;*

*Pseudoperonospora* species, such as, for example, *Pseudoperonospora humuli* or *Pseudoperonospora cubensis;*

*Plasmopara* species, such as, for example, *Plasmopara viticola;*

*Bremia* species, such as, for example, *Bremia lactucae;*

*Peronospora* species, such as, for example, *Peronospora pisi* or *P. brassicae;*

*Erysiphe* species, such as, for example, *Erysiphe graminis;*

*Sphaerotheca* species, such as, for example, *Sphaerotheca fuliginea*;

*Podosphaera* species, such as, for example, *Podosphaera leucotricha*;

*Venturia* species, such as, for example, *Venturia inaequalis*;

*Pyrenophora* species, such as, for example, *Pyrenophora teres* or *P. graminea* (conidia form: *Drechslera*, syn: *Helminthosporium*);

*Cochliobolus* species, such as, for example, *Cochliobolus sativus* (conidia form: *Drechslera*, syn: *Helminthosporium*);

*Uromyces* species, such as, for example, *Uromyces appendiculatus*;

*Puccinia* species, such as, for example, *Puccinia recondita*;

*Sclerotinia* species, such as, for example, *Sclerotinia sclerotiorum*;

*Tilletia* species, such as, for example, *Tilletia caries*;

*Ustilago* species, such as, for example, *Ustilago nuda* or *Ustilago avenae*;

*Pellicularia* species, such as, for example, *Pellicularia sasakii*;

*Pyricularia* species, such as, for example, *Pyricularia oryzae*;

*Fusarium* species, such as, for example, *Fusarium culmorum*;

*Botrytis* species, such as, for example, *Botrytis cinerea*;

*Septoria* species, such as, for example, *Septoria nodorum*;

*Leptosphaeria* species, such as, for example, *Leptosphaeria nodorum*;

*Cercospora* species, such as, for example, *Cercospora canescens*;

*Alternaria* species, such as, for example, *Alternaria brassicae*; and

*Pseudocercosporella* species, such as, for example, *Pseudocercosporella herpotrichoides*.

The active compounds/active compound combinations according to the invention also have very good fortifying action in plants. Accordingly, they can be used for mobilizing the defenses of the plant against attack by unwanted microorganisms.

In the present context, plant-fortifying (resistance-inducing) substances are to be understood as meaning those substances which are capable of stimulating the defense system of plants such that, when the treated plants are subsequently inoculated with unwanted microorganisms, they show substantial resistance against these microorganisms.

In the present case, unwanted microorganisms are to be understood as meaning phytopathogenic fungi, bacteria and viruses. Accordingly, the substances according to the invention can be used to protect plants for a certain period after the treatment against attack by the pathogens mentioned.

The period for which protection is provided generally extends over 1 to 10 days, preferably 1 to 7 days, after the treatment of the plants with the active compounds.

The fact that the active compounds/active compound combinations are well tolerated by plants at the concentrations required for controlling plant diseases permits the treatment of above-ground parts of plants, of propagation stock and seeds, and of the soil.

The active compounds/active compound combinations according to the invention are also suitable for increasing the yield of crops. In addition, they show reduced toxicity and are well tolerated by plants.

At certain concentrations and application rates, the active compounds/active compound combinations according to the invention can if appropriate also be used as herbicides, for influencing plant growth and for controlling animal pests. If appropriate, they can also be used as intermediates and precursors for the synthesis of further active compounds.

In the protection of materials, the compounds according to the invention can be employed for protecting industrial materials against infection with, and destruction by, unwanted microorganisms.

Industrial materials in the present context are understood as meaning non-living materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably adhesives, sizes, paper and board, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (Basidiomycetes), and against slime organisms and algae.

Microorganisms of the following genera may be mentioned as examples:

*Alternaria*, such as *Alternaria tenuis*,

*Aspergillus*, such as *Aspergillus niger*,

*Chaetomium*, such as *Chaetomium globosum*,

*Coniophora*, such as *Coniophora puetana*,

*Lentinus*, such as *Lentinus tigrinus*,

*Penicillium*, such as *Penicillium glaucum*,

*Polyporus*, such as *Polyporus versicolor*,

*Aureobasidium*, such as *Aureobasidium pullulans*,

*Sclerophoma*, such as *Sclerophoma pityophila*,

*Trichoderma*, such as *Trichoderma viride*,

*Escherichia*, such as *Escherichia coli*,

*Pseudomonas*, such as *Pseudomonas aeruginosa*, and

*Staphylococcus*, such as *Staphylococcus aureus*.

Depending on their particular physical and/or chemical properties, the active compounds/active compound combinations can be converted into the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds/active compound combinations with extenders, that is liquid solvents, liquefied gases under pressure, and/or solid carriers, optionally with the use of surfactants, that is emulsifiers and/or dispersants and/or foam-formers. If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignosulphite waste liquors and methylcellulose.

Tackifiers such as carboxymethylcellulose and natural and synthetic polymers in the form of powders, granules or lattices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

The formulations generally comprise between 0.1 and 95% by weight of active compound, preferably between 0.5 and 90%.

The active compounds according to the invention can be used as such or in their formulations, also in a mixture with known fungicides, bactericides, acaricides, nematicides or insecticides, to broaden, for example, the activity spectrum or to prevent development of resistance. In many cases, synergistic effects are obtained, i.e. the activity of the mixture is greater than the activity of the individual components.

Fungicides:

2-phenylphenol; 8-hydroxyquinoline sulphate; acibenzolar-S-methyl; aldimorph; amidoflumet; ampropylfos; ampropylfos-potassium; andoprim; anilazine; azaconazole; azoxystrobin; benalaxyl; benodanil; benomyl; benthiavalicarb-isopropyl; benzamacril; benzamacril-isobutyl; bilanafos; binapacryl; biphenyl; bitertanol; blasticidin-S; bromuconazole; bupirimate; buthiobate; butylamine; calcium polysulphide; capsimycin; captafol; captan; carbendazim; carboxin; carpropamid; carvone; quinomethionate; chlobenthiazone; chlorfenazole; chloroneb; chlorothalonil; chlozolinate; clozylacon; cyazofamid; cyflufenamid; cymoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulfamide; flutolanil; flutriafol; folpet; fosetyl-Al; fosetyl-sodium; fuberidazole; furalaxyl; furametpyr; furcarbanil; furmecyclox; guazatine; hexachlorobenzene; hexaconazole; hymexazol; imazalil; imibenconazole; iminoctadine triacetate; iminoctadine tris(albesilate); iodocarb; ipconazole; iprobenfos; iprodione; iprovalicarb; irumamycin; isoprothiolane; isovaledione; kasugamycin; kresoxim-methyl; mancozeb; maneb; meferimzone; mepanipyrim; mepronil; metalaxyl; metalaxyl-M; metconazole; methasulfocarb; methfuroxam; metiram; metominostrobin; metsulfovax; mildiomycin; myclobutanil; myclozolin; natamycin; nicobifen; nitrothal-isopropyl; noviflumuron; nuarimol; ofurace; orysastrobin; oxadixyl; oxolinic acid; oxpoconazole; oxycarboxin; oxyfenthiin; paclobutrazol; pefurazoate; penconazole; pencycuron; phosdiphen; phthalide; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolnitrin; quinconazole; quinoxyfen; quintozene; simeconazole; spiroxamine; sulphur; tebuconazole; tecloftalam; tecnazene; tetcyclacis; tetraconazole; thiabendazole; thicyofen; thifluzamide; thiophanate-methyl; thiram; tioxymid; tolclofos-methyl; tolylfluanid; triadimefon; triadimenol; triazbutil; triazoxide; tricyclamide; tricyclazole; tridemorph; trifloxystrobin; triflumizole; triforine; tritiiconazole; uniconazole; validamycin A; vinclozolin; zineb; ziram; zoxamide; (2S)—N-[2-[4-[[3-(4-chlorophenyl)-2-propynyl]oxy]-3-methoxyphenyl]ethyl]-3-methyl-2-[(methylsulphonyl)amino]butanamide; 1-(1-naphthalenyl)-1H-pyrrole-2,5-dione; 2,3,5,6-tetrachloro-4-(methylsulphonyl)pyridine; 2-amino-4-methyl-N-phenyl-5-thiazolecarboxamide; 2-chloro-N-(2,3-dihydro-1,1,3-trimethyl-1H-inden-4-yl)-3-pyridinecarboxamide; 3,4,5-trichloro-2,6-pyridinedicarbonitrile; Actinovate; cis-1-(4-chlorophenyl)-2-(1H-1,2,4-triazol-1-yl)-cycloheptanol; methyl 1-(2,3-dihydro-2,2-dimethyl-1H-inden-1-yl)-1H-imidazole-5-carboxylate; monopotassium carbonate; N-(6-methoxy-3-pyridinyl)cyclopropanecarboxamide; N-butyl-8-(1,1-dimethylethyl)-1-oxaspiro[4.5]decan-3-amine; sodium tetrathiocarbonate;

and copper salts and preparations such as Bordeaux mixture; copper hydroxide; copper naphthenate; copper oxychloride; copper sulphate; cufraneb; cuprous oxide; mancopper; oxine-copper.

Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:

abamectin, ABG-9008, acephate, acequinocyl, acetamiprid, acetoprole, acrinathrin, AKD-1022, AKD-3059, AKD-3088, alanycarb, aldicarb, aldoxycarb, allethrin 1R-isomers, alpha-cypermethrin (alphamethrin), amidoflumet, aminocarb, amitraz, avermectin, AZ-60541, azadirachtin, azamethiphos, azinphos-methyl, azinphos-ethyl, azocyclotin,

*Bacillus popilliae, Bacillus sphaericus, Bacillus subtilis, Bacillus thuringiensis, Bacillus thuringiensis* strain EG-2348, *Bacillus thuringiensis* strain GC-91, *Bacillus thuringiensis* strain NCTC-11821, baculoviruses, *Beauveria bassiana, Beauveria tenella*, bendiocarb, benfuracarb, bensultap, benzoximate, beta-cyfluthrin, beta-cypermethrin, bifenazate, bifenthrin, binapacryl, bioallethrin, bioallethrin S-cyclopentyl isomer, bioethanomethrin, biopermethrin, bioresmethrin, bistrifluoron, BPMC, brofenprox, bromophos-ethyl, bromopropylate, bromfenvinfos (-methyl), BTG-504, BTG-505, bufencarb, buprofezin, butathiofos, butocarboxim, butoxycarboxim, butylpyridaben, cadusafos, camphechlor, carbaryl, carbofuran, carbophenothion, carbosulfan, cartap, CGA-50439, quinomethionate, chlordane, chlordimeform, chloethocarb, chlorethoxyfos, chlorfenapyr, chlorfenvinphos, chlorfluazuron, chlormephos, chlorobenzilate, chloropicrin, chlorproxyfen, chlorpyrifos-methyl, chlorpyrifos (-ethyl), chlovaporthrin, chromafenozide, cis-cypermethrin, cis-resmethrin, cis-permethrin, clocythrin, cloethocarb, clofentezine, clothianidin, clothiazoben, codlemone, coumaphos, cyanofenphos, cyanophos, cycloprene, cycloprothrin, *Cydia pomonella*, cyfluthrin, cyhalothrin, cyhexatin, cypermethrin, cyphenothrin (1R-trans isomer), cyromazine, DDT, deltamethrin, demeton-S-methyl, demeton-S-methyl-sulphone, diafenthiuron, dialifos, diazinon, dichlofenthion, dichlorvos, dicofol, dicrotophos, dicyclanil, diflubenzuron, dimethoate, dimethylvinphos, dinobuton, dinocap, dinotefuran, diofenolan, disulfoton, docusate-sodium, dofenapyn, DOWCO-439, eflusilanate, emamectin, emamectin benzoate, empenthrin (1R isomer), endosulfan, *Entomophthora* spp., EPN, esfenvalerate, ethiofencarb, ethiprole, ethion, ethoprophos, etofenprox, etoxazole, etrimfos, famphur, fenamiphos, fenazaquin, fenbutatin oxide, fenfluthrin, fenitrothion, fenobucarb, fenothiocarb, fenoxacrim, fenoxycarb, fenpropathrin, fenpyrad, fenpyrithrin, fenpyroximate, fensulfothion, fenthion, fentrifanil, fenvalerate, fipronil, flonicamid, fluacrypyrim, fluazuron, flubenzimine, flubrocythrinate, flucycloxuron, flucythrinate, flufenerim, flufenoxuron, flufenprox, flumethrin, flupyrazofos, flutenzin (flufenzine), fluvalinate, fonofos, formetanate, formothion, fosmethilan, fosthiazate, fubfenprox (fluproxyfen), furathiocarb, gamma-HCH, gossyplure, grandlure, granulosis viruses, halfenprox, halofenozide, HCH, HCN-801, heptenophos, hexaflumuron, hexythiazox, hydramethylnone, hydroprene, IKA-2002, imidacloprid, imiprothrin, indoxacarb, iodofenphos, iprobenfos, isazofos, isofenphos, isoprocarb, isoxathion, ivermectin, japonilure, kadethrin, nuclear polyhedrosis viruses, kinoprene, lambda-cyhalothrin, lindane, lufenuron, malathion, mecarbam, mesulfenfos, metaldehyde, metamsodium, methacrifos, methamidophos, *Metarhizium anisopliae, Metarhizium flavoviride*, methidathion, methiocarb, methomyl, methoprene, methoxychlor, methoxy-fenozide, metolcarb, metoxadiazone, mevinphos, milbemectin, milbemycin, MKI-245, MON45700, monocrotophos, moxidectin, MTI-800, naled, NC-104, NC-170, NC-184, NC-194, NC-196, niclosamide, nicotine, nitenpyram, nithiazine, NNI-0001, NNI-0101, NNI-0250, NNI-9768, novaluron, noviflumuron, OK-5101, OK-5201, OK-9601, OK-9602, OK-9701, OK-9802, omethoate, oxamyl, oxydemeton-methyl,

*Paecilomyces fumosoroseus*, parathion-methyl, parathion (-ethyl), permethrin (cis-, trans-), petroleum, PH-6045, phenothrin (1R-trans isomer), phenthoate, phorate, phosalone, phosmet, phosphamidon, phosphocarb, phoxim, piperonyl butoxide, pirimicarb, pirimiphos-methyl, pirimiphos-ethyl, prallethrin, profenofos, promecarb, propaphos, propargite, propetamphos, propoxur, prothiofos, prothoate, protrifenbute, pymetrozine, pyraclofos, pyresmethrin, pyrethrum, pyridaben, pyridalyl, pyridaphenthion, pyridathion, pyrimidifen, pyriproxyfen, quinalphos, resmethrin, RH-5849, ribavirin, RU-12457, RU-15525, S-421, S-1833, salithion, sebufos, SI-0009, silafluofen, spinosad, spirodiclofen, spiromesifen, sulfluramid, sulfotep, sulprofos, SZI-121, tau-fluvalinate, tebufenozide, tebufenpyrad, tebupirimfos, teflubenzuron, tefluthrin, temephos, temivinphos, terbam, terbufos, tetrachlorvinphos, tetradifon, tetramethrin, tetramethrin (1R isomer), tetrasul, theta-cypermethrin, thiacloprid, thiamethoxam, thiapronil, thiatriphos, thiocyclam hydrogen oxalate, thiodicarb, thiofanox, thiometon, thiosultap-sodium, thuringiensin, tolfenpyrad, tralocythrin, tralomethrin, transfluthrin, triarathene, triazamate, triazophos, triazuron, trichlophenidine, trichlorfon, triflumuron, trimethacarb, vamidothion, vaniliprole, verbutin, *Verticillium lecanii*,

WL-108477, WL-40027,

YI-5201, YI-5301, YI-5302,

XMC, xylylcarb,

ZA-3274, zeta-cypermethrin, zolaprofos, ZXI-8901, the compound 3-methylphenyl propylcarbamate (Tsumacide Z), the compound 3-(5-chloro-3-pyridinyl)-8-(2,2,2-trifluoroethyl)-8-azabicyclo[3.2.1]octane-3-carbonitrile (CAS Reg. No. 185982-80-3) and the corresponding 3-endo isomer (CAS Reg. No. 185984-60-5) (cf. WO 96/37494, WO 98/25923), and preparations which contain insecticidally active plant extracts, nematodes, fungi or viruses.

A mixture with other known active compounds, such as herbicides, or with fertilizers and growth regulators, is also possible.

In addition, the compounds of the formula (I)/active compound combinations according to the invention also have very good antimycotic activity. They have a very broad antimycotic activity spectrum in particular against dermatophytes and yeasts, moulds and diphasic fungi (for example against *Candida* species, such as *Candida albicans, Candida glabrata*), and *Epidermophyton floccosum, Aspergillus* species, such as *Aspergillus niger* and *Aspergillus fumigatus, Trichophyton* species, such as *Trichophyton mentagrophytes*, Microsporon species such as *Microsporon canis* and *audouinii*. The listing of these fungi by no means limits the mycotic spectrum that can be covered, but is only for illustration.

The active compounds/active compound combinations can be used as such, in the form of their formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, spreading, etc. It is further possible to apply the active compounds by the ultra-low-volume method, or to inject the active compound preparation or the active compound itself into the soil. It is also possible to treat the seeds of the plants.

When using the active compounds/active compound combinations according to the invention as fungicides, the application rates can be varied within a relatively wide range, depending on the kind of application. For the treatment of parts of plants, the active compound application rates are generally between 0.1 and 10 000 g/ha, preferably between 10 and 1000 g/ha. For seed dressing, the active compound application rates are generally between 0.001 and 50 g per kilogram of seed, preferably between 0.01 and 10 g per kilogram of seed. For the treatment of the soil, the active compound application rates are generally between 0.1 and 10 000 g/ha, preferably between 1 and 5000 g/ha.

The preparation and the use of the active compounds/active compound combinations according to the invention are illustrated by the examples below.

PREPARATION EXAMPLES

Example I-1-a-1

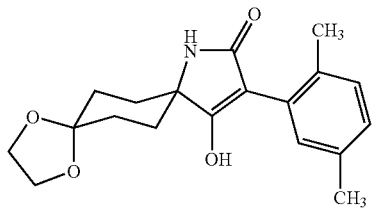

4.88 g (0.042 mol) of potassium tert-butoxide are initially charged in 13 ml of anhydrous dimethylformamide (DMF), 6.82 g of Example II-1 in 14 ml of anhydrous DMF are added dropwise at 60° C. and the mixture is stirred at 80° C. and monitored by thin-layer chromatography.

After the reaction has ended, the reaction solution is poured into 150 ml of ice-water and, at 0 to 10° C., acidified to pH=2 using concentrated hydrochloric acid, and the precipitate is filtered off with suction, washed with ice-water and then dried. This is followed by purification by silica gel column chromatography (dichloromethane/acetone=5:1).

Yield: 2.5 g (40% of theory), m.p. 233° C.

Example I-1-a-8

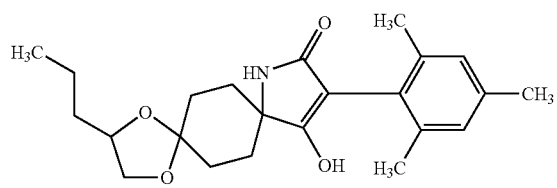

Under argon protective gas, 0.644 g (2 mmol) of the compound of Example XIV-1-1 is initially charged in 30 ml of xylene, 2.083 g (20 mmol) of 1,2-pentanediol and 0.059 g (0.29 mmol) of p-toluenesulphonic acid are added at room temperature, 0.5 g of molecular sieve 4 Å (powder) is added and the mixture is stirred under reflux for three days and monitored by thin-layer chromatography.

After reaction has ended, the solvent is distilled off. The product is purified by silica gel column chromatography (dichloromethane/acetone=5:1).

Yield: 0.27 g (≈35% of theory), m.p. 273° C.

The following compounds of the formula (I-1-a) are obtained analogously to Example (I-1-a-1) and in accordance with the general statements on the preparation (I-1-a)

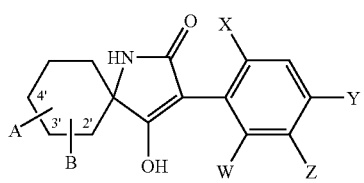

| Ex. No. | W | X | V | Z | A | B | m.p. ° C. | Isomer |
|---|---|---|---|---|---|---|---|---|
| I-1-a-2 | CH₃ | CH₃ | CH₃ | H | 4'-O—(CH₂)₂—O— | | >220 | — |
| I-1-a-3 | CH₃ | CH₃ | CH₃ | CH₃ | 4'-O—(CH₂)₂—O— | | >240 | — |
| I-1-a-4 | CH₃ | CH₃ | Cl | H | 4'-O—(CH₂)₂—O— | | >240 | — |
| I-1-a-5 | H | CH₃ | CH₃ | CH₃ | 4'-O—(CH₂)₂—O— | | 240 | — |
| I-1-a-6 | CH₃ | Cl | Cl | H | 4'-O—(CH₂)₂—O— | | >245 | — |
| I-1-a-7 | CH₃ | CH₃ | CH₃ | H | 4'-O—CHCH₃—CHCH₃—O— | | * | mixture |
| I-1-a-8 | CH₃ | CH₃ | CH₃ | H | 4'-O—CHC₃H₇—CH₂—O— | | 273 | A logP 2.73 |

-continued (I-1-a)

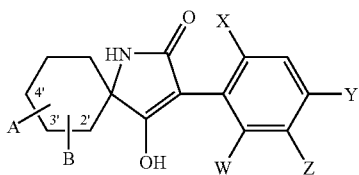

| Ex. No. | W | X | V | Z | A | B | m.p. °C. | Isomer |
|---|---|---|---|---|---|---|---|---|
| I-1-a-9 | CH₃ | CH₃ | CH₃ | H | 4'-O—CHC₃H₇—CH₂—O— | | decomp. | B logP 2.78 |
| I-1-a-10 | CH₃ | CH₃ | CH₃ | H | 4'-O—CHCH₃—CHCH₃—O— | | 275 | mixture |
| I-1-a-11 | CH₃ | Cl | Cl | H | 4'-O—(CH₂)₃—O— | | 262 | — |
| I-1-a-12 | H | CH₃ | H | CH₃ | 4'-O—(CH₂)₃—O— | | 166 | — |
| I-1-a-13 | CH₃ | CH₃ | CH₃ | CH₃ | 4'-O—(CH₂)₃—O— | | 263 | — |
| I-1-a-14 | CH₃ | CH₃ | Cl | H | 4'-O—(CH₂)₃—O— | | 312 | — |
| I-1-a-15 | H | Cl | H | 4-Cl—Ph | 4'-O—(CH₂)₃—O— | | 133 | — |
| I-1-a-16 | H | CH₃ | H | 4-Cl—Ph | 4'-O—(CH₂)₃—O— | | 210 | — |
| I-1-a-17 | H | CH₃ | CH₃ | CH₃ | 4'-O—(CH₂)₃—O— | | 189 | — |
| I-1-a-18 | CH₃ | CH₃ | CH₃ | H | 4'-O—(CH₂)₃—O— | | 229 | — |
| I-1-a-19 | CH₃ | CH₃ | Br | H | 4'-O—(CH₂)₃—O— | | 255 | — |
| I-1-a-20 | CH₃ | CH₃ | Cl | H | 4'-O—CH₂—C(CH₃)₂—CH₂—O— | | 273 | — |
| I-1-a-21 | CH₃ | CH₃ | CH₃ | H | 4'-O—CHCH₃—CH₂—CHCH₃—O— | | 265 | mixture |
| I-1-a-22 | CH₃ | CH₃ | CH₃ | H | 4'-O—CHCH₃—C(CH₂)₂—O— | | 230 | mixture |
| I-1-a-23 | CH₃ | CH₃ | CH₃ | H | 4'-O—CH₂—C(CH₃)₂—CH₂—O— | | 230 | — |
| I-1-a-24 | CH₃ | OCH₃ | CH₃ | H | 4'-O—(CH₂)₃—O— | | 202 | — |
| I-1-a-25 | CH₃ | C₂H₅ | CH₃ | H | 4'-O—(CH₂)₂—O— | | decomp. | — |
| I-1-a-26 | CH₃ | CH₃ | Br | H | 4'-O—(CH₂)₂—O— | | 306 | — |
| I-1-a-27 | H | CH₃ | H | 5-(4-Cl—Ph) | 4'-O—(CH₂)₂—O— | | 154 | — |
| I-1-a-28 | H | CH₃ | H | CH₃ | 4'-O—CHCH₃—CH₂—O— | | wax | mixture |
| I-1-a-29 | H | CH₃ | H | CH₃ | 4'-O—CHCH₃—CHCH₃—O— | | 84 | mixture |
| I-1-a-30 | CH₃ | CH₃ | Cl | H | 4'-O—CHCH₃—CHCH₃—O— | | 268 | mixture |
| I-1-a-31 | CH₃ | CH₃ | Cl | H | -4'O—CHCH₃—CH₂—O— | | 301 | mixture |
| I-1-a-32 | CH₃ | CH₃ | Br | H | 4'-O—CH₂—CHCH₃—CH₂—O— | | 171 | mixture |
| I-1-a-33 | CH₃ | CH₃ | Br | H | 4'-O—CH₂-C(CH₃)₂—CH₂—O— | | 266 | — |
| I-1-a-34 | CH₃ | CH₃ | Cl | H | 4'-O—CH₂—CHCH₃—CH₂—O— | | 265 | mixture |
| I-1-a-35 | CH₃ | CH₃ | Cl | H | 4'-O—CHCH₃—(CH₂)₂—O— | | 243 | mixture |
| I-1-a-36 | H | CH₃ | H | CH₃ | 4'-O—CHCH₃—CH₂—CHCH₃—O— | | 161 | mixture |
| I-1-a-37 | H | CH₃ | H | CH₃ | 4'-O—(CH₂)₂—O— | | oil | mixture |
| I-1-a-38 | CH₃ | CH₃ | Cl | H | 4'-O—CHCH₃—CH₂—CHCH₃—O— | | 276 | mixture |
| I-1-a-39 | CH₃ | C₂H₅ | Br | H | 4'-O—(CH₂)₂—O— | | 293 | — |
| I-1-a-40 | C₂H₅ | C₂H₅ | CH₃ | H | 4'-O—(CH₂)₂—O— | | 269 | — |
| I-1-a-41 | H | CH₃ | Cl | CH₃ | 4'-O—(CH₂)₂—O— | | 236 | — |
| I-1-a-42 | C₂H₅ | OCH₃ | Cl | H | 4'-O—(CH₂)₂—O— | | 234 | — |
| I-1-a-43 | CH₃ | OCH₃ | CH₃ | H | 4'-O—(CH₂)₂—O— | | 237 | — |
| I-1-a-44 | C₂H₅ | Cl | Cl | H | 4'-O—(CH₂)₂—O— | | 305 | — |
| I-1-a-45 | C₂H₅ | CH₃ | CH₃ | H | 4'-O—CHCH₃—CHCH₃—O— | | 148 | mixture |
| I-1-a-46 | CH₃ | CH₃ | Br | H | 4'-O—CHCH₃—CHCH₃—O— | | 275 | mixture |
| I-1-a-47 | CH₃ | CH₃ | Br | H | 4'-O—CHCH₃—CH₂—O— | | 292 | mixture |
| I-1-a-48 | C₂H₅ | Br | CH₃ | H | 4'-O—(CH₂)₂—O— | | 296 | — |
| I-1-a-49 | H | Cl | H | 4-Cl—Ph | 4'-O—(CH₂)₂—O— | | 257 | — |
| I-1-a-50 | CH₃ | CH₃ | Br | H | 4'-O—CH—CH₂—O—<br>\|<br>CH₂—OCH₃ | | 116 | mixture |
| I-l-a-51 | CH₃ | CH₃ | H | 4-Cl-Ph | 4'-O—CHCH₃—CH₂—O— | | 288 | mixture |
| I-l-a-52 | H | CH₃ | H | 4-Cl-Ph | 4'-O—CHCH₃—CH₂—O— | | 198 | mixture |
| I-l-a-53 | CH₃ | C₂H₅ | Br | H | 4'-O—CHCH₃—CH₂—O— | | 255 | mixture |
| I-l-a-54 | H | CH₃ | H | 4-Cl-Ph | 4'-O—CHCH₃—CHCH₃—O— | | 213 | mixture |
| I-l-a-55 | H | CH₃ | Cl | CH₃ | 4'-O—CHCH₃—CH₂—O— | | 272 | mixture |
| I-l-a-56 | CH₃ | CH₃ | Br | H | 4'-O—CHCH₃—CH₂—CHCH₃—O— | | 262 | mixture |
| I-l-a-57 | H | Cl | Cl | H | 4'-O—(CH₂)₃—O— | | 237 | |
| I-l-a-58 | CH₃ | CH₃ | Br | H | 4'-O—CHCH₃—(CH₂)₂—O— | | 80 | mixture |
| I-l-a-59 | CH₃ | Cl | Cl | H | 4'-O—C(CH₃)₂—CH₂—O— | | 264 | |
| I-l-a-60 | CH₃ | C₂H₅ | Br | H | 4'-O—CHCH₃—(CH₂)₂—O— | | 190 | mixture |
| I-l-a-61 | H | CH₃ | H | CH₃ | 4'-O—CH₂—C(CH₃)₂—CH2—O— | | 240 | |
| I-l-a-62 | H | CH₃ | H | CH₃ | 4'-O—CH₂—CHCH₃—CH₂—O— | | 276 | mixture |
| I-l-a-63 | CH₃ | C₂H₅ | Br | H | 4'-O—CH₂—CHCH₃—CHCH₃—O— | | >300 | mixture |
| I-l-a-64 | H | CH₃ | H | 4-Cl-Ph | 4'-O—CH₂—C(CH₃)₂—CH₂—O— | | 276 | - |
| I-l-a-65 | H | Cl | H | 4-Cl-Ph | 4'-O—CH₂-CHCH₃—CH₂—O— | | 79 | mixture |
| I-l-a-66 | H | CH₃ | H | 4-Cl-Ph | 4'-O—CHCH₃—(CH₂)₂—O— | | 67 | mixture |
| I-l-a-67 | H | CH₃ | H | 4-Cl-Ph | 4'-O—CH₂—C(CH₃)₂—CH2—O— | | 234 | |
| I-l-a-68 | H | CH₃ | H | CH₃ | 4'-O—(CH₂)₂—O— | | 211 | |
| I-l-a-69 | C₂H₅ | Br | CH₃ | H | 3'-O—(CH₂)₂—O— | | decomp. | |

-continued

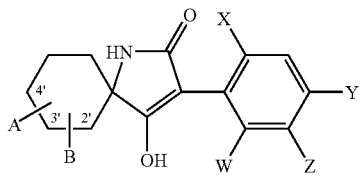

(I-1-a)

| Ex. No. | W | X | Y | Z | A | B | m.p. ° C. | Isomer |
|---|---|---|---|---|---|---|---|---|
| I-1-a-70 | CH$_3$ | CH$_3$ | Cl | H | 3'-O—(CH$_2$)$_2$—O— | | 260 | — |
| I-1-a-71 | CH$_3$ | CH$_3$ | CH$_3$ | H | 3'-O—CH(CH$_2$—OCH$_3$)—CH$_2$—O— | | oil | mixture |
| I-1-a-72 | C$_2$H$_5$ | Br | CH$_3$ | H | 3'-O—CH(CH$_2$—OCH$_3$)—CH$_2$—O— | | oil | mixture |
| I-1-a-73 | H | CH$_3$ | H | CH$_3$ | 3'-O—CH(CH$_2$—OCH$_3$)—CH$_2$—O— | | oil | mixture |
| I-1-a-74 | CH$_3$ | CH$_3$ | Cl | H | 3'-O—CH(CH$_2$—OCH$_3$)—CH$_2$—O— | | 82 | mixture |
| I-1-a-75 | CH$_3$ | CH$_3$ | Cl | H | 4'-O—CH(CH$_2$—OCH$_3$)—CH$_2$—O— | | 67 | mixture |
| I-1-a-76 | H | Cl | H | 4-Cl—Ph | 4'-O—CHCH$_3$—CH$_2$—O— | | 68 | mixture |
| I-1-a-77 | C$_2$H$_5$ | Br | CH$_3$ | H | 4'-O—CHCH$_3$—CH$_2$—O— | | 281 | mixture |
| I-1-a-78 | H | Cl | H | 4-Cl—Ph | 4'-O—CHCH$_3$—(CH$_2$)$_2$—O— | | 232 | mixture |
| I-1-a-79 | H | Cl | H | 4-Cl—Ph | 4'-O—CH$_2$—CHCH$_3$—CH$_2$—O— | | 160 | mixture |
| I-1-a-80 | H | Cl | H | 4-Cl—Ph | 4'-O—CHCH$_3$—CH$_2$—CHCH$_3$—O— | | 268 | mixture |
| I-1-a-81 | H | Cl | H | 4-Cl—Ph | 4'-O—CH$_2$—C(CH$_3$)$_2$—CH$_2$—O— | | 151 | — |
| I-1-a-82 | CH$_3$ | C$_2$H$_5$ | Br | H | 4'-O—(CH$_2$)$_3$—O— | | 244 | — |
| I-1-a-83 | CH$_3$ | CH$_3$ | Cl | H | 3'-O—CHCH$_3$—CH$_2$—O— | | 167 | mixture |
| I-1-a-84 | CH$_3$ | CH$_3$ | Cl | H | 3'-O—CH$_2$—C(CH$_3$)$_2$—CH$_2$—O— | | 266 | mixture |
| I-1-a-85 | CH$_3$ | CH$_3$ | Cl | H | 3'-O—(CH$_2$)$_3$—O— | | 261 | mixture |
| I-1-a-86 | CH$_3$ | C$_2$H$_5$ | 4-Cl—Ph | H | 4'-O—CHCH$_3$—CH$_2$—O— | | 219-222 | mixture |

Ph = 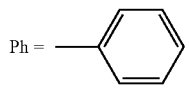

*$^1$H-NMR (400 MHz, d$_6$-DMSO): δ = 1.05-1.09 (2 d, 6 H, 2 × CH$\underline{CH_3}$); 4.18-4.23 (m, 2 H, 2 × $\underline{CH}$CH$_3$) ppm
decomp. = decomposition Example I-1-b-1

1.82 g of the compound of Example I-1-a-4 are initially charged in 50 ml of anhydrous ethyl acetate and 0.77 ml (5.5 mmol) of triethylamine under reflux. 0.55 ml (0.0055 mol) of isobutyryl chloride in 5 ml of anhydrous ethyl acetate is added, and the mixture is stirred under reflux.

After the reaction has ended (monitored by thin-layer chromatography) the solvent is distilled off and the residue is taken up in dichloromethane. The mixture is washed twice with 30 ml of 0.5 N NaOH and dried, and the solvent is distilled off.

The product is purified by silica gel column chromatography (dichloromethane/ethyl acetate=3:1).

Yield: 0.3 g (14% of theory), m.p. 215° C.

The following compounds of the formula (I-1-b) are obtained analogously to Example (I-1-b-1) and in accordance with the general statements on the preparation

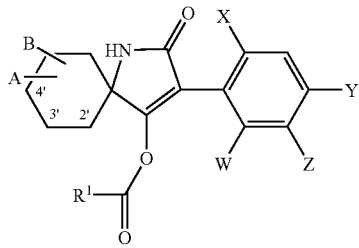

(I-1-b)

| Ex. No. | W | X | Y | Z | A | B | R¹ | m.p. °C. | Isomer |
|---|---|---|---|---|---|---|---|---|---|
| I-1-b-2 | $CH_3$ | $C_2H_5$ | Br | H | 4'-O—$(CH_2)_2$—O— | | $H_3CO$—$CH_2$— | *3.23 (s, 3 H, O$CH_3$) 7.21 (s, 2 H, —Ar—$H$) | — |
| I-1-b-3 | $CH_3$ | $C_2H_5$ | Br | H | 4'-O—$(CH_2)_2$—O— | | $i$-$C_3H_7$ | solidified foam | — |
| I-1-b-4 | $C_2H_5$ | Cl | Cl | H | 4'-O—$(CH_2)_2$—O— | | $i$-$C_3H_7$ | 106-112 | — |
| I-1-b-5 | $C_2H_5$ | Br | $CH_3$ | H | 4'-O—$CHCH_3$—$CHCH_3$—O— | | $i$-$C_3H_7$ | 198-200 | mixture |
| I-1-b-6 | $C_2H_5$ | Cl | Cl | H | 4'-O—$(CH_2)_2$—O— | | $H_3CO$—$CH_2$— | *2.63 (m, 2 H, Ar—$CH_2$) 3.29 (s, 3 H, O$CH_3$) | — |
| I-1-b-7 | $C_2H_5$ | $OCH_3$ | Cl | H | 4'-O—$(CH_2)_2$—O— | | $H_3CO$—$CH_2$— | 170-175 | — |
| I-1-b-8 | $C_2H_5$ | Br | $CH_3$ | H | 3'-O—$(CH_2)_2$—O— | | $i$-$C_3H_7$ | solidified foam **1.07 (m, 6 H, CH$(CH_3)_2$) 2.28 (s, 3 H, Ar$CH_3$) | — |
| I-1-b-9 | $C_2H_5$ | Br | $CH_3$ | H | 3'-O—$(CH_2)_2$—O— | | $H_3CO$—$CH_2$— | *2.29 (s, 3 H, Ar—$CH_3$) 3.26 (s, 3 H, O$CH_3$) | — |
| I-1-b-10 | $C_2H_5$ | Br | $CH_3$ | H | 3'-O—CH—$CH_2$—O— $\mid$ $CH_2$—$OCH_3$ | | $i$-$C_3H_7$ | oil **1.05 (m, 6 H, CH$(CH_3)_2$) 2.29 (s, 3 H, Ar$CH_3$) | mixture |
| I-1-b-11 | $C_2H_5$ | Br | $CH_3$ | H | 3'-O—CH—$CH_2$—O— $\mid$ $CH_2$—$OCH_3$ | | $H_3CO$—$CH_2$— | oil **2.29 (s, 3 H, Ar$CH_3$) 3.26 (s, 3 H, O$CH_3$) | mixture |
| I-1-b-12 | $CH_3$ | $C_2H_5$ | Br | H | 4'-O—$CHCH_3$—$CH_2$—$CHCH_3$—O— | | cyclopropyl | 225 | mixture |
| I-1-b-13 | $CH_3$ | $C_2H_5$ | Br | H | 4'-O—$CHCH_3$—$(CH_2)_2$—O— | | 2-Cl—Ph | 225 | mixture |
| I-1-b-14 | $CH_3$ | $C_2H_5$ | Br | H | 4'-O—$CHCH_3$—$CHCH_3$—O— | | 2-thienyl | 246 | mixture |
| I-1-b-15 | $CH_3$ | $C_2H_5$ | Br | H | 3'-O—CH—$CH_2$—O— $\mid$ $CH_2$—$OCH_3$ | | $t$-$C_4H_9$ | solidified foam | mixture |
| I-1-b-16 | $CH_3$ | $C_2H_5$ | Br | H | 4'-O—$CHCH_3$—$CH_2$—O— | | $i$-$C_3H_7$ | 194 | mixture |
| I-1-b-17 | $CH_3$ | $C_2H_5$ | Br | H | 4'-O—$CHCH_3$—$(CH_2)_2$—O— | | $i$-$C_3H_7$ | *1.06 (m, 6 H, CH($CH_3)_2$) 7.21 (s, 2 H, Ar$H$) | mixture |
| I-1-b-18 | $C_2H_5$ | $CH_3$ | Br | H | 4'-O—$CHCH_3$—$CHCH_3$—O— | | $H_3CO$—$CH_2$ | *3.24 (s, 3 H, O$CH_3$) 7.21 (s, 2 H, Ar—$H$) | mixture |
| I-1-b-19 | $C_2H_5$ | $CH_3$ | $CH_3$ | H | 4'-O—$(CH_2)_2$—O— | | $i$-$C_3H_7$ | *0.98 (dd, 6 H, CH($CH_3)_2$) 3.98 (m, 4 H, $CH_2$O) 6.86 (s, 2 H, Ar—$H$) | — |
| I-1-b-20 | $C_2H_5$ | $CH_3$ | Br | H | 4'-O—$CHCH_3$—$CH_2$—$CHCH_3$—O— | | $i$-$C_3H_7$ | 120 | mixture |

*¹H-NMR (400 MHz, CDCl₃): shifts δ in ppm
**¹H-NMR (300 MHz, CDCl₃): shifts δ in ppm

Example I-1-c-1

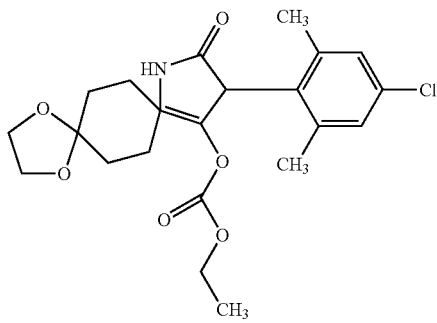

1.82 g of the compound of Example I-1-a-4 are stirred at 10 to 20° C. in 30 ml of anhydrous dichloromethane and 0.7 ml of triethylamine. 0.5 ml of ethyl chloroformate in 2 ml of anhydrous dichloromethane is added, and the mixture is stirred at room temperature.

After the reaction has ended (monitored by thin-layer chromatography), the mixture is washed twice with 10 ml of 0.5 N NaOH and dried over magnesium sulphate. The solvent is then distilled off.

The product is purified by silica gel column chromatography (dichloromethane/ethanol=30:1).

Yield: 1.15 g (52% of theory), m.p. 198° C.

The following compounds of the formula (I-1-c) are obtained analogously to Example (I-1-c-1) and in accordance with the general statements on the preparation:

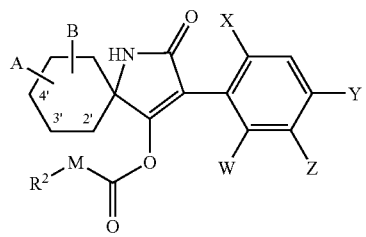

(I-1-c)

| Ex. No. | W | X | Y | Z | A B | M | $R^2$ | m.p. ° C. | Isomer |
|---|---|---|---|---|---|---|---|---|---|
| I-1-c-2 | $CH_3$ | $CH_3$ | $CH_3$ | H | 4'-O—$(CH_2)_2$—O— | O | $C_2H_5$ | 181 | — |
| I-1-c-3 | H | $CH_3$ | $CH_3$ | $CH_3$ | 4'-O—$(CH_2)_2$—O— | O | $C_2H_5$ | 221 | — |
| I-1-c-4 | $CH_3$ | Cl | Cl | H | 4'-O—$(CH_2)_2$—O— | O | $C_2H_5$ | 233 | — |
| I-1-c-5 | $CH_3$ | $CH_3$ | $CH_3$ | $CH_3$ | 4'-O—$(CH_2)_2$—O— | O | $C_2H_5$ | 209 | — |
| I-1-c-6 | $CH_3$ | $CH_3$ | $CH_3$ | H | 4'-O—$CHCH_3$—$CH_2$—O— | O | $C_2H_5$ | 218 | mixture |
| I-1-c-7 | $CH_3$ | Cl | Cl | H | 4'-O—$(CH_2)_3$—O— | O | $C_2H_5$ | 235 | — |
| I-1-c-8 | $CH_3$ | $CH_3$ | Cl | H | 4'-O—$(CH_2)_3$—O— | O | $C_2H_5$ | 195 | — |
| I-1-c-9 | H | $CH_3$ | $CH_3$ | $CH_3$ | 4'-O—$(CH_2)_3$—O— | O | $C_2H_5$ | 235 | — |
| I-1-c-10 | $CH_3$ | $CH_3$ | Br | H | 4'-O—$(CH_2)_3$—O— | O | $C_2H_5$ | 234 | — |
| I-1-c-11 | $CH_3$ | $CH_3$ | $CH_3$ | H | 4'-O—$(CH_2)_3$—O— | O | $C_2H_5$ | 229 | — |
| I-1-c-12 | $CH_3$ | $CH_3$ | Cl | H | 4'-O—$CH_2$—$CHCH_3$—$CH_2$—O— | O | $C_2H_5$ | 241 | mixture |
| I-1-c-13 | $CH_3$ | $CH_3$ | Cl | H | 4'-O—$CH_2$—$C(CH_3)_2$—$CH_2$—O— | O | $C_2H_5$ | 247 | — |
| I-1-c-14 | $CH_3$ | $C_2H_5$ | Br | H | 4'-O—$(CH_2)_2$—O— | O | $C_2H_5$ | 200-201 | — |
| I-1-c-15 | $CH_3$ | $C_2H_5$ | $CH_3$ | H | 4'-O—$(CH_2)_2$—O— | O | $C_2H_5$ | oil | — |
| I-1-c-16 | H | $CH_3$ | H | 4-Cl—Ph | 4'-O—$(CH_2)_2$—O— | O | $C_2H_5$ | 197 | — |
| I-1-c-17 | $CH_3$ | $CH_3$ | Cl | H | 4'-O—$CHCH_3$—$CH_2$—O— | O | $C_2H_5$ | 223 | mixture |
| I-1-c-18 | $CH_3$ | $CH_3$ | Cl | H | 4'-O—$CHCH_3$—$CHCH_3$—O— | O | $C_2H_5$ | 232 | mixture |
| I-1-c-19 | H | $CH_3$ | H | $CH_3$ | 4'-O—$CHCH_3$—$CH_2$—O— | O | $C_2H_5$ | 141 | mixture |
| I-1-c-20 | $CH_3$ | $CH_3$ | Br | H | 4'-O—$(CH_2)_2$—O— | O | $C_2H_5$ | 222 | — |
| I-1-c-21 | H | $CH_3$ | Cl | $CH_3$ | 4'-O—$(CH_2)_2$—O— | O | $C_2H_5$ | 187 | — |
| I-1-c-22 | H | $CH_3$ | H | $CH_3$ | 4'-O—$CHCH_3$—$CHCH_3$—O— | O | $C_2H_5$ | 180 | mixture |
| I-1-c-23 | $C_2H_5$ | $C_2H_5$ | $CH_3$ | H | 4'-O—$(CH_2)_2$—O— | O | $C_2H_5$ | 179 | — |
| I-1-c-24 | $CH_3$ | O—$CH_3$ | $CH_3$ | H | 4'-O—$(CH_2)_2$—O— | O | $C_2H_5$ | 176 | — |
| I-1-c-25 | $C_2H_5$ | O—$CH_3$ | Cl | H | 4'-O—$(CH_2)_2$—O— | O | $C_2H_5$ | **1.16 ("q", 6 H, —Ar—$CH_2$—$CH_3$ and O—$CH_2$—$CH_3$) 3.79 (s, 3 H, Ar—$OCH_3$) | — |
| I-1-c-26 | $C_2H_5$ | Cl | Cl | H | 4'-O—$(CH_2)_2$—O— | O | $C_2H_5$ | 175-183 | — |
| I-1-c-27 | $CH_3$ | $C_2H_5$ | Br | H | 4'-O—$CHCH_3$—$CH_2$—O— | O | $C_2H_5$ | 181 | mixture |
| I-1-c-28 | $C_2H_5$ | Cl | Cl | H | 4'-O—$(CH_2)_2$—O— | O | $C_6H_5$—$CH_2$— | 173 | — |
| I-1-c-29 | $CH_3$ | $C_2H_5$ | Br | H | 4'-O—$CHCH_3$—$CHCH_3$—O— | O | $CH_2$=CH—$CH_2$— | 187 | mixture |
| I-1-c-30 | $CH_3$ | $CH_3$ | Cl | H | 4'-O—$CHCH_3$—$(CH_2)_2$—O— | O | $C_2H_5$ | 229 | mixture |

-continued

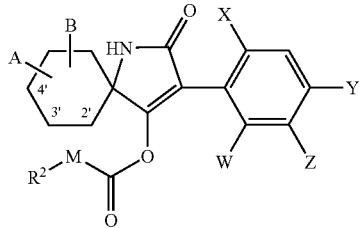

(I-1-c)

| Ex. No. | W | X | Y | Z | A B | M | R² | m.p. °C. | Isomer |
|---|---|---|---|---|---|---|---|---|---|
| I-1-c-31 | H | $CH_3$ | H | 4-Cl—Ph | 4'-O—$(CH_2)_3$—O— | O | $C_2H_5$ | 207 | — |
| I-1-c-32 | $CH_3$ | $CH_3$ | Br | H | 4'-O—$CH_2$—$CHCH_3$—$CH_2$—O— | O | $C_2H_5$ | 242 | mixture |
| I-1-c-33 | $CH_3$ | $CH_3$ | Br | H | 4'-O—$CH_2$—$C(CH_3)_2$—$CH_2$—O— | O | $C_2H_5$ | 250 | — |
| I-1-c-34 | $CH_3$ | O—$CH_3$ | $CH_3$ | H | 4'-O—$(CH_2)_3$—O— | O | $C_2H_5$ | 222 | — |
| I-1-c-35 | H | $CH_3$ | H | $CH_3$ | 4'-O—$CH_2$—$C(CH_3)_2$—$CH_2$—O— | O | $C_2H_5$ | 194 | — |
| I-1-c-36 | H | $CH_3$ | H | $CH_3$ | 4'-O—$CH_2$—$CHCH_3$—$CH_2$—O— | O | $C_2H_5$ | 169 | mixture |
| I-1-c-37 | $CH_3$ | $C_2H_5$ | Br | H | 4'-O—$CHCH_3$—$CH_2$—$CHCH_3$—O— | O | $C_2H_5$ | 175-178 | mixture |
| I-1-c-38 | $CH_3$ | $C_2H_5$ | Br | H | 4'-O—$CHCH_3$—$(CH_2)_2$—O— | O | $C_2H_5$ | 97 | mixture |
| I-1-c-39 | H | Cl | H | 4-Cl—Ph | 4'-O—$(CH_2)_3$—O— | O | $C_2H_5$ | 237 | — |
| I-1-c-40 | H | $CH_3$ | H | $CH_3$ | 3'-O—$(CH_2)_2$—O— | O | $C_2H_5$ | 156 | — |
| I-1-c-41 | $CH_3$ | $CH_3$ | Cl | H | 3'-O—$(CH_2)_2$—O— | O | $C_2H_5$ | 193 | — |
| I-1-c-42 | $C_2H_5$ | Br | $CH_3$ | H | 3'-O—$(CH_2)_2$—O— | O | $C_2H_5$ | **2.58 (m, 2 H, Ar—$CH_2$—), 4.08 (q, 2 H, O$CH_2$—$CH_3$) | — |
| I-1-c-43 | $C_2H_5$ | Br | $CH_3$ | H | 3'-O—CH—$CH_2$—O—<br>             \|<br>           $CH_2$—$OCH_3$ | O | $C_2H_5$ | oil **1.18 ("q", 6 H, Ar—$CH_2$—$CH_3$ and O—$CH_2$—$CH_3$) 2.32 (s, 3 H, Ar—$CH_3$) | mixture |
| I-1-c-44 | $C_2H_5$ | Br | $CH_3$ | H | 3'-O—$(CH_2)_2$—O— | O | $(H_3C)_3$C—$CH_2$— | foam **0.8 (s, 9 H, $C(CH_3)_3$) 2.28 (s, 3 H, Ar—$CH_3$) | — |
| I-1-c-45 | H | Cl | H | 4-Cl—Ph | 4'-O—$CHCH_3$—$CH_2$—O— | O | $C_2H_5$ | 219 | mixture |
| I-1-c-46 | H | Cl | H | 4-Cl—Ph | 4'-O—$(CH_2)_2$—O— | O | $C_2H_5$ | 239 | — |

*¹H-NMR (400 MHz, CDCl₃): shifts δ in ppm
**¹H-NMR (300 MHz, CDCl₃): shifts δ in ppm Example I-1-d-1

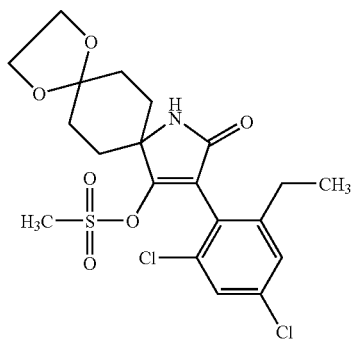

0.159 g of the compound of Example I-1-a-44 is initially charged in 10 ml of trichloromethane, 0.098 ml of diisopropylethylamine and 1.5 mg of DMAP are added at room temperature, 0.037 ml of methanesulphonyl chloride is added and the mixture is stirred for 20 hours, 5 ml of NaCl solution are added, the mixture is stirred at room temperature for about 0.5 hours and the organic phase is separated off, dried with sodium sulphate and concentrated using a rotary evaporator. The resulting crude product is purified by column chromatography on silica gel using an n-heptane/ethyl acetate gradient of from 4:1 to 0:100.

Yield: 0.07 g (37% of theory), m.p.: 217° C.

Example I-1-g-1

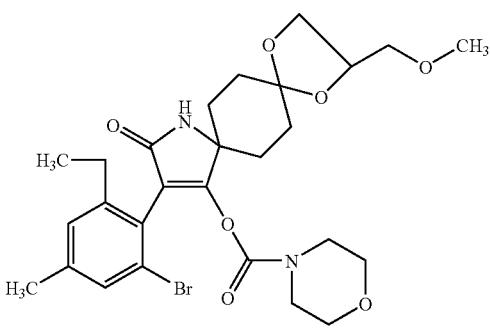

0.233 g of the compound of Example I-1-a-72 is initially charged in 8 ml of chloroform, 0.098 ml of diisopropylethylamine and 1.5 mg of DMAP are added, 0.056 ml of morpholinecarbonyl chloride is then added, the mixture is stirred at room temperature for 20 hours, 5 ml of 5% strength sodium bicarbonate solution are added, the mixture is stirred for another 0.5 hours and the organic phase is separated off, dried with sodium sulphate and concentrated using a rotary evaporator. The crude product is purified by column chromatography on silica gel using an n-heptane/ethyl acetate gradient from 4:1 to 0:100.

Yield: 0.148 g (64% of theory), oil $^1$H-NMR (400 MHz, CDCl$_3$): δ=2.31 (2, 3H, Ar—CH$_3$), 3.1, 3.2 (each m, 2H, CH$_2$O) ppm.

Example II-1

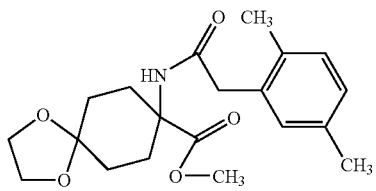

9.56 g of 8-aminomethyl 1,4-dioxaspiro[4.5]decane-8-carboxylate hydrochloride are initially charged in 38 ml of anhydrous acetonitrile, and 17.5 g (0.127 mol) of ground potassium carbonate are added at from 5 to 10° C. 6.94 g of 2,5-dimethylphenylacetyl chloride in 10 ml of anhydrous acetonitrile are then added dropwise over a period of 12 minutes.

The mixture is stirred at room temperature for 3 h.

The reaction solution is poured into 250 ml of ice-water, and the precipitate is filtered off with suction. The precipitate is washed with water and taken up in dichloromethane, the mixture is dried and the solvent is distilled off. The product is purified by column chromatography on silica gel (dichloromethane/ethyl acetate=3:1).

Yield: 6.82 g (49% of theory), m.p. 115° C.

Example (II-2)

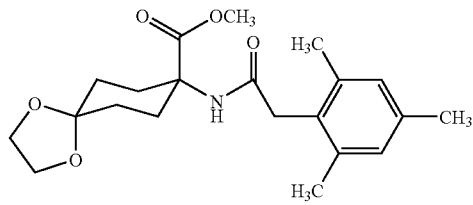

154.6 g (1.579 mol) of concentrated sulphuric acid are initially charged, and at an internal temperature of from 30 to 40° C., 107.9 g of the compound of Example (XXI-1) in 630 ml of methylene chloride are added dropwise as a suspension. The mixture is stirred at from 30 to 40° C. for 2 h, and 220 ml of anhydrous methanol are then added dropwise such that an internal temperature of 40° C. is obtained.

The mixture is stirred at an external temperature of 40 to 70° C. for a further 6 h.

The reaction solution is poured onto 1.5 kg of ice, extracted with dichloromethane and washed with NaHCO$_3$ solution. The mixture is dried and the solvent is distilled off.

The product is purified by column chromatography on silica gel (toluene/ethyl acetate=1:1).

Yield: 11.4 g (10% of theory).

The following compounds of the formula (II) are obtained analogously to Examples (II-1) and (II-2) and in accordance with the general statements on the preparation

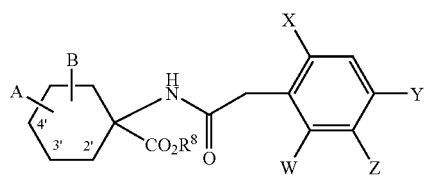

(II)

| Ex. No. | W | X | Y | Z | A | B | R$^8$ | m.p. ° C. |
|---|---|---|---|---|---|---|---|---|
| II-2 | CH$_3$ | CH$_3$ | CH$_3$ | H | 4'-O—(CH$_2$)$_2$—O— | | CH$_3$ | log P 2.68 |
| II-3 | CH$_3$ | CH$_3$ | CH$_3$ | CH$_3$ | 4'-O—(CH$_2$)$_2$—O— | | CH$_3$ | 141 |
| II-4 | CH$_3$ | CH$_3$ | Cl | H | 4'-O—(CH$_2$)$_2$—O— | | CH$_3$ | 181 |
| II-5 | H | CH$_3$ | CH$_3$ | CH$_3$ | 4'-O—(CH$_2$)$_2$—O— | | CH$_3$ | 129 |
| II-6 | CH$_3$ | Cl | Cl | H | 4'-O—(CH$_2$)$_2$—O— | | CH$_3$ | 159 |

-continued

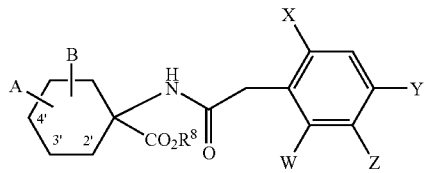

(II)

| Ex. No. | W | X | Y | Z | A | B | R⁸ | m.p. ° C. |
|---|---|---|---|---|---|---|---|---|
| II-7 | $CH_3$ | $CH_3$ | Br | H | 4'-O—$(CH_2)_2$—O— | | $CH_3$ | wax log P 2.81* |
| II-8 | $CH_3$ | $C_2H_5$ | $CH_3$ | H | 4'-O—$(CH_2)_2$—O— | | $CH_3$ | wax log P 2.95* |
| II-9 | $CH_3$ | $C_2H_5$ | Br | H | 4'-O—$(CH_2)_2$—O— | | $CH_3$ | wax log P 3.19* |
| II-11 | $CH_3$ | Cl | Cl | H | 4'-O—$(CH_2)_3$—O— | | $CH_3$ | 175 |
| II-12 | H | $CH_3$ | H | $CH_3$ | 4'-O—$(CH_2)_3$—O— | | $CH_3$ | 144 |
| II-13 | $CH_3$ | $CH_3$ | $CH_3$ | $CH_3$ | 4'-O—$(CH_2)_3$—O— | | $CH_3$ | 148 |
| II-14 | $CH_3$ | $CH_3$ | Cl | H | 4'-O—$(CH_2)_3$—O— | | $CH_3$ | 184 |
| II-15 | H | Cl | H | 4-Cl—Ph | 4'-O—$(CH_2)_3$—O— | | $CH_3$ | 177 |
| II-16 | H | $CH_3$ | H | 4-Cl—Ph | 4'-O—$(CH_2)_3$—O— | | $CH_3$ | 181 |
| II-17 | H | $CH_3$ | $CH_3$ | $CH_3$ | 4'-O—$(CH_2)_3$—O— | | $CH_3$ | log P 2.59* |
| II-18 | $CH_3$ | $CH_3$ | $CH_3$ | H | 4'-O—$(CH_2)_3$—O— | | $CH_3$ | 143 |
| II-19 | $CH_3$ | $CH_3$ | Br | H | 4'-O—$(CH_2)_3$—O— | | $CH_3$ | 189 |
| II-20 | $CH_3$ | $CH_3$ | Cl | H | 4'-O—$CH_2$—$C(CH_3)_2$—$CH_2$—O— | | $CH_3$ | 178 |
| II-21 | $CH_3$ | $CH_3$ | Cl | H | 4'-O—$CH_2$—$CHCH_3$—$CH_2$—O— | | $CH_3$ | 170 |
| II-22 | $CH_3$ | $CH_3$ | Br | H | 4'-O—$CH_2$—$C(CH_3)_2$—$CH_2$—O— | | $CH_3$ | 181 |
| II-23 | $CH_3$ | $CH_3$ | Br | H | 4'-O—$CH_2$—$CHCH_3$—$CH_2$—O— | | $CH_3$ | 177 |
| II-24 | $CH_3$ | $OCH_3$ | $CH_3$ | H | 4'-O—$(CH_2)_3$—O— | | $CH_3$ | log P 2.49* |
| II-25 | $CH_3$ | $CH_3$ | Br | H | 4'-O-$CHCH_3$—$CHCH_3$—O— | | $CH_3$ | 189 |
| II-26 | $CH_3$ | $CH_3$ | Br | H | 4'-O—$CHCH_3$—$CH_2$—O— | | $CH_3$ | 161 |
| II-27 | H | $CH_3$ | H | $CH_3$ | 4'-O—$CHCH_3$—$CHCH_3$—O— | | $CH_3$ | 166 |
| II-28 | $CH_3$ | $CH_3$ | Cl | H | 4'-O—$CHCH_3$—$CHCH_3$—O— | | $CH_3$ | 183 |
| II-29 | $CH_3$ | $CH_3$ | Cl | H | 4'-O—$CHCH_3$—$CH_2$—O— | | $CH_3$ | 170 |
| II-30 | H | $CH_3$ | H | $CH_3$ | 4'-O—$CHCH_3$—$CH_2$—O— | | $CH_3$ | 141 |
| II-31 | H | $CH_3$ | H | 5-(4-Cl—Ph) | 4'-O—$(CH_2)_2$—O— | | $CH_3$ | log P 3.47* |
| II-32 | $C_2H_5$ | $C_2H_5$ | $CH_3$ | H | 4'-O—$(CH_2)_2$—O— | | $CH_3$ | log P 3.28* |
| II-33 | $CH_3$ | $OCH_3$ | $CH_3$ | H | 4'-O—$(CH_2)_2$—O— | | $CH_3$ | 139 |
| II-34 | H | $CH_3$ | Cl | $CH_3$ | 4'-O—$(CH_2)_2$—O— | | $CH_3$ | 182 |
| II-35 | $C_2H_5$ | $OCH_3$ | Cl | H | 4'-O—$(CH_2)_2$—O— | | $CH_3$ | 153 |
| II-36 | $C_2H_5$ | Br | $CH_3$ | H | 4'-O—$(CH_2)_2$—O— | | $CH_3$ | log P 3.04* |
| II-37 | H | $CH_3$ | H | $CH_3$ | 4'-O—$CHCH_3$—$CH_2$—$CHCH_3$—O— | | $CH_3$ | 122 |
| II-38 | $CH_3$ | $CH_3$ | Cl | H | 4'-O—$CHCH_3$—$CH_2$—$CHCH_3$—O— | | $CH_3$ | 208 |
| II-39 | H | $CH_3$ | H | $CH_3$ | 4'-O—$CHCH_3$—$(CH_2)_2$—O— | | $CH_3$ | 144 |
| II-40 | $CH_3$ | $CH_3$ | Cl | H | 4'-O—$CHCH_3$—$(CH_2)_2$—O— | | $CH_3$ | 174 |
| II-41 | $CH_3$ | $CH_3$ | Br | H | 4'-O—$CHCH_3$—$(CH_2)_2$—O— | | $CH_3$ | 175 |
| II-42 | $CH_3$ | $CH_3$ | Br | H | 4'-O—$CHCH_3$—$CH_2$—$CHCH_3$—O— | | $CH_3$ | 202 |
| II-43 | $CH_3$ | $C_2H_5$ | Br | H | 4'-O—$CHCH_3$—$CH_2$—$CHCH_3$—O— | | $CH_3$ | 200 |
| II-44 | H | $CH_3$ | H | $CH_3$ | 4'-O—$CH_2$—$C(CH_3)_2$—$CH_2$—O— | | $CH_3$ | 157 |
| II-45 | H | $CH_3$ | H | $CH_3$ | 4'-O—$CH_2$—$CHCH_3$—$CH_2$—O— | | $CH_3$ | 154 |
| II-46 | $CH_3$ | $C_2H_5$ | Br | H | 4'-O—$CHCH_3$—$(CH_2)_2$—O— | | $CH_3$ | 158 |
| II-47 | $CH_3$ | Cl | Cl | H | 4'-O—$CH_2$—$C(CH_3)_2$—$CH_2$—O— | | $CH_3$ | 197 |
| II-48 | $CH_3$ | Cl | Cl | H | 4'-O—$CHCH_3$—$CH_2$—O— | | $CH_3$ | 174 |
| II-49 | H | Cl | H | 4-Cl—Ph | 4'-O—$CH_2$—$C(CH_3)_2$—$CH_2$—O— | | $CH_3$ | 205 |
| II-50 | H | Cl | H | 4-Cl—Ph | 4'-O—$CH_2$—$CHCH_3$—$CH_2$—O— | | $CH_3$ | 166 |
| II-51 | H | $CH_3$ | H | 4-Cl—Ph | 4'-O—$CH_2$—$C(CH_3)_2$—$CH_2$—O— | | $CH_3$ | 184 |
| II-52 | H | $CH_3$ | H | 4-Cl—Ph | 4'-O—$CH_2$—$CHCH_3$—$CH_2$—O— | | $CH_3$ | 163 |
| II-53 | H | $CH_3$ | H | 4-Cl—Ph | 4'-O—$CHCH_3$—$CH_2$—$CHCH_3$—O— | | $CH_3$ | 149 |
| II-54 | $CH_3$ | $C_2H_5$ | Br | H | 4'-O—$CH_2$—$C(CH_3)_2$—$CH_2$—O— | | $CH_3$ | 241 |
| II-55 | $CH_3$ | $C_2H_5$ | Br | H | 4'-O—$CH_2$—$CHCH_3$—$CH_2$—O— | | $CH_3$ | 147 |
| II-56 | $CH_3$ | $C_2H_5$ | Br | H | 4'-O—$CHCH_3$—$CH_2$—O— | | $CH_3$ | 157 |
| II-57 | $CH_3$ | $C_2H_5$ | Br | H | 4'-O—$CHCH_3$—$CHCH_3$—O— | | $CH_3$ | 167 |
| II-58 | $C_2H_5$ | Cl | Cl | H | 4'-O—$(CH_2)_2$—O— | | $CH_3$ | 281 |
| II-59 | H | Cl | H | 4-Cl—Ph | 4'-O—$(CH_2)_2$—O— | | $CH_3$ | |
| II-60 | $CH_3$ | $CH_3$ | H | 4-Cl—Ph | 4'-O—$CHCH_3$—$CH_2$—O— | | $CH_3$ | 173 |
| II-61 | H | $CH_3$ | Cl | $CH_3$ | 4'-O—$CHCH_3$—$CH_2$—O— | | $CH_3$ | 165 |
| II-62 | H | $CH_3$ | H | 4-Cl—Ph | 4'-O—$CHCH_3$—$CH_2$—O— | | $CH_3$ | 174 |
| II-63 | H | $CH_3$ | H | 4-Cl—Ph | 4'-O—$CHCH_3$—$CHCH_3$—O— | | $CH_3$ | 151 |
| II-64 | H | Cl | H | 4-Cl—Ph | 4'-O—$CHCH_3$—$CH_2$—O— | | $CH_3$ | 181 |
| II-65 | H | Cl | H | 4-Cl—Ph | 4'-O—$CHCH_3$—$CHCH_3$—O— | | $CH_3$ | 182 |

-continued

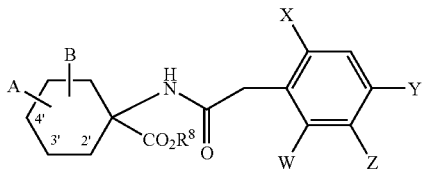

(II)

| Ex. No. | W | X | Y | Z | A | B | R⁸ | m.p. °C. |
|---|---|---|---|---|---|---|---|---|
| II-66 | H | $CH_3$ | H | $CH_3$ | 3'-O—$(CH_2)_2$—O— | | $CH_3$ | 111 |
| II-67 | $C_2H_5$ | Br | $CH_3$ | H | 3'-O—$(CH_2)_2$—O— | | $CH_3$ | 174 |
| II-68 | $CH_3$ | $CH_3$ | Cl | H | 3'-O—$(CH_2)_2$—O— | | $CH_3$ | 154 |
| II-69 | $CH_3$ | $CH_3$ | Cl | H | 3'-O—CH—$CH_2$—O—<br>               $CH_2$—$OCH_3$ | | $CH_3$ | oil |
| II-70 | $CH_3$ | $CH_3$ | $CH_3$ | H | 3'-O—CH—$CH_2$—O—<br>               $CH_2$—$OCH_3$ | | $CH_3$ | oil |
| II-71 | H | $CH_3$ | H | $CH_3$ | 3'-O—CH—$CH_2$—O—<br>               $CH_2$—$OCH_3$ | | $CH_3$ | oil |
| II-72 | $C_2H_5$ | Br | $CH_3$ | H | 3'-O—CH—$CH_2$—O—<br>               $CH_2$—$OCH_3$ | | $CH_3$ | oil |
| II-73 | $C_2H_5$ | Br | $CH_3$ | H | 4'-O—$CHCH_3$—$CH_2$—O— | | $CH_3$ | 143 |
| II-74 | H | Cl | H | 4-Cl—Ph | 4'-O—$CH_2$—$CHCH_3$—$CH_2$—O— | | $CH_3$ | 169 |
| II-75 | $CH_3$ | $C_2H_5$ | Br | H | 4'-O—$(CH_2)_3$—O— | | $CH_3$ | 165 |
| II-76 | H | Cl | H | 4-Cl—Ph | 4'-O—$CHCH_3$—$(CH_2)_2$—O— | | $CH_3$ | 161 |
| II-77 | H | Cl | H | 4-Cl—Ph | 4'-O—$CHCH_3$—$CH_2$—$CHCH_3$—O— | | $CH_3$ | 74 |
| II-78 | $C_2H_5$ | Br | $CH_3$ | H | 4'-O—$CHCH_3$—$CH_2$—$CHCH_3$—O— | | $CH_3$ | 84 |

*The logP values given in the Preparation Examples and Tables above are determined in accordance with EEC Directive 79/831 Annex V.A8 by HPLC (High Performance Liquid Chromatography) on a reversed-phase column (C 18). Temperature: 43° C.

In the acidic range, the determination is carried out at pH 2.3 using 0.1% aqueous phosphoric acid and acetonitrile as mobile phases; linear gradient from 10% acetonitrile to 95% acetonitrile.

The determination by LC-MS in the acidic range is carried out at pH 2.7 using 0.1% aqueous formic acid and acetonitrile (comprises 0.1% formic acid) as mobile phases; linear gradient from 10% acetonitrile to 95% acetonitrile.

The determination by LC-MS in the neutral range is carried out at pH 7.8 using 0.001 molar aqueous ammonium bicarbonate solution and acetonitrile as mobile phases; linear gradient from 10% acetonitrile to 95% acetonitrile.

Calibration is carried out using unbranched alkan-2-ones (having 3 to 16 carbon atoms) with known log P values (determination of the log P values by the retention times using linear interpolation between two successive alkanones).

The lambda-max values were determined in the maxima of the chromatographic signals using the UV spectra from 200 nm to 400 nm.

Example (XXI-1)

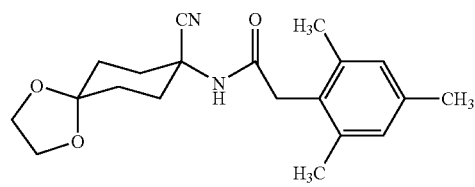

49.4 ml of triethylamine are added to 65 g of 1,4-dioxaspiro [4.5]decane-8-amino-8-carbonitrile in 800 ml of anhydrous tetrahydrofuran (THF). At 0 to 10° C., 70.2 g of mesitylene acetyl chloride in 80 ml of anhydrous THF are added dropwise.

The mixture is stirred at room temperature.

After the reaction has ended (monitored by thin-layer chromatography), the reaction solution is added with stirring to 1.2 l of ice-water, 200 ml of 1N HCl are added and the precipitate is filtered off with suction. The latter is taken up in dichloromethane, and the aqueous phase is removed. The organic phase is dried, the solvent is distilled off and the residue is recrystallized from 320 ml of toluene/640 ml of n-hexane.

Yield: 107.9 g (88% of theory), m.p. >220° C.

Example XIV-1-1

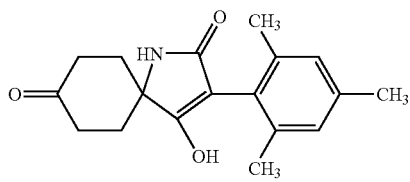

At room temperature, 20.6 g of the compound of Example I-1-c-2 in 24 g of semiconcentrated aqueous sodium hydroxide solution and about 100 ml of ethanol are stirred under argon protective gas for one hour, and the ethanol is then evaporated off. The solution is then acidified using hydrochloric acid, the entire mixture is dissolved in methylene chloride and the organic phase is separated off and concentrated by evaporation. The residue is stirred at 60° C. in 4 N hydrochloric acid for two hours.

The precipitate is separated off and stirred in ethyl acetate.

Yield: 6.67 g; m.p.: 293.9° C.

Example XVI-1

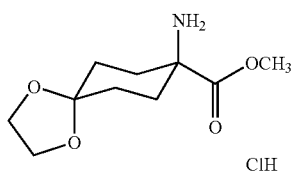

46 g of 1,4-dioxa[4.5]decane-8-amino-8-carboxylic acid are initially charged in 350 ml of anhydrous methanol, and 32.6 g (0.275 mol) of thionyl chloride are added dropwise at from 0 to 5° C. The mixture is stirred at 0° C. for 30 minutes (suspension) and then at 40° C. overnight.

The mixture is cooled, the potassium chloride is filtered off with suction and the solvent is distilled off. The residue is triturated with MTB ether and filtered off with suction.

Yield: 48.63 g (83% of theory), m.p.: decomposition

The following novel compounds of the formula (XVI) are obtained analogously to Example XVI-1

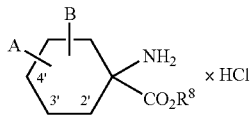
(XVI)

| Ex. No. | A | B | $R^8$ | m.p. ° C. |
|---|---|---|---|---|
| XVI-2 | 4'-O—CHCH$_3$—CH$_2$—O— | | CH$_3$ | *1.18-1.19 (2 d, 3 H, CH$CH_3$) 3.76 (2 s, 3 H, OCH$_3$) |
| XVI-3 | 4'-O—CHCH$_3$—CHCH$_3$—O— | | CH$_3$ | *3.76 (s, 3 H, OCH$_3$) 4.18-4.23 (m, 2 H, 2 × $CH$—O) |
| XVI | 4'-O—(CH$_2$)$_3$—O— | | CH$_3$ | resin |
| XVI-5 | 4'-O—CHCH$_3$—(CH$_2$)$_2$—O— | | CH$_3$ | *1.07-1.08 (d, 3 H, CH$CH_3$) 3.77 (s, 3 H, OCH$_3$) |
| XVI-6 | —O—CH$_2$—CHCH$_3$—CH$_2$—O— | | CH$_3$ | *0.77 (d, 3 H, CH$CH_3$) 8.71 (3 H, br, N$H_3^+$) |
| XVI-7 | 4'-O—CHCH$_3$—CH$_2$—CHCH$_3$—O— | | CH$_3$ | *1.07-1.15 (m, 6 H, 2 × CH$CH_3$) 3.93-4.0 (m, 2 H, O—$CH$) |
| XVI-8 | 4'-O—CH$_2$—C(CH$_3$)$_2$—CH$_2$—O— | | CH$_3$ | *0.9 (s, 6 H, C(CH$_3$)$_2$) 3.76 (s, 3 H, OC$H_3$) |
| XVI-9 | 3'-O—(CH$_2$)$_2$—O— | | CH$_3$ | *3.74, 3.75 (2 s, 3 H, CO$_2CH_3$) 3.79-3.99 (m, 4 H, —O—($CH_2$)$_2$—O—) |
| XVI-10 | 3'-O—CH—CH$_2$—O—         \|         CH$_2$—OCH$_3$ | | CH$_3$ | *3.28 (2 s, 3 H, OC$H_3$) 3.73-3.75 (4 s, 3 H, CO$_2CH_3$) |

*$^1$H-NMR (400 MHz, d$_6$-DMSO): shift δ in ppm

The substituted 1,4-dioxa[4,5]decane-8-amino-8-carboxylic esters and their salts of the formula (XVI'), the optionally substituted 1,4-dioxa[4,5]decane-7-amino-7-carboxylic esters and their salts of the formula (XVI") and the optionally substituted 1,5-dioxa[5,5]undecane-9-amino-9-carboxylic esters and their salts of the formula (XVI'''), possible substituents being the substituents mentioned at the outset in the definition of A, B, are novel and form part of the subject-matter of the invention:

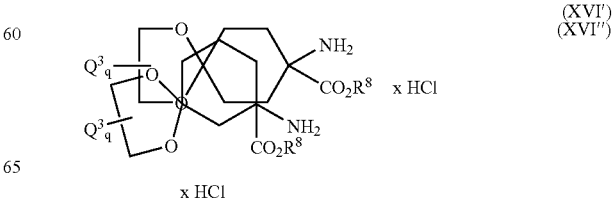
(XVI')
(XVI")

-continued

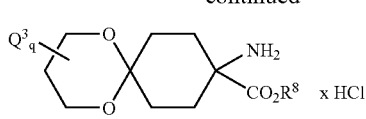
(XVI''')

in which
Q³ represents C₁-C₄-alkyl, C₁-C₃-haloalkyl, C₁-C₄-alkoxy or C₁-C₄-alkoxy-C₁-C₂-alkyl,
q represents 1, 2 or 3 and, in the case of the compounds of the formulae (XVI'') and (XVI'''), may also represent 0,
R⁸ is as defined above.

Example XIX-1

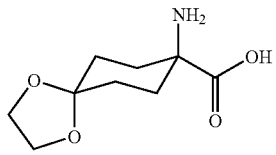

112 g of the compound of Example XXIII-8 are suspended in 710 ml of 30% strength KOH and, under reflux, stirred under an atmosphere of nitrogen.

At from 0 to 20° C., the mixture is acidified with concentrated HCl to a pH of from 5.2 to 5.3 and filtered off with suction, the filtrate is subjected to an azeotropic distillation with methanol until a volume of about 0.5 l is obtained, the potassium chloride is filtered off with suction and the filtrate is concentrated using a rotary evaporator and dehydrated azeotropically with methanol.

Yield: 46 g (46% of theory).

The following novel compounds of the formula (XIX) are obtained analogously to Example XIX-1

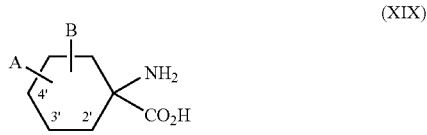
(XIX)

| Ex. No. | A | B |
|---|---|---|
| XIX-2 | 4'-O—CHCH₃—CH₂—O— | |
| XIX-3 | 4'-O—CHCH₃—CHCH₃—O— | |
| XIX-4 | 4'-O—(CH₂)₃—O— | |
| XIX-5 | 4'-O—CHCH₃—(CH₂)₂—O— | |
| XIX-6 | 4'-O—CH₂—CHCH₃—CH₂—O— | |
| XIX-7 | 4'-O—CHCH₃—CH₂—CHCH₃—O— | |
| XIX-8 | 4'-O—CH₂—C(CH₃)₂—CH₂—O— | |
| XIX-9 | 3'-O—(CH₂)₂—O— | |
| XIX-10 | 3'-O—CH—CH₂—O—<br>            \|<br>          CH₂—OCH₃ | |

Without further purification, the amino acids were directly esterified to give the compounds (XVI). These were characterized. The substituted 1,4-dioxa[4,5]decane-8-amino-8-carboxylic acids (XIX'), the optionally substituted 1,4-dioxa[4,5]decane-7-amino-7-carboxylic acids of the formula (XIX'') and the optionally substituted 1,5-dioxa[5,5]undecane-9-aminocarboxylic acids of the formula (XIX'''), possible substituents of which are the substituents mentioned at the outset in the definition of the radicals A, B, are novel and also form part of the subject-matter of the invention:

(XIX')

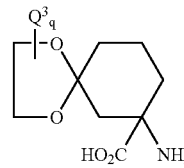
(XIX'')

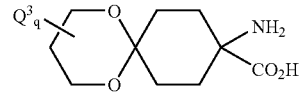
(XIX''')

in which
Q³ is as defined above and
q represents 1, 2 or 3 and, in the case of the compounds of the formulae (XIX'') and (XIX'''), also 0.

Example XXIII-1

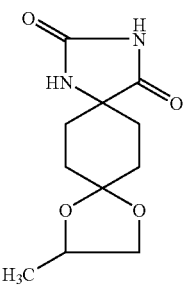

16.4 g (335 mmol) of sodium cyanide and 128.7 g (1339 mmol) of ammonium carbonate are initially charged in 600 ml of water and, at room temperature, 57 g (335 mmol) of 1,4-dioxa[4,5]decane-2-methyl-8-one (XXIV-1), dissolved in 30 ml of ethanol, are slowly added dropwise.

The mixture is stirred at from 55 to 60° C. for about 12 to 15 hours.

The mixture is cooled to 0° C., the solid is filtered off with suction and resuspended in water, the suspension is filtered off with suction and the product is washed with hexane and dried.

Yield: 73.6 g (92% of theory). 2 Isomers 1:1.

The following novel compounds of the formula (XXI) are obtained analogously to Example (XXIII-1)

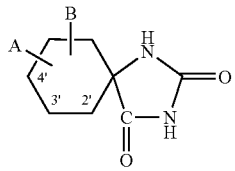

(XXIII)

| Ex. No. | A B | $^1$H-NMR (400 MHz) | Shifts δ in ppm |
|---|---|---|---|
| XXIII-1 | 4'-O—CHCH$_3$—CH$_2$—O— | d$_6$-DMSO | 10.53 (s); 8.35 (s); 4.15 (m, 1H); 4.02 (m, 1 H); 3.37 (m, 1 H); 1.93-1.50 (6 m, 8 H); 1.18 (dd, J = 6.2 Hz, 6.5 Hz. 3 H) |
| XXIII-2 | 4'-O—CHCH$_3$—CHCH$_3$—O— | d$_6$-DMSO 2 diastereomers 2:1 | 10.52 (s); 8.35 (s); 4.18 (m) + 3.59 (m): Σ2 H; 1.90-1.50 (bm, Σ8 H); 1.18 (dd, J = 6.3 Hz, 5.8 Hz) + 1.06 (dd, J = 6.1 Hz, 7.7 Hz): Σ6 H |
| XXIII-3 | 4'-O—(CH$_2$)$_3$—O— | d$_6$-DMSO | 10.50 (s); 8.35 (s); 3.81 (m, 4 H); 2.12 (m, 2 H); 1.78 (m, 2 H); 1.60 (m, 4 H); 1.48 (m, 2 H) |
| XXIII-4 | 4'-O—CHCH$_3$—(CH$_2$)$_2$—O— | d$_6$-DMSO 2 diastereomers | 10.50 (s); 8.31/8.30 (each s.); 4.09-3.67 (6 m, 3 H); 2.54 (m, 1 H); 1.88 (m, 1 H); 1.76-1.39 (6 m, 8 H); 1.08 (dd, J = 6 Hz) |
| XXIII-5 | 4'-O—CH$_2$—CHCH$_3$—CH$_2$—O— | d$_6$-DMSO | 10.51 (s); 8.34 (s); 3.73 (m, 2 H); 3.51 (dd, J = 9.7 Hz, 11.5 Hz, 1 H); 3.43 (dd, J = 9.7 Hz, 11.5 Hz, 1 H); 2.41 (m, 1 H); 1.88-1.41 (bm, 8 H); 0.76 (d, J = 6.8 Hz, 3 H) |
| XXIII-6 | 4'-O—CHCH$_3$—CH$_2$—CHCH$_3$—O— | d$_6$-DMSO 2 diastereomers 2:1 | 10.53 (s); 8.28 (s); 4.02 + 3.92 (each m, Σ2 H); 1.95 (6 m) + 1.75-1.40 (bm): Σ10 H; 1.12 (dd, J = 6.3 Hz, 10.8 Hz) + 1.08 (dd, J = 6.1 Hz, 11.3 Hz): Σ6 H |
| XXIII-7 | 4'-O—CH$_2$—C(CH$_3$)$_2$—CH$_2$—O— | d$_6$-DMSO | 10.50 (s); 8.34 (s); 3.45 (s, 2 H); 3.43 (s, 2 H); 2.11 (m, 2 H); 1.78 (m, 2 H); 1.62 (m, 2 H); 1.50 (m, 2 H); 0.89 (s, 6 H) |
| XXIII-8 | 3'-O—(CH$_2$)$_2$—O— | d$_6$-DMSO | 10.6 (bm, 1 H), 7.32 (bm, 1 H), 3.9 (m, 4 H), 1.71 (m, 4 H), 1.61 (m, 1 H), 1.52 (m, 3 H) |
| XXIII-9 | 3'-O—CH—CH$_2$—O— <br> \| <br> CH$_2$—OCH$_3$ | d$_6$-DMSO isomer mixtures | 10.5 (bm), 7.16 (bm), 6.98 (bm), 6.87 (bm), 6.60 (bm), 4.22 (m), 4.01 (m), 3.64 (m), 3.34 (m), 3.27 (m), 3.17 (s), 2.40 (m), 2.22 (m), 2.01 (m), 1.90-1.60 (bm) |

The compounds of the formulae (XXIII'), (XXIII'') and (XXIII''')

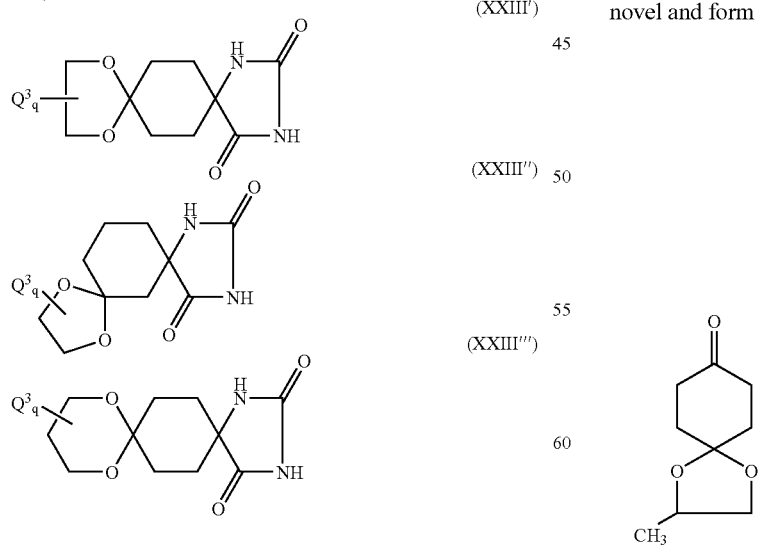

in which
Q$^3$ is as defined above and
q represents 1, 2 or 3 and, in the case of the compounds of the formulae (XXIII'') and (XXIII'''), may also represent 0, are novel and form part of the subject-matter of the invention.

Example XXIV-1

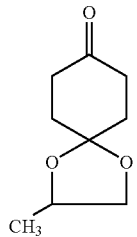

53.7 g (423 mmol) of oxalyl chloride are initially charged in 1000 ml of dichloromethane. At −70° C., a solution of 60 ml of dimethyl sulphoxide in 100 ml of dichloromethane is added dropwise, and the mixture is stirred for 20 min. 66 g (385 mmol) of 1,4-dioxa[4,5]decane-2-methyl-8-ol are dissolved in 300 ml of dichloromethane and, at the same temperature, added dropwise over a period of 1 h to the reaction solution. The mixture is stirred for another hour, the ice bath is then removed and the mixture is allowed to warm to −40° C. over a period of 30 min. The mixture is stirred at this temperature for 30 min, triethylamine (140 ml) is then added and the mixture is allowed to warm to room temperature (1 h) and stirred overnight.

The reaction is quenched with 500 ml of water and the mixture is stirred for another 15 minutes.

The organic phase is separated off and the aqueous solution is extracted 3× with 200 ml of dichloromethane. The combined organic phases are dried with sodium sulphate and the solvent is distilled off. Purification by chromatography on silica gel, hexane/ethyl acetate 2:1.

Yield: 58 g (88% of theory)

$^1$H-NMR (400 MHz, d$_6$-DMSO): δ=4.24 (m, 1H), 3.46 (t, 1H), 4.10 (dd, 1H), 2.36 (m, 4H), 1.94 (m, 4H), 1.23 (d, 3H) ppm.

Example XXIV-7

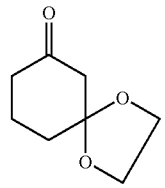

50 g of cyclohexane-1,3-dione, 27.67 g of 1,2-ethanediol, 500 ml of toluene and 0.849 g of 4-toluenesulphonic acid monohydrate are mixed and, on a water separator, boiled under reflux for 3 to 4 h. The mixture is washed with 100 ml of sat. NaHCO$_3$ solution and 2× with sat. NaCl solution, dried and concentrated using a rotary evaporator. The mixture is then subjected to fractional distillation under high vacuum (distillation of the product at 85° C./1 mbar or 62-75° C./0.15 mmHg).

Yield: 21.9 g (27% of theory)

$^1$H-NMR (400 MHz, CD$_3$CN): δ=3.9 (m, 4H), 2.52 (s, 2H), 2.27 (m, 2H), 1.87 (m, 2H), 1.79 (m, 2H) ppm.

The following novel compounds of the formula (XXIV) are obtained analogously to Examples (XXIV-1) and (XXIV-7)

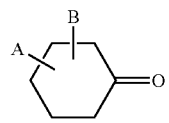

(XXIV)

| Ex. No. | A | B | 1H-NMR (400 MHz) | Shifts δ in ppm |
|---|---|---|---|---|
| XXIV-1 | 4'-O—CHCH$_3$—CH$_2$—O— | | d$_6$-DMSO | 4.24 (m, 1 H); 3.46 (t, 1 H, J = 7.7 Hz); 4.10 (dd, 1 H, J = 5.8 HZ, 7.9 Hz); 2.36 (m, 4 H); 1.94 (m, 4 H); 1.23 (d, J = 6 Hz/3 H) |
| XXIV-2 | 4'-O—CHCH$_3$—CHCH$_3$—O— | | d$_6$-DMSO 2 isomers 2:1 | 4.28/3.68 (each m, Σ2 H); 2.35/1.94 (each m, Σ8 H); 1.22 (d. J = 5.7 Hz) + 1.10 (d, J = 6.1 Hz); Σ6 H |
| XXIV-3 | 4'-O—(CH$_2$)$_3$—O— | | d$_6$-DMSO | 3.88 (dd, J = 5.6 Hz, 4 H); 2.25 (m, 4 H), 2.08 (m, 4 H); 1.64 (m, 2 H) |
| XXIV-4 | 4'-O—CHCH$_3$—(CH$_2$)$_2$—O— | | in d$_6$-DMSO | 4.03 (m, 1 H); 3.93 (m, 1 H); 3.80 (m, 1 H); 2.30 (m, 2 H); 2.22 (m, 4 H); 1.87 (m, 2 H); 1.51 (m, 2 H); 1.10 (d, 3 H, J = 6.1 Hz) |
| XXIV-5 | 4'-O—CH$_2$—CHCH$_3$—CH$_2$—O— | | d$_6$-DMSO 1 isomer | 3.81 (dd, J = 4.7 Hz, 12.0 Hz, 2 H); 3.52 (dd, 2 H, J = 9.7 Hz); 2.28 (m, 2 H); 2.21 (m, 4 H); 1.95 (m, 2 H); 1.91 (m, 1 H); 0.80 (d, J = 6.8 Hz, 1 H) |
| XXIV-6 | 4'-O—CHCH$_3$—CH$_2$—CHCH$_3$—O— | | d$_6$-DMSO 2 isomers = 45:55 | 4.02 (m, 2 H); 2.31/2.21/1.97/1.87/1.61 (in each case m, Σ10 H); 1.17 (d, 3 H, J = 6.3 Hz); 1.12 (d, 3 H, J = 6.1 Hz) |
| XXIV-8 | 3'-O—CH(CH$_2$—OCH$_3$)—CH$_2$—O— | | CD$_3$CN isomer mixture | 4.23 (m), 4.01 (m), 3.66 (m), 3.38 (m), 3.31 (s), 2.54 (s), 2.26 (m), 1.87 (m), 1.78 (m), 1.56 (m) |

Some of the ketones of the formula (XXIV) are commercially available, some are known (JACS 108, 2691-2699; 1986; JACS 109, 1363-1370, 1987) and some are novel.

Some of the compounds of the formula (XXV) are commercially available, some are known (J. Med. Chem. 24, 341-346, 1981) and some are novel.

Example XXV-1

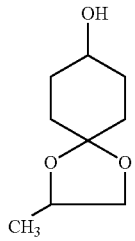

114 g of 4-hydroxycyclohexanone, 80 g of 1,2 propanediol (77 ml) and 2 g of 4-toluenesulphonic acid dihydrate are added to 500 ml of toluene. The mixture is boiled on a water separator until no more water separates out. For work-up, 1 ml of triethylamine is added, and the reaction solution is washed with 200 ml of water, dried and concentrated using a rotary evaporator. The residue (104 g) is distilled under reduced pressure.

Yield: 76.3 g ≙44% of theory

The following novel compounds of the formula (XXIV) are obtained analogously to Example (XXIV-1)

Example I-2-a-1

0.32 g (1.00 mmol) of the compound of Example XIV-2-1, 0.62 g (10 mmol) of ethylene glycol and 50 mg of 4-toluenesulphonic acid in 15 ml of toluene are heated under reflux overnight.

For work-up, the mixture is cooled and the solid is filtered off with suction and dried.

Yield: 0.35 g (96% of theory), m.p. 267° C.

The following compounds of the formula (I-2-a) are obtained analogously to Example (I-2-a-1) and in accordance with the general statements on the preparation:

(XXIV)

| Ex. No. | A | B | 1H-NMR (400 MHz, $d_6$-DMSO) Shift δ in ppm |
|---|---|---|---|
| XXV-1 | —O—CHCH$_3$—CH$_2$—O— | | 4.38 (dd, 1 H J = 4.2 Hz, 5.3 Hz); 4.12 (m, 1 H); 3.97 (m, 1 H); 3.54 (6 s, 1 H); 3.33 (m, 1 H); 1.67 (m, 4 H); 1.44 (m, 4 H); 1.16 (dd, J = 6.1 HZ, 3 H); |
| XXV-2 | —O—CHCH$_3$—CHCH$_3$—O— | | 4.35 (m); 4.16 (m); 3.54 (m); 1.67 (m); 1.44 (m); 1.15 (dd, J = 5.7 Hz); 1.03 (dd, J = 6.1 Hz) |
| XXV-3 | —O—(CH$_2$)$_3$—O— | | 4.35 (OH); 3.77 (m, 4 H); 3.52 (m, 1 H); 1.96 (m, 2 H); 1.57 (m, 4 H); 1.50-128 (m, 4 H) |
| XXV-4 | —O—CHCH$_3$—(CH$_2$)$_2$—O— | | 4.34 (m, 1 H); 3.95 (m, 1 H); 3.87 (m, 1 H); 3.67 (m, 1 H); 3.53 (m, 1 H); 2.25 (m, 1 H); 2.66-2.20 (m, 10 H); 1.06 (dd, J = 6.1 Hz, 3 H) |
| XXV-5 | —O—CH$_2$—CHCH$_3$—CH$_2$—O— | | 4.41 (bs, OH); 3.69 (m) + 3.53 (m) + 3.43 (m) + 3.35 (m) + 3.25 (m): Σ5 H; 2.12 (m, 1 H); 1.74 (m, 2 H); 1.62-1.23 (m, 5 H); 0.80 (d. J = 6.8 Hz) + 0.75 (d, J = 6.8 Hz): Σ3 H |
| XXV-6 | —O—CHCH$_3$—CH$_2$—CHCH$_3$—O— | | 4.34 (s, OH); 3.94 (m); 3.53 (m) 2.20 (m); 1.78 (m); 2.65-2.20 (bm); 1.10 (dd, J = 6.3 Hz); 1.05 (dd, J = 6 Hz) |

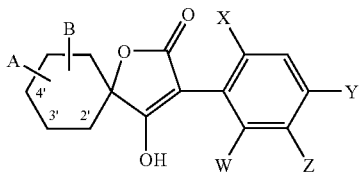

(I-2-a)

| Ex. No. | W | X | Y | Z | A | B | m.p. °C. |
|---|---|---|---|---|---|---|---|
| I-2-a-2 | CH₃ | CH₃ | CH₃ | H | 4'—O—(CH₂)₂—O— | | >250 |
| I-2-a-3 | CH₃ | CH₃ | Cl | H | 4'-O—CHCH₃—CH₂—O— | | 198 |
| I-2-a-4 | CH₃ | CH₃ | Cl | H | 4'-O—CHCH₂Cl—CH₂—O— | | 248 |
| I-2-a-5 | CH₃ | CH₃ | Br | H | 4'—O—(CH₂)₂—O— | | 266 |
| I-2-a-6 | CH₃ | CH₃ | Cl | H | 4'-O—(CH₂)₃—O— | | 227 |
| I-2-a-7 | CH₃ | CH₃ | Cl | H | 4'-O—CH₂—C(CH₃)₂—CH₂—O— | | 270 |
| I-2-a-8 | H | CH₃ | H | 4-Cl—Ph | 4'—O—(CH₂)₂—O— | | * |

Ph = 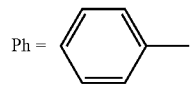

*¹H-NMR (400 MHz, d₆-DMSO): δ = 2.19 (s, 3 H, Ar—C$\underline{H}$₃), 3.92 (s, 4 H, (O—C$\underline{H}$₂—)₂), 7.3 (m, 1 H, Ar—$\underline{H}$), 7.4 (m, 1 H, Ar—$\underline{H}$), 7.5 (m, 3 H, Ar—H), 7.65 (m, 2 H—Ar—$\underline{H}$) ppm.

Example I-2-b-1

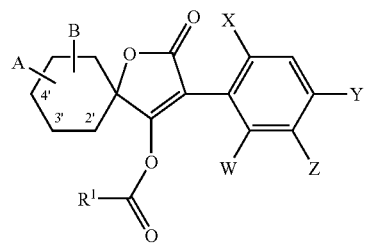

0.22 g (0.60 mmol) of the compound of Example (I-2-a-1) is initially charged in 10 ml of dichloromethane, 0.067 g (0.66 mmol) of triethylamine is added, 0.071 g (0.66 mmol) of isobutyryl chloride is added dropwise with ice-cooling and the mixture is stirred at room temperature overnight.

For work-up, the mixture is extracted with 10% strength citric acid solution and saturated sodium bicarbonate solution and the organic phase is dried with sodium sulphate and concentrated using a rotary evaporator.

Yield: 0.22 g (77% of theory), m.p. 142° C.

The following compounds of the formula (I-2-b) are obtained analogously to Example (I-2-b-1) and in accordance with the general statements on the preparation:

(I-2-b)

| Ex. No. | W | X | Y | Z | A | B | R¹ | m.p. °C. |
|---|---|---|---|---|---|---|---|---|
| I-2-b-2 | CH₃ | CH₃ | CH₃ | H | 4'—O—(CH₂)₂—O— | | t-C₄H₉ | 165-169 |
| I-2-b-3 | CH₃ | CH₃ | Cl | H | 4'-O—CHCH₂Cl—CH₂—O— | | i-C₃H₇ | 240-243 |
| I-2-b-4 | CH₃ | CH₃ | Cl | H | 4'-O—CHCH₃—CH₂—O— | | i-C₃H₇ | 232 |

Example XIV-2-1

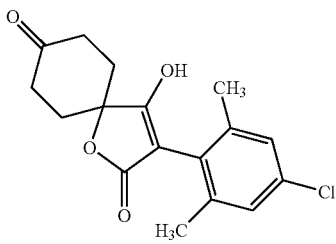

4.59 g (40.89 mmol) of potassium tert-butoxide are initially charged in 35 ml of dimethylformamide, with ice-cooling, a solution of 10.00 g (27.26 mmol) of the compound of Example (III-A-1) in 15 ml of dimethylformamide is added dropwise at from 0 to 10° C. and the mixture is stirred at room temperature overnight.

For work-up, most of the DMF is distilled off using a rotary evaporator, and the residue is partitioned between water and ethyl acetate. The aqueous phase is acidified with hydrochloric acid and the precipitated product is filtered off with suction, washed with water and dried.

Further purification is carried out by preparative HPLC (silica gel RP-18, mobile phase acetonitrile/water).

Yield: 2.20 g (25% of theory), m.p. 210° C.

The following compounds of the formula (XIV-2) are obtained analogously to Example (XIV-2-1) and in accordance with the general statements on the preparation of compounds of the formula (XIV-2) in WO 99/16 748:

(XIV-2)

| Ex. No. | W | X | Y | Z | A | B | m.p. ° C. |
|---|---|---|---|---|---|---|---|
| XIV-2-2 | $CH_3$ | $CH_3$ | $CH_3$ | H | | 4'-C=O | 187-190 |
| XIV-2-3 | $CH_3$ | $CH_3$ | Br | H | | 4'-C=O | 222 |

Example III-A-1

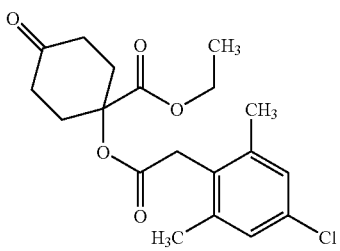

5.00 g (26.85 mmol) of ethyl 4-oxo-1-hydroxycyclohexanecarboxylate and 3.26 g (32.22 mmol) of triethylamine are initially charged in 35 ml of dichloromethane, with ice-cooling, a solution of 6.41 g (29.53 mmol) of 2,6-dimethyl-4-chlorophenylacetyl chloride in 15 ml of dichloromethane is added at from 0 to 10° C. and the mixture is stirred at room temperature overnight.

For work-up, the mixture is extracted with 10% strength citric acid solution and saturated sodium bicarbonate solution and the organic phase is dried with sodium sulphate and concentrated using a rotary evaporator.

Yield: 10.00 g of an oil (67% of theory).

The following compounds of the formula (III-A) are obtained analogously to Example (III-A-1) and in accordance with the general statements on the preparation:

(III-A)

| Ex. No. | W | X | Y | Z | $R^8$ | m.p. ° C. |
|---|---|---|---|---|---|---|
| III-A-2 | $CH_3$ | $CH_3$ | $CH_3$ | H | $C_2H_5$ | oil |
| III-A-3 | $CH_3$ | $CH_3$ | Br | H | $C_2H_5$ | oil |

The oils were used without further characterization for synthesizing compounds of the formula (XIV-2).

Example A

*Myzus persicae* Test (7:1)

| Solvent: | 7 parts by weight of dimethylformamide |
|---|---|
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) which are heavily infested by the green peach aphid (*Myzus persicae*) are treated by being dipped into the preparation of active compound of the desired concentration.

After the desired period of time, the kill in % is determined. 100% means that all aphids have been killed; 0% means that none of the aphids have been killed.

In this test, for example, the following compounds of the Preparation Examples show an activity of ≧80% at a concentration of 1000 ppm: Ex. I-1-a-2, Ex. I-1-a-1, Ex. I-1-a-3, Ex. I-1-a-4, Ex. I-1-b-1, Ex. I-1-c-3, Ex. I-1-c-4, Ex. I-1-c-1.

Example B

*Aphis gossypii* Test (7:1)

| Solvent: | 7 parts by weight of dimethylformamide |
|---|---|
| Emulsifier: | 1 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cotton leaves (*Gossypium hirsutum*) which are heavily infested by the cotton aphid (*Aphis gossypii*) are treated by being dipped into the preparation of active compound of the desired concentration.

After the desired period of time, the kill in % is determined. 100% means that all aphids have been killed; 0% means that none of the aphids have been killed.

In this test, for example, the following compounds of the Preparation Examples show an activity of ≧80% at a concentration of 200 ppm: Ex. I-1-a-2, Ex. I-1-a-3, Ex. I-1-a-4, Ex. I-1-c-1.

Example C

| *Phaedon cochleariae* - larvae Test (7:1) | |
| --- | --- |
| Solvent: | 7 parts by weight of dimethylformamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with larvae of the mustard beetle (*Phaedon cochleariae*) while the leaves are still moist.

After the desired period of time, the kill in % is determined. 100% means that all beetle larvae have been killed; 0% means that none of the beetle larvae have been killed.

In this test, for example, the following compounds of the Preparation Examples show an activity of ≧90% at a concentration of 1000 ppm: Ex. I-2-a-2, Ex. I-2-b-2, Ex. I-1-a-2, Ex. I-1-a-1, Ex. I-1-a-3, Ex. I-1-a-4, Ex. I-1-c-3, Ex. I-1-c-4, Ex. I-1-c-5, Ex. I-1-b-1, Ex. I-1-c-1.

Example D

| *Plutella* Test (7:1) | |
| --- | --- |
| Solvent: | 7 parts by weight of dimethylformamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the diamond back moth (*Plutella xylostella*) while the leaves are still moist.

After the desired period of time, the kill in % is determined. 100% means that all caterpillars have been killed; 0% means that none of the caterpillars have been killed.

In this test, for example, the following compounds of the Preparation Examples show an activity of 100% at a concentration of 1000 ppm: Ex. I-2-a-2, Ex. I-2-b-2, Ex. I-1-a-2.

Example E

| *Spodoptera frugiperda* Test (7:1) | |
| --- | --- |
| Solvent: | 7 parts by weight of dimethylformamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the army worm (*Spodoptera frugiperda*) while the leaves are still moist.

After the desired period of time, the kill in % is determined. 100% means that all caterpillars have been killed; 0% means that none of the caterpillars have been killed.

In this test, for example, the following compounds of the Preparation Examples show an activity of ≧85% at a concentration of 1000 ppm: Ex. I-2-a-2, Ex. I-2-b-2, Ex. I-1-a-2, Ex. I-1-a-3, Ex. I-1-c-3.

Example F

| *Nephotettix* Test (7:1) | |
| --- | --- |
| Solvent: | 7 parts by weight of dimethylformamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Rice seedlings (*Oryza sativa*) are treated by being dipped into the preparation of active compound of the desired concentration and are populated with the green rice leaf hopper (*Nephotettix cincticeps*) while the leaves are still moist.

After the desired period of time, the kill in % is determined. 100% means that all leaf hoppers have been killed; 0% means that none of the leaf hoppers have been killed.

In this test, for example, the following compounds of the Preparation Examples show an activity of 100% at a concentration of 1000 ppm: Ex. I-2-a-2, Ex. I-2-b-2, Ex. I-1-a-2.

Example G

| *Tetranychus* Test (7:1) (OP resistant/dip treatment) | |
| --- | --- |
| Solvent: | 7 parts by weight of dimethylformamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Bean plants (*Phaseolus vulgaris*) which are heavily infested by all stages of the greenhouse red spider mite (*Tetranychus urticae*) are treated by dipped into a preparation of active compound of the desired concentration.

After the desired period of time, the activity in % is determined. 100% means that all spider mites have been killed; 0% means that none of the spider mites have been killed.

In this test, for example, the following compounds of the Preparation Examples show an activity of ≧98% at a concentration of 100 ppm: Ex. I-1-a-1, Ex. I-1-a-3, Ex. I-1-a-4, Ex. I-1-c-4.

Example H

| *Meloidogyne* Test (7:1) | |
| --- | --- |
| Solvent: | 7 parts by weight of dimethylformamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

Vessels are filled with sand, solution of active compound, *Meloidogyne incognita* egg/larvae suspension and lettuce seeds. The lettuce seeds germinate and the plants develop. On the roots, galls are formed.

After the desired period of time, the nematicidal activity is determined in % by the formation of galls. 100% means that no galls have been found; 0% means that the number of galls on the treated plants corresponds to that of the untreated control.

In this test, for example, the following compound of the Preparation Examples shows an activity of 95% at a concentration of 20 ppm: Ex. I-1-a-4.

Example I

| *Myzus persicae* Test | |
| --- | --- |
| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) which are heavily infested by the green peach aphid (*Myzus persicae*) are treated by being dipped into the preparation of active compound of the desired concentration.

After the desired period of time, the kill in % is determined. 100% means that all aphids have been killed; 0% means that none of the aphids have been killed.

In this test, for example, the following compounds of the Preparation Examples show an activity of ≧80% at a concentration of 100 ppm: Ex. I-2-a-5, Ex. I-1-a-11, Ex. I-1-a-14, Ex. I-1-a-12, Ex. I-1-a-13.

Example J

| *Tetranychus* Test (OP resistant/dip treatment) | |
| --- | --- |
| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Bean plants (*Phaseolus vulgaris*) which are heavily infested by all stages of the greenhouse red spider mite (*Tetranychus urticae*) are treated by being dipped into a preparation of active compound of the desired concentration.

After the desired period of time, the activity in % is determined. 100% means that all spider mites have been killed; 0% means that none of the spider mites have been killed.

In this test, for example, the following compounds of the Preparation Examples show an activity ≧90% at a concentration of 100 ppm: Ex. I-1-a-11, Ex. I-1-a-14, Ex. I-1-a-12, Ex. I-1-a-21, Ex. I-1-a-22, Ex. I-1-a-9, Ex. I-1-a-43, Ex. I-1-a-46, Ex. I-1-a-53, Ex. I-1-a-70, Ex. I-1-c-16, Ex. I-1-c-20.

Example K

| *Meloidogyne* Test | |
| --- | --- |
| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

Vessels are filled with sand, solution of active compound, *Meloidogyne incognita* egg/larvae suspension and lettuce seeds. The lettuce seeds germinate and the plants develop. On the roots, galls are formed.

After the desired period of time, the nematicidal activity is determined in % by the formation of galls. 100% means that no galls have been found; 0% means that the number of galls on the treated plants corresponds to that of the untreated control.

In this test, for example, the following compound of the Preparation Examples shows an activity of 80% at a concentration of 20 ppm: Ex. I-1-a-12.

Example L

| Aphis gossypii Test | |
|---|---|
| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cotton leaves (*Gossypium hirsutum*) which are heavily infested by the cotton aphid (*Aphis gossypii*) are treated by being dipped into the preparation of active compound of the desired concentration.

After the desired period of time, the kill in % is determined. 100% means that all aphids have been killed; 0% means that none of the aphids have been killed.

In this test, for example, the following compounds of the Preparation Examples show an activity of ≧80% at a concentration of 100 ppm: Ex. I-1-a-19, Ex. I-1-a-7, Ex. I-1-a-14, Ex. I-1-a-30, Ex. I-1-a-31, Ex. I-1-a-38, Ex. I-1-a-48, Ex. I-1-a-50, Ex. I-1-a-53, Ex. I-1-a-56, Ex. I-1-a-58, Ex. I-1-a-63, Ex. I-1-b-4, Ex. I-1-c-15, Bsp.I-1-c-19, Bsp.I-1-c-20, Bsp.I-1-c-32, Bsp.I-2-a-5.

Example M

| Phaedon cochleariae Larvae Test | |
|---|---|
| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with larvae of the mustard beetle (*Phaedon cochleariae*) while the leaves are still moist.

After the desired period of time, the kill in % is determined. 100% means that all beetle larvae have been killed; 0% means that none of the beetle larvae have been killed.

In this test, for example, the following compound of the Preparation Examples shows an activity of 100% at a concentration of 100 ppm: Ex. I-1-a-23.

Example N

| Phaedon Test (spray treatment) | |
|---|---|
| Solvents: | 78 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvents and emulsifier, and the concentrate is diluted with emulsifier-containing water to the desired concentration.

Discs of Chinese cabbage (*Brassica pekinensis*) are sprayed with a preparation of active compound of the desired concentration and, after drying, populated with larvae of the mustard beetle (*Phaedon cochleariae*).

After the desired period of time, the activity in % is determined. 100% means that all beetle larvae have been killed; 0% means that none of the beetle larvae have been killed.

In this test, for example, the following compounds of the Preparation Examples show an activity of ≧80% at an application rate of 100 g/ha: Ex. I-1-a-15, Ex. I-1-c-9, Ex. I-1-a-21 and an activity of 100% at an application rate 500 g/ha: Ex. I-1-a-18, Ex. I-1-a-20, Ex. I-1-a-22, Ex. I-1-a-8, Ex. I-1-a-10, Ex. I-1-a-7, Ex. I-1-a-9, Ex. I-1-c-6, Ex. I-1-a-16, Ex. I-1-a-24, Ex. I-1-a-27, Ex. I-1-a-30, Ex. I-1-a-31, Ex. I-1-a-32, Ex. I-1-a-33, Ex. I-1-a-34, Ex. I-1-a-38, Ex. I-1-a-39, Ex. I-1-a-43, Ex. I-1-a-45, Ex. I-1-a-46, Ex. I-1-a-47, Ex. I-1-a-49, Ex. I-1-a-51, Ex. I-1-a-52, Ex. I-1-a-53, Ex. I-1-a-54, Ex. I-1-a-56, Ex. I-1-a-61, Ex. I-1-a-63, Ex. I-1-a-64, Ex. I-1-a-65, Ex. I-1-a-66, Ex. I-1-a-67, Ex. I-1-a-68, Ex. I-1-a-71, Ex. I-1-c-19, Ex. I-1-c-31, Ex. I-1-c-34.

Example O

| Tetranychus Test (OP resistant/spray treatment) | |
|---|---|
| Solvents: | 78 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvents and emulsifier, and the concentrate is diluted with emulsifier-containing water to the desired concentration.

Bean plants (*Phaseolus vulgaris*) which are heavily infested by all stages of the greenhouse red spider mite (*Tetranychus urticae*) are treated by being dipped into a preparation of active compound of the desired concentration.

After the desired period of time, the activity in % is determined. 100% means that all spider mites have been killed; 0% means that none of the spider mites have been killed.

In this test, for example, the following compounds of the Preparation Examples show an activity of ≧80% at an application rate of 100 g/ha: Ex. I-2-b-1, Ex. I-1-a-16, Ex. I-1-a-15, Ex. I-1-c-9, Ex. I-1-c-11, Ex. I-1-a-23, Ex. I-1-c-6, Ex. I-1-a-24, Ex. I-1-a-27 and Ex. I-1-a-38, Ex. I-1-a-50, Ex. I-1-a-58, Ex. I-1-c-24, Ex. I-1-c-43.

Example P

| Meloidogyne Test (spray treatment) | |
|---|---|
| Solvent: | 80 parts by weight of acetone |

To produce a suitable preparation of active compound, 1 part by weight of active compound is mixed with the stated amount of solvent, and the concentrate is diluted with water to the desired concentration.

Vessels are filled with sand, solution of active compound, *Meloidogyne incognita* egg/larvae suspension and lettuce seeds. The lettuce seeds germinate and the plants develop. On the roots, galls are formed.

After the desired period of time, the nematicidal activity is determined in % by the formation of galls. 100% means that no galls have been found; 0% means that the number of galls on the treated plants corresponds to that of the untreated control.

In this test, for example, the following compound of the Preparation Examples shows an activity of 100% at a concentration of 20 ppm: Ex. I-1-a-15.

Example Q

| *Myzus* Test (spray treatment) | |
|---|---|
| Solvents: | 78 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvents and emulsifier, and the concentrate is diluted with emulsifying-containing water to the desired concentration.

Discs of Chinese cabbage (*Brassica pekinensis*) which are infested by all stages of the green peach aphid (*Myzus persicae*) are sprayed with a preparation of active compound of the desired concentration.

After the desired period of time, the activity in % is determined. 100% means that all aphids have been killed; 0% means that none of the aphids have been killed.

In this test, for example, the following compounds of the Preparation Examples show an activity of ≧90% at an application rate of 500 g/ha: Ex. I-1-a-18, Ex. I-1-a-19, Ex. I-1-c-10, Ex. I-1-a-20, Ex. I-1-c-11, Ex. I-1-a-23, Ex. I-1-a-21, Ex. I-1-a-22, Ex. I-1-a-8, Ex. I-1-a-10, Ex. I-1-a-7, Ex. I-1-a-9, Ex. I-1-c-6, Ex. I-2-a-1, Ex. I-2-a-3, Ex. I-2-a-4, Ex. I-2-a-7, Ex. I-2-b-1, Ex. I-2-b-3, Ex. I-2-b-4, Ex. I-2-a-5, Ex. I-1-a-16, Ex. I-1-a-24, Ex. I-1-a-26, Ex. I-1-a-28, Ex. I-1-a-29, Ex. I-1-a-30, Ex. I-1-a-31, Ex. I-1-a-32, Ex. I-1-a-33, Ex. I-1-a-34, Ex. I-1-a-35, Ex. I-1-a-36, Ex. I-1-a-37, Ex. I-1-a-38, Ex. I-1-a-39, Ex. I-1-a-40, Ex. I-1-a-41, Ex. I-1-a-42, Ex. I-1-a-43, Ex. I-1-a-44, Ex. I-1-a-45, Ex. I-1-a-46, Ex. I-1-a-47, Ex. I-1-a-48, Ex. I-1-a-49, Ex. I-1-a-50, Ex. I-1-a-51, Ex. I-1-a-52, Ex. I-1-a-53, Ex. I-1-a-54, Ex. I-1-a-56, Ex. I-1-a-57, Ex. I-1-a-58, Ex. I-1-a-59, Ex. I-1-a-60, Ex. I-1-a-61, Ex. I-1-a-62, Ex. I-1-a-63, Ex. I-1-a-64, Ex. I-1-a-65, Ex. I-1-a-66, Ex. I-1-a-67, Ex. I-1-a-69, Ex. I-1-a-70, Ex. I-1-a-71, Ex. I-1-b-4, Ex. I-1-b-6, Ex. I-1-b-7, Ex. I-1-b-8, Ex. I-1-b-10, Ex. I-1-b-11, Ex. I-1-c-14, Ex. I-1-c-15, Ex. I-1-c-16, Ex. I-1-c-17, Ex. I-1-c-18, Ex. I-1-c-19, Ex. I-1-c-20, Ex. I-1-c-21, Ex. I-1-c-22, Ex. I-1-c-23, Ex. I-1-c-24, Ex. I-1-c-25, Ex. I-1-c-26, Ex. I-1-c-30, Ex. I-1-c-31, Ex. I-1-c-32, Ex. I-1-c-33, Ex. I-1-c-34, Ex. I-1-c-35, Ex. I-1-c-36, Ex. I-1-c-40, Ex. I-1-c-41, Ex. I-1-c-42, Ex. I-1-c-43.

Example R

| *Spodoptera frugiperda* Test (spray treatment) | |
|---|---|
| Solvents: | 78 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvents and emulsifier, and the concentrate is diluted with emulsifier-containing water to the desired concentration.

Discs of maize leaves (*Zea mays*) are sprayed with a preparation of active compound of the desired concentration and, after drying, populated with caterpillars of the army worm (*Spodoptera frugiperda*).

After the desired period of time, the activity in % is determined. 100% means that all caterpillars have been killed; 0% means that none of the caterpillars have been killed.

In this test, for example, the following compounds of the Preparation Examples show an activity of ≧80% at an application rate of 500 g/ha: Ex. I-2-a-7, Ex. I-1-a-16, Ex. I-1-a-21, Ex. I-1-a-22, Ex. I-1-a-8, Ex. I-1-a-10, Ex. I-1-a-27, Ex. I-1-a-31, Ex. I-1-a-49, Ex. I-1-a-51, Ex. I-1-a-52, Ex. I-1-a-54, Ex. I-1-a-64, Ex. I-1-a-65, Ex. I-1-a-66, Ex. I-1-a-67, Ex. I-1-c-16, Ex. I-1-c-19, Ex. I-1-c-31, Ex. I-1-c-36, Ex. I-1-c-40.

Example S

| *Myzus persicae* Test (hydroponic treatment) | |
|---|---|
| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

The preparation of active compound is mixed with water. The stated concentration relates to the amount of active compound per volume unit of water (mg/l=ppm). The treated water is filled into vessels containing a pea plant (*Pisum sativum*). After the desired period of time, the plant is infected with the green peach aphid (*Myzus persicae*).

After the desired period of time, the kill in % is determined. 100% means that all aphids have been killed; 0% means that none of the aphids have been killed.

In this test, for example, the following compounds of the Preparation Examples show an activity of ≧95% at a concentration of 20 ppm: Ex. I-1-a-23, Ex. I-1-a-21, Ex. I-1-a-7, Ex. I-1-a-24, Ex. I-1-a-26, Ex. I-1-a-30, Ex. I-1-a-32, Ex. I-1-a-34, Ex. I-1-a-35, Ex. I-1-a-36, Ex. I-1-a-38, Ex. I-1-a-39, Ex. I-1-a-40, Ex. I-1-a-42, Ex. I-1-a-43, Ex. I-1-a-44, Ex. I-1-a-45, Ex. I-1-a-46, Ex. I-1-a-47, Ex. I-1-a-48, Ex. I-1-a-50, Ex. I-1-a-53, Ex. I-1-a-56, Ex. I-1-a-57, Ex. I-1-a-58, Ex. I-1-a-59, Ex. I-1-a-69, Ex. I-1-a-70, Ex. I-1-a-71, Ex. I-1-b-4, Ex. I-1-b-8, Ex. I-1-b-10, Ex. I-1-b-11, Ex. I-1-c-15, Ex. I-1-c-17, Ex. I-1-c-19, Ex. I-1-c-20, Ex. I-1-c-23, Ex. I-1-c-24, Ex. I-1-c-25, Ex. I-1-c-32, Ex. I-1-c-43.

Example T

| Post-emergence Test | |
|---|---|
| Solvent: | 5 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Test plants of a height of 5-15 cm are sprayed with the preparation of active compounds such that the particular amounts of active compound desired are applied per unit area. The concentration of the spray liquor is chosen such that the particular amounts of active compound desired are applied in 1000 l of water/ha.

After three weeks, the degree of damage to the plants is rated in % damage in comparison to the development of the untreated control.

The figures denote

0%=no effect (like untreated control)

100%=total destruction

Example U

| Pre-emergence Test (examination of active compounds herbicides Monheim) | |
|---|---|
| Solvent: | 5 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is sprayed with the preparation of active compound such that the particular amounts of active compound desired are applied per unit area. The concentration of the spray liquor is chosen such that the particular amounts of active compound desired are applied in 1000 l of water/ha.

After three weeks, the degree of damage to the plants is rated in % damage in comparison to the development of the untreated control.

The figures denote:

0%=no effect (like untreated control)

100%=total destruction

| Greenhouse | Concentration of active compound g of a.i./ha | *Echinochloa* | *Setaria* | *Amaranthus* | *Galium* | *Sinapis* |
|---|---|---|---|---|---|---|
| Ex. I-1-a-4 | 250 | 100 | 100 | 95 | 70 | 70 |

| Greenhouse | Concentration of active compound g of a.i./ha | *Alopecurus* | *Avena fatua* | *Echinochloa* | *Setaria* | *Sinapis* |
|---|---|---|---|---|---|---|
| Ex. I-1-c-4 | 250 | 80 | — | 90 | 99 | 80 |
| Ex. I-1-b-1 | 250 | 70 | 70 | 80 | 95 | 70 |
| Ex. I-1-a-11 | 250 | 90 | 70 | 80 | 90 | — |

| Greenhouse | Concentration of active compound g of a.i./ha | Sugar beet | *Alopecurus* | *Avena fatua* | *Echinochloa* | *Setaria* |
|---|---|---|---|---|---|---|
| Ex. I-1-a-14 | 250 | 0 | 95 | 80 | 80 | 90 |
| Ex. I-1-a-15 | 250 | 0 | 95 | 80 | 99 | 70 |

| Greenhouse | Concentration of active compound g of a.i./ha | *Alopecurus* | *Echinochloa* | *Setaria* |
|---|---|---|---|---|
| Ex. I-1-a-11 | 250 | 80 | 80 | 100 |

Example V

1. Herbicidal Pre-Emergence Action

Seeds of monocotyledonous and dicotyledonous weed and crop plants are placed in sandy loam in wood fibre pots and covered with soil. The test compounds, formulated in the form of wettable powders (WP), are then, as an aqueous suspension with a water application rate of 600 l/ha (converted), with 0.2% of wetting agent added, applied to the surface of the covering soil in various dosages.

After the treatment, the pots are placed in a greenhouse and kept under good growth conditions for the test plants. The visual assessment of the emergence damage on the test plants is carried out after a trial period of 3 weeks by comparison with untreated controls (herbicidal effect in percent (%): 100% effect=the plants have died, 0% effect=like control plants).

In addition to the compounds mentioned above, the following compounds, applied by the pre-emergence method at 320 g of a.i./ha, show an activity of ≧80% against *Solium multiflorum* and *Setaria viridis*: Ex. I-1-a-24, Ex. I-1-a-39, Ex. I-1-a-40, Ex. I-1-a-42, Ex. I-1-a-43, Ex. I-1-a-44, Ex. I-1-a-45, Ex. I-1-a-48, Ex. I-1-a-69, Ex. I-1-a-71, Ex. I-1-b-4, Ex. I-1-b-5, Ex. I-1-b-8, Ex. I-1-b-9, Ex. I-1-b-10, Ex. I-1-c-14, Ex. I-1-c-15, Ex. I-1-c-23, Ex. I-1-c-25, Ex. I-1-c-42 and Ex. I-1-c-43.

2. Herbicidal Post-Emergence Action

Seeds of monocotyledonous and dicotyledonous weed and crop plants are placed into sandy loam in wood fibre pots, covered with soil and cultivated in a greenhouse under good growth conditions. 2-3 weeks after sowing, the test plants are treated at the one-leaf stage. The test compounds, formulated as wettable powders (WP), are then, in various dosages with a water application rate of 600 l/ha (converted), with 0.2% of wetting agent added, sprayed onto the green parts of the plants. After the test plants have been kept in the greenhouse under optimum growth conditions for about 3 weeks, the effect of the preparations is rated visually in comparison to untreated controls (herbicidal effect in percent (%): 100% effect=the plants have died, 0% effect=like control plants).

Use of Safeners:

If it is additionally to be tested as to whether safeners can improve the plant compatibility of test substances in the case of crop plants, the following options are used for applying the safener:

- seeds of the crop plants are, before sowing, dressed with the safener substance (the amount of safener stated in percent, based on the weight of the seed)
- before the application of the test substances, the crop plants are sprayed with the safener at a certain application rate per hectar (usually 1 day before the application of the test substances)
- the safener is applied together with the test substance as a tank mix (the amount of safener is stated in g/ha or as a ratio, based on the herbicide).

| Greenhouse | Concentration of active compound g of a.i./ha | Lolium | Setaria | Sinapis | Echinochloa |
|---|---|---|---|---|---|
| Ex. I-1-a-18 | 320 | 80 | 100 | — | 90 |
| Ex. I-1-a-19 | 320 | 90 | 90 | 70 | 90 |
| Ex. I-2-a-6 | 320 | 80 | 80 | 60 | 60 |
| Ex. I-2-b-3 | 320 | 100 | 90 | — | 80 |
| Ex. I-1-a-2 | 320 | 70 | 90 | 60 | 80 |
| Ex. I-1-a-7 | 320 | 80 | 80 | 60 | 60 |
| Ex. I-1-a-21 | 320 | 80 | 90 | 70 | 80 |
| Ex. I-1-a-22 | 320 | 70 | 80 | 70 | 100 |
| Ex. I-1-c-6 | 320 | 90 | 90 | 60 | 80 |

| Greenhouse | Concentration of active compound g of a.i./ha | Lolium | Setaria | Amaranthus | Sinapis | Echinochloa |
|---|---|---|---|---|---|---|
| Ex. I-2-a-2 | 320 | 90 | 100 | 60 | 70 | 80 |

| Greenhouse | Concentration of active compound g of a.i./ha | Lolium | Setaria | Amaranthus | Stellaria |
|---|---|---|---|---|---|
| Ex. I-2-a-5 | 320 | 100 | 70 | 70 | 60 |

In addition to the compounds mentioned above, the following compounds, applied by the post-emergence method at 320 g of a.i./ha, show an activity of ≧80% against *Echinocloa crus-galli*, *Lolium multiflorum* and *Setaria viridis*: Ex. I-1-a-10, Ex. I-1-a-18, Ex. I-1-a-19, Ex. I-1-a-21, Ex. I-1-a-24, Ex. I-1-a-25, Ex. I-1-a-27, Ex. I-1-a-39, Ex. I-1-a-40, Ex. I-1-a-42, Ex. I-1-a-45, Ex. I-1-a-48, Ex. I-1-a-71, Ex. I-1-b-8, Ex. I-1-b-9, Ex. I-1-b-10, Ex. I-1-b-11, Ex. I-1-c-6, Ex. I-1-c-15, Ex. I-1-c-23, Ex. I-1-c-25, Ex. I-1-c-26, Ex. I-1-c-42, Ex. I-1-c-43, Ex. I-2-a-2, and Ex. I-2-b-3.

Test Description for Profiling Tests

2. Herbicidal Post-Emergence Action

Seeds of monocotyledonous and dicotyledonous weed and crop plants are placed into sandy loam in wood fibre pots or in plastic pots, covered with soil and cultivated in a greenhouse, during the vegetation period also outdoors outside of the greenhouse, under good growth conditions. 2-3 weeks after sowing, the test plants are treated at the one- to three-leaf stage. The test compounds, formulated as wettable powders (WP) or emulsifiable concentrates (EC) are, in various dosages with a water application rate of 300 l/ha (converted), with wetting agent (0.2 to 0.3%) added, sprayed onto the plants and the surface of the soil. 34 weeks after the treatment of the test plants, the effect of the preparations is rated visually in comparison to untreated controls (herbicidal effect in percent (%): 100% effect=the plants have died, 0% effect=like control plants).

By comparing the effect of the test substances on crop plants without or with safener treatment, it is possible to assess the effect of the safener substance.

Container Trials with Cereal in a Greenhouse

Mefenpyr 1 Day Prior to Herbicide Application

TABLE 1

| | 10 days after application | | |
|---|---|---|---|
| | Application rate g of a.i./ha | Summer barley observed (%) | Summer wheat observed (%) |
| I-1-a-25 | 25 | 50 | 40 |
| | 12.5 | 30 | 20 |
| I-1-a-25 + mefenpyr | 25 + 100 | 15 | 10 |
| | 12.5 + 100 | 10 | 5 |

TABLE 2

| | days after application | |
|---|---|---|
| | Application rate g of a.i./ha | Summer wheat observed (%) |
| I-1-a-25 | 50 | 60 |
| | 25 | 20 |
| | 12.5 | 10 |

TABLE 2-continued

|  | days after application | |
| --- | --- | --- |
|  | Application rate<br>g of a.i./ha | Summer wheat<br>observed (%) |
| I-1-a-25 +<br>mefenpyr | 50 + 100<br>25 + 100<br>12.5 + 100 | 10<br>5<br>0 |

TABLE 3

|  | 28 days after application | | |
| --- | --- | --- | --- |
|  | Application rate<br>g of a.i./ha | Summer barley<br>observed (%) | Summer wheat<br>observed (%) |
| I-1-c-25 | 23.8<br>11.9 | 50 | 70<br>20 |
| I-1-c-25 +<br>mefenpyr | 23.8<br>11.9 | 20 | 20<br>10 |

Example W

| Critical concentration test/soil insects - treatment of transgenic plants |  |
| --- | --- |
| Test insect: | *Diabrotica balteata* - larvae in the soil |
| Solvent: | 7 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

The preparation of active compound is poured onto the soil. Here, the concentration of active compound in the preparation is virtually immaterial; only the amount by weight of active compound per volume unit of soil, which is stated in ppm (mg/l), matters. The soil is filled into 0.25 l pots, and these are allowed to stand at 20° C.

Immediately after the preparation, 5 pregerminated maize corns of the cultivar YIELD GUARD (trademark, of Monsanto Comp., USA) are placed into each pot. After 2 days, the appropriate test insects are placed into the treated soil. After a further 7 days, the efficacy of the active compound is determined by counting the maize plants that have emerged (1 plant=20% activity).

Example X

| *Heliothis virescens* Test - treatment of transgenic plants |  |
| --- | --- |
| Solvent: | 7 parts by weight of acetone |
| Emulsifier: | 1 part by weight of alkylaryl polyglycol ether |

To produce a suitable preparation of active compound, 1 part by weight of active compound is mixed with the stated amounts of solvent and the stated amount of emulsifier, and the concentrate is diluted with water to the desired concentration.

Soybean shoots (*Glycine max*) of the cultivar Roundup Ready (trademark of Monsanto Comp. USA) are treated by being dipped into the preparation of active compound of the desired concentration and are populated with the tobacco bud worm *Heliothis virescens* while the leaves are still moist.

After the desired period of time, the kill of the insects is determined.

The invention claimed is:

1. A compound of the formula (I)

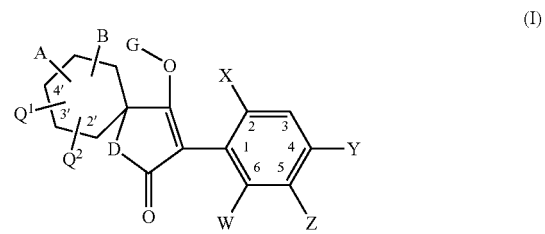

in which

W represents hydrogen, alkyl, alkenyl, alkynyl, alkoxy, halogen, alkenyloxy, haloalkyl, haloalkoxy or cyano, X represents halogen, alkyl, alkenyl, alkynyl, alkoxy, alkenyloxy, alkylthio, alkylsulphinyl, alkylsulphonyl, haloalkyl, haloalkoxy, haloalkenyloxy, nitro or cyano, Y and Z independently of one another represent hydrogen, alkyl, alkenyl, alkynyl, alkoxy, halogen, haloalkyl, haloalkoxy, cyano, or nitro, or represent in each case optionally substituted aryl or heteroaryl, with the proviso that at least one of the radicals W or Z is different from hydrogen if X and Y represent methyl, A and B and the carbon atom to which they are attached represent a five- to seven-membered ketal, thioketal or dithioketal which is optionally interrupted by a further heteroatom, each of which radicals is optionally substituted by alkyl, haloalkyl, alkoxy, alkoxyalkyl or optionally substituted phenyl, D represents NH or oxygen, $Q^1$ and $Q^2$ independently of one another represent hydrogen, alkyl, haloalkyl or alkoxy, G represents hydrogen (a), or

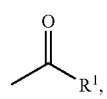

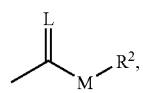

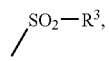

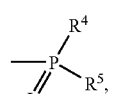

E, or

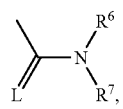

in which
E represents a metal ion or an ammonium ion,
L represents oxygen or sulphur,
M represents oxygen or sulphur,
$R^1$ represents in each case optionally halogen- or cyano-substituted alkyl, alkenyl, alkoxyalkyl, alkylthioalkyl or polyalkoxyalkyl, or represents in each case optionally halogen-, alkyl- or alkoxy-substituted cycloalkyl or heterocyclyl, or represents in each case optionally substituted phenyl, phenylalkyl, heteroaryl, phenoxyalkyl or heteroaryloxyalkyl,
$R^2$ represents in each case optionally halogen- or cyano-substituted alkyl, alkenyl, alkoxyalkyl or polyalkoxyalkyl, or represents in each case optionally substituted cycloalkyl, phenyl or benzyl,
$R^3$, $R^4$ and $R^5$ independently of one another represent in each case optionally halogen-substituted alkyl, alkoxy, alkylamino, dialkylamino, alkylthio, alkenylthio or cycloalkylthio, or represent in each case optionally substituted phenyl, benzyl, phenoxy or phenylthio,
$R^6$ and $R^7$ independently of one another represent hydrogen, in each case optionally halogen- or cyano-substituted alkyl, cycloalkyl, alkenyl, alkoxy, or alkoxyalkyl, or represent in each case optionally substituted phenyl or benzyl, or $R^6$ and $R^7$ together with the N atom to which they are attached form an optionally substituted cycle which optionally contains oxygen or sulphur.

2. The compound according to claim 1 in which
W represents hydrogen, $C_1$-$C_6$-alkyl, $C_2$-$C_6$-alkenyl, $C_2$-$C_6$-alkynyl, halogen, $C_1$-$C_6$-alkoxy, $C_1$-$C_4$-haloalkoxy or cyano,
X represents halogen, $C_1$-$C_6$-alkyl, $C_2$-$C_6$-alkenyl, $C_2$-$C_6$-alkynyl, $C_1$-$C_6$-haloalkyl, $C_1$-$C_6$-alkoxy, $C_3$-$C_6$-alkenyloxy, $C_1$-$C_6$-alkylthio, $C_1$-$C_6$-alkylsulphinyl, $C_1$-$C_6$-alkylsulphonyl, $C_1$-$C_6$-haloalkoxy, $C_3$-$C_6$-haloalkenyloxy, nitro or cyano,
Y and Z independently of one another represent hydrogen, halogen, $C_1$-$C_6$-alkyl, $C_2$-$C_6$-alkenyl, $C_2$-$C_6$-alkynyl, $C_1$-$C_6$-alkoxy, $C_1$-$C_6$-haloalkoxy, $C_1$-$C_6$-haloalkoxy, cyano, $C_2$-$C_6$-alkenyl, or $C_2$-$C_6$-alkynyl, or a heteroaryl or an aryl radical selected from the group consisting of

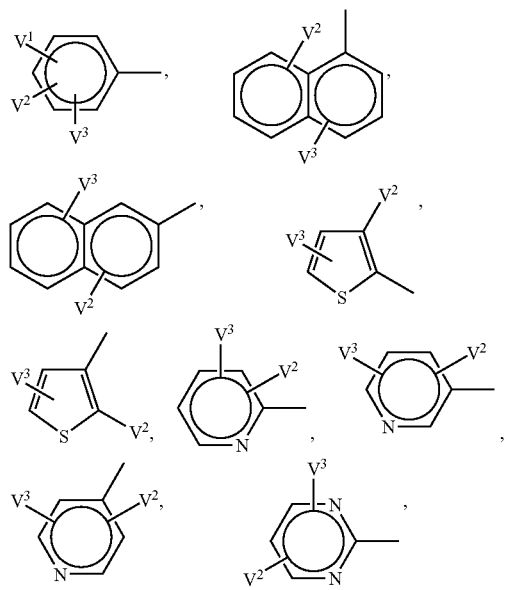

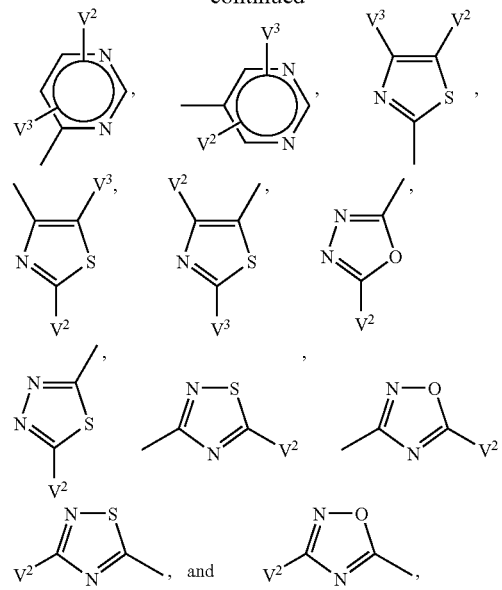

provided that only one of the radicals Y or Z can represent heteroaryl or aryl,
$V^1$ represents hydrogen, halogen, $C_1$-$C_{12}$-alkyl, $C_1$-$C_6$-alkoxy, $C_1$-$C_6$-alkylthio, $C_1$-$C_6$-alkylsulphinyl, $C_1$-$C_6$-alkylsulphonyl, $C_1$-$C_4$-haloalkyl, $C_1$-$C_4$-haloalkoxy, nitro, cyano, or represents phenyl, phenoxy, phenoxy-$C_1$-$C_4$-alkyl, phenyl-$C_1$-$C_4$-alkoxy, phenylthio-$C_1$-$C_4$-alkyl or phenyl-$C_1$-$C_4$-alkylthio, each of which is optionally substituted by one or more substituents selected from the group consisting of halogen, $C_1$-$C_6$-alkyl, $C_1$-$C_6$-alkoxy, $C_1$-$C_4$-haloalkyl, $C_1$-$C_4$-haloalkoxy, nitro and cyano,
$V^2$ and $V^3$ independently of one another represent hydrogen, halogen, $C_1$-$C_6$-alkyl, $C_1$-$C_6$-alkoxy, $C_1$-$C_4$-haloalkyl or $C_1$-$C_4$-haloalkoxy,
with the proviso that at least one of the radicals W or Z is different from hydrogen if X and Y represent methyl,
A and B and the carbon atom to which they are attached represent a five- to seven-membered ketal, thioketal, or dithioketal which is optionally interrupted by a further oxygen atom, sulphur atom or by the group

each of which radicals is optionally substituted by one to four substituents selected from the group consisting of $C_1$-$C_6$-alkyl, $C_1$-$C_4$-haloalkyl, $C_1$-$C_6$-alkoxy and $C_1$-$C_4$-alkoxy-$C_1$-$C_4$-alkyl,
$V^4$ represents hydrogen, $C_1$-$C_6$-alkyl, $C_3$-$C_6$-alkenyl, —CO—$V^5$, —$CO_2V^5$, CO—NH—$V^5$ or CO—NH—O—$V^5$,
$V^5$ represents $C_1$-$C_6$-alkyl,
D represents NH or oxygen,
$Q^1$ and $Q^2$ independently of one another represent hydrogen, $C_1$-$C_6$-alkyl, $C_1$-$C_2$-haloalkyl or $C_1$-$C_4$-alkoxy,
G represents hydrogen (a), or

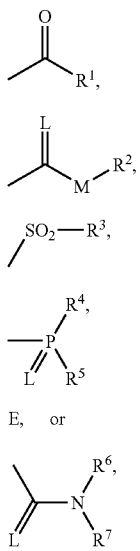

(b), (c), (d), (e), (f), (g)

in which
E represents a metal ion or an ammonium ion,
L represents oxygen or sulphur and
M represents oxygen or sulphur,
$R^1$ represents in each case optionally halogen- or cyano-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl or poly-$C_1$-$C_8$-alkoxy-$C_1$-$C_8$-alkyl, or represents optionally halogen-, $C_1$-$C_6$-alkyl- or $C_1$-$C_6$-alkoxy-substituted $C_3$-$C_8$-cycloalkyl in which optionally one or two not directly adjacent methylene groups are replaced by oxygen or sulphur,
represents optionally halogen-, cyano-, nitro-, $C_1$-$C_6$-alkyl-, $C_1$-$C_6$-alkoxy-, $C_1$-$C_6$-haloalkyl-, $C_1$-$C_6$-haloalkoxy-, $C_1$-$C_6$-alkylthio- or $C_1$-$C_6$-alkylsulphonyl-substituted phenyl,
represents optionally halogen-, nitro-, cyano-, $C_1$-$C_6$-alkyl-, $C_1$-$C_6$-alkoxy-, $C_1$-$C_6$-haloalkyl- or $C_1$-$C_6$-haloalkoxy-substituted phenyl-$C_1$-$C_6$-alkyl,
represents optionally halogen- or $C_1$-$C_6$-alkyl-substituted 5- or 6-membered heteroaryl having one or two heteroatoms selected from the group consisting of oxygen, sulphur and nitrogen,
represents optionally halogen- or $C_1$-$C_6$-alkyl-substituted phenoxy-$C_1$-$C_6$-alkyl or
represents optionally halogen-, amino- or $C_1$-$C_6$-alkyl-substituted 5- or 6-membered heteroaryloxy-$C_1$-$C_6$-alkyl having one or two heteroatoms selected from the group consisting of oxygen, sulphur and nitrogen,
$R^2$ represents in each case optionally halogen- or cyano-substituted $C_1$-$C_{20}$-alkyl, $C_2$-$C_{20}$-alkenyl, $C_1$-$C_8$-alkoxy-$C_2$-$C_8$-alkyl or poly-$C_1$-$C_8$-alkoxy-$C_2$-$C_8$-alkyl,
represents optionally halogen-, $C_1$-$C_6$-alkyl- or $C_1$-$C_6$-alkoxy-substituted $C_3$-$C_8$-cycloalkyl or
represents in each case optionally halogen-, cyano-, nitro-, $C_1$-$C_6$-alkyl-, $C_1$-$C_6$-alkoxy-, $C_1$-$C_6$-haloalkyl- or $C_1$-$C_6$-haloalkoxy-substituted phenyl or benzyl,
$R^3$ represents optionally halogen-substituted $C_1$-$C_8$-alkyl or in each case optionally halogen-, $C_1$-$C_6$-alkyl-, $C_1$-$C_6$-alkoxy-, $C_1$-$C_4$-haloalkyl-, $C_1$-$C_4$-haloalkoxy-, cyano- or nitro-substituted phenyl or benzyl, $R^4$ and $R^5$ independently of one another represent in each case optionally halogen-substituted $C_1$-$C_8$-alkyl, $C_1$-$C_8$-alkoxy, $C_1$-$C_8$-alkylamino, di($C_1$-$C_8$-alkyl)amino, $C_1$-$C_8$-alkylthio or $C_3$-$C_8$-alkenylthio or represent in each case optionally halogen-, nitro-, cyano-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkyl- or $C_1$-$C_4$-haloalkyl-substituted phenyl, phenoxy or phenylthio,
$R^6$ and $R^7$ independently of one another represent hydrogen, represent in each case optionally halogen- or cyano-substituted $C_1$-$C_8$-alkyl, $C_3$-$C_8$-cycloalkyl, $C_1$-$C_8$-alkoxy, $C_3$-$C_8$-alkenyl or $C_1$-$C_8$-alkoxy-$C_2$-$C_8$-alkyl, represent in each case optionally halogen-, $C_1$-$C_8$-alkyl-, $C_1$-$C_8$-haloalkyl- or $C_1$-$C_8$-alkoxy-substituted phenyl or benzyl or $R^6$ and $R^7$ together represent an optionally $C_1$-$C_6$-alkyl-substituted $C_3$-$C_6$-alkylene radical in which optionally one methylene group is replaced by oxygen or sulphur.

3. The compound according to claim 1 in which
W represents hydrogen, chlorine, bromine, $C_1$-$C_4$-alkyl, $C_2$-$C_4$-alkenyl, $C_2$-$C_4$-alkynyl, $C_1$-$C_4$-alkoxy, $C_1$-$C_2$-haloalkyl or $C_1$-$C_2$-haloalkoxy,
X represents chlorine, bromine, $C_1$-$C_4$-alkyl, $C_2$-$C_4$-alkenyl, $C_2$-$C_4$-alkynyl, $C_1$-$C_4$-alkoxy, $C_1$-$C_4$-haloalkyl, $C_1$-$C_4$-haloalkoxy or cyano,
Y and Z independently of one another represent hydrogen, fluorine, chlorine, bromine, $C_1$-$C_4$-alkyl, $C_2$-$C_4$-alkenyl, $C_2$-$C_4$-alkynyl, $C_1$-$C_6$-alkoxy, $C_1$-$C_4$-haloalkyl, $C_1$-$C_4$-haloalkoxy, cyano, $C_2$-$C_4$-alkenyl, or $C_2$-$C_4$-alkynyl, or a heteroaryl or an aryl radical selected from the group consisting of

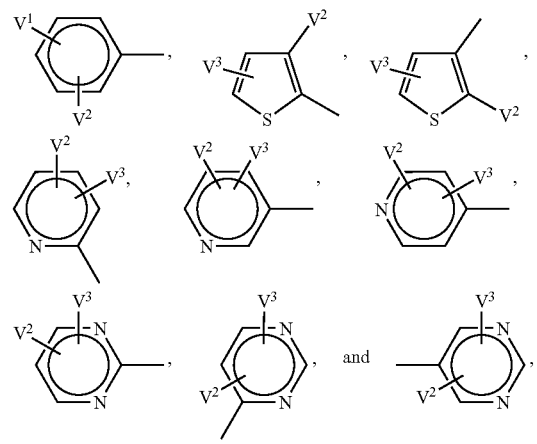

provided that only one of the radicals Y or Z can represent heteroaryl or aryl,
$V^1$ represents hydrogen, fluorine, chlorine, bromine, $C_1$-$C_6$-alkyl, $C_1$-$C_4$-alkoxy, $C_1$-$C_2$-haloalkyl, $C_1$-$C_2$-haloalkoxy, nitro, cyano, or represents phenyl which is optionally substituted by one or two substituents selected from the group consisting of fluorine, chlorine, bromine, $C_1$-$C_4$-alkyl, $C_1$-$C_4$-alkoxy, $C_1$-$C_2$-haloalkyl, $C_1$-$C_2$-haloalkoxy, nitro and cyano,
$V^2$ and $V^3$ independently of one another represent hydrogen, fluorine, chlorine, bromine, $C_1$-$C_4$-alkyl, $C_1$-$C_4$-alkoxy, $C_1$-$C_2$-haloalkyl or $C_1$-$C_2$-haloalkoxy,
with the proviso that at least one of the radicals W or Z is different from hydrogen if X and Y represent methyl, A and B and the carbon atom to which they are attached represent a five-, six- or seven-membered ketal which is optionally interrupted by a further oxygen atom and which is optionally substituted by one, two or three substituents selected from the group consisting of $C_1$-$C_4$-alkyl, $C_1$-$C_4$-alkoxy and $C_1$-$C_4$-alkoxy-$C_1$-$C_2$-alkyl, D represents NH or oxygen, $Q^1$ and $Q^2$ independently of one another represent hydrogen, methyl, ethyl, trifluoromethyl, methoxy or ethoxy, G represents hydrogen (a), or

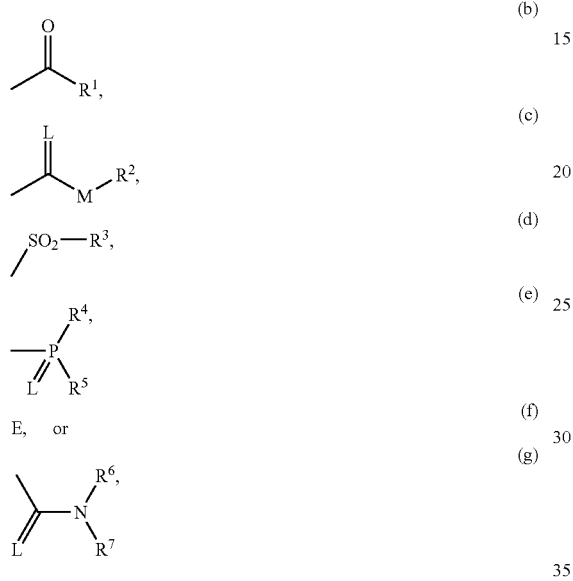

in which

E represents a metal ion or an ammonium ion,

L represents oxygen or sulphur,

M represents oxygen or sulphur, $R^1$ represents $C_1$-$C_{16}$-alkyl, $C_2$-$C_{16}$-alkenyl, $C_1$-$C_6$-alkoxy-$C_1$-$C_4$-alkyl, $C_1$-$C_6$-alkylthio-$C_1$-$C_4$-alkyl or poly-$C_1$-$C_6$-alkoxy-$C_1$-$C_4$-alkyl, each of which is optionally substituted by one, two or three substituents selected from the group consisting of fluorine and chlorine, or represents $C_3$-$C_7$-cycloalkyl which is optionally substituted by one or two substituents selected from the group consisting of fluorine, chlorine, $C_1$-$C_5$-alkyl and $C_1$-$C_5$-alkoxy, and in which optionally one or two not directly adjacent methylene groups are replaced by oxygen or sulphur, represents phenyl which is optionally substituted by one, two or three substituents selected from the group consisting of fluorine, chlorine, bromine, cyano, nitro, $C_1$-$C_4$-alkyl, $C_1$-$C_4$-alkoxy, $C_1$-$C_3$-haloalkyl, $C_1$-$C_3$-haloalkoxy, $C_1$-$C_4$-alkylthio and $C_1$-$C_4$-alkylsulphonyl, represents phenyl-$C_1$-$C_4$-alkyl which is optionally substituted by one or two substituents selected from the group consisting of fluorine, chlorine, bromine, $C_1$-$C_4$-alkyl, $C_1$-$C_4$-alkoxy, $C_1$-$C_3$-haloalkyl and $C_1$-$C_3$-haloalkoxy, represents pyrazolyl, thiazolyl, pyridyl, pyrimidyl, furanyl or thienyl, each of which is optionally substituted by one or two substituents selected from the group consisting of fluorine, chlorine, bromine and $C_1$-$C_4$-alkyl, represents phenoxy-$C_1$-$C_5$-alkyl which is optionally substituted by one or two substituents selected from the group consisting of fluorine, chlorine, bromine and $C_1$-$C_4$-alkyl or represents pyridyloxy-$C_1$-$C_5$-alkyl, pyrimidyloxy-$C_1$-$C_5$-alkyl or thiazolyloxy-$C_1$-$C_5$-alkyl, each of which is optionally substituted by one or two substituents selected from the group consisting of fluorine, chlorine, bromine, amino and $C_1$-$C_4$-alkyl, $R^2$ represents $C_1$-$C_{16}$-alkyl, $C_2$-$C_{16}$-alkenyl, $C_1$-$C_6$-alkoxy-$C_2$-$C_6$-alkyl or poly-$C_1$-$C_6$-alkoxy-$C_2$-$C_6$-alkyl, each of which is optionally substituted by one, two or three substituents selected from the group consisting of fluorine and chlorine, represents $C_3$-$C_7$-cycloalkyl which is optionally substituted by one or two substituents selected from the group consisting of fluorine, chlorine, $C_1$-$C_4$-alkyl and $C_1$-$C_4$-alkoxy or represents phenyl or benzyl, each of which is optionally substituted by one, two or three substituents selected from the group consisting of fluorine, chlorine, bromine, cyano, nitro, $C_1$-$C_4$-alkyl, $C_1$-$C_3$-alkoxy, $C_1$-$C_3$-haloalkyl and $C_1$-$C_3$-haloalkoxy, $R^3$ represents $C_1$-$C_6$-alkyl which is optionally substituted by one, two or three substituents selected from the group consisting of fluorine and chlorine, or represents phenyl or benzyl, each of which is optionally substituted by one or two substituents selected from the group consisting of fluorine, chlorine, bromine, $C_1$-$C_4$-alkyl, $C_1$-$C_4$-alkoxy, $C_1$-$C_2$-haloalkoxy, $C_1$-$C_2$-haloalkyl, cyano and nitro, $R^4$ and $R^5$ independently of one another represent $C_1$-$C_6$-alkyl, $C_1$-$C_6$-alkoxy, $C_1$-$C_6$-alkylamino, di($C_1$-$C_6$-alkyl)amino, $C_1$-$C_6$-alkylthio or $C_3$-$C_4$-alkenylthio, each of which is optionally substituted by one, two or three substituents selected from the group consisting of fluorine and chlorine, or represent phenyl, phenoxy or phenylthio, each of which is optionally substituted by one or two substituents selected from the group consisting of fluorine, chlorine, bromine, nitro, cyano, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkyl and $C_1$-$C_3$-haloalkyl, $R^6$ and $R^7$ independently of one another represent hydrogen, represent $C_1$-$C_6$-alkyl, $C_3$-$C_6$-cycloalkyl, $C_1$-$C_6$-alkoxy, $C_3$-$C_6$-alkenyl or $C_1$-$C_6$-alkoxy-$C_2$-$C_6$-alkyl, each of which is optionally substituted by one, two or three substituents selected from the group consisting of fluorine and chlorine, represent phenyl or benzyl, each of which is optionally substituted by one, two or three substituents selected from the group consisting of fluorine, chlorine, bromine, $C_1$-$C_5$-haloalkyl, $C_1$-$C_5$-alkyl and $C_1$-$C_5$-alkoxy, or $R^6$ and $R^7$ together represent an optionally $C_1$-$C_4$-alkyl-substituted $C_3$-$C_6$-alkylene radical in which optionally one methylene group is replaced by oxygen or sulphur.

4. The compound according to claim 1 in which

W represents hydrogen, chlorine, bromine, methyl, ethyl, vinyl, ethynyl, propynyl, methoxy, ethoxy or trifluoromethyl, X represents chlorine, bromine, methyl, ethyl, propyl, isopropyl, vinyl, ethynyl, propynyl, methoxy, ethoxy, trifluoromethyl, difluoromethoxy, trifluoromethoxy or cyano, Y and Z independently of one another represent hydrogen, fluorine, chlorine, bromine, methyl, ethyl, vinyl, ethynyl, propynyl, methoxy, trifluoromethyl, trifluoromethoxy, cyano or a phenyl radical

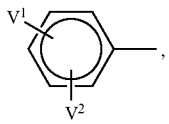, provided that only one of the radicals Y or Z can represent phenyl,
$V^1$ represents hydrogen, fluorine, chlorine, bromine, methyl, ethyl, n-propyl, isopropyl, tert-butyl, methoxy, ethoxy, n-propoxy, isopropoxy, trifluoromethyl or trifluoromethoxy,
$V^2$ represents hydrogen, fluorine, chlorine, methyl, ethyl, n-propyl, isopropyl, methoxy, ethoxy or trifluoromethyl, with the proviso that at least one of the radicals W or Z is different from hydrogen if X and Y represent methyl,
A and B and the carbon atom to which they are attached represent a five-, six- or seven-membered ketal which is optionally interrupted by a further oxygen atom and which is optionally substituted by one or two substituents selected from the group consisting of methyl, ethyl, propyl, trifluoromethyl, monochloromethyl, methoxy, ethoxy, methoxymethyl and ethoxymethyl,
D represents NH or oxygen,
$Q^1$ and $Q^2$ represent hydrogen,
G represents hydrogen (a) or (b) 

(c) 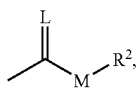

(d) 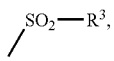

(e) 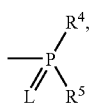

(f) E, or (g) 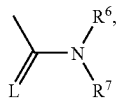

in which
E represents a metal ion or an ammonium ion,
L represents oxygen or sulphur,
M represents oxygen or sulphur,
$R^1$ represents $C_1$-$C_{10}$-alkyl, $C_2$-$C_{10}$-alkenyl, $C_1$-$C_4$-alkoxy-$C_1$-$C_2$-alkyl, $C_1$-$C_4$-alkylthio-$C_1$-$C_2$-alkyl, each of which is optionally substituted by one, two or three substituents selected from the group consisting of fluorine and chlorine, or represents $C_3$-$C_6$-cycloalkyl which is optionally monosubstituted by fluorine, chlorine, methyl, ethyl or methoxy,
represents phenyl which is optionally substituted by one or two substituents selected from the group consisting of fluorine, chlorine, bromine, cyano, nitro, methyl, ethyl, n-propyl, isopropyl, methoxy, ethoxy, trifluoromethyl and trifluoromethoxy, or
represents furanyl, thienyl or pyridyl, each of which is optionally monosubstituted by chlorine, bromine or methyl,
$R^2$ represents $C_1$-$C_{10}$-alkyl, $C_2$-$C_{10}$-alkenyl or $C_1$-$C_4$-alkoxy-$C_2$-$C_4$-alkyl, each of which is optionally substituted by one, two or three substituents selected from the group consisting of fluorine and chlorine,
represents cyclopentyl or cyclohexyl,
or represents phenyl or benzyl, each of which is optionally substituted by one or two substituents selected from the group consisting of fluorine, chlorine, cyano, nitro, methyl, ethyl, methoxy, trifluoromethyl and trifluoromethoxy,
$R^3$ represents methyl, ethyl, propyl or isopropyl, each of which is optionally substituted by one, two or three substituents selected from the group consisting of fluorine and chlorine, or represents phenyl which is optionally monosubstituted by fluorine, chlorine, bromine, methyl, ethyl, isopropyl, tert-butyl, methoxy, ethoxy, isopropoxy, trifluoromethyl, trifluoromethoxy, cyano or nitro,
$R^4$ and $R^5$ independently of one another represent $C_1$-$C_4$-alkoxy or $C_1$-$C_4$-alkylthio, or represent phenyl, phenoxy or phenylthio, each of which is optionally monosubstituted by fluorine, chlorine, bromine, nitro, cyano, methyl, methoxy, trifluoromethyl or trifluoromethoxy,
$R^6$ and $R^7$ independently of one another represent hydrogen, $C_1$-$C_4$-alkyl, $C_3$-$C_6$-cycloalkyl, $C_1$-$C_4$-alkoxy, $C_3$-$C_4$-alkenyl or $C_1$-$C_4$-alkoxy-$C_2$-$C_4$-alkyl, represent phenyl which is optionally substituted by one or two substituents selected from the group consisting of fluorine, chlorine, bromine, methyl, methoxy and trifluoromethyl, or $R^6$ and $R^7$ together represent a $C_5$-$C_6$-alkylene radical in which optionally one methylene group is replaced by oxygen or sulphur.

5. The compound according to claim 1 in which
W represents hydrogen, chlorine, bromine, methyl, ethyl or methoxy,
X represents chlorine, bromine, methyl, ethyl or methoxy,
Y and Z independently of one another represent hydrogen, chlorine, bromine, methyl or

provided that only one of the radicals Y or Z can represent

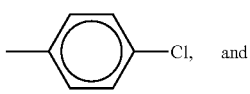

and
with the proviso that at least one of the radicals W or Z is different from hydrogen if X and Y represent methyl,
A and B and the carbon atom to which they are attached represent a five- or six-membered ketal which is optionally substituted by one or two substituents selected from the group consisting of methyl, ethyl, propyl, and monochloromethyl,
D represents NH or oxygen,
$Q^1$ and $Q^2$ represent hydrogen,
G represents hydrogen (a), or

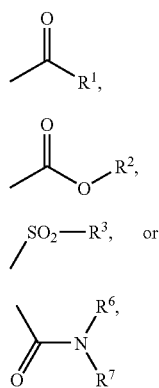

R[1] represents $C_1$-$C_{10}$-alkyl, $C_1$-$C_4$-alkoxy-$C_1$-$C_2$-alkyl, $C_3$-$C_6$-cycloalkyl,
represents phenyl which is optionally monosubstituted by chlorine, or represents thienyl,
R[2] represents $C_1$-$C_{10}$-alkyl, $C_2$-$C_{10}$-alkenyl or benzyl,
R[3] represents methyl,
R[6] and R[7] together represent a $C_5$-$C_6$-alkylene radical in which optionally one methylene group is replaced by oxygen or sulphur.

6. A process for preparing a compound of the formula (I) according to claim 1, comprising
(A) condensing intramolecularly a compound of the formula (II)

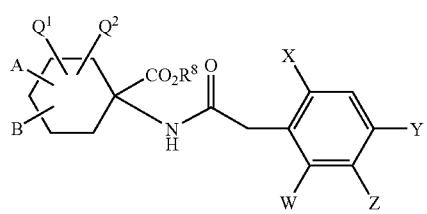

in which
A, B, Q[1], Q[2], W, X, Y and Z are as defined in claim 1, and
R[8] represents alkyl
in the presence of a diluent and in the presence of a base, to obtain a compound of the formula (I-1-a),

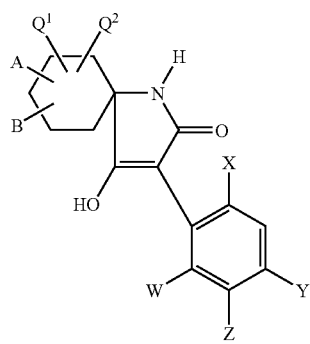

wherein A, B, Q[1], Q[2], W, X, Y and Z are as defined in claim 1,
(B) condensing intramolecularly a compound of the formula (III)

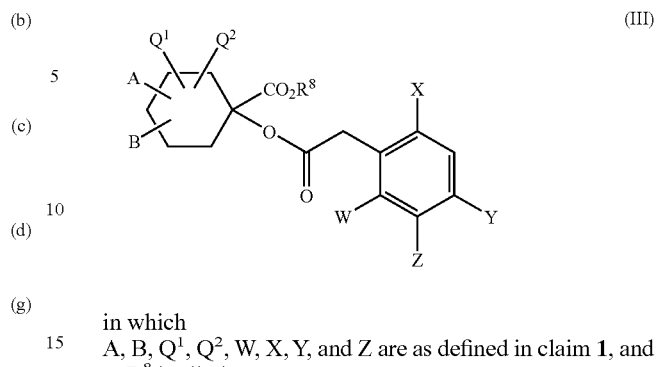

in which
A, B, Q[1], Q[2], W, X, Y, and Z are as defined in claim 1, and
R[8] is alkyl,
in the presence of a diluent and in the presence of a base, to obtain a compound of the formula (I-2-a)

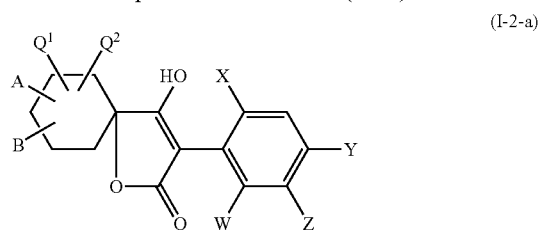

in which
A, B, Q[1], Q[2], W, X, Y and Z are as defined in claim 1,
(C) reacting a compound of the formula (I-1-a)

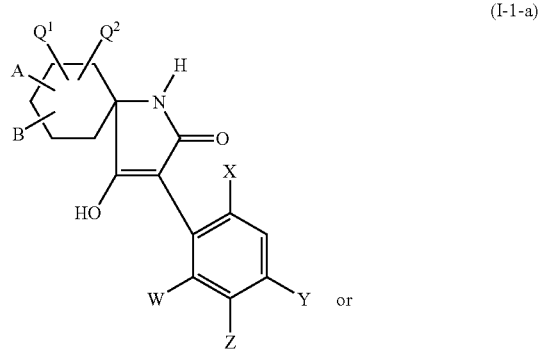

a compound of the formula (I-2-a)

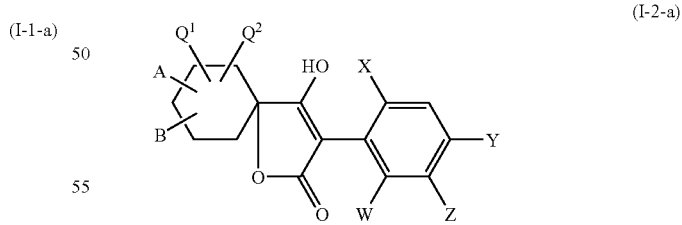

wherein A, B, Q[1], Q[2], W, X, Y, and Z are as defined in claim 1,
α) with a compound of the formula (IV)

in which
R¹ is defined in claim 1 and
Hal represents halogen or

β) with a carboxylic anhydride of the formula (V)

$$R^1\text{—CO—O—CO—}R^1 \quad (V)$$

in which
R¹ is defined in claim 1,
optionally in the presence of a diluent and optionally in the presence of an acid binder, to obtain a compound of the formula (I-1-b)

(I-1-b)

or a compound of the formula (I-2-b)

(I-2-b)

respectively, wherein R¹, A, B, Q Q², W, X, Y and Z are as defined in claim 1;

(D) reacting a compound of the formula (I-1-a)

(I-1-a)

or a compound of the formula (I-2-a)

(I-2-a)

wherein A, B, Q¹, Q², W, X, Y, and Z are as defined in claim 1,
with a chloroformic ester or a chloroformic thioester of the formula (VI)

$$R^2\text{-M-CO—Cl} \quad (VI)$$

in which
R² and M are as defined in claim 1,
optionally in the presence of a diluent and optionally in the presence of an acid binder, to obtain a compound of the formula (I-1-c)

(I-1-c)

or a compound of the formula (I-2-c)

(I-2-c)

respectively, wherein R², M, A, B, Q¹, Q², W, X, Y and Z are as defined in claim 1 and L represents oxygen;

(E) reacting a compound of the formula (I-1-a)

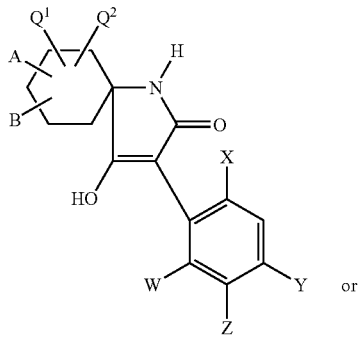
(I-1-a)

a compound of the formula (I-2-a)

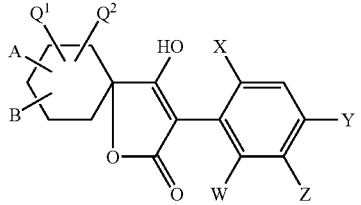
(I-2-a)

wherein A, B, $Q^1$, $Q^2$, W, X, Y, and Z are as defined in claim 1, with a chloromonothioformic ester or a chlorodithioformic ester of the formula (VII)

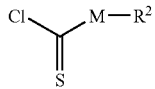
(VII)

in which

M and $R^2$ are as defined in claim 1, optionally in the presence of a diluent and optionally in the presence of an acid binder, to obtain a compound of the formula (I-1-c)

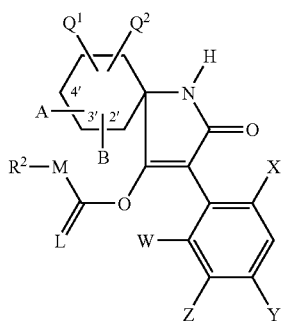
(I-1-c)

or a compound of the formula (I-2-c)

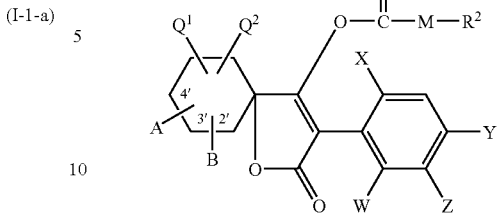
(I-2-c)

respectively, wherein $R^2$, M, A, B, $Q^1$, $Q^2$, W, X, Y and Z are as defined in claim 1 and L represents sulphur;

(F) reacting a compound of the formula (I-1-a)

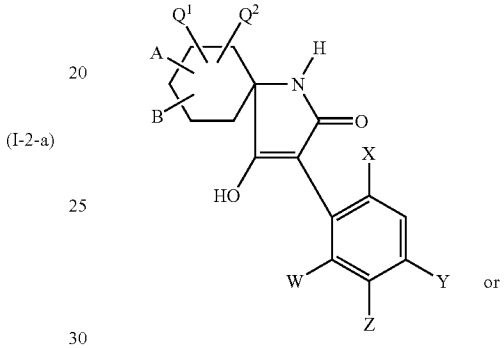
(I-1-a)

a compound of the formula (I-2-a)

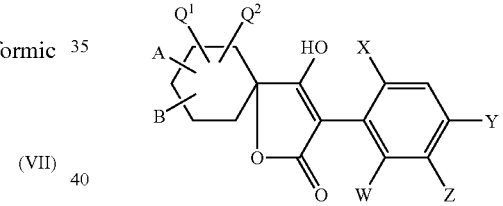
(I-2-a)

wherein A, B, $Q^1$, $Q^2$, W, X, Y, and Z are as defined in claim 1, with a sulphonyl chloride of the formula (VIII)

$R^3$—$SO_2$—Cl (VIII)

in which $R^3$ is defined in claim 1, optionally in the presence of a diluent and optionally in the presence of an acid binder, to obtain a compound of the formula (I-1-d)

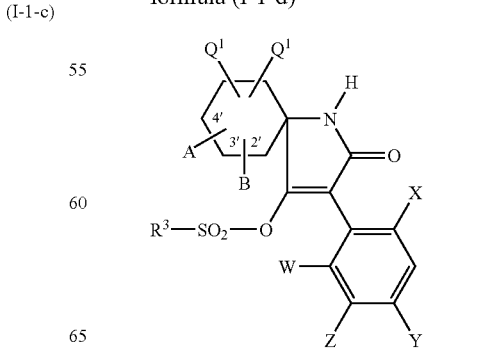
(I-1-d)

or a compound of the formula (I-2-d)

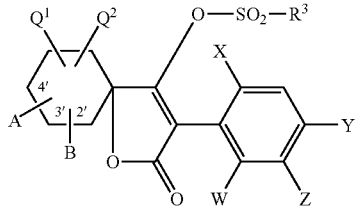
(I-2-d)

respectively, wherein $R^3$, A, B, $Q^1$, $Q^2$, W, X, Y and Z are as defined in claim 1;

(G) reacting a compound of the formula (I-1-a)

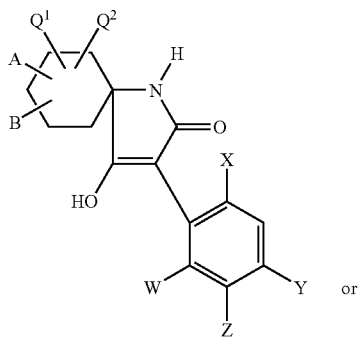
(I-1-a)

a compound of the formula (I-2-a)

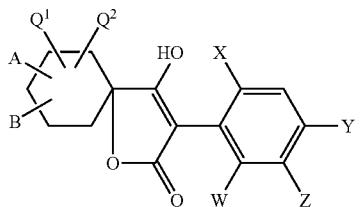
(I-2-a)

wherein A, B, $Q^1$, $Q^2$, W, X, Y, and Z are as defined in claim 1, with a phosphorus compound of the formula (IX)

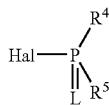
(IX)

in which
L, $R^4$ and $R^5$ are as defined in claim 1 and
Hal represents halogen,
optionally in the presence of a diluent and optionally in the presence of an acid binder, to obtain a compound of the formula (I-1-e)

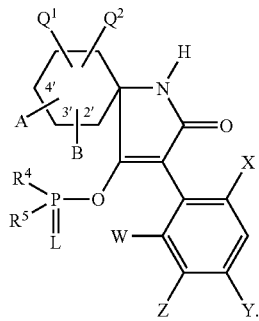
(I-1-e)

or a compound of the formula (I-2-e)

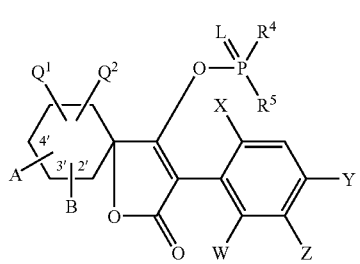
(I-2-e)

respectively, wherein L, $R^4$, $R^5$, A, B, $Q^1$, $Q^2$, W, X, Y and Z are as defined in claim 1;

(H) reacting a compound of the formula (I-1-a)

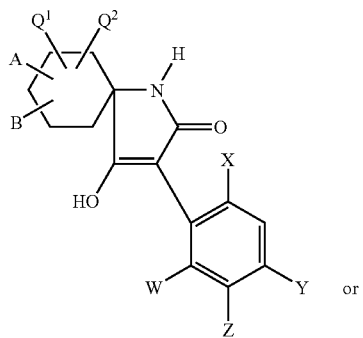
(I-1-a)

or a compound of the formula (I-2-a)

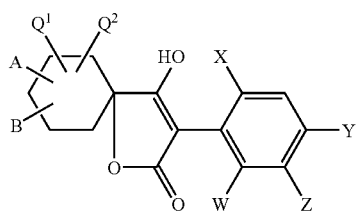
(I-2-a)

wherein A, B, $Q^1$, $Q^2$, W, X, Y, and Z are as defined in claim 1,
with a metal compound or amine of the formula (X) or (XI), respectively, $$Me(OR^{10})_t \quad (X)$$

-continued

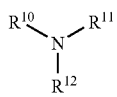
(XI)

in which

Me represents a mono- or divalent metal, t represents the number 1 or 2 and $R^{10}$, $R^{11}$, and $R^{12}$ independently of one another represent hydrogen or alkyl, optionally in the presence of a diluent, to obtain a compound of the formula (I-1-f)

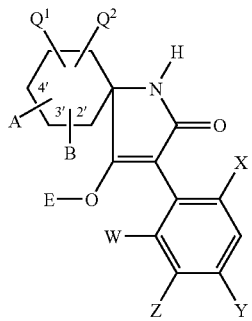
(I-1-f)

or a compound of the formula (I-2-f)

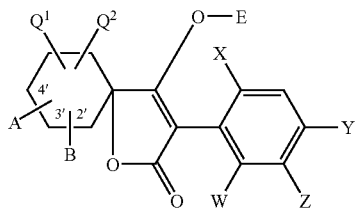
(I-2-f)

respectively, wherein E, A, B, $Q^1$, $Q^2$, W, X, Y and Z are as defined in claim 1;

(I) reacting a compound of the formula (I-1-a)

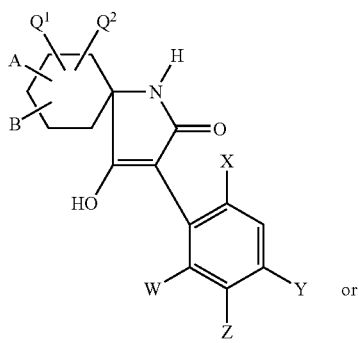
(I-1-a)

or a compound of the formula (I-2-a)

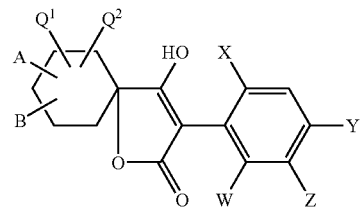
(I-2-a)

wherein A, B, $Q^1$, $Q^2$, W, X, Y, and Z are as defined in claim 1,

α) with an isocyanate or an isothiocyanate of the formula (XII)

$$R^6\!-\!N\!=\!C\!=\!L \qquad (XII)$$

in which $R^6$ and L are as defined in claim 1, optionally in the presence of a diluent and optionally in the presence of a catalyst, or β) with a carbamoyl chloride or a thiocarbamoyl chloride of the formula (XIII)

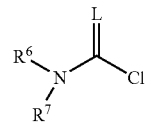
(XIII)

in which

L, $R^6$ and $R^7$ are as defined in claim 1, optionally in the presence of a diluent and optionally in the presence of an acid binder, to obtain a compound of the formula (I-1-g)

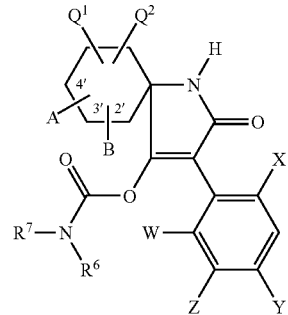
(I-1-g)

or a compound of the formula (I-2-g)

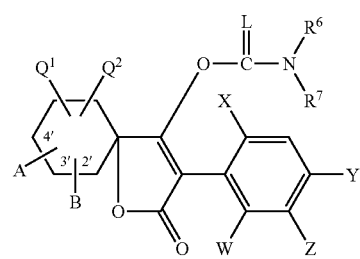
(I-2-g)

respectively, wherein L, $R^6$, $R^7$, A, B, $Q^1$, $Q^2$, W, X, Y and Z are as defined in claim 1; or (J) reacting a compound of the formula (XIV)

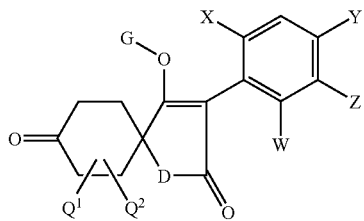
(XIV)

in which
D, G, $Q^1$, $Q^2$, W, X, Y and Z are as defined in claim 1,
with a diol of the formula (XV)

 (XV)

in which
A and B are as defined in claim 1,
optionally in the presence of a diluent, in the presence of an acidic catalyst and under dehydrating conditions, to obtain a compound of the formula (I-1-a)-(I-1-g):

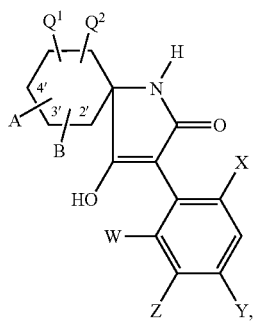 (I-1-a)

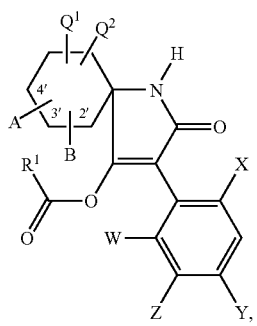 (I-1-b)

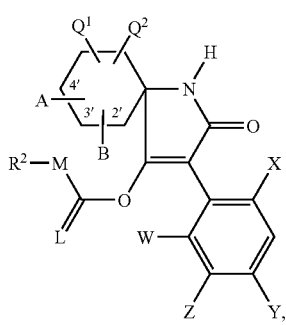 (I-1-c)

-continued

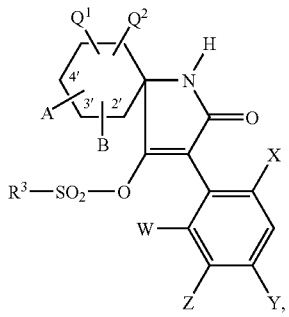 (I-1-d)

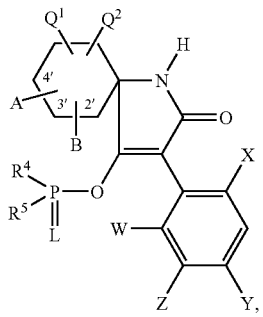 (I-1-e)

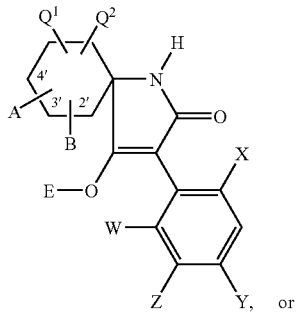 (I-1-f)

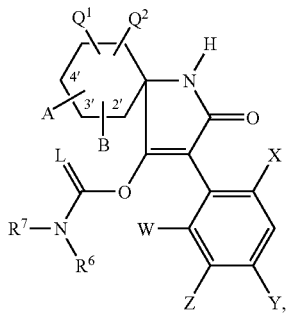 (I-1-g)

or a compound of the formula (I-2-a)-(I-2-g):

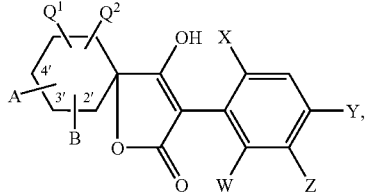 (I-2-a)

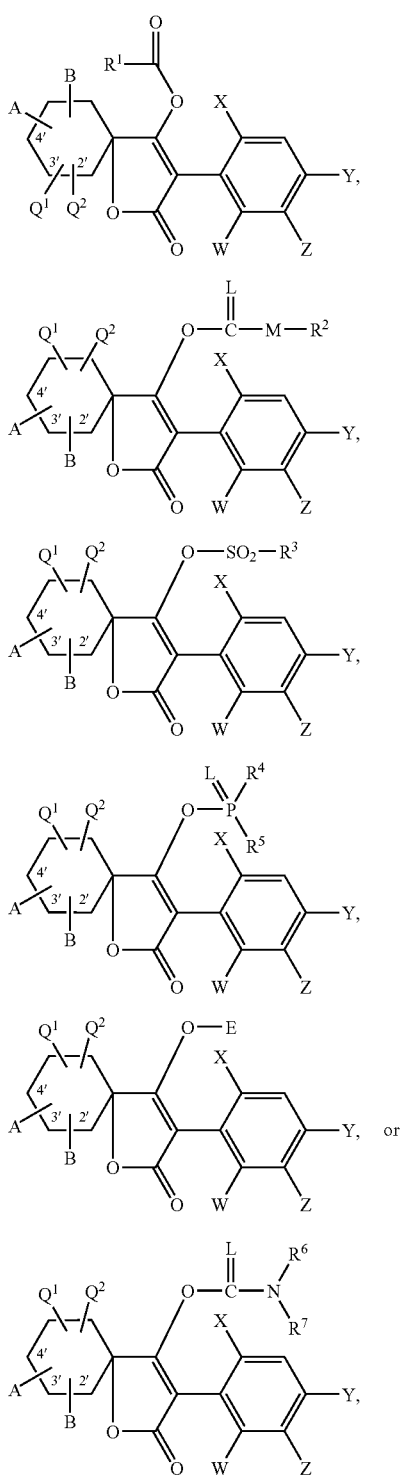

wherein $R^1$-$R^7$, M, L, E, A, B, D, G, $Q^1$, $Q^2$, W, X, Y and Z are as defined in claim 1.

7. A composition for controlling plant pests, unwanted vegetation or unwanted microorganisms, comprising at least one compound according to claim 1.

8. A method for controlling plant pests, unwanted vegetation or unwanted microorganisms, comprising contacting a compound according to claim 1 with pests, unwanted vegetation, unwanted microorganisms or their habitat.

9. A process for preparing a composition for controlling plant pests, unwanted vegetation or unwanted microorganisms, comprising mixing a compound according to claim 1 with one or more extenders, surfactants, or combinations thereof.

10. A composition comprising an effective amount of an active compound combination comprising,
(a') at least one compound according to claim 1 and
(b') at least one crop plant compatibility-improving compound selected from the group consisting of
4-dichloroacetyl-1-oxa-4-azaspiro[4.5]decane (AD-67, MON-4660), 1-dichloro-acetylhexahydro-3,3,8a-trimethylpyrrolo[1,2-a]pyrimidin-6(2H)-one (dicyclonon, BAS-145138), 4-dichloroacetyl-3,4-dihydro-3-methyl-2H-1,4-benzoxazine (benoxacor), 1-methylhexyl 5-chloroquinoline-8-oxyacetate (cloquintocet-mexyl), 3-(2-chlorobenzyl)-1-(1-methyl-1-phenylethyl)urea (cumyluron), α-(cyanomethoximino)phenylacetonitrile (cyometrinil), 2,4-dichlorophenoxyacetic acid (2,4-D), 4-(2,4-dichlorophenoxy)butyric acid (2,4-DB), 1-(1-methyl-1-phenylethyl)-3-(4-methylphenyl)urea (daimuron, dymron), 3,6-dichloro-2-methoxybenzoic acid (dicamba), S-1-methyl-1-phenylethyl piperidine-1-thiocarboxylate (dimepiperate), 2,2-dichloro-N-(2-oxo-2-(2-propenylamino)ethyl)-N-(2-propenyl)acetamide (DKA-24), 2,2-dichloro-N,N-di-2-propenylacetamide (dichlormid), 4,6-dichloro-2-phenylpyrimidine (fenclorim), ethyl 1-(2,4-dichlorophenyl)-5-trichloromethyl-1H-1,2,4-triazole-3-carboxylate (fenchlorazole-ethyl), phenylmethyl 2-chloro-4-trifluoromethylthiazole-5-carboxylate (flurazole), 4-chloro-N-(1,3-dioxolan-2-yl-methoxy)-α-trifluoroacetophenone oxime (fluxofenim), 3-dichloroacetyl-5-(2-furanyl)-2,2-dimethyloxazolidine (furilazole, MON-13900), ethyl 4,5-dihydro-5,5-diphenyl-3-isoxazolecarboxylate (isoxadifen-ethyl), 1-(ethoxycarbonyl)ethyl 3,6-dichloro-2-methoxybenzoate (lactidichlor), (4-chloro-o-tolyloxy)acetic acid (MCPA), 2-(4-chloro-o-tolyloxy)propionic acid (mecoprop), diethyl 1-(2,4-dichorophenyl)-4,5-dihydro-5-methyl-1H-pyrazole-3, 5-dicarboxylate (mefenpyr-diethyl), 2-dichloromethyl-2-methyl-1,3-dioxolane (MG-191), 2-propenyl-1-oxa-4-azaspiro[4.5]decane-4-carbodithioate (MG-838), 1,8-naphthalic anhydride, α-(1,3-dioxolan-2-ylmethoximino)phenylacetonitrile (oxabetrinil), 2,2-dichloro-N-(1,3-dioxolan-2-ylmethyl)-N-(2-propenyl) acetamide (PPG-1292), 3-dichloroacetyl-2,2-dimethyloxazolidine (R-28725), 3-dichloroacetyl-2,2,5-trimethyloxazolidine (R-29148), 4-(4-chloro-o-tolyl) butyric acid, 4-(4-chlorophenoxy)butyric acid, diphenylmethoxyacetic acid, methyl diphenylmethoxyacetate, ethyl diphenylmethoxyacetate, methyl 1-(2-chlorophenyl)-5-phenyl-1H-pyrazole-3-carboxylate, ethyl 1-(2,4-dichloro-phenyl)-5-methyl-1H-pyrazole-3-carboxylate, ethyl 1-(2,4-dichlorophenyl)-5-isopropyl-1H-pyrazole-3-carboxylate, ethyl 1-(2,4-dichlorophenyl)-5-(1,1-di-methylethyl)-1H-pyrazole-3-carboxylate, ethyl 1-(2,4-dichlorophenyl)-5-phenyl-1H-pyrazole-3-carboxylate, ethyl 5-(2,4-dichlorobenzyl)-2-isoxazoline-3-carboxylate, ethyl 5-phenyl-2-isoxazoline-3-carboxylate, ethyl 5-(4-fluorophenyl)-5-phenyl-2-isoxazoline-3-carboxylate, 1,3-dimethylbut-1-yl 5-chloroquinoline-8-oxyacetate, 4-allyloxybutyl 5-chloroquinoline-8-oxyacetate, 1-allyloxyprop-2-yl 5-chloroquinoline-8-oxyacetate, methyl 5-chloroquinoxaline-8-oxyacetate, ethyl 5-chloroquinoline-8-oxyacetate, allyl 5-chloroquinoxaline-8-oxyacetate, 2-oxoprop-1-yl 5-chloroquinoline-8-oxyacetate, diethyl 5-chloroquinoline-8-oxymalonate, diallyl 5-chloroquinoxaline-8-oxymalonate, diethyl 5-chloroquinoline-8-oxymalonate, 4-carboxychroman-4-ylacetic acid (AC-304415), 4-chlorophenoxyacetic acid, 3,3'-dimethyl-4-methoxy-benzophenone, 1-bromo-4-chloromethylsulphonylbenzene, 1-[4-(N-2-methoxybenzoylsulphamoyl)phenyl]-3-methylurea (also known as N-(2-methoxybenzoyl)-4-[(methylaminocarbonyl)amino]benzenesulphonamide), 1-[4-(N-2-methoxybenzoylsulphamoyl)phenyl]-3,3-dimethylurea, 1-[4-(N-4,5-dimethylbenzoylsulphamoyl)phenyl]-3-methylurea, 1-[4-(N-naphthyl-sulphamoyl)phenyl]-3,3-dimethylurea, and N-(2-methoxy-5-methylbenzoyl)-4-(cyclopropylaminocarbonyl)benzenesulphonamide, a compound of the general formula (IIa)

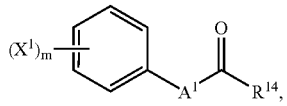

(IIa)

a compound of the general formula (IIb)

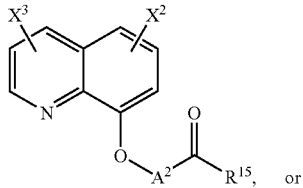

(IIb)

a compound of the formula (IIc)

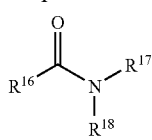

where m represents a number 0, 1, 2, 3, 4 or 5, $A^1$ represents one of the following divalent heterocyclic groups

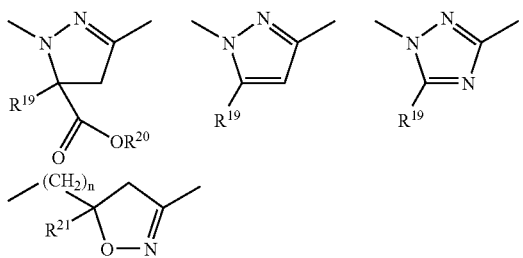

n represents a number 0, 1, 2, 3, 4 or 5, $A^2$ represents alkanediyl having 1 or 2 carbon atoms optionally substituted with one or more substituents selected from the group consisting of $C_1$-$C_4$-alkyl, $C_1$-$C_4$-alkoxy-carbonyl, and $C_1$-$C_4$-alkenyloxy-carbonyl, $R^{14}$ represents hydroxy, mercapto, amino, $C_1$-$C_6$-alkoxy, $C_1$-$C_6$-alkylthio, $C_1$-$C_6$-alkylamino or di($C_1$-$C_4$-alkyl)-amino, $R^{15}$ represents hydroxy, mercapto, amino, $C_1$-$C_7$-alkoxy, $C_1$-$C_6$-alkylthio, $C_1$-$C_6$-alkenyloxy, $C_1$-$C_6$-alkenyloxy-$C_1$-$C_6$-alkoxy, $C_1$-$C_6$-alkylamino or di($C_1$-$C_4$-alkyl)-amino, $R^{16}$ represents $C_1$-$C_4$-alkyl optionally substituted with one or more substituents selected from the group consisting of fluorine, chlorine, and bromine, $R^{17}$ represents hydrogen, represents $C_1$-$C_6$-alkyl, $C_2$-$C_6$-alkenyl or $C_2$-$C_6$-alkynyl in each case optionally substituted with one or more substituents selected from the group consisting of fluorine, chlorine and bromine, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, phenyl optionally substituted with one or more substituents selected from the group consisting of fluorine, chlorine and bromine, or $C_1$-$C_4$-alkyl-substituted phenyl, $R^{18}$ represents hydrogen, represents $C_1$-$C_6$-alkyl, $C_2$-$C_6$-alkenyl or $C_2$-$C_6$-alkynyl in each case optionally substituted with one or more substituents selected from the group consisting of fluorine, chlorine and bromine, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, phenyl optionally substituted with one or more substituents selected from the group consisting of fluorine, chlorine and bromine, or $C_1$-$C_4$-alkyl-substituted phenyl, or $R^{17}$ and $R^{18}$ together represent $C_3$-$C_6$-alkanediyl or $C_2$-$C_5$-oxaalkanediyl, each of which is optionally substituted by $C_1$-$C_4$-alkyl, phenyl, furyl, a fused benzene ring or by two substituents which, together with the C atom to which they are attached, form a 5- or 6-membered carbocycle, $R^{19}$ represents hydrogen, cyano, or halogen, or represents $C_1$-$C_4$-alkyl, $C_3$-$C_6$-cycloalkyl or phenyl in each case optionally substituted with one or more substituents selected from the group consisting of fluorine, chlorine and bromine, $R^{20}$ represents hydrogen, or in each case optionally hydroxy-, cyano-, halogen- or $C_1$-$C_4$-alkoxy-substituted $C_3$-$C_6$-cycloalkyl or tri-($C_1$-$C_4$-alkyl)silyl, $R^{21}$ represents hydrogen, cyano, or halogen, or represents $C_1$-$C_4$-alkyl, $C_3$-$C_6$-cycloalkyl or phenyl in each case optionally substituted with one or more substituents selected from the group consisting of fluorine, chlorine and bromine, $X^1$ represents nitro, cyano, halogen, $C_1$-$C_4$-alkyl, $C_1$-$C_4$-alkoxy or $C_1$-$C_4$-haloalkoxy, $X^2$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, $X^3$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, or a compound selected from the group consisting of a compound of the general formula (IId)

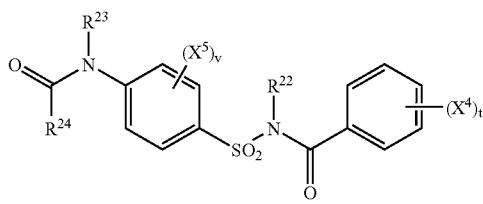

(IId)

and a compound of the general formula (IIe)

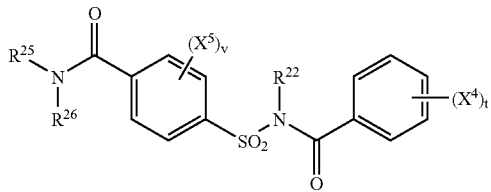

(IIe)

where t represents a number 0, 1, 2, 3, 4, or 5, v represents a number 0, 1, 2, 3, 4, or 5, $R^{22}$ represents hydrogen or $C_1$-$C_4$-alkyl, $R^{23}$ represents hydrogen or $C_1$-$C_4$-alkyl, $R^{24}$ represents hydrogen, in each case optionally cyano-, halogen- or $C_1$-$C_4$-alkoxy-substituted $C_1$-$C_6$-alkyl, $C_1$-$C_6$-alkoxy, $C_1$-$C_6$-alkylthio, $C_1$-$C_6$-alkylamino or di($C_1$-$C_4$-alkyl)-amino, or in each case optionally cyano-, halogen- or $C_1$-$C_4$-alkyl-substituted $C_3$-$C_6$-cycloalkyl, $C_3$-$C_6$-cycloalkyloxy, $C_3$-$C_6$-cycloalkylthio or $C_3$-$C_6$-cycloalkylamino, $R^{25}$ represents hydrogen, optionally cyano-, hydroxy-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, or optionally cyano-, halogen- or $C_1$-$C_4$-alkyl-substituted $C_3$-$C_6$-cycloalkyl, $R^{26}$ represents hydrogen, optionally cyano-, hydroxy-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, optionally cyano-, halogen- or $C_1$-$C_4$-alkyl-substituted $C_3$-$C_6$-cycloalkyl, or optionally nitro-, cyano-, halogen-, $C_1$-$C_4$-alkyl-, $C_1$-$C_4$-haloalkyl-, $C_1$-$C_4$-alkoxy- or $C_1$-$C_4$-haloalkoxy-substituted phenyl, or $R^{26}$ together with $R^{25}$ represents in each case optionally $C_1$-$C_4$-alkyl-substituted $C_2$-$C_6$-alkanediyl or $C_2$-$C_5$-oxaalkanediyl, $X^4$ represents nitro, cyano, carboxyl, carbamoyl, formyl, sulphamoyl, hydroxy, amino, halogen, $C_1$-$C_4$-alkyl, $C_1$-$C_4$-haloalkyl, $C_1$-$C_4$-alkoxy or $C_1$-$C_4$-haloalkoxy, and $X^5$ represents nitro, cyano, carboxyl, carbamoyl, formyl, sulphamoyl, hydroxy, amino, halogen, $C_1$-$C_4$-alkyl, $C_1$-$C_4$-haloalkyl, $C_1$-$C_4$-alkoxy or $C_1$-$C_4$-haloalkoxy.

11. A composition according to claim 10, in which the crop plant compatibility-improving compound is selected from the group consisting of cloquintocet-mexyl, fenchlorazole-ethyl, isoxadifen-ethyl, mefenpyr-diethyl, furilazole, fenclorim, cumyluron, dymron,

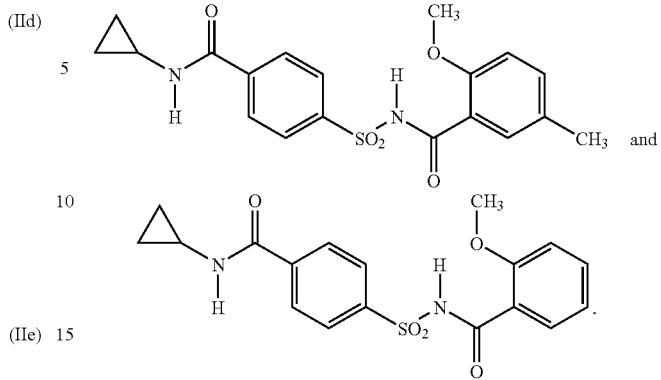

12. The composition according to claim 11, in which the crop plant compatibility-improving compound is cloquintocet-mexyl.

13. The composition according to claim 11, in which the crop plant compatibility-improving compound is mefenpyr-diethyl.

14. A method for controlling unwanted vegetation, comprising contacting unwanted vegetation or their habitat with a composition according to claim 10.

15. A method for controlling unwanted vegetation, comprising contacting unwanted vegetation or their habitat, separately in close temporal succession, with a compound according to claim 1 and a crop plant compatibility-improving compound selected from the group consisting of 4-dichloroacetyl-1-oxa-4-azaspiro[4.5]decane (AD-67, MON-4660), 1-dichloroacetylhexahydro-3,3,8a-trimethylpyrrolo[1,2-a]pyrimidin-6(2H)-one (dicyclonon, BAS-145138), 4-dichloroacetyl-3,4-dihydro-3-methyl-2H-1,4-benzoxazine (benoxacor), 1-methylhexyl 5-chloroquinoline-8-oxyacetate (cloquintocet-mexyl), 3-(2-chlorobenzyl)-1-(1-methyl-1-phenylethyl)urea (cumyluron), α-(cyanomethoximino)phenylacetonitrile (cyometrinil), 2,4-dichlorophenoxyacetic acid (2,4-D), 4-(2,4-dichlorophenoxy)butyric acid (2,4-DB), 1-(1-methyl-1-phenylethyl)-3-(4-methylphenyl)urea (daimuron, dymron), 3,6-dichloro-2-methoxybenzoic acid (dicamba), S-1-methyl-1-phenylethyl piperidine-1-thiocarboxylate (dimepiperate), 2,2-dichloro-N-(2-oxo-2-(2-propenylamino)ethyl)-N-(2-propenyl)acetamide (DKA-24), 2,2-dichloro-N,N-di-2-propenylacetamide (dichlormid), 4,6-dichloro-2-phenylpyrimidine (fenclorim), ethyl 1-(2,4-dichlorophenyl)-5-trichloromethyl-1H-1,2,4-triazole-3-carboxylate (fenchlorazole-ethyl), phenylmethyl 2-chloro-4-trifluoromethylthiazole-5-carboxylate (flurazole), 4-chloro-N-(1,3-dioxolan-2-ylmethoxy)-α-trifluoroacetophenone oxime (fluxofenim), 3-dichloroacetyl-5-(2-furanyl)-2,2-dimethyloxazolidine (furilazole, MON-13900), ethyl 4,5-dihydro-5,5-diphenyl-3-isoxazolecarboxylate (isoxadifen-ethyl), 1-(ethoxycarbonyl)ethyl 3,6-dichloro-2-methoxybenzoate (lactidichlor), (4-chloro-o-tolyloxy)acetic acid (MCPA), 2-(4-chloro-o-tolyloxy)propionic acid (mecoprop), diethyl 1-(2,4-dichorophenyl)-4,5-dihydro-5-methyl-1H-pyrazole-3,5-dicarboxylate (mefenpyr-diethyl), 2-dichloromethyl-2-methyl-1,3-dioxo lane (MG-191), 2-propenyl-1-oxa-4-azaspiro[4.5]decane-4-carbodithioate (MG-838), 1,8-naphthalic anhydride, α-(1,3-dioxolan-2-ylmethoximino)phenylacetonitrile (oxabetrinil), 2,2-dichloro-N-(1,3-dioxolan-2-ylmethyl)-N-(2-propenyl)acetamide (PPG-1292), 3-dichloroacetyl-2,2-dimethyloxazolidine (R-28725), 3-dichloroacetyl-2,2,5-trimethyl-oxazolidine (R-29148), 4-(4-chloro-o-tolyl)butyric acid, 4-(4-chloro-phenoxy)butyric acid, diphenylmethoxyacetic acid, methyl diphenylmethoxy-acetate, ethyl diphenylmethoxyacetate, methyl 1-(2-chlorophenyl)-5-phenyl-1H-pyrazole-3-carboxylate, ethyl 1-(2,4-dichlorophenyl)-5-methyl-1H-pyrazole-3-carboxylate, ethyl 1-(2,4-dichlorophenyl)-5-isopropyl-1H-pyrazole-3-carboxylate, ethyl 1-(2,4-dichlorophenyl)-5-(1,1-dimethylethyl)-1H-pyrazole-3-carboxylate, ethyl 1-(2,4-dichlorophenyl)-5-phenyl-1H-pyrazole-3-carboxylate, ethyl 5-(2,4-dichlorobenzyl)-2-isoxazoline-3-carboxylate, ethyl 5-phenyl-2-isoxazoline-3-carboxylate, ethyl 5-(4-fluorophenyl)-5-phenyl-2-isoxazoline-3-carboxylate, 1,3-dimethylbut-1-yl 5-chloroquinoline-8-oxyacetate, 4-allyl-oxybutyl 5-chloroquinoline-8-oxyacetate, 1-allyloxyprop-2-yl 5-chloroquinoline-8-oxyacetate, methyl 5-chloroquinoxaline-8-oxyacetate, ethyl 5-chloroquinoline-8-oxyacetate, allyl 5-chloroquinoxaline-8-oxyacetate, 2-oxoprop-1-yl 5-chloroquinoline-8-oxyacetate, diethyl 5-chloroquinoline-8-oxymalonate, diallyl 5-chloroquinoxaline-8-oxymalonate, diethyl 5-chloroquinoline-8-oxymalonate, 4-carboxychroman-4-ylacetic acid (AC-304415), 4-chlorophenoxyacetic acid, 3,3-dimethyl-4-methoxybenzophenone, 1-bromo-4-chloromethyl-sulphonylbenzene, 1-[4-(N-2-methoxybenzoylsulphamoyl)phenyl]-3-methylurea (also known as N-(2-methoxybenzoyl)-4-[(methylaminocarbonyl)amino]benzene-sulphonamide), 1-[4-(N-2-methoxybenzoylsulphamoyl)phenyl]-3,3-dimethylurea, 1-[4-(N-4,5-dimethylbenzoylsulphamoyl)phenyl]-3-methylurea, 1-[4-(N-naphthylsulphamoyl)phenyl]-3,3-dimethylurea, N-(2-methoxy-5-methylbenzoyl)-4-(cyclopropylaminocarbonyl)benzenesulphonamide, a compound of the general formula (IIa)

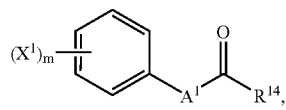

(IIa)

a compound of the general formula (IIb)

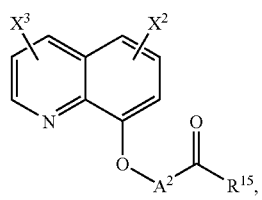

(IIb)

a compound of the formula (IIc)

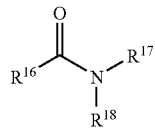

(IIc)

where m represents a number 0, 1, 2, 3, 4 or 5, $A^1$ represents one of the following divalent heterocyclic groups

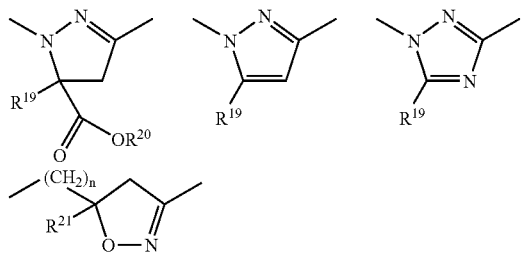

n represents a number 0, 1, 2, 3, 4 or 5, $A^2$ represents alkanediyl having 1 or 2 carbon atoms optionally substituted with one or more substituents selected from the group consisting of $C_1$-$C_4$-alkyl, $C_1$-$C_4$-alkoxy-carbonyl, and $C_1$-$C_4$-alkenyloxy-carbonyl, $R^{14}$ represents hydroxy, mercapto, amino, $C_1$-$C_6$-alkoxy, $C_1$-$C_6$-alkylthio, $C_1$-$C_6$-alkylamino or di($C_1$-$C_4$-alkyl)-amino, $R^{15}$ represents hydroxy, mercapto, amino, $C_1$-$C_4$-alkoxy, $C_1$-$C_6$-alkylthio, $C_1$-$C_6$-alkenyloxy, $C_1$-$C_6$-alkenyloxy-$C_1$-$C_6$-alkoxy, $C_1$-$C_6$-alkylamino or di($C_1$-$C_4$-alkyl)-amino, $R^{16}$ represents $C_1$-$C_4$-alkyl optionally substituted with one or more substituents selected from the group consisting of fluorine, chlorine, and bromine, $R^{17}$ represents hydrogen, represents $C_1$-$C_6$-alkyl, $C_2$-$C_6$-alkenyl or $C_2$-$C_6$-alkynyl in each case optionally substituted with one or more substituents selected from the group consisting of fluorine, chlorine and bromine, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, phenyl optionally substituted with one or more substituents selected from the group consisting of fluorine, chlorine and bromine, or $C_1$-$C_4$-alkyl-substituted phenyl, $R^{18}$ represents hydrogen, represents $C_1$-$C_6$-alkyl, $C_2$-$C_6$-alkenyl or $C_2$-$C_6$-alkynyl in each case optionally substituted with one or more substituents selected from the group consisting of fluorine, chlorine and bromine, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, phenyl optionally substituted with one or more substituents selected from the group consisting of fluorine, chlorine and bromine, or $C_1$-$C_4$-alkyl-substituted phenyl, or $R^{17}$ and $R^{18}$ together represent $C_3$-$C_6$-alkanediyl or $C_2$-$C_5$-oxaalkanediyl, each of which is optionally substituted by $C_1$-$C_4$-alkyl, phenyl, furyl, a fused benzene ring or by two substituents which, together with the C atom to which they are attached, form a 5- or 6-membered carbocycle, $R^{19}$ represents hydrogen, cyano, or halogen, or represents $C_1$-$C_4$-alkyl, $C_3$-$C_6$-cycloalkyl or phenyl in each case optionally substituted with one or more substituents selected from the group consisting of fluorine, chlorine and bromine, $R^{20}$ represents hydrogen, or in each case optionally hydroxy-, cyano-, halogen- or $C_1$-$C_4$-alkoxy-substituted $C_1$-$C_6$-alkyl, $C_3$-$C_6$-cycloalkyl or tri-($C_1$-$C_4$-alkyl)-silyl, $R^{21}$ represents hydrogen, cyano, or halogen, or represents $C_1$-$C_4$-alkyl, $C_3$-$C_6$-cycloalkyl or phenyl in each case optionally substituted with one or more substituents selected from the group consisting of fluorine, chlorine and bromine, $X^1$ represents nitro, cyano, halogen, $C_1$-$C_4$-alkyl, $C_1$-$C_4$-haloalkyl, $C_1$-$C_4$-alkoxy or $C_1$-$C_4$-haloalkoxy, $X^2$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, $X^3$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, a compound of the general formula (IId)

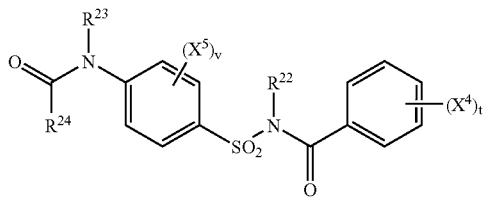

(IId)

and a compound of the general formula (IIe)

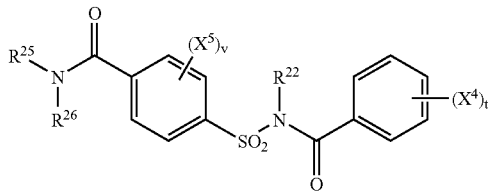

(IIe)

where t represents a number 0, 1, 2, 3, 4, or 5, v represents a number 0, 1, 2, 3, 4, or 5, $R^{22}$ represents hydrogen or $C_1$-$C_4$-alkyl, $R^{23}$ represents hydrogen or $C_1$-$C_4$-alkyl, $R^{24}$ represents hydrogen, in each case optionally cyano-, halogen- or $C_1$-$C_4$-alkoxy-substituted $C_1$-$C_6$-alkyl, $C_1$-$C_6$-alkoxy, $C_1$-$C_6$-alkylthio, $C_1$-$C_6$-alkylamino or di($C_1$-$C_4$-alkyl)-amino, or in each case optionally cyano-, halogen- or $C_1$-$C_4$-alkyl-substituted $C_3$-$C_6$-cycloalkyl, $C_3$-$C_6$-cycloalkyloxy, $C_3$-$C_6$-cycloalkylthio or $C_3$-$C_6$-cycloalkylamino, $R^{25}$ represents hydrogen, optionally cyano-, hydroxy-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, or optionally cyano-, halogen- or $C_1$-$C_4$-alkyl-substituted $C_3$-$C_6$-cycloalkyl, $R^{26}$ represents hydrogen, optionally cyano-, hydroxy-, halogen- or $C_1$-$C_4$-alkoxy-substituted $C_1$-$C_6$-alkyl, in each case optionally cyano- or halogen-substituted $C_3$-$C_6$-alkenyl or $C_3$-$C_6$-alkynyl, optionally cyano-, halogen- or $C_1$-$C_4$-alkyl-substituted $C_3$-$C_6$-cycloalkyl, or optionally nitro-, cyano-, halogen-, $C_1$-$C_4$-alkyl-, $C_1$-$C_4$-haloalkyl-, $C_1$-$C_4$-alkoxy- or $C_1$-$C_4$-haloalkoxy-substituted phenyl, or $R^{26}$ together with $R^{25}$ represents in each case optionally $C_1$-$C_4$-alkyl-substituted $C_2$-$C_6$-alkanediyl or $C_2$-$C_5$-oxaalkanediyl, $X^4$ represents nitro, cyano, carboxyl, carbamoyl, formyl, sulphamoyl, hydroxy, amino, halogen, $C_1$-$C_4$-alkyl, $C_1$-$C_4$-alkoxy or $C_1$-$C_4$-haloalkoxy, and $X^5$ represents nitro, cyano, carboxyl, carbamoyl, formyl, sulphamoyl, hydroxy, amino, halogen, $C_1$-$C_4$-alkyl, $C_1$-$C_4$-haloalkyl, $C_1$-$C_4$-alkoxy or $C_1$-$C_4$-haloalkoxy, are allowed to act, separately in close temporal succession, on the unwanted vegetation or their habitat.

16. The compound according to claim 1, wherein W, X, Y, Z, D, $Q^1$, $Q^2$, G, A and B are defined by one of the following combinations:

| W | X | Y | Z | D | $Q^1$ | $Q^2$ | G | A | B |
|---|---|---|---|---|---|---|---|---|---|
| $CH_3$ | $CH_3$ | $CH_3$ | H | NH | H | H | H | 4'-O— | —$(CH_2)_2$—O— |
| $CH_3$ | $CH_3$ | Cl | H | NH | H | H | H | 4'-O— | —$(CH_2)_2$—O— |
| $CH_3$ | $CH_3$ | Br | H | NH | H | H | H | 4'-O— | —$(CH_2)_2$—O— |
| $CH_3$ | $CH_3$ | $CH_3$ | H | NH | H | H | H | 4'-O— | —$(CH_2)_3$—O— |
| $CH_3$ | $CH_3$ | Cl | H | NH | H | H | H | 4'-O— | —$(CH_2)_3$—O— |
| $CH_3$ | $CH_3$ | Br | H | NH | H | H | H | 4'-O— | —$(CH_2)_3$—O— |

* * * * *